United States Patent
Genov et al.

(10) Patent No.: US 9,481,667 B2
(45) Date of Patent: Nov. 1, 2016

(54) SALTS AND SOLID FORMS OF ISOQUINOLINONES AND COMPOSITION COMPRISING AND METHODS OF USING THE SAME

(71) Applicant: Infinity Pharmaceuticals, Inc., Cambridge, MA (US)

(72) Inventors: Daniel G. Genov, Boston, MA (US); Louis Grenier, Newton, MA (US); Andrew B. Hague, Chelmsford, MA (US); Alexander Redvers Eberlin, Cambridge (GB); Ludovic Sylvain Marc Renou, Cambridge (GB); Susana Del Rio Gancedo, Cambridge (GB)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 112 days.

(21) Appl. No.: 14/209,842

(22) Filed: Mar. 13, 2014

(65) Prior Publication Data

US 2014/0275135 A1 Sep. 18, 2014

Related U.S. Application Data

(60) Provisional application No. 61/789,740, filed on Mar. 15, 2013.

(51) Int. Cl.
*C07D 401/14* (2006.01)
*A61K 31/4725* (2006.01)

(52) U.S. Cl.
CPC ......... *C07D 401/14* (2013.01); *A61K 31/4725* (2013.01)

(58) Field of Classification Search
CPC .................... C07D 401/14; A61K 31/4725
USPC .......................................... 544/324; 514/275
See application file for complete search history.

(56) References Cited

U.S. PATENT DOCUMENTS

| | | | |
|---|---|---|---|
| 4,547,508 A | 10/1985 | Konz et al. |
| 4,656,159 A | 4/1987 | McPherson et al. |
| 4,704,381 A | 11/1987 | Schaumann et al. |
| 4,795,627 A | 1/1989 | Fisher et al. |
| 5,240,941 A | 8/1993 | Bruneau |
| 5,294,612 A | 3/1994 | Bacon et al. |
| 5,310,731 A | 5/1994 | Olsson et al. |
| 5,364,862 A | 11/1994 | Spada et al. |
| 5,420,419 A | 5/1995 | Wood |
| 5,428,125 A | 6/1995 | Hefner, Jr. et al. |
| 5,442,039 A | 8/1995 | Hefner, Jr. et al. |
| 5,446,040 A | 8/1995 | Walter |
| 5,504,103 A | 4/1996 | Bonjouklian et al. |
| 5,506,347 A | 4/1996 | Erion et al. |
| 5,525,604 A | 6/1996 | Lee et al. |
| 5,561,134 A | 10/1996 | Spada et al. |
| 5,563,257 A | 10/1996 | Zilch et al. |
| 5,593,997 A | 1/1997 | Dow et al. |
| 5,646,128 A | 7/1997 | Firestein et al. |
| 5,652,366 A | 7/1997 | Spada et al. |
| 5,654,307 A | 8/1997 | Bridges et al. |
| 5,665,721 A | 9/1997 | Bhagwat et al. |
| 5,674,998 A | 10/1997 | Boyer et al. |
| 5,686,455 A | 11/1997 | Adams et al. |
| 5,736,554 A | 4/1998 | Spada et al. |
| 5,747,235 A | 5/1998 | Farid et al. |
| 5,756,711 A | 5/1998 | Zilch et al. |
| 5,763,596 A | 6/1998 | Boyer et al. |
| 5,763,597 A | 6/1998 | Ugarkar et al. |
| 5,763,885 A | 6/1998 | Murphy et al. |
| 5,795,977 A | 8/1998 | Ugarkar et al. |
| 5,811,454 A | 9/1998 | Springer |
| 5,824,492 A | 10/1998 | Hiles et al. |
| 5,858,753 A | 1/1999 | Chantry et al. |
| 5,914,488 A | 6/1999 | Sone |
| 5,919,808 A | 7/1999 | Petrie et al. |
| 5,922,753 A | 7/1999 | Petrie et al. |
| 5,948,776 A | 9/1999 | Petrie et al. |
| 5,965,573 A | 10/1999 | Petrie et al. |
| 5,977,061 A | 11/1999 | Holy et al. |
| 5,981,533 A | 11/1999 | Traxler et al. |
| 5,985,589 A | 11/1999 | Chantry et al. |
| 5,990,169 A | 11/1999 | Petrie et al. |
| 5,994,358 A | 11/1999 | Petrie et al. |
| 6,001,839 A | 12/1999 | Calderwood et al. |
| 6,057,305 A | 5/2000 | Holy et al. |
| 6,063,930 A | 5/2000 | Dinsmore et al. |

(Continued)

FOREIGN PATENT DOCUMENTS

CA 1338379 C 6/1996
CN 101602768 A 12/2009

(Continued)

OTHER PUBLICATIONS

Stahl et al., eds., Handbook of pharmaceutical salts. Properties, selection and use (Wiley-VCH, 2008), pp. 265-327.*
Serajuddin, Advanced Drug Delivery Reviews 59 (2007) 603-616.*
Liu, Rong, ed., Water-Insoluble Drug Formulation (CRC Press, 2008) Chapter 15 pp. 417-435.*
Bastin et al., Organic Process Research & Development 2000, 4,427-435.*
Morris, et al., International Journal of Pharmaceutics 105 (1994) 209-217.*
Adeyeye, Moji, ed., Preformulation in Solid Dosage Form Development (Informa Healthcare, 2008) Chapter 2.3, pp. 63-80.*

(Continued)

*Primary Examiner* — Deepak Rao
(74) *Attorney, Agent, or Firm* — Jones Day

(57) ABSTRACT

Solid forms of chemical compounds that modulate kinase activity, including PI3 kinase activity, and compounds, pharmaceutical compositions, and methods of treatment of diseases and conditions associated with kinase activity, including PI3 kinase activity, are described herein. Also provided herein are processes for preparing compounds, solid forms thereof, and pharmaceutical compositions thereof.

35 Claims, 54 Drawing Sheets

(56) References Cited

U.S. PATENT DOCUMENTS

Figure 2A:
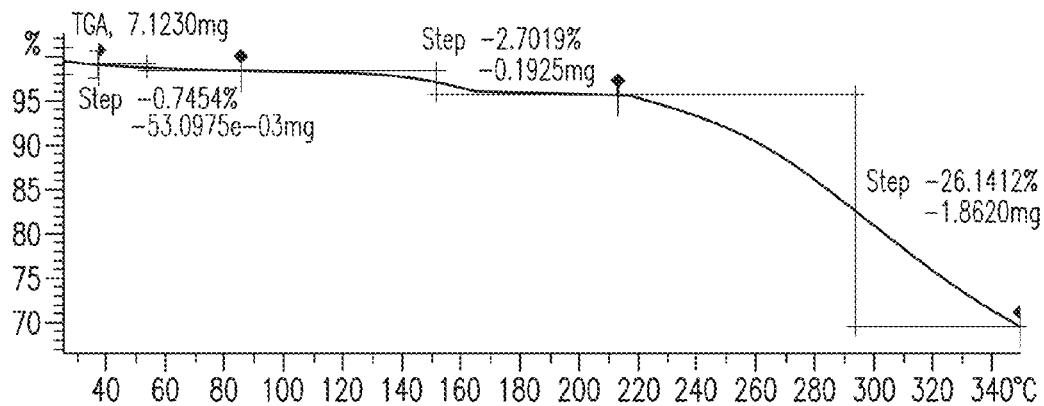

| | | |
|---|---|---|
| 6,084,095 A | 7/2000 | Bridges et al. |
| 6,093,737 A | 7/2000 | Anthony et al. |
| 6,127,121 A | 10/2000 | Meyer, Jr. et al. |
| 6,150,352 A | 11/2000 | Goulet et al. |
| 6,153,631 A | 11/2000 | Petrie et al. |
| 6,191,170 B1 | 2/2001 | Medina |
| 6,251,901 B1 | 6/2001 | Petrie et al. |
| 6,265,410 B1 | 7/2001 | Bridges et al. |
| 6,268,370 B1 | 7/2001 | Adams et al. |
| 6,312,894 B1 | 11/2001 | Hedgpeth et al. |
| 6,323,201 B1 | 11/2001 | Carson et al. |
| 6,342,514 B1 | 1/2002 | Petrie et al. |
| 6,350,741 B1 | 2/2002 | Golec et al. |
| 6,383,790 B1 | 5/2002 | Shokat |
| 6,384,039 B1 | 5/2002 | Fossa |
| 6,387,894 B1 | 5/2002 | Fossa |
| 6,390,821 B1 | 5/2002 | Shokat |
| 6,455,534 B2 | 9/2002 | Bridges et al. |
| 6,472,153 B1 | 10/2002 | Dempcy et al. |
| 6,482,623 B1 | 11/2002 | Vanhaesebroeck et al. |
| 6,485,906 B2 | 11/2002 | Meyer, Jr. et al. |
| 6,492,346 B1 | 12/2002 | Hedgpeth et al. |
| 6,506,769 B2 | 1/2003 | Snow et al. |
| 6,518,277 B1 | 2/2003 | Sadhu et al. |
| 6,521,417 B1 | 2/2003 | Shokat |
| 6,521,620 B1 | 2/2003 | Bridges et al. |
| 6,531,491 B1 | 3/2003 | Kania et al. |
| 6,534,524 B1 | 3/2003 | Kania et al. |
| 6,545,005 B1 | 4/2003 | Baxter et al. |
| 6,552,192 B1 | 4/2003 | Hanus et al. |
| 6,562,819 B2 | 5/2003 | Carson et al. |
| 6,583,161 B1 | 6/2003 | Medina |
| 6,586,441 B2 | 7/2003 | Borroni et al. |
| 6,613,798 B1 | 9/2003 | Porter et al. |
| 6,630,495 B1 | 10/2003 | Cooke et al. |
| 6,632,789 B1 | 10/2003 | June |
| 6,645,989 B2 | 11/2003 | Adams et al. |
| 6,649,631 B1 | 11/2003 | Orme et al. |
| 6,653,296 B1 | 11/2003 | Holy et al. |
| 6,653,306 B1 | 11/2003 | Alexander et al. |
| 6,660,744 B1 | 12/2003 | Hirst et al. |
| 6,660,845 B1 | 12/2003 | Gall et al. |
| 6,664,269 B2 | 12/2003 | Martin et al. |
| 6,667,300 B2 | 12/2003 | Sadhu et al. |
| 6,690,583 B1 | 2/2004 | Bergstedt et al. |
| 6,710,058 B2 | 3/2004 | Jacobson et al. |
| 6,713,484 B2 | 3/2004 | Bridges et al. |
| 6,720,344 B2 | 4/2004 | Kerwin et al. |
| 6,734,187 B1 | 5/2004 | Tanaka et al. |
| 6,770,639 B2 | 8/2004 | Snow et al. |
| 6,777,425 B2 | 8/2004 | Burli et al. |
| 6,777,439 B2 | 8/2004 | Durden |
| 6,790,844 B2 | 9/2004 | Ueno et al. |
| 6,800,620 B2 | 10/2004 | Sadhu et al. |
| 6,849,420 B2 | 2/2005 | Vanhasebroeck et al. |
| 6,849,713 B2 | 2/2005 | Zhang et al. |
| 6,852,727 B2 | 2/2005 | Goulet et al. |
| 6,906,103 B2 | 6/2005 | Zhang et al. |
| 6,916,949 B2 | 7/2005 | Springer et al. |
| 6,919,332 B2 | 7/2005 | Noe et al. |
| 6,921,763 B2 | 7/2005 | Hirst et al. |
| 6,949,535 B2 | 9/2005 | Sadhu et al. |
| 7,026,461 B1 | 4/2006 | Shokat |
| 7,041,676 B2 | 5/2006 | McDonald et al. |
| 7,049,116 B2 | 5/2006 | Shokat |
| 7,049,312 B1 | 5/2006 | Rafferty et al. |
| 7,064,218 B2 | 6/2006 | Dyatkina et al. |
| 7,071,355 B2 | 7/2006 | Leban et al. |
| 7,087,614 B2 | 8/2006 | Guo et al. |
| 7,115,627 B2 | 10/2006 | Pinto et al. |
| 7,115,653 B2 | 10/2006 | Baxter et al. |
| 7,144,903 B2 | 12/2006 | Collins et al. |
| 7,157,487 B2 | 1/2007 | Nakayama et al. |
| 7,166,293 B2 | 1/2007 | Teng et al. |
| 7,173,028 B2 | 2/2007 | Dahmann et al. |
| 7,208,601 B2 | 4/2007 | Mjalli et al. |
| 7,217,794 B2 | 5/2007 | Abdel-Meguid et al. |
| 7,235,585 B2 | 6/2007 | Springer et al. |
| 7,244,741 B2 | 7/2007 | Simon et al. |
| 7,247,736 B2 | 7/2007 | Leban et al. |
| 7,262,204 B2 | 8/2007 | Collins et al. |
| 7,265,111 B2 | 9/2007 | Bigot et al. |
| 7,265,131 B2 | 9/2007 | Johnson et al. |
| 7,273,868 B2 | 9/2007 | Yamada et al. |
| 7,329,765 B2 | 2/2008 | Burli et al. |
| 7,332,497 B2 | 2/2008 | Hirst et al. |
| 7,338,959 B2 | 3/2008 | Chamberlain et al. |
| 7,348,427 B2 | 3/2008 | Burli et al. |
| 7,365,094 B2 | 4/2008 | Leban et al. |
| 7,384,967 B2 | 6/2008 | Polisetti et al. |
| 7,396,836 B2 | 7/2008 | Harada et al. |
| 7,414,036 B2 | 8/2008 | Sevillano et al. |
| 7,429,596 B2 | 9/2008 | Tanaka et al. |
| 7,439,254 B2 | 10/2008 | Bergnes |
| 7,449,456 B2 | 11/2008 | Nagashima et al. |
| 7,449,477 B2 | 11/2008 | Barda et al. |
| 7,459,462 B2 | 12/2008 | Simon et al. |
| 7,459,472 B2 | 12/2008 | Mjalli et al. |
| 7,470,721 B2 | 12/2008 | Durden |
| 7,501,538 B2 | 3/2009 | Mjalli et al. |
| 7,514,445 B2 | 4/2009 | Freyne et al. |
| 7,517,889 B2 | 4/2009 | Harris et al. |
| 7,534,797 B2 | 5/2009 | Arnold et al. |
| 7,541,373 B2 | 6/2009 | Polisetti et al. |
| 7,569,571 B2 | 8/2009 | Dong et al. |
| 7,572,913 B2 | 8/2009 | McKerracher et al. |
| 7,579,348 B2 | 8/2009 | Wang et al. |
| 7,585,868 B2 | 9/2009 | Knight et al. |
| 7,608,594 B2 | 10/2009 | Blagg et al. |
| 7,615,552 B2 | 11/2009 | Ono et al. |
| 7,622,451 B2 | 11/2009 | Blagg et al. |
| 7,678,803 B2 | 3/2010 | Huang et al. |
| 7,700,607 B2 | 4/2010 | Hu et al. |
| 7,700,620 B2 | 4/2010 | Sutton et al. |
| 7,705,018 B2 | 4/2010 | Chen et al. |
| 7,728,008 B2 | 6/2010 | Qiao et al. |
| 7,745,485 B2 | 6/2010 | Durden |
| 7,932,260 B2 | 4/2011 | Fowler et al. |
| 7,989,458 B2 | 8/2011 | Leblanc et al. |
| 8,053,603 B2 | 11/2011 | Shao et al. |
| 8,106,146 B2 | 1/2012 | Benz et al. |
| 8,173,639 B2 | 5/2012 | Simonsen et al. |
| 8,193,182 B2 | 6/2012 | Ren et al. |
| 8,399,483 B2 | 3/2013 | Allen et al. |
| 8,415,365 B2 | 4/2013 | Li et al. |
| 8,420,667 B2 | 4/2013 | Khyanzhin et al. |
| 8,461,147 B2 | 6/2013 | Sapountzis et al. |
| 8,604,032 B2 | 12/2013 | Ren et al. |
| 8,785,470 B2 | 7/2014 | Ren et al. |
| 2001/0019829 A1 | 9/2001 | Nelson et al. |
| 2001/0027197 A1 | 10/2001 | Bridges et al. |
| 2002/0016460 A1 | 2/2002 | Snow et al. |
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0127625 A1 | 9/2002 | Oxelius |
| 2002/0146690 A1 | 10/2002 | Meyer et al. |
| 2002/0147160 A1 | 10/2002 | Bhat et al. |
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 | 4/2003 | Shokat |
| 2003/0083268 A1 | 5/2003 | Burli et al. |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer et al. |
| 2003/0166929 A1 | 9/2003 | Snow et al. |

(56) References Cited

U.S. PATENT DOCUMENTS

| | | |
|---|---|---|
| 2003/0180924 A1 | 9/2003 | DeSimone |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |
| 2003/0199516 A1 | 10/2003 | Moser et al. |
| 2003/0208800 A1 | 11/2003 | Eby et al. |
| 2003/0212113 A1 | 11/2003 | Dyatkina et al. |
| 2003/0232849 A1 | 12/2003 | Noe et al. |
| 2003/0235822 A1 | 12/2003 | Lokhov et al. |
| 2004/0039035 A1 | 2/2004 | Collins et al. |
| 2004/0043959 A1 | 3/2004 | Bloom et al. |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0102423 A1 | 5/2004 | McLaughlan et al. |
| 2004/0102437 A1 | 5/2004 | Takami et al. |
| 2004/0110717 A1 | 6/2004 | Carroll et al. |
| 2004/0110945 A1 | 6/2004 | Nakayama et al. |
| 2004/0116689 A1 | 6/2004 | Gall et al. |
| 2004/0122235 A1 | 6/2004 | Polisetti et al. |
| 2004/0127434 A1 | 7/2004 | Bigot et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0266780 A1 | 12/2004 | Sadhu et al. |
| 2005/0004149 A1 | 1/2005 | Harada et al. |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0153997 A1 | 7/2005 | Simon et al. |
| 2005/0171148 A1 | 8/2005 | Mjalli et al. |
| 2005/0182045 A1 | 8/2005 | Nagase et al. |
| 2005/0187418 A1 | 8/2005 | Small et al. |
| 2005/0197340 A1 | 9/2005 | Arora et al. |
| 2005/0214310 A1 | 9/2005 | Toki et al. |
| 2005/0215579 A1 | 9/2005 | Simon et al. |
| 2005/0239809 A1 | 10/2005 | Watts et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2006/0019988 A1 | 1/2006 | McDonald et al. |
| 2006/0069034 A1 | 3/2006 | Burli et al. |
| 2006/0079538 A1 | 4/2006 | Hallahan et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0183783 A1 | 8/2006 | Polisetti et al. |
| 2006/0199776 A1 | 9/2006 | Blagg et al. |
| 2006/0205694 A1 | 9/2006 | Alonso et al. |
| 2006/0235031 A1 | 10/2006 | Arnold et al. |
| 2006/0276470 A1 | 12/2006 | Jackson et al. |
| 2006/0287295 A1 | 12/2006 | Barlaam et al. |
| 2006/0293274 A1 | 12/2006 | Wu |
| 2007/0015773 A1 | 1/2007 | Bergeron et al. |
| 2007/0017915 A1 | 1/2007 | Weder et al. |
| 2007/0027193 A1 | 2/2007 | Leban et al. |
| 2007/0032640 A1 | 2/2007 | Varghese et al. |
| 2007/0054915 A1 | 3/2007 | Arora et al. |
| 2007/0072897 A1 | 3/2007 | Mahaney et al. |
| 2007/0099871 A1 | 5/2007 | Davis et al. |
| 2007/0142405 A1 | 6/2007 | Dong et al. |
| 2007/0179151 A1 | 8/2007 | Chen et al. |
| 2007/0224672 A1 | 9/2007 | Leban et al. |
| 2007/0249598 A1 | 10/2007 | Wang et al. |
| 2007/0270452 A1 | 11/2007 | Blagg et al. |
| 2008/0032960 A1 | 2/2008 | Knight et al. |
| 2008/0058521 A1 | 3/2008 | Krishnan et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0200465 A1 | 8/2008 | Burli et al. |
| 2008/0249090 A1 | 10/2008 | Hu et al. |
| 2008/0261956 A1 | 10/2008 | Choi et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0306053 A1 | 12/2008 | Tachdjian et al. |
| 2008/0306093 A1 | 12/2008 | Servant et al. |
| 2008/0306099 A1 | 12/2008 | Li et al. |
| 2008/0312180 A1 | 12/2008 | Liang et al. |
| 2008/0318942 A1 | 12/2008 | Simon et al. |
| 2009/0023729 A1 | 1/2009 | Nakamura et al. |
| 2009/0030023 A1 | 1/2009 | Harada et al. |
| 2009/0053192 A1 | 2/2009 | Millan et al. |
| 2009/0088452 A1 | 4/2009 | Coleman et al. |
| 2009/0099214 A1 | 4/2009 | Fairhurst et al. |
| 2009/0105233 A1 | 4/2009 | Chua et al. |
| 2009/0118283 A1 | 5/2009 | Defert et al. |
| 2009/0124638 A1 | 5/2009 | Shokat et al. |
| 2009/0124654 A1 | 5/2009 | Mjalli et al. |
| 2009/0137581 A1 | 5/2009 | Chen et al. |
| 2009/0143402 A1 | 6/2009 | Simonsen et al. |
| 2009/0163481 A1 | 6/2009 | Murphy et al. |
| 2009/0163709 A1 | 6/2009 | Blagg |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0209539 A1 | 8/2009 | Leblanc et al. |
| 2009/0232768 A1 | 9/2009 | Birkus et al. |
| 2009/0247513 A1 | 10/2009 | Burli et al. |
| 2009/0253694 A1 | 10/2009 | Ono et al. |
| 2009/0264409 A1 | 10/2009 | Dong et al. |
| 2009/0264423 A2 | 10/2009 | Chua et al. |
| 2009/0270426 A1 | 10/2009 | Knight et al. |
| 2009/0270567 A1 | 10/2009 | Small et al. |
| 2009/0312319 A1* | 12/2009 | Ren .................. C07D 487/04 514/234.2 |
| 2009/0312406 A1 | 12/2009 | Hsieh et al. |
| 2009/0318411 A1 | 12/2009 | Castanedo et al. |
| 2009/0325967 A1 | 12/2009 | Fairhurst et al. |
| 2010/0009963 A1 | 1/2010 | Knight et al. |
| 2010/0022585 A1 | 1/2010 | deLong et al. |
| 2010/0028280 A1 | 2/2010 | Philippe et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0105630 A1 | 4/2010 | Blagg |
| 2010/0163070 A1 | 7/2010 | Malle et al. |
| 2010/0168153 A1 | 7/2010 | Stowasser et al. |
| 2010/0179167 A1 | 7/2010 | Xu et al. |
| 2010/0190749 A1 | 7/2010 | Ren et al. |
| 2010/0280067 A1 | 11/2010 | Sarma et al. |
| 2010/0305099 A1 | 12/2010 | Sapountzias et al. |
| 2010/0324074 A1 | 12/2010 | Zhang |
| 2010/0331306 A1 | 12/2010 | Bui et al. |
| 2011/0009378 A1 | 1/2011 | Lange et al. |
| 2011/0046165 A1 | 2/2011 | Ren et al. |
| 2011/0105508 A1 | 5/2011 | Allen et al. |
| 2011/0124641 A1 | 5/2011 | Ren et al. |
| 2011/0130306 A1 | 6/2011 | Chang |
| 2011/0130420 A1 | 6/2011 | Khanzhin et al. |
| 2011/0135655 A1 | 6/2011 | Katsikis et al. |
| 2011/0144134 A1 | 6/2011 | Shokat et al. |
| 2011/0172228 A1 | 7/2011 | Ren et al. |
| 2011/0172335 A1 | 7/2011 | Deshpande |
| 2011/0224223 A1 | 9/2011 | Shokat et al. |
| 2011/0251182 A1 | 10/2011 | Sun et al. |
| 2011/0269779 A1 | 11/2011 | Wilson et al. |
| 2011/0281866 A1 | 11/2011 | Ren et al. |
| 2011/0301144 A1 | 12/2011 | Knight et al. |

(56) References Cited

U.S. PATENT DOCUMENTS

| | | | |
|---|---|---|---|
| 2012/0059000 A1 | 3/2012 | Ren et al. | |
| 2012/0065154 A1 | 3/2012 | Tanaka et al. | |
| 2012/0077815 A1* | 3/2012 | Allen | C07D 401/12 514/245 |
| 2012/0122838 A1 | 5/2012 | Ren et al. | |
| 2012/0149701 A1 | 6/2012 | Ren et al. | |
| 2012/0184568 A1 | 7/2012 | Ren et al. | |
| 2012/0202784 A1 | 8/2012 | Aronov et al. | |
| 2012/0220575 A1 | 8/2012 | Chang et al. | |
| 2012/0245169 A1 | 9/2012 | Ren et al. | |
| 2012/0329776 A1 | 12/2012 | Ren et al. | |
| 2013/0029982 A1 | 1/2013 | Castro et al. | |
| 2013/0029984 A1 | 1/2013 | Castro et al. | |
| 2013/0053362 A1 | 2/2013 | Castro et al. | |
| 2014/0275135 A1 | 9/2014 | Genov et al. | |
| 2014/0288048 A1 | 9/2014 | Castro et al. | |

FOREIGN PATENT DOCUMENTS

| | | |
|---|---|---|
| DE | 2139107 A1 | 2/1973 |
| EP | 0530149 A1 | 3/1993 |
| EP | 0640599 A1 | 3/1995 |
| EP | 773023 A1 | 5/1997 |
| EP | 1020445 B1 | 8/2008 |
| EP | 2433636 A1 | 3/2012 |
| GB | 812366 A | 4/1959 |
| GB | 937725 A | 9/1963 |
| JP | 61-109797 A | 5/1986 |
| JP | 05-256693 A | 10/1993 |
| JP | 08295667 A | 11/1996 |
| JP | 09143163 A | 6/1997 |
| JP | 10206995 A | 8/1998 |
| JP | 2000072773 A | 3/2000 |
| JP | 2002131859 A | 5/2002 |
| JP | 2003073357 A | 3/2003 |
| JP | 2004161716 A | 6/2004 |
| JP | 4834699 | 12/2011 |
| JP | 4846769 | 12/2011 |
| WO | WO 83/01446 A1 | 4/1983 |
| WO | WO 91/17161 A1 | 11/1991 |
| WO | WO 92/14733 A1 | 9/1992 |
| WO | WO 93/16091 A1 | 8/1993 |
| WO | WO 93/16092 A1 | 8/1993 |
| WO | WO 93/18035 A1 | 9/1993 |
| WO | WO 93/19767 A1 | 10/1993 |
| WO | WO 93/22443 A1 | 11/1993 |
| WO | WO 94/13677 A1 | 6/1994 |
| WO | WO 94/17803 A1 | 8/1994 |
| WO | WO 94/19340 A1 | 9/1994 |
| WO | WO 94/20490 A1 | 9/1994 |
| WO | WO 94/29436 A1 | 12/1994 |
| WO | WO 95/01975 A1 | 1/1995 |
| WO | WO 95/07278 A1 | 3/1995 |
| WO | WO 95/10628 A2 | 4/1995 |
| WO | WO 95/12588 A1 | 5/1995 |
| WO | WO 95/29673 A1 | 11/1995 |
| WO | WO 95/32984 A1 | 12/1995 |
| WO | WO 95/10628 A3 | 9/1996 |
| WO | WO 96/40706 A1 | 12/1996 |
| WO | WO 97/28133 A1 | 8/1997 |
| WO | WO 97/28161 A1 | 8/1997 |
| WO | WO 98/41525 A1 | 9/1998 |
| WO | WO 98/52611 A1 | 11/1998 |
| WO | WO 98/57952 A1 | 12/1998 |
| WO | WO 00/17202 A1 | 3/2000 |
| WO | WO 01/02369 A2 | 1/2001 |
| WO | WO 01/16114 A2 | 3/2001 |
| WO | WO 01/19829 A2 | 3/2001 |
| WO | WO 01/25238 A2 | 4/2001 |
| WO | WO 01/31063 A1 | 5/2001 |
| WO | WO 01/38584 A2 | 5/2001 |
| WO | WO 01/16114 A3 | 8/2001 |
| WO | WO 01/55140 A1 | 8/2001 |
| WO | WO 01/55143 A1 | 8/2001 |
| WO | WO 01/56988 A1 | 8/2001 |
| WO | WO 01/19829 A3 | 9/2001 |
| WO | WO 01/25238 A3 | 10/2001 |
| WO | WO 01/38584 A3 | 10/2001 |
| WO | WO 01/81346 A2 | 11/2001 |
| WO | WO 02/06192 A1 | 1/2002 |
| WO | WO 01/81346 A3 | 3/2002 |
| WO | WO 01/02369 A3 | 4/2002 |
| WO | WO 02/30944 A2 | 4/2002 |
| WO | WO 02/057425 A2 | 7/2002 |
| WO | WO 02/076986 A1 | 10/2002 |
| WO | WO 02/080926 A1 | 10/2002 |
| WO | WO 02/083143 A1 | 10/2002 |
| WO | WO 02/088025 A1 | 11/2002 |
| WO | WO 02/090334 A1 | 11/2002 |
| WO | WO 02/030944 A3 | 1/2003 |
| WO | WO 03/000187 A2 | 1/2003 |
| WO | WO 03/016275 A1 | 2/2003 |
| WO | WO 03/020880 A2 | 3/2003 |
| WO | WO 03/024969 A1 | 3/2003 |
| WO | WO 03/028341 A2 | 4/2003 |
| WO | WO 03/035075 A1 | 5/2003 |
| WO | WO 03/059884 A1 | 7/2003 |
| WO | WO 03/020880 A3 | 10/2003 |
| WO | WO 03/082341 A1 | 10/2003 |
| WO | WO 03/106426 A1 | 12/2003 |
| WO | WO 2004/006906 A2 | 1/2004 |
| WO | WO 2004/006906 A3 | 3/2004 |
| WO | WO 2004/018058 A2 | 3/2004 |
| WO | WO 2004/031177 A1 | 4/2004 |
| WO | WO 2004/039774 A2 | 5/2004 |
| WO | WO 2004/018058 A3 | 7/2004 |
| WO | WO 2004/039774 A3 | 7/2004 |
| WO | WO 2004/058717 A1 | 7/2004 |
| WO | WO 03/000187 A3 | 8/2004 |
| WO | WO 2004/087053 A2 | 10/2004 |
| WO | WO 2004/111014 A1 | 12/2004 |
| WO | WO 2005/002585 A1 | 1/2005 |
| WO | WO 2005/007085 A2 | 1/2005 |
| WO | WO 2005/012323 A2 | 2/2005 |
| WO | WO 2005/016348 A1 | 2/2005 |
| WO | WO 2005/016349 A1 | 2/2005 |
| WO | WO 2005/016528 A2 | 2/2005 |
| WO | WO 2005/021533 A1 | 3/2005 |
| WO | WO 2002/057425 A3 | 4/2005 |
| WO | WO 2005/012323 A3 | 5/2005 |
| WO | WO 2005/016528 A3 | 5/2005 |
| WO | WO 2005/044181 A2 | 5/2005 |
| WO | WO 2005/047289 A1 | 5/2005 |
| WO | WO 2005/061460 A1 | 7/2005 |
| WO | WO 2005/063258 A1 | 7/2005 |
| WO | WO 2005/067901 A2 | 7/2005 |
| WO | WO 2005/074603 A2 | 8/2005 |
| WO | WO 2005/007085 A3 | 9/2005 |
| WO | WO 2005/097800 A1 | 10/2005 |
| WO | WO 2005/105760 A1 | 11/2005 |
| WO | WO 2005/067901 A3 | 12/2005 |
| WO | WO 2005/112935 A1 | 12/2005 |
| WO | WO 2005/113556 A1 | 12/2005 |
| WO | WO 2005/117889 A1 | 12/2005 |
| WO | WO 2005/120511 A1 | 12/2005 |
| WO | WO 2005/044181 A3 | 3/2006 |
| WO | WO 2006/030032 A1 | 3/2006 |
| WO | WO 2006/038865 A1 | 4/2006 |
| WO | WO 2006/050501 A2 | 5/2006 |
| WO | WO 2006/050946 A1 | 5/2006 |
| WO | WO 2006/068760 A2 | 6/2006 |
| WO | WO 2004/087053 A3 | 8/2006 |
| WO | WO 2006/089106 A2 | 8/2006 |
| WO | WO 2006/108107 A1 | 10/2006 |
| WO | WO 2006/112666 A1 | 10/2006 |
| WO | WO 2005/074603 A3 | 11/2006 |
| WO | WO 2006/114064 A2 | 11/2006 |
| WO | WO 2006/114065 A2 | 11/2006 |
| WO | WO 2006/068760 A3 | 12/2006 |
| WO | WO 2006/089106 A3 | 12/2006 |
| WO | WO 2007/002293 A2 | 1/2007 |
| WO | WO 2007/006547 A1 | 1/2007 |
| WO | WO 2007/020046 A1 | 2/2007 |
| WO | WO 2007/002293 A3 | 3/2007 |

(56) References Cited

FOREIGN PATENT DOCUMENTS

| | | |
|---|---|---|
| WO | WO 2007/025090 A2 | 3/2007 |
| WO | WO 2006/050501 A3 | 5/2007 |
| WO | WO 2007/061737 A2 | 5/2007 |
| WO | WO 2006/114064 A3 | 6/2007 |
| WO | WO 2006/114065 A3 | 6/2007 |
| WO | WO 2007/025090 A3 | 6/2007 |
| WO | WO 2007/075554 A2 | 7/2007 |
| WO | WO 2007/079164 A2 | 7/2007 |
| WO | WO 2007/079164 A3 | 9/2007 |
| WO | WO 2007/103308 A2 | 9/2007 |
| WO | WO 2007/112005 A2 | 10/2007 |
| WO | WO 2007/114926 A2 | 10/2007 |
| WO | WO 2007/121453 A2 | 10/2007 |
| WO | WO 2007/121920 A2 | 11/2007 |
| WO | WO 2007/121924 A2 | 11/2007 |
| WO | WO 2007/124854 A1 | 11/2007 |
| WO | WO 2007/125310 A2 | 11/2007 |
| WO | WO 2007/125315 A2 | 11/2007 |
| WO | WO 2007/126841 A2 | 11/2007 |
| WO | WO 2007/134828 A1 | 11/2007 |
| WO | WO 2007/135380 A2 | 11/2007 |
| WO | WO 2007/135398 A1 | 11/2007 |
| WO | WO 2007/061737 A3 | 12/2007 |
| WO | WO 2007/125315 A3 | 12/2007 |
| WO | WO 2007/121920 A3 | 1/2008 |
| WO | WO 2008/001236 A2 | 1/2008 |
| WO | WO 2008/012326 A1 | 1/2008 |
| WO | WO 2007/103308 A3 | 2/2008 |
| WO | WO 2007/112005 A3 | 2/2008 |
| WO | WO 2007/125310 A3 | 3/2008 |
| WO | WO 2008/025755 A1 | 3/2008 |
| WO | WO 2008/039882 A1 | 4/2008 |
| WO | WO 2008/047821 A1 | 4/2008 |
| WO | WO 2008/063625 A2 | 5/2008 |
| WO | WO 2008/064018 A1 | 5/2008 |
| WO | WO 2008/070507 A2 | 6/2008 |
| WO | WO 2007/121453 A3 | 7/2008 |
| WO | WO 2008/079028 A1 | 7/2008 |
| WO | WO 2008/082487 A2 | 7/2008 |
| WO | WO 2008/094737 A2 | 8/2008 |
| WO | WO 2007/121924 A3 | 9/2008 |
| WO | WO 2008/112715 A2 | 9/2008 |
| WO | WO 2007/114926 A3 | 10/2008 |
| WO | WO 2008/118454 A2 | 10/2008 |
| WO | WO 2008/118455 A1 | 10/2008 |
| WO | WO 2008/118468 A1 | 10/2008 |
| WO | WO 2008/125014 A1 | 10/2008 |
| WO | WO 2008/125207 A1 | 10/2008 |
| WO | WO 2008/127226 A2 | 10/2008 |
| WO | WO 2007/126841 A3 | 11/2008 |
| WO | WO 2008/112715 A3 | 11/2008 |
| WO | WO 2008/118454 A3 | 11/2008 |
| WO | WO 2008/136457 A1 | 11/2008 |
| WO | WO 2008/082487 A3 | 12/2008 |
| WO | WO 2008/127226 A3 | 12/2008 |
| WO | WO 2009/000412 A1 | 12/2008 |
| WO | WO 2009/004621 A1 | 1/2009 |
| WO | WO 2009/010925 A2 | 1/2009 |
| WO | WO 2009/023718 A2 | 2/2009 |
| WO | WO 2008/094737 A3 | 3/2009 |
| WO | WO 2009/029617 A1 | 3/2009 |
| WO | WO 2009/023718 A3 | 4/2009 |
| WO | WO 2009/044707 A1 | 4/2009 |
| WO | WO 2009/050506 A2 | 4/2009 |
| WO | WO 2009/064802 A2 | 5/2009 |
| WO | WO 2009/010925 A3 | 7/2009 |
| WO | WO 2009/064802 A3 | 7/2009 |
| WO | WO 2009/088986 A1 | 7/2009 |
| WO | WO 2009/088990 A1 | 7/2009 |
| WO | WO 2009/100406 A2 | 8/2009 |
| WO | WO 2009/103022 A1 | 8/2009 |
| WO | WO 2009/117157 A1 | 9/2009 |
| WO | WO 2009/117985 A1 | 10/2009 |
| WO | WO 2009/050506 A3 | 11/2009 |
| WO | WO 2009/100406 A3 | 11/2009 |
| WO | WO 2010/006086 A2 | 1/2010 |
| WO | WO 2010/009207 A1 | 1/2010 |
| WO | WO 2010/019210 A2 | 2/2010 |
| WO | WO 2010/024430 A1 | 3/2010 |
| WO | WO 2010/036380 A1 | 4/2010 |
| WO | WO 2010/039534 A2 | 4/2010 |
| WO | WO 2010/019210 A3 | 5/2010 |
| WO | WO 2010/065923 A2 | 6/2010 |
| WO | WO 2010/070032 A1 | 6/2010 |
| WO | WO 2010/039534 A3 | 8/2010 |
| WO | WO 2010/092340 A1 | 8/2010 |
| WO | WO 2010/101949 A1 | 9/2010 |
| WO | WO 2010/106436 A2 | 9/2010 |
| WO | WO 2010/119050 A1 | 10/2010 |
| WO | WO 2010/129816 A2 | 11/2010 |
| WO | WO 2010/133836 A1 | 11/2010 |
| WO | WO 2010/151735 A2 | 12/2010 |
| WO | WO 2011/008302 A1 | 1/2011 |
| WO | WO 2011/017296 A1 | 2/2011 |
| WO | WO 2011/045353 A1 | 4/2011 |
| WO | WO 2011/058108 A1 | 5/2011 |
| WO | WO 2011/058109 A1 | 5/2011 |
| WO | WO 2011/058110 A1 | 5/2011 |
| WO | WO 2011/058113 A1 | 5/2011 |
| WO | WO 2011/075628 A1 | 6/2011 |
| WO | WO 2011/133722 A2 | 10/2011 |
| WO | WO 2011/144742 A1 | 11/2011 |
| WO | WO 2011/146882 A1 | 11/2011 |
| WO | WO 2012/003271 A1 | 1/2012 |
| WO | WO 2012/003274 A1 | 1/2012 |
| WO | WO 2012/032334 A1 | 3/2012 |
| WO | WO 2012/061696 A1 | 5/2012 |
| WO | WO 2012/064973 A2 | 5/2012 |
| WO | WO 2012/097000 A1 | 7/2012 |
| WO | WO 2013/012915 A1 | 1/2013 |
| WO | WO 2013/032591 A1 | 3/2013 |
| WO | WO 2013/116562 A1 | 8/2013 |
| WO | WO 2014/100767 A1 | 6/2014 |
| WO | WO 2014/151386 | 9/2014 |
| WO | WO 2014/201409 A1 | 12/2014 |
| WO | WO 2015/010641 | 1/2015 |

OTHER PUBLICATIONS

Gould, International J. of Therapeutics 33, pp. 201-213 & 217 (1986).*

Swarbrick et al., eds. Encyclopedia of Pharmaceutical Technology 13 (Marcel Dekker, NY 1996) pp. 453-499.*

Abdel-Mohsen, "Synthesis, Reactions and Antimicrobial Activity of 2-Amino-4-(8-quinolinol-5-yl)-1-(p-tolyl)-pyrrole-3-carbonitrile," *Bull. Korean Chem. Soc.* 26(5):719-728 (2005).

Abe et al., "T cell receptor-mediated recognition of self-ligand induces signaling in immature thymocytes before negative selection," *J. Exp. Med.* 176(2):459-468 (1992).

Abrahamian et al., "Immunological and Clinical Profile of Adult Patients with Selective Immunoglobulin Subclass deficiency: response to intravenous immunoglobulin therapy," *Clin. Exp. Immunol.* 159(3):344-350 (2010).

Abraham, T., "Thermally induced intramolecular cycloaddition reaction of N-phenyl-2-phenylethynlbenzamide potential cure reaction for thermosetting polymers," *J. Polym. Sci. Polym. Chem. Ed.* 20(7):1953-1957 (1982).

Ames et al., "Heterocyclic Syntheses from o-Halogeno-acids. Part II. Thienopyridinones and Thienopyranones from 3-Bromothiophen-2- and 4-Bromothiophen-3-carboxylic Acids," *J.C.S. Perkin I* 1390-1395 (1975).

Anderson et al., "Paradoxical inhibition of T-cell function in response to CTLA-4 blockade; heterogeneity within the human T-cell population," *Nat. Med.* 6(2):211-214 (2000).

Andrews et al., "Effects of the 11β-hydroxysteroid dehydrogenase inhibitor carbenoxolone on insulin sensitive in men with type 2 diabetes," *J. Clin. Endocrinol. Metab.* 88(1):285-291 (2003).

Arcaro et al., "Wortmannin is a potent phosphatidylinositol 3-kinase inhibitor: the role of phosphatidylinositol 3,4,5-triphosphate in neutrophil responses," *Biochem. J.*, 296(Pt 2):297-301 (1993).

(56) References Cited

OTHER PUBLICATIONS

Arnold et al., "Pyrrolo[2,3-d]pyrimidines containing an extended 5-substituent as potent and selective inhibitors of lck I," *Bioorg. Med. Chem. Lett.* 10(19):2167-2170 (2000).
Augustine et al., "Interleukin 2- and polyomavirus middle T antigen-induced modification of phosphatidylinositol 3-kinase activity in activated T lymphocytes," *Mol. Cell. Biol.* 11(9):4431-4440 (1991).
Baggiolini et al., "Inhibition of the phagocytosis-induced respiratory burst by the fungal metabolite wortmannin and some analogues," *Exp. Cell. Res.* 169(2): 408-418 (1987).
Ballell et al. "New Thiopyrazolo[3,4-d] pyrimidine derivatives as anti-mycobacterial agents," *Bioorg. Med. Chem. Lett.* 17(6):1736-1740 (2007).
Banker et al., Modern Pharmaceutics, pp. 451, 596, 3$^{rd}$ ed, Marcel Dekker, New York (1996).
Bansal et al., "The Molecular Biology of Endometrial Cancers and the Implications for Pathogenesis, Classification, and Targeted Therapies," *Cancer Control* 16(1):8-13 (2009).
Barber et al., "PI3Kgamma inhibition blocks glomerulonephritis and extends lifespan in a mouse model of systemic lupus," *Nat. Med.* 11(9):933-935 (2005). (Epub Aug. 28, 2005).
Barf et al., "Arylsulfonamidothiazoles as a new class of potential antidiabetic drugs. Discovery of potent and selective inhibitors of the 11β-hydroxysteroid dehydrogenase Type 1," *J. Med. Chem.* 45(18):3813-3815 (2002).
Barnes et al., "Efficacy and Safety of Inhaled Corticosteroids in Asthma—Report of a Workshop Held in Eze, France Oct. 1992," *Am. Rev. Respir. Dis.* 148:S1-S26 (1993).
Bartholomeusz et al., "Targeting the PI3K Signaling Pathway in Cancer Therapy," *Expert Opin. Ther. Targets* 16(1):121-130 (2012).
Basotest®, Test Kit for the Quantitative Determination of the Degranulation of Basophilic Granulocytes in Heparinized Human Whole Blood, version 04/02, pp. 1-10, [www.biocarta.com/TDS/10-0500.pdf], Retreived from the Internet Nov. 29, 2011.
Beeram et al., "Akt-induced endocrine therapy resistance is reversed by inhibition of mTOR signaling," *Ann Oncol.* 18(8):1323-1328 (2007).
Bell et al., "Glucokinase mutations insulin secretion, and diabetes mellitus", *Annu. Rev. Physiol.* 58:171-186 (1996).
Berndt et al., "The p110δ crystal structure uncovers mechanisms for selectivity and potency of novel PI3K inhibitors," *Nat. Chem. Biol.* 6(2):117-124 (2010).
Bhat et al., "Pyrazolopyrimidine nucleosides. 12. Synthesis and biological activity of certain pyrazolo[3,4-d]pyrimidine nucleosides related to adenosine," *J. Med. Chem.* 24(10):1165-1172 (1981).
Bhatt et al., "Dual inhibition of PI3K and mTOR inhibits autocrine and paracrine proliferative loops in PI3K/Akt/mTOR-addicted lymphomas," *Blood* 115(22):4455-4463 (2010).
Bi et al., "Proliferative defect and embryonic lethality in mice homozygous for a deletion in the p110α subunit of phosphoinositide 3-kinase," *J. Biol. Chem.* 274:10963-10968 (1999).
Billottet et al., "A selective inhibitor of the p110δ isoform of PI 3-kinase inhibits AML cell proliferation and survival and increases the cytotoxic effects of VP16," *Oncogene* 25:6648-6659 (2006).
Billottet et al , "Inhibition of Class 1 Phosphoinositide 3-Kinase Activity Impairs Proliferation and Triggers Apoptosis in Acute Promyelocytic Leukemia without Affecting Atra-Induced Differentiation," *Cancer Res.* 69(3):1027-1036 (2009).
Bishop et al., "Generation of monospecific nanomolar tyrosine kinase inhibitors via a chemical genetic approach," *J. Am. Chem. Soc.* 121(4):627-631 (1999).
Blunden et al., "Mycotoxins in food," *Med. Lab. Sci.* 48(4):271-282 (1991).
Bochner et al., "Immunological aspects of allergic asthma," *Annu. Rev. Immunol.* 12:295-335 (1994).
Bohren et al., "Expression, crystallization and preliminary crystallographic analysis of human carbonyl reductase," *J. Mol. Biol.* 224:659-664 (1994).

Bone et al., "Phosphoinositide 3-kinase signalling regulates early development and developmental haemopoiesis," *J. Cell. Sci.* 120(Pt 10):1752-1762 (2007).
Bowers et al., "A platelet biomarker for assessing phosphoinositide 3-kinase inhibition during cancer chemotherapy," *Mol. Cancer Ther.* 6(9):2600-2607 (2007).
Brzezianska et al., "A Minireview: The Role of MAPK/ERK and PI3K/Akt Pathways in Thyroid Follicular Cell-Derived Neoplasm," *Front. Biosci.* 16:422-439 (2011).
Buitenhuis et al., "The role of the PI3k-PKB signaling module in regulation of hematopoiesis," *Cell Cycle* 8(4):560-566 (2009).
Burger et al., "High-level expression of the T-cell chemokines CCL3 and CCL4 by chronic lymphocytic leukemia B cells in nurselike cell cocultures and after BCR stimulation," *Blood* 113(13):3050-3058 (2009).
Burger et al., "Phosphoinositide 3'-kinase delta: turning off BCR signaling in Chronic Lymphocytic Leukemia," *Oncotarget* 2(10):737-738 (2011).
Burger, "Inhibiting B-Cell Receptor Signaling Pathways in Chronic Lymphocytic Leukemia," *Curr. Mematol. Malig. Rep.* 7:26-33 (2012).
Byrd et al., "Translating PI3K-Delta Inhibitors to the Clinic in Chronic Lymphocytic Leukemia: The Story of CAL-101 (GS1101)," *ASCO Program Proceedings*, pp. 691-694 (2012).
Campora et al., "Binuclear complexes of nickel bridged by hydrocarbon ligands. Isocyanide insertion chemistry and amide formation by intramolecular coupling of acyl and imidoyl functionalities," *Organometallics* 11(1):11-13 (1992).
Campora et al., "Isocyanide insertion chemistry. Synthesis and structural characterization of bridging imidoyl complexes of nickel and amide formation by intramolecular coupling of acyl and imidoyl functionalities," *Organometallics* 12(10):4025-4031 (1993).
Camps et al., "Blockade of PI3Kγ suppresses joint inflammation and damage in mouse models of rheumatoid arthritis," *Nat. Med.* 11(9):936-943 (2005).
Chaisuparat et al., "Dual inhibition of P13Kα and mTOR as an alternative treatment for Kaposi's Sarcoma," *Cancer Res.* 68:8361-8368 (2008).
Chang et al., "The Bruton tyrosine kinase inhibitor PCI-32765 ameliorates autoimmune arthritis by inhibition of multiple effector cells," *Arthritis Research & Therapy* 13:R115 (2011).
Chappelow et al., "Neovascular age-related macular degeneration: potential therapies," *Drugs* 68(8):1029-1036 (2008).
Chapuis et al., "Dual Inhibition of PI3K and mTORC1/2 Signaling by NVP-BEZ235 as a New Therapeutic Strategy for Acute Myeloid Leukemia," *Clin. Cancer Res.* 16(22):5424-5435 (2010).
Chawla et. al., "Challenges in Polymorphism of Pharmaceuticals," *Current Research & Information on Pharmaceutical Science* 5(1):9-12 (2004).
Chen et al., "Characterization of Structurally Distinct, Isoform-Selective Phosphoinositide 3'-Kinase Inhibitors in Combination with Radiation in the Treatment of Glioblastoma," *Mol. Cancer Ther.* 7(4):841-850 (2008).
Cheson et al., "Bendamustine: Rebirth of an Old Drug," *J. Clin. Oncol.* 27(9):1492-1501 (2009).
Chiarini et al., "Activity of the Novel Dual Phosphatidylinositol 3-Kinase/Mammalian Target of Rapamycin Inhibitor NVP-BEZ235 against T-Cell Acute Lymphoblastic Leukemia," *Cancer Res.* 70(20):8097-8107 (2010).
Chiarini et al., "Dual Inhibition of Class IA Phosphatidylinositol 3-Kinase and Mammalian Target of Rapamycin as a New Therapeutic Option for T-Cell Acute Lymphoblastic Leukemia," *Cancer Res.* 69(8): 3520-3528 (2009).
Cho et al., "A novel synthesis of benzo[c]phenanthridine skeleton and biological evaluation of isoquinoline derivatives," *Chem. Pharm. Bull.(Tokyo)* 47(6):900-902 (1999).
Clayton et al., "A crucial role for the p110delta subunit of phosphatidylinositol 3-kinase in B cell development and activation," *J. Exp. Med.* 196:753-763 (2002).
Closse et al., "2,3-dihydrobenzofuran-2-ones: a new class of highly potent antiinflammatory agents," *J. Med. Chem.* 24:1465-1471 (1981).

(56) References Cited

OTHER PUBLICATIONS

Courtney et al., "The PI3K Pathway as Drug Target in Human Cancer," *J. Clin. Oncol.* 28(6):1075-1083 (2010).
Cox et al., "Human colorectal cancer cells efficiently conjugate the cyclopentenone prostaglandin, prostaglandin J$_2$, to glutathione," *Biochem. Biophys. Acta.* 1584:37-45 (2002).
Cushing et al., "PI3Kδ and PI3Kγ as Targets for Autoimmune and Inflammatory Diseases," *J. Med. Chem.* 55:8559-8581 (2012).
Dai et al., "Distinct Roles of Phosphoinositide-3 Kinase and Phospholipase Cγ2 in B-Cell Receptor-Mediated Signal Transduction," *Mol. Cell. Biol.* 26(1):88-99 (2006).
Davids et al., "Decreased mitochondrial apoptotic priming underlies stroma-mediated treatment resistance in chronic lymphocytic leukemia," *Blood* 120(17):3501-3509 (2012).
Davies et al., "The Human T3 γ Chain is Phosphorylated at Serine 126 in Response to T Lymphocyte Activation," *J. Biol. Chem.* 262(23):10918-10921 (1987).
Davis et al., "The preparation of substituted 1(2H)-isoquinolinones from dilithiated 2-methyl-N-arylbenzamides, 2-methyl-N-(arylmethyl)-benzamides, or 2-methylbenzoic acid, 2,2-dimethylhydrazide," *Synthetic Commun.* 27(17):2961-2969 (1997).
Davis et al., "Chronic active B-cell-receptor signaling in diffuse large B-cell lymphoma," *Nature* 463:88-92 (2010).
De Weers et al., "The Bruton's tyrosine kinase gene is expressed throughout B cell differentiation, from early precursor B cell stages preceding immunoglobulin gene rearrangement up to mature B cell stages," *Eur. J. Immunol.* 23:3109-3114 (1993).
Diederich et al., "In search for specific inhibitors of human 11β-hydroxysteroid-dehydrogenases (11βHSDs): chenodeoxycholic acid selectively inhibits 11β-HSD-I," *Eur. J. Endocrinol.* 142(2):200-207 (2000).
Dijksman et al., "271.1: 2-dihydro-2-thianaphthalene derivatives. Part I. Preparation and reactions of 1 : 2-dihydro-1-keto-2-thianaphthalenes," *J. Chem. Soc.* 1213-1218 (1951).
Ding et al., "A combinatorial scaffold approach toward kinase-directed heterocycle libraries," *J. Am. Chem. Soc.* 124(8):1594-1596 (2002).
Ding et al., "A concise and traceless linker strategy toward combinatorial libraries of 2,6,9-substituted purines," *J. Org. Chem.* 66(24):8273-8276 (2001).
Ding et al., "Resin-capture and release strategy toward combinatorial libraries of 2,6,9-substituted purines," *J. Comb. Chem.* 4(2):183-186 (2002).
Donati, G., "Emerging therapies for neovascular age-related macular degeneration: state of the art," *Ophthalmologica* 221(6):366-377 (2007).
European Examination Report for EP Application No. 07873406.8 dated Sep. 14, 2011.
European Search Report for EP Application No. 05857011.0 dated Feb. 4, 2011.
European Search Report for EP Application No. 09700784.3 dated Oct. 28, 2011.
European Search Report and Search Opinion for EP Application No. 09700424.6 dated Oct. 26, 2011.
European Search Report for EP Application No. 07873406.8 dated Mar. 1, 2010.
European Search Report for EP Application No. 07754845.1 dated Sep. 20, 2011.
Examination Report for GB Application No. GB 0819947.3 dated Oct. 27, 2010.
Extended European Search Report for EP Application No. 09816603.6 dated Mar. 19, 2012.
Extended European Search Report from European Application No. 09700784.3 dated Oct. 28, 2011.
Fajans et al., "Maturity onset diabetes of the young (MODY)," *Diabet. Med.* 13(9 Suppl 6):S90-S95 (1996).
Feinstein et al., "Regulation of the action of hydrocotisone in airway epithelial cells by 11b-hydroxysteroid dehydrogenase," *Am. J. Respir. Cell. Mol. Biol.* 21(3):403-408 (1999).

Feldman et al., "Active-Site Inhibitors of mTOR Target Rapamycin-Resistant Outputs of mTORC1 and mTORC2," *PLoS Biol.* 7(2):371-383 (2009).
Fingl et al., "Chapter 1—General Principles," The Pharmacological Basis of Therapeutics, 5th edition, Goodman and Gilman editors, MacMillan Publishings Co., Inc., New York, pp. 1-46, (1975).
Flinn et al., "Preliminary Evidence of Clinical Activity in a Phase I Study of CAL-101, a Selective Inhibitor of the p110δ Isoform of Phosphatidylinositol 3-Kinase (PI3K), in Patients with Select Hematologic Malignancies," *J. Clin. Oncol.* 27(15s) (Suppl: Abstr 3543) (2009).
Forrest et al., "Carbonyl Reductase," *Chem. Biol. Interact.* 129(1-2): 21-40 (2000).
Forrest et al., "Induction of a human carbonyl reductase gene located on chromosome 21," *Biochem. Biophys. Acta.* 1048(2-3):149-155 (1990).
Franzen, "The Suzuki, the Heck, and the Stille reaction—three versatile methods for the introduction of new C—C bonds on solid support," *Can. J. Chem.* 78:957-962 (2000).
Funder et al., "Mineralocorticoid action: target tissue specificity is enzyme, not receptor, mediated," *Science* 242:583-585 (1998).
Fling-Leung, W. P., "Phosphoinositide 3-kinase delta (PI3Kδ) in leukocyte signaling and function," *Cell Signal* 23:603-608 (2011).
Furukawa, T., "Molecular Targeting Therapy for Pancreatic Cancer: Current Knowledge and Perspectives from Bench to Bedside," *J. Gastroenterol.* 43(12):905-911 (2008).
Garber et al., "Diversity of gene expression in adenocarcinoma of the lung," *Proc. Natl. Acad. Sci. U.S.A.* 98(24):13784-13789 (2001).
Gillespie et al., "Antagonists of the human adenosine $A_{2A}$ receptor. Part 3: Design and synthesis of pyrazolo[3,4-d]pyrimidines, pyrrolo[2,3-d]pyrimidines and 6-arylpurines," *Bioorg. Med. Chem. Lett.* 18(9):2924-2929 (2008).
Gonzalez et al., "Protection against daunorubicin cytotoxicity by expression of a cloned human carbonyl reductase cDNA in K562 leukemia cells," *Cancer Res.* 55(20):4646-4650 (1995).
Graber et al., "The protein tyrosine kinase inhibitor herbimycin A, but not genistein, specifically inhibits signal transduction by the T cell antigen receptor," *Int. Immunol.* 4(1):1201-1210 (1992).
Graupera et al., "Angiogenesis selectively requires the p110α isoform of PI3K to control endothelial cell migration," *Nature* 453(7195):662-666 (2008).
Gunther et al., "Acute pathological effects on rats of orally administered wortmannin-containing preparations and purified wortmannin from Fusarium oxysporum," *Food Chem. Toxicol.* 27(3):173-179 (1989).
Gunther et al., "Immunosuppressive effects of dietary wortmannin on rats and mice," *Immunopharmacol. Immunotoxicol.* 11(4):559-570 (1989).
Haase et al., "Detection of viral nucleic acids by in situ hybridization," *Methods in Virology* 7:189-226 (1984).
Haluska et al., "The RTK/RAS/BRAF/PI3K Pathways in Melanoma: Biology, Small Molecule Inhibitors, and Potential Applications," *Semin. Oncol.* 34(6):546-554 (2007).
Hanefeld et al., "One-pot synthesis of tetrasubstituted pyrazoles proof of regiochemistry," *J. Chem. Soc. Perkin* 1 1545-1552 (1996).
Harada et al., "Novel role of phosphatidylinositol 3-kinase in CD28-mediated costimulation," *J. Biol. Chem.* 276(12):9003-9008 (2001).
Harding et al., "CD28-mediated signalling co-stimulates murine T cells and prevents induction of anergy in T-cell clones," *Nature* 356(6370):607-609 (1992).
Has Selblom et al., "High immunohistochemical expression of p-AKT predicts inferior survival in patients with diffuse large B-cell lymphoma treated with immunochemotherapy," *Brit. J. Haematol.* 149:560-568 (2010).
Haylock-Jacobs et al., "PI3Kδ drives the pathogenesis of experimental autoimmune encephalomyelitis by inhibiting effector T cell apoptosis and promoting Th17 differentiation," *J. Autoimmun.* 36:278-287 (2011).
Hellwinkel et al., "Heterocyclensynthesen mit MF/Al2O3-basensystemen; 2-arylbenzofurane and 2,3-diarylisochinolin-1(2H)-one," *Synthesis* 1995( 9):1135-1141 (1995).

(56) References Cited

OTHER PUBLICATIONS

Herishanu et al., "The lymph node microenvironment promotes B-cell receptor signaling, NF-κb activation, and tumor proliferation in chronic lymphocytic leukemia," *Blood* 117(2):563-574 (2011).
Herman et al., "Phosphatidylinositol 3-kinase-δ inhibitor CAL-101 shows promising preclinical activity in chronic lymphocytic leukemia by antagonizing intrinsic and extrinsic cellular survival signals," *Blood* 116(12):2078-2088 (2010).
Herman et al., "The role of phosphatidylinositol 3-kinase-δ in the immunomodulatory effects of lenalidomide in chronic lymphocytic leukemia," *Blood* 117(16):4323-4327 (2011).
Herrera et al., "The dual PI3K/mTOR inhibitor BEZ235 is effective in lung cancer cell lines," *Anticancer Res.* 31:849-854 (2011).
Hickey et al., "BCR-ABL Regulates Phosphatidylinositol 3-Kinase-p110γ Transcription and Activation and Is Required for Proliferation and Drug Resistance," *J. Biol. Chem.* 281(5):2441-2450 (2006).
Hirsch et al., "CALming Down T Cell Acute Leukemia," *Cancer Cell* 21:449-450 (2012).
Hirsch et al., "Central Role for G Protein-Coupled Phosphoinositide 3-Kinase γ in Inflammation," *Science* 287:1049-1053 (2000).
Hoellenriegel and Burger, "Phosphoinositide 3'-kinase delta: turning off BCR signaling in Chronic Lymphocytic Leukemia," *Oncotarget* 2(10):737-738 (2011).
Hoellenriegel et al., "The phosphoinositide 3'-kinase delta inhibitor, CAL-101, inhibits B-cell receptor signaling and chemokine networks in chronic lymphocytic leukemia," *Blood* 118(13):3603-3612 (2011).
Hoellenriegel et al., "Phosphoinositide 3'-kinase (PI3K) Delta Inhibition with CAL-101 Blocks B-cell Receptor (BCR) Signaling and the Prosurvival Actions of Nurse-Like Cells (NLC) in Chronic Lymphocytic Leukemia (CLL)," (ASH Annual Meeting 2010).
Honigberg et al., "The Bruton tyrosine kinase inhibitor PCI-32765 blocks B-Cell activation and is efficacious in models of autoimmune disease and B-cell malignancy," *PNAS* 107(29):13075-13080 (2010).
Ikeda et al., "PI3K/p110δ is a novel therapeutic target in multiple myeloma," *Blood* 116(9):1460-1468 (2010).
International Preliminary Report on Patentability and Written Opinion for PCT/US2005/042524 dated May 22, 2007.
International Preliminary Report on Patentability and Written Opinion for PCT/US2007/008355 dated Nov. 4, 2008.
International Preliminary Report on Patentability and Written Opinion for PCT/US2007/008395 dated Oct. 8, 2008.
International Preliminary Report on Patentability and Written Opinion for PCT/US2009/049969 dated Jan. 11, 2011.
International Preliminary Report on Patentability and Written Opinion for PCT/US2009/060985 dated Apr. 19, 2011.
International Preliminary Report on Patentability for PCT/US2009/000038 dated Jul. 6, 2010.
International Preliminary Report on Patentability for PCT/US2009/005380 dated Apr. 7, 2011.
International Preliminary Report on Patentability for PCT/US2010/002020 dated Jan. 26, 2012.
International Preliminary Report on Patentability for PCT/US2009/000042 dated Jul. 6, 2010.
International Search Report & Written Opinion for PCT/US2011/060212 dated Jun. 1, 2012.
International Search Report & Written Opinion issued after Submission of Request for Additional Search for PCT/US2011/060212 dated Jul. 6, 2012.
International Search Report and Written Opinion for PCT/US2009/005380 dated Nov. 20, 2009.
International Search Report and Written Opinion for PCT/US2009/049969 dated Mar. 15, 2010.
International Search Report and Written Opinion for PCT/US2010/033939, dated Nov. 5, 2010.
International Search Report and Written Opinion for PCT/US2012/047190 dated Oct. 2, 2012.
International Search Report and Written Opinion for PCT/US2012/020831 dated May 2, 2012.
International Search Report for PCT/US2011/037412 dated Aug. 22, 2011.
International Search Report for PCT/US1995/005213 dated Aug. 21, 1995.
International Search Report for PCT/US2007/008395 (4 pages) dated Aug. 27, 2008.
International Search Report for PCT/US2009/000038 dated Mar. 11, 2009.
International Search Report for PCT/US2009/000042 dated Mar. 23, 2009.
International Search Report for PCT/US2005/042524 (7 pages) dated Oct. 2, 2006.
International Search Report for PCT/US2007/008355 dated Sep. 25, 2008.
International Search Report for PCT/US2009/060985 dated Jun. 28, 2010.
International Search Report for PCT/US2010/002020 dated Nov. 2, 2010.
Ishiyama et al., "A stoichiometric aromatic C—H borylation catalyzed by iridium(I)/2,2'-bipyridine complexes at room temperature," *Angew. Chem. Int. Ed. Engl.* 41(16):3056-3058 (2002).
Ishiyama et al., "Mild iridium-catalyzed borylation of arenes. High turnover numbers, room temperature reactions, and isolation of a potential intermediate," *J. Am. Chem. Soc.* 124(3):390-391 (2002).
Jackson et al., "PI 3-kinase p110β: a new target for antithrombotic therapy," *Nat. Med.* 11:507-514 (2005).
Jimeno et al., "Phase I Trial of PX-866, a Novel Phosphoinositide-3-Kinase (PI-3K) Inhibitor," *J. Clin. Oncol.* 27:15s (Suppl; Abstract 3542) (2009).
Johnson et al., "Accessory cell-derived signals required for T cell activation," *Immunol. Res.* 48-64 (1993).
Jou et al., "Essential, nonredundant role for the phosphoinositide 3-kinase p110delta in signaling by the B-cell receptor complex," *Mol. Cell. Biol.* 22:8580-8591 (2002).
June et al., "Evidence for the involvement of three distinct signals in the induction of IL-2 gene expression in human T lymphocytes," *J. Immunol.* 143(1):153-161 (1989).
June et al, "Inhibition of tyrosine phosphorylation prevents T-cell receptor mediated signal transduction," *Proc. Natl. Acad. Sci. U.S.A.* 87:7722-7726 (1990).
June et al., "Role of CD28 receptor in T-cell activation," *Immunol Today* 11(6):211-216 (1990).
June, C.H., "Signaling transduction in T cells," *Curr. Opin. Immunol.* 3(3):287-293 (1991).
Kajita et al., "Nickel-catalyzed decarbonylative addition of phthalimides to alkynes," *J. Am. Chem. Soc.* 130(19):6058-6059 (2008).
Kallberg et al., "Short-chain dehydrogenase/reductase (SDR) relationships: a large family with eight clusters common to human, animal, and plant genomes," *Protein Sci.* 11(3):636-641 (2002).
Kallberg et al., "Short-Chain Dehydrogenases/Reductases (SDRs)—Coenzyme-Based Functional Assignments in Completed Genomes," *Eur. J. Biochem.* 269(18):4409-4417 (2002).
Kang et al., "Oncogenic transformation induced by the p110β, -γ, and -δ isoforms of class I phosphoinositide 3-kinase," *PNAS* 103(5):1289-1294 (2006).
Karpeiskii et al., "Pyridoxal-5'-Derivatives of Nucleobases," *Bioorganicheskaya Khimiya* 11(8): 1097-1104 (1985).
Khwaja, A., "PI3K as a Target for Therapy in Haematological Malignancies," *Curr. Top. Microbiol. Immunol.* 347:169-188 (2010).
Kim et al., "Activation and Function of the mTORC1 Pathway in Mast Cells," *J. Immunol.* 180(7):4586-4595 (2008).
Knight et al., "A Pharmacological Map of the PI3-K Family Defines a Role for p110α in Insulin Signaling," *Cell* 125(4):733-747 (2006).
Kong, D. and Yamori, T., "Advances in Development of Phosphatidylinositol 3-Kinase Inhibitors," *Curr. Med. Chem.* 16:2839-2854 (2009).
Kost et al., "Recyclization of 3-Alkyl- and 1,3-Dialkylisoquinolinium Salts to Naphthylamines," *Chemistry of Heterocyclic Compounds* 16(9): 965-970 (1981).
Kraybill et al., "Inhibitor scaffolds as new allele specific kinase substrates," *J. Am. Chem. Soc.* 124(41):12118-12128 (2002).

(56) References Cited

OTHER PUBLICATIONS

Kreutzberger et al. "5-Substituierte 4-Aminopyrimidine durch Aminomethinylierung von Acetonitrilen," *Liebigs Ann. Chem.* 537-544 (1977).
Kulkarni et al., "PI3Kbeta plays a critical role in neutrophil activation by immune complexes," *Sci. Signal* 2011, vol. 4, ra23.
Kumar et al., "Keten Dithioacetals. Part 11. Reaction of 3-Cyano-4-Methylthio-2(1H)-pyridones with Hydrazine and Guanidine: Synthesis of Novel Substituted and Fused Pyrazolo[4,3-c]pyridone and Pyrido[4,3-d]pyrimidine derivatives," *J. Chem. Soc. Perkin* 1 8:857-862 (1978).
Kundu et al., "Palladium-catalysed heteroannualation with terminal alkynes; a highly regio- and stereoselective synthesis of (Z)-3-aryl(alykl)idene isoindolin-1-ones," *Tetrahedron* 56(27):4777-4792 (2000).
Kurtova et al., "Diverse marrow stromal cells protect CLL cells from spontaneous and drug-induced apoptosis: development of a reliable and reproducible system to assess stromal cell adhesion-mediated drug resistance," *Blood* 114(20): 4441-4450 (2009).
Kwok et al., "The anti-inflammatory natural product parthenolide from the medicinal herb Feverfew directly binds to and inhibits Iκb kinase," *Chem. Biol.* 8(8):759-766 (2001).
Lannutti et al., "CAL-101 a p110δ selective phosphatidylinositol-3-kinase inhibitor for the treatment of B-cell malignancies, inhibits PI3K signaling and cellular viability," *Blood* 117(2):591-594 (2011).
Larabi et al., "Crystal Structure and Mechanism of Activation of TANK-Binding Kinase 1," *Cell Reports* 3:734-746 (2013).
Ledbetter et al., "CD28 ligation in T-cell activation: evidence for two signal transduction pathways," *Blood* 75(7):1531-1539 (1990).
Ledbetter et al., "Crosslinking of surface antigens causes mobilization of intracellular ionized calcium in T lymphocytes," *Proc. Natl. Acad. Sci. U. S. A.* 84(5):1384-1388 (1987).
Lee et al., "All roads lead to mTOR: integrating inflammation and tumor angiogenesis," *Cell Cycle* 6(24):3011-3014 (2007).
Lee et al., "The CD28 signal transduction pathway in T cell activation", Advances in Cell Regulation of Cell Growth, vol. 2, pp. 141-160, New York: Raven Press, Ltd. (1991).
Ley et al., "The T cell receptor/CD3 complex and CD2 stimulate the tyrosine phosphorylation of indistinguishable patterns of polypeptides in the human T leukemic cell line Jurkat," *Eur. J. Immunol.* 21(9):2203-2209 (1991).
Li et al., "Roles of PLC-beta2 and -beta3 and PI3Kgamma in chemoattractant-mediated signal transduction," *Science* 287(5455):1046-1049 (2000).
Liu et al., "Costimulation of T-cell growth," *Curr. Opin. Immunol.* 4(3):265-270 (1992).
Lu et al., "CD28-induced T cell activation. Evidence for a protein-tyrosine kinase signal transduction pathway," *J. Immunol.* 149(1):24-29 (1992).
Majumder et al., "mTOR inhibition reverses Akt-dependent prostate intraepithelial neoplasia through regulation of apoptotic and HIF-1-dependent pathways," *Nat. Med.* 10(6):594-601 (2004).
Markman et al., "Status of PI3K inhibition and biomarker development in cancer therapeutics," *Ann. Oncol.* 21(4):683-691 (2010).
Martelli et al., "The emerging role of the phosphatidylinositol 3-kinase/Akt/mammalian target of rapamycin signaling network in normal myelopoiesis and leukemogenesis," *Biochim. Biophys. Acta.* 803:991-1002 (2010).
Martinez et al., "The Molecular Signature of Mantle Cell Lymphoma Reveals Multiple Signals Favoring Cell Survival," *Cancer Res.* 63:8226-8232 (2003).
Martin-Sanchez et al., "PI3K Inhibition as a Potential Therapeutic Strategy in Peripheral T-Cell Lymphomas," *Blood (ASH Annual Meeting Abstracts)* 118: Abstract 3493 (2011).
Mattes et al., "DNA sequence selectivity of guanine-N7 alkylation by nitrogen mustards," *Nucleic Acids Res.* 14(7):2971-2987 (1986).
Maxwell et al., "Attenuation of phosphoinositide 3-kinase δ signaling restrains autoimmune disease," *J. Autoimmun.* 38:381-391 (2012).

Mayer et al., "Small molecule inhibitor of mitotic spindle bipolarity identified in a phenotype-based screen," *Science* 286(5441):971-974 (1999).
Mazzoletti and Broggini, "PI3K/AKT/mTOR inhibitors in ovarian cancer," *Curr. Med. Chem.* 17(36):4433-4447 (2010).
Meadows, S.A., et al., "CAL-101, a Potent Selective Inhibitor of the p110δ Isoform of Phosphatidylinositol 3-Kinase, Attenuates Pathway Signaling, Induces Apoptosis, and Overcomes Signals From the Microenvironment in Cellular Models of Hodgkin Lymphoma," *Blood* (ASH Annual Meeting Abstracts), 116:Abstract 3926 (2010).
Mellinghoff et al., "TORward AKTually useful mouse models," *Nat. Med.* 10(6):579-580 (2004).
Merida et al., "IL-2 binding activates a tyrosine-phosphorylated phosphatidylinositol-3-kinase," *J. Immunol.* 147(7): 2202-2207 (1991).
Miyaura et al., "Palladium-catalyzed cross-coupling reactions of organoboron compounds," *Chem. Rev.* 95(7):2457-2483 (1995).
Modi et al., "Isoquinolones; part IV-synthesis of methyl, 3-formyl & other 3-substituted N-arylisoquinolones." *Indian J. Chem.* 18B:304-306 (1979).
Moon et al., "A novel microtubule destabilizing entity from orthogonal synthesis of triazine library and zebrafish embryo screening," *J. Am. Chem. Soc.* 124(39):11608-11609 (2002).
Mosmann et al., "The expanding universe of T-cell subsets: Th1, Th2 and more," *Immunology Today* 17(3):138-146 (1996).
Nakanishi et al., "Cloning and sequence analysis of a cDNA encoding tetrameric carbonyl reductase of pig lung," *Biochem. Biophys. Res. Commun.* (3):1311-1316 (1993).
Nemazanyi et al., "3-Amino-4-aryl-1(2H)-isoquinolones," *Chemistry of Heterocyclic Compounds* 27(3):307-308 (1991).
Newman et al., "Solid state analysis of the active pharmaceutical ingredient in drug products," *Drug Discov. Today* 8(19):898-905 (2003).
Nisitani et al., "Posttranscriptional regulation of Bruton's tyrosine kinase expression in antigen receptor-stimulated splenic B cells," *PNAS* 97(6):2737-2742 (2000).
Niswender et al., "Protein engineering of protein kinase a catalytic subunits results in the acquisition of novel inhibitor sensitivity," *J. Biol. Chem.* 277(32):28916-28922 (2002).
Nobel et al., "Purification of full-length recombinant human and rat type 1 11β-hydroxysteroid dehydrogenases with retained oxidoreductase activities," *Protein Expr. Purif.* 26(3):349-356 (2002).
Norman, "Selective PI3K-delta Inhibitors, a Review of the Patent Literature," Expert Opinion on Therapeutic Patents, 21(11): 1773-1790 (2011).
Nunes et al., "Signalling through CD28 T-cell activation pathway involves an inositol phospholipid-specific phospholipase C activity," *Biochem. J.* 293(Pt 3):835-842 (1993).
Oda et al., "PIK3CA cooperates with other phosphatidylinositol 3'-kinase pathway mutations to effect oncogenic transformation," *Cancer Res.* 68(19):8127-8136 (2008).
Office Action dated Dec. 13, 2012 for U.S. Appl. No. 13/112,611.
Okada et al., "Essential role of phosphatidylinositol 3-kinase in insulin-induced glucose transport and antilipolysis in rat adipocytes. Studies with a selective inhibitor wortmannin," *J. Biol. Chem.* 269(5):3568-3573 (1994).
Okada et al., "Blockage of chemotactic peptide-induced stimulation of neutrophils by wortmannin as a result of selective inhibition of phosphatidylinositol 3-kinase," *J. Biol. Chem.* 269(5):3563-3567 (1994).
Oppermann et al., "Forms and functions of human SDR enzymes," *Chem. Biol. Interact.* 130-132(1-3):699-705 (2001).
O'Shea et al., "Activation of human peripheral blood T lymphocytes by pharmacological induction of protein-tyrosine phosphorylation," *Proc. Natl. Acad. Sci. U. S. A.* 89(21):10306-10310 (1992).
Ozaki et al., "Studies on 4(1H)-quinazolinones. IV. Convenient synthesis of 12-methyl-6H-isoquino [2,1-a] quinazolin-6-one and 6-methyl-13H-quinazolino [3,4-a] quinazolin-13-one," *Chem. Pharm. Bull.* 32(6):2160-2164 (1984).
Ozol et al., "Autoxidative transformations of 2-substituted 3-alkyl-4-hydroxy-1-oxo-1, 2-dihydroisoquinolines," *Chemistry of Heterocyclic Compounds* 14(6):644-648 (1978).

(56) References Cited

OTHER PUBLICATIONS

Patel et al., "Immunopathological aspects of age-related macular degeneration," *Semin. Immunopathol.* 30(2):97-110 (2008).
Perez-Blas et al., "Impaired T cell signal transduction through CD28 in a patient with idiopathic thrombocytopenia," *Clin. Exp. Immunol.* 85(3):424-428 (1991).
Persson, "Glucocorticoids for asthma—early contributions," *Pulm. Pharmacol.* 2(3):163-166 (1989).
Petrie et al., "Novel biotinylated adenylate analogue derived from pyrazolo[3,4-d]pyrimidine for labeling DNA probes," *Bioconjug. Chem.* 2(6):441-446 (1991).
Pighi et al., "Phospho-proteomic analysis of mantle cell lymphoma cells suggests a pro-survival role of B-cell receptor signaling," *Cell Oncol. (Dordr)* 34(2):141-153 (2011).
Polak et al., "The PI3K/PKB signaling module as key regulator of hematopoiesis: implications for therapeutic strategies in leukemia," *Blood* 119(4):911-923 (2012).
Porta and Figlin, "Phosphatidylinositol-3-kinase/Akt signaling pathway and kidney cancer, and the therapeutic potential of phosphatidylinositol-3-kinase/Akt inhibitors," *J. Urol.* 182(6):2569-2577 (2009).
Prasad et al., "Phosphatidylinositol (PI) 3-kinase and PI 4-kinase binding to the CD4-p56$^{lck}$ complex: the p56$^{lck}$ SH3 domain binds to PI 3-kinase but not PI 4-kinase," *Mol. Cell. Biol.* 13(12): 7708-7717 (1993).
Prasad et al., "Src-homology 3 domain of protein kinase p59$^{fyn}$ mediates binding to phosphatidylinositol 3-kinase in T cells," *Proc. Natl. Acad. Sci. U. S. A.* 90(15): 7366-7370 (1993).
Prasad et al., "T-cell antigen CD28 interacts with the lipid kinase phosphatidylinositol 3-kinase by a cytoplasmic Tyr(P)-Met-Xaa-Met motif," *Proc. Natl. Acad. Sci. U. S. A.* 91(7): 2834-2838 (1994).
Pudlo et al., "Synthesis, antiproliferative, and antiviral activity of certain 4-substituted and 4,5 disubstituted 7-[1,3-dihydroxy-2-propoxy)methyl]pyrrolo[2,3-d]pyrimidines," *J. Med. Chem.* 33(7):1984-1992 (1990).
Puri and Gold, "Selective inhibitors of phosphoinositide 3-kinase delta: modulators of B-cell function with potential for treating autoimmune inflammatory disease and B-cell malignancies," *Front. Immunol.* 3.256 (2012).
Quiroga et al., "B-cell antigen receptor signaling enhances chronic lymphocytic leukemia cell migration and survival: specific targeting with a novel spleen tyrosine kinase inhibitor, R406," *Blood* 114(5):1029-1037 (2009).
Reif et al., "Divergent regulation of phosphatidylinositol 3-kinase P85α and P85β isoforms upon T cell activation," *J. Biol. Chem.* 268(15):10780-10788 (1993).
Report of the Expert Committee on the Diagnosis and Classification of Diabetes Mellitus, *Diabetes Care* 2( Suppl. 1):S5-S19 (1992).
Rizzatti et al., "Gene expression profiling of mantle cell lymphoma cells reveals aberrant expression of genes from the PI3K-AKT, WNT and TGFβ signalling pathways," *Brit. J. Haematol.* 130:516-526 (2005).
Robertson, "Eicosanoids and human disease", Harrison's Principles of Internal Medicine, Isselbacher K.J. et al. (eds.), vol. 1, pp. 431-435, McGraw-Hill, New York City (1994).
Roller et al., "Blockade of Phosphatidylinositol 3-Kinase (PI3K)δ or PI3Kγ Reduces IL-17 and Ameliorates Imiquimod-Induced Psoriasis-like Dermatitis," *J. Immunol.* 189:4612-4620 (2012).
Romero et al., "Cloning and expression of the bovine 11b-hydroxysteroid dehydrogenase type-2," *J. Steroid Biochem. Mol. Biol.* 72(5):231-237 (2000).
Rommel et al., "PI3Kδ and PI3Kγ: partners in crime in inflammation in rheumatoid arthritis and beyond?" *Nat. Rev. Immunol.* 7:191-201 (2007).
Rott et al., "Recent developments in the use of biologics in psoriasis and autoimmune disorders. The role of autoantibodies," *BMJ* 330(7493):716-720 (2005).
Rudelius et al., "Constitutive activation of Akt contributes to the pathogenesis and survival of mantle cell lymphoma," *Blood* 108(5):1668-1676 (2006).

Saif and Chu, "Biology of colorectal cancer," *Cancer J.* 16(3):196-201 (2010).
Salmena et al., "Tenets of PTEN Tumor Suppression," *Cell* 133(3):403-414 (2008).
Sarker et al., "Targeting the PI3K/AKT pathway for the treatment of prostate cancer," *Clin. Cancer Res.* 15(15):4799-4805 (2009).
Sasaki et al., "Function of PI3Kγ in Thymocyte Development, T Cell Activation, and Neutrophil Migration," *Science* 287:1040-1046 (2000).
Schwartz et al., "Quercetin inhibition of the induction and function of cytotoxic T lymphocytes," *Immunopharmacology* 4(2):125-138 (1982).
Schwartz, "A cell culture model for T lymphocyte clonal anergy," *Science* 248(4961):1349-1356 (1990).
Shapiro et al., "Phase I Dose-Escalation Study of XL147, a PI3K Inhibitor Administered Orally to Patients with Solid Tumors," *J. Clin. Oncol.* 27:146x (Suppl Abstr 3500) (2009).
Shibasaki et al., "Different properties of monomer and heterodimer forms of phosphatidylinositol 3-kinases," *Biochem. J.* 289 ( Pt 1):227-231 (1993).
Sinclair et al., "Phosphatidylinositol-3 Kinase Delta (PI3Kδ) Inhibitor AMG 319 Is a Potent, Selective and Orally Bioavailable Small Molecule Inhibitor That Suppresses PI3K-Mediated Signaling and Viability in Neoplastic B Cells," *Blood (ASH Annual Meeting Abstracts)* 118:Abstract 4964 (2011).
Singer et al., "Optimization of in situ hybridization using isotopic and non-isotopic detection methods," *Biotechniques* 4(3):230-250 (1986).
Smith et al., "Expression of Bruton's Agammaglobulinemia Tyrosine Kinase Gene, BTK, Is Selectively Down-Regulated in T Lymphocytes and Plasma Cells," *J. Immunol.* 152:557-565 (1994).
Soldan et al., "Induction of daunorubicin carbonyl reducing enzymes by daunorubicin in sensitive and resistant pancreas carcinoma cells," *Biochem. Pharmacol.* 51(2):117-123 (1996).
Soond et al., "PI3K p110δ regulates T-cell cytokine production during primary and secondary immune responses in mice and humans," *Blood* 115(11):2203-2213 (2010).
Srinivasan et al., "PI3 Kinase Signals BCR-Dependent Mature B Cell Survival," *Cell* 139:573-586 (2009).
Stanoeva et al., "Homophthalic anhydrides and their application to the synthesis of heterocyclic compounds (review)," *Chemistry of Heterocyclic Compounds* 20(12):1305-1315 (1984).
Subramaniam et al., "Targeting Nonclassical Oncogenes for Therapy in T-ALL," *Cancer Cell* 21:459-472 (2012).
Sujobert et al., "Essential role for the p110δ isoform in phosphoinositide 3-kinase activation and cell proliferation in acute myeloid leukemia," *Blood* 106(3):1063-1066 (2005).
Supplementary European Examination Report EP Application No. 07754845.1 dated Sep. 20, 2011.
Supplementary European Search Report for EP Application No. 07754845 (4 pages) dated Feb. 24, 2010.
Supplementary European Search Report for EP Application No. 10800175.1 dated Nov. 7, 2012.
Sykes et al., "Treatment of severe autoimmune disease by stem-cell transplantation," *Nature* 35(7042):620-627 (2005).
Takeuchi et al., "Synergistic Augmentation of Rapamycin-Induced Autophagy in Malignant Glioma Cells by Phosphatidylinositol 3-Kinase/Protein Kinase B Inhibitors," *Cancer Res.* 65(8):3336-3346 (2005).
Tanaka et al., "An unbiased cell morphology-based screen for new, biologically active small molecules," *PLoS Biol.* 3(5):0764-0776 (2005).
Thompson et al., "Identification of distinct populations of PI-3 kinase activity following T-cell activation," *Oncogene* 7(4):719-725 (1992).
Torbett et al., "A chemical screen in diverse breast cancer cell lines reveals genetic enhancers and suppressors of sensitivity to PI3K isoform-selective inhibition," *Biochem. J.* 415(1):97-110 (2008).
Truitt et al., "Stimulation of CD28 triggers an association between CD28 and phosphatidylinositol 3-kinase in Jurkat T cells," *J. Exp. Med.* 179(3):1071-1076 (1994).
Tyukavkina et al., Bioorganicheskaya Khimiya, Moskva, DROFA, pp. 83-85 (2004).

(56) References Cited

OTHER PUBLICATIONS

Uddin et al., "Role of phosphatidylinositol 3'-kinase/AKT pathway in diffuse large B-cell lymphoma survival," *Blood* 108(13):4178-4186 (2006).
Ugarkar et al., "Adenosine kinase inhibitors. 2. Synthesis, enzyme inhibition, and antiseizure activity of diaryltubercidin analogues," *J. Med. Chem.* 43(15):2894-2905 (2000).
Vandenberghe et al., "Antibody and B7/BB1-mediated ligation of the CD28 receptor induces tyrosine phosphorylation in human T cells," *J. Exp. Med.* 175(4):951-960 (1992).
Vanhaesebroeck et al., "PI3K: from the bench to the clinic and back," *Curr. Top. Microbiol. Immunol.* 347:1-19 (2010).
Vara et al., "PI3K/Akt Signalling Pathway and Cancer," *Cancer Treat. Rev.* 30(2):193-204 (2004).
Vasilevsky et al., "Study of the Heterocyclization of vic-Substituted Hydrazides of Acetylenylpyrazolecarboxylic Acids into N-Amino Pyrazolopyridinones," *Journal of Heterocyclic Chemistry* 39(6): 1229-1233 (2002).
Vasilevsky et al., "Unexpected results in the heterocyclization of 5-acetylenylpyrazole-4-carboxylic acid hydrazides under the influence of CuCl: formation of a diazepinone and dehydrodimerization into the corresponding bis(pyrazolo [4,3-d] [1,2] diazepinone)," *Tetrahedron Lett.* 46(26):4457-4459 (2005).
Vippagunta et al., "Crystalline Solids," *Adv. Drug Deliv. Rev.* 48(1):3-26 (2001).
Vitali et al., "Immunotherapy in rheumatoid arthritis: a review," *Int. J. Artif. Organs* 16 Suppl. 5:196-200 (1993).
Vlahos et al., "A specific inhibitor of phosphatidylinositol 3-kinase, 2-(4-morpholinyl)-8-phenyl-4H-1-benzopyran-4-one (LY294002)," *J. Biol. Chem.* 269(7):5241-5248 (1994).
Vogt et al., "Phosphatidylinositol 3-kinase: the oncoprotein," *Curr. Top. Microbiol. Immunol.* 347:79-104 (2010).
Vogt et al., "Phosphoinositide 3-kinase: from viral oncoprotein to drug target," *Virology* 344(1):131-138 (2006).
Wagner et al., "A First-in-Human Phase I Study to Evaluate the Pan-PI3K Inhibitor GDC-0941 Administered QD or BID in Patients with Advanced Solid Tumors," *J. Clin. Oncol.* 27:146s (Suppl, Abstr 3501) (2009).
Wahlstrom et al., "Aberrant MAPK and PI3K Signaling Contribute to Chemotherapy Resistance in T Cell Acute Lymphobalstic Leukemia by Altering the Balance of Apoptosis Mediators," *Blood (ASH Annual Meeting Abstracts)* 118: Abstract 3490 (2011).
Ward et al, "Inhibition of CD28-mediated T cell costimulation by the phosphoinositide 3-kinase inhibitor wortmannin," *Eur. J. Immunol.* 25(2):526-532 (1995).
Ward et al., "Ligation of CD28 receptor by B7 induces formation of D-3 phosphoinositides in T lymphocytes independently of T cell receptor/CD3 activation," *Eur. J. Immunol.* 23(10):2572-2577 (1993).
Ward et al., "Regulation of D-3 phosphoinositides during T cell activation via the T cell antigen receptor/CD3 complex and CD2 antigens," *Eur. J. Immunol.* 22(1):45-49 (1992).
Ward et al., "Regulation of phosphoinositide kinases in T cells. Evidence that phosphatidylinositol 3-kinase is not a substrate for T cell antigen receptor-regulated tyrosine kinases," *J. Biol. Chem.* 267(33):23862-23869 (1992).
Ward et al., "Therapeutic potential of phosphoinositide 3-kinase inhibitors," *Chem. Biol.* 10(3):207-213 (2003).
White et al., "11β-Hydroxysteroid Dehyrdogenase and the Syndrome of Apparent Mineralocorticoid Excess," *Endocr. Rev.* 18(1):135-156 (1997).
Widler et al., "7-alkyl- and 7-Cycloalkyl-5-aryl-pyrrolo[2,3-d]pyrimidines—potent inhibitors of the tyrosine kinase c-Src," *Bioorg. Med. Chem. Lett.* 11(6):849-852 (2001).
Wiesinger et al., "Antiinflammatory activity of the new mould metabolite 11-desacetoxy-wortmannin and of some of its derivatives," *Experientia* 30(2):135-136 (1974).

Wolff, Burger's Medicinal Chemistry, 5$^{th}$ ed, Part 1, pp. 975-977, John Wiley & Sons (1995).
Woscholski et al., "A comparison of demethoxyviridin and wortmannin as inhibitors of phosphatidylinositol 3-kinase," *FEBS Lett.* 342(2):109-114 (1994).
Wu et al., "Decreased immunological responses by wortmannin-containing rice culture of Fusarium oxysporum and by purified wortmannin in avian species," *Immunopharmacol. Immunotoxicol.* 14(4):913-923 (1992).
Wu et al., "Wortmannin (a mycotoxin) inhibited immune responses in chickens," *Poultry Sci.* Vo. 71, Suppl 1, pp. 13 (1992).
Yaguchi et al., "Antitumor activity of ZSTK474, a new phosphatidylinositol 3-kinase inhibitor," *J. Natl. Cancer Inst.* 98(8):545-556 (2006).
Yang et al., "A novel activation pathway for mature thymocytes. Costimulation of CD2 (T,p50) and CD28 (T,p44) induces autocrine interleukin 2/interleukin 2 receptor-mediated cell proliferation," *J. Exp. Med.* 168(4):1457-1468 (1988).
Yano et al , "Inhibition of histamine secretion by wortmannin through the blockade of phosphatidylinositol 3-kinase in RBL-2H3 cells," *J. Biol. Chem.* 268(34):25846-25856 (1993).
Yoshida et al., "Quercetin arrests human leukemic T-cells in late G1 phase of the cell cycle," *Cancer Res.* 52(23):6676-6681 (1992).
Zhao and Vogt, "Class I PI3K in oncogenic cellular transformation," *Oncogene* 27(41):5486-5496 (2008).
Gadhachanda et al., "4-Aminopyrimidines as novel HIV-1 inhibitors," *Bioorg. Med. Chem. Lett.* 17(1):260-265 (2007). (Epub Oct. 10, 2006).
Koeberle et al., "Pirinixic acid derivatives as novel dual inhibitors of microsomal prostaglandin E2 synthase-1 and 5-lipoxygenase," *J. Med. Chem.* 51(24):8068-8076 (2008).
Popescu et al., "Quinoline-based derivatives of pirinixic acid as dual PPAR alpha/gamma agonists," *Arch. Pharm. (Weinheim)* 340(7):367-371 (2007).
Waltenberger et al., "Pharmacophore modeling and virtual screening for novel acidic inhibitors of microsomal prostaglandin $E_2$ synthase-1 (mPGES-1)," *J. Med. Chem.* 54(9):3163-3174 (2011). (Epub Apr. 20, 2011).
Werz et al., "Novel and potent inhibitors of 5-lipoxygenase product synthesis based on the structure of pirinixic acid," *J. Med. Chem.* 51(17):5449-5453 (2008). (Epub Aug. 19, 2008).
Doukas et al., "Aerosolized Phosphoinositide 3-Kinase γ/δ InhibitorTG1 00-115 [3-[2,4-Diamino-6-(3-hydroxyphenyl)pteridin-7-yl]phenol] as a Therapeutic Candidate for Asthma and Chronic Obstructive Pulmonary Disease", Journal of Pharmacology and Experimental Therapeutics, vol. 328, No. 3, Dec. 4, 2008, pp. 758-765.
Hackam et al., "Translation of Research Evidence from Animals to Humans", JAMA, vol. 296(14), 2006, pp. 1731-1732.
Jordan et al., "Tamoxifen: A Most Unlikely Pioneering Medicine", Nature Reviews: Drug Discovery, vol. 2, 2003, pp. 205-213.
Adeyeye, M. ed., Preformulation in Solid Dosage Form Development (Informa Healthcare, 2008) Chapter 2.3, pp. 63-80.
Bastin et al., "Salt Selection and Optimisation Procedures for Pharmaceutical New Chemical Entities", Organic Process Research & Development 2000, 4, pp. 427-435.
Gould et al., "Salt selection for basic drugs", International J. of Therapeutics 33, pp. 201-213 & 217 (1986).
Liu, R. ed., Water-insoluble drug formulation (CRC Press, 2008), Chapter 15, pp. 417-435.
Morris et al., "An integrated approach to the selection of optimal salt form for a new drug candidate", International Journal of Pharmaceutics, vol. 105, Issue 3, May 9, 1994, pp. 209-217.
Serajuddin, "Salt formation to improve drug solubility", Advanced Drug Delivery Reviews, 59 (2007) 603-616.
Stahl et al., eds , Handbook of pharmaceutical salts. Properties, selection and use. (Wiley-VCH 2008), pp. 265-327.
Swarbrick et al., eds., Encyclopedia of Pharmaceutical Technology 13 (Marcel Dekker, NY 1996), pp. 453-499.

\* cited by examiner

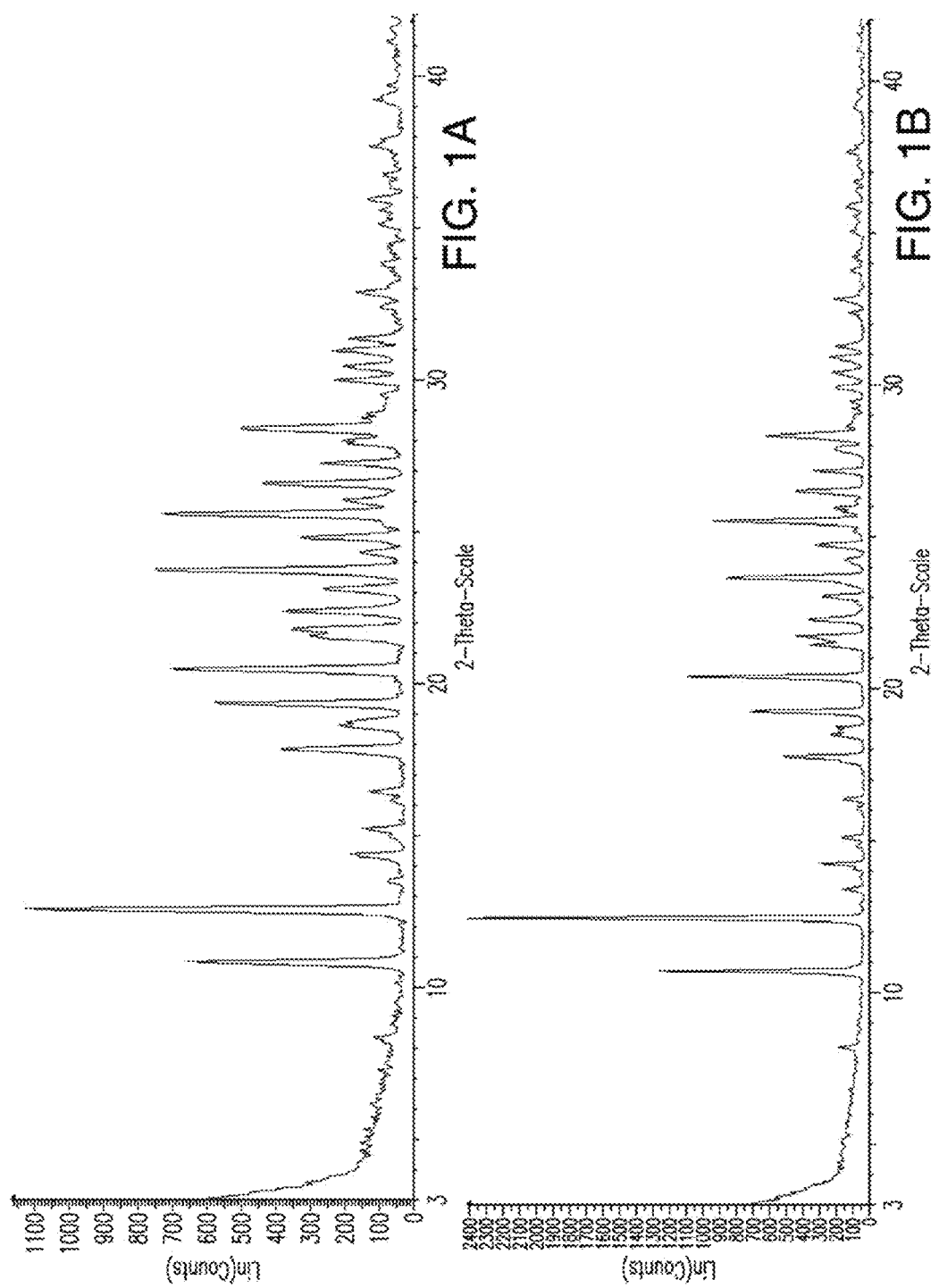

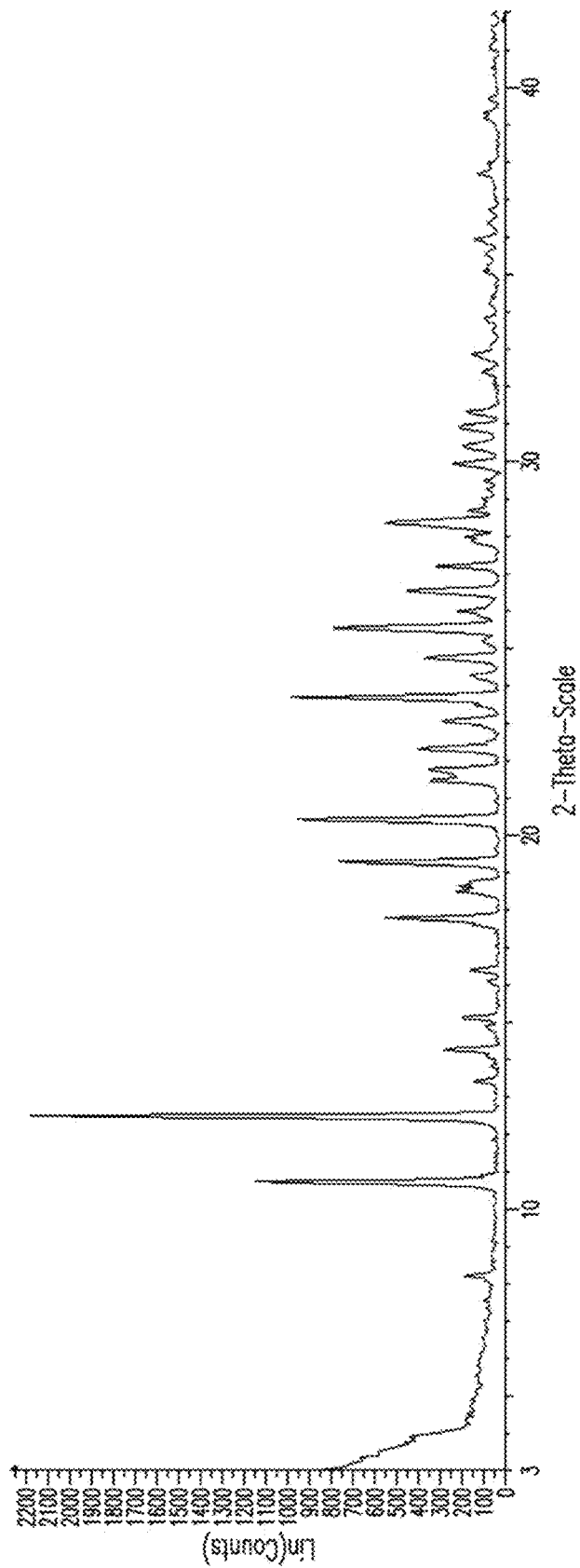

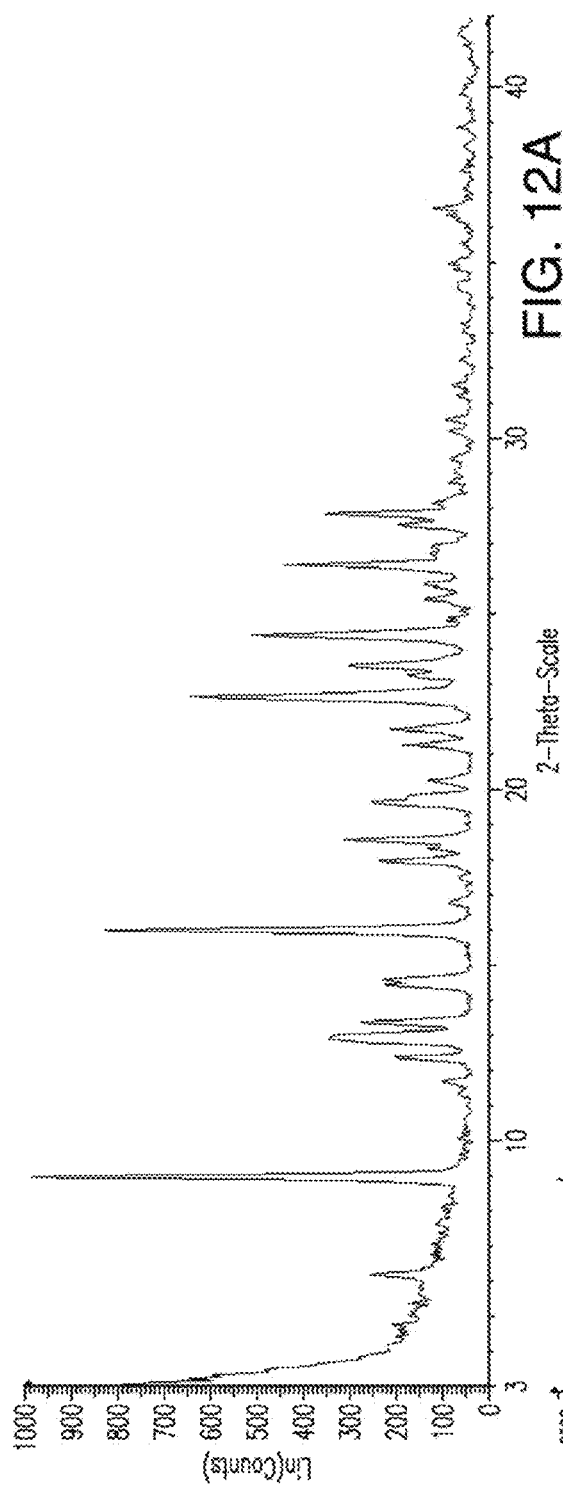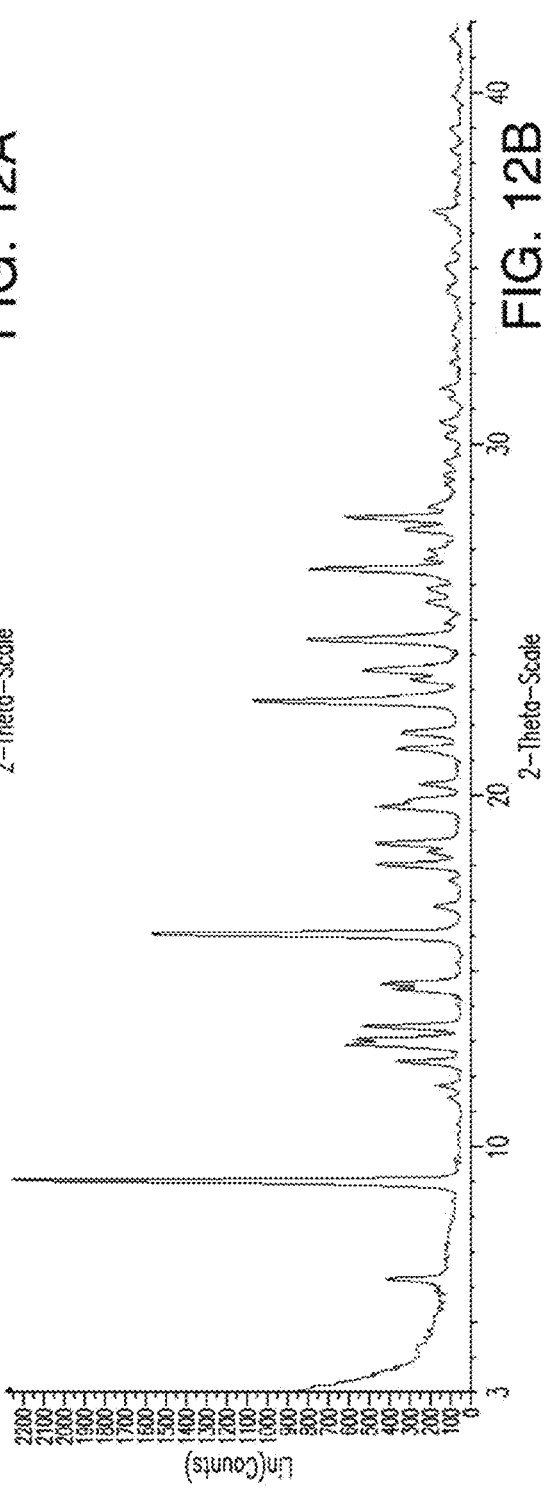

SALTS AND SOLID FORMS OF ISOQUINOLINONES AND COMPOSITION COMPRISING AND METHODS OF USING THE SAME

This application claims priority to U.S. Provisional Application No. 61/789,740, filed Mar. 15, 2013, the entirety of which is incorporated herein by reference.

1. BACKGROUND

The activity of cells can be regulated by external signals that stimulate or inhibit intracellular events. The process by which stimulatory or inhibitory signals are transmitted into and within a cell to elicit an intracellular response is referred to as signal transduction. Over the past decades, cascades of signal transduction events have been elucidated and found to play a central role in a variety of biological responses. Defects in various components of signal transduction pathways have been found to account for a vast number of diseases, including numerous forms of cancer, inflammatory disorders, metabolic disorders, vascular and neuronal diseases (Gaestel et al. *Current Medicinal Chemistry* (2007) 14:2214-2234).

Kinases represent a class of important signaling molecules. Kinases can generally be classified into protein kinases and lipid kinases, and certain kinases exhibit dual specificities. Protein kinases are enzymes that phosphorylate other proteins and/or themselves (i.e., autophosphorylation). Protein kinases can be generally classified into three major groups based upon their substrate utilization: tyrosine kinases which predominantly phosphorylate substrates on tyrosine residues (e.g., erb2, PDGF receptor, EGF receptor, VEGF receptor, src, abl), serine/threonine kinases which predominantly phosphorylate substrates on serine and/or threonine residues (e.g., mTorC1, mTorC2, ATM, ATR, DNA-PK, Akt), and dual-specificity kinases which phosphorylate substrates on tyrosine, serine and/or threonine residues.

Lipid kinases are enzymes that catalyze the phosphorylation of lipids. These enzymes, and the resulting phosphorylated lipids and lipid-derived biologically active organic molecules play a role in many different physiological processes, including cell proliferation, migration, adhesion, and differentiation. Certain lipid kinases are membrane associated and they catalyze the phosphorylation of lipids contained in or associated with cell membranes. Examples of such enzymes include phosphoinositide(s) kinases (e.g., PI3-kinases, PI4-Kinases), diacylglycerol kinases, and sphingosine kinases.

Phosphoinositide 3-kinases (PI3Ks) constitute a unique and conserved family of intracellular lipid kinases that phosphorylate the 3'-OH group on phosphatidylinositols or phosphoinositides. The PI3K family comprises 15 kinases with distinct substrate specificities, expression patterns, and modes of regulation. The class I PI3Ks (p110α, p110β, p110δ, and p110γ) are typically activated by tyrosine kinases or G-protein coupled receptors to generate a lipid product termed PIP$_3$, which engages downstream effectors such as those in the Akt/PDK1 pathway, mTOR, the Tec family kinases, and the Rho family GTPases. The class II and III PI3Ks play a key role in intracellular trafficking through the synthesis of PI(3)P and PI(3,4)P2.

The PI3K signaling pathway is one of the most highly mutated systems in human cancers. PI3K signaling is also a key factor in many other diseases in humans. PI3K signaling is involved in many disease states including allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

Many inhibitors of PI3Ks have been generated. While such compounds are often initially evaluated for their activity when dissolved in solution, solid state characteristics such as polymorphism play an important role. Polymorphic forms of a drug substance, such as an inhibitor of PI3K, can have different chemical and physical properties, including crystallinity, melting point, chemical reactivity, solubility, dissolution rate, optical and mechanical properties, vapor pressure, and density. These properties can have a direct effect on the ability to process or manufacture a drug substance and the drug product. Moreover, polymorphism is often a factor under regulatory review of the "sameness" of drug products from various manufacturers. For example, polymorphism has been evaluated in compounds such as warfarin sodium, famotidine, and ranitidine. Polymorphism can affect the quality, safety, and/or efficacy of a drug product, such as a kinase inhibitor. Thus, research directed towards polymorphs of PI3K inhibitors and processes for preparing polymorphs of PI3K inhibitors represents a significantly useful field of investigation in the development of active pharmaceutical ingredients (APIs).

In addition, PI3K inhibitors have been used to treat various diseases and disorders in humans (e.g., in clinical trials). For the production of a drug substance intended for use in humans, current Good Manufacturing Practices (GMP) are applicable. Procedures need to be in place that can control the levels of impurities and ensure that API products are produced which consistently meet their predetermined specifications. Thus, a significant need exists for a process to prepare PI3K inhibitors suitable for human use, particularly on a commercial scale, that is, inter alia, safe, scalable, efficient, economically viable, and/or having other desirable properties. Among other entities, disclosed herein are polymorphic forms of PI3K inhibitors which address these needs and provide exemplary advantages.

2. SUMMARY

Provided herein are salts and solid forms of a compound of formula (I) (also referred as Compound 1 herein), solid forms of the salts, and methods of synthesizing the salts and solid forms.

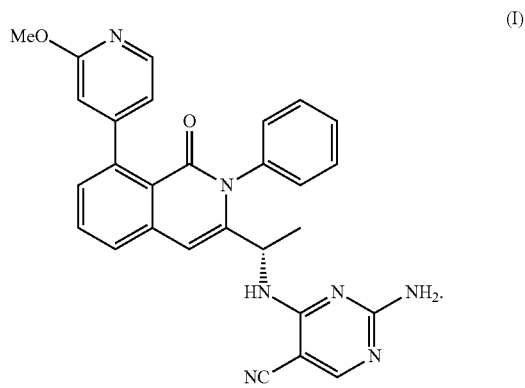 [SMILES: COc1cc(-c2cccc3cc([C@H](C)Nc4nc(N)ncc4C#N)n(-c4ccccc4)c(=O)c23)ccn1]

(I)

The solid forms provided herein include, but are not limited to, hydrates, anhydrates, solvates, as well as crystal and amorphous forms. The solid forms provided herein are useful as active pharmaceutical ingredients for the preparation of formulations for use in animals or humans. Thus, embodiments herein encompass the use of these solid forms as a final drug product. Certain embodiments provide solid forms useful in making final dosage forms with improved properties, e.g., powder flow properties, compaction properties, tableting properties, stability properties, and excipient compatibility properties, among others, that are needed for manufacturing, processing, formulation and/or storage of final drug products. Certain embodiments herein provide pharmaceutical compositions comprising a single-component crystal form, a multiple-component crystal form, a single-component amorphous form and/or a multiple-component amorphous form comprising the compound of formula (I) and a pharmaceutically acceptable diluent, excipient or carrier.

Provided herein are methods for preparing a solid form of a salt of Compound 1, or a solvate thereof; comprising (a) contacting Compound 1 with an acid in a solvent system or exposing a material comprising a salt of Compound 1 to a solvent system; and (b) producing and/or recovering the solid form of the salt of Compound 1 from the mixture resulted from step (a).

Provided herein are methods for preparing a solid form of a free base of Compound 1, or a solvate thereof; comprising (a) exposing a material comprising a salt or free base of Compound 1 to a solvent system; and (b) producing and/or recovering the solid form of the free base of Compound 1 from the mixture resulted from step (a).

In certain embodiments, step (b) comprises one or more of the following steps: (i) cooling a solution containing a salt or free base of Compound 1; (ii) adding an anti-solvent, with or without a cooling step, to cause precipitation of a solid material comprising a salt or free base of Compound 1; (iii) evaporating (e.g., slow evaporation or fast evaporation) a solution containing a salt or free base of Compound 1; (iv) slurrying a material comprising a salt or free base of Compound 1 in a solvent system; and (v) subjecting a material comprising a salt or free base of Compound 1 to maturation in a solvent system.

Provided herein are also pharmaceutical compositions, single unit dosage forms, dosing regimens and kits comprising the salts and solid forms.

Provided herein are also methods for treating, preventing, and managing various disorders using the compositions, salts, and solid forms. The methods comprise administering to a patient in need of such treatment or management a therapeutically effective amount of a salt or solid form provided herein. Further provided are methods of preventing various diseases and disorders, which comprise administering to a patient in need of such prevention a prophylactically effective amount of a salt or solid form provided herein.

Provided herein are also methods for analyzing a material for the presence or amount of a solid form provided herein, comprising providing a material comprising a compound of formula (I), or a salt, solvate, or solvate of a salt thereof, or a mixture thereof; and using a characterization method to determine whether a signatory characteristic associated with the solid form is present in the material by comparing the characteristic obtained from the material with a reference signatory characteristic; wherein the existence of a characteristic substantially identical to the reference signatory characteristic indicates the presence of the solid form in the material.

3. INCORPORATION BY REFERENCE

All publications, patents, and patent applications mentioned in this specification are herein incorporated by reference in their entireties and to the same extent as if each individual publication, patent, or patent application was specifically and individually indicated to be incorporated by reference.

4. BRIEF DESCRIPTION OF THE DRAWINGS

FIG. 1A, FIG. 1B, and FIG. 1C provide representative X-ray powder diffraction (XRPD) patterns of a solid form comprising Form 1 of a sulfuric acid salt of Compound 1.

Figure 2B:
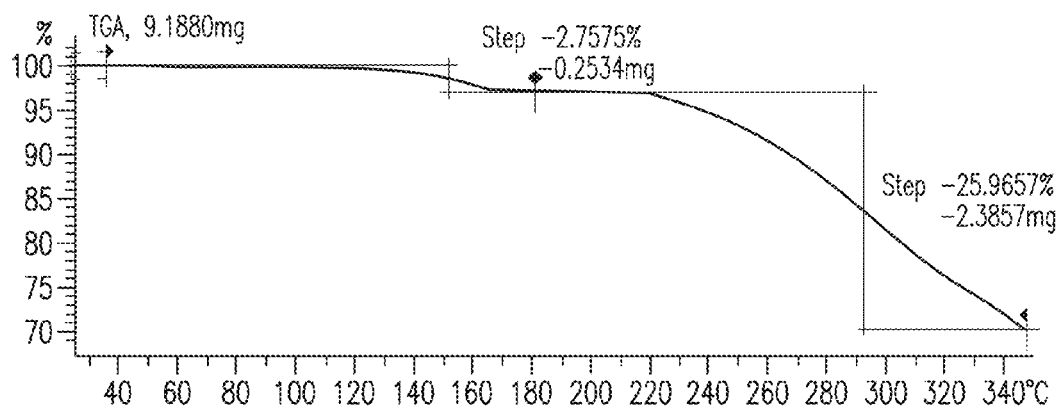
Figure 2C:
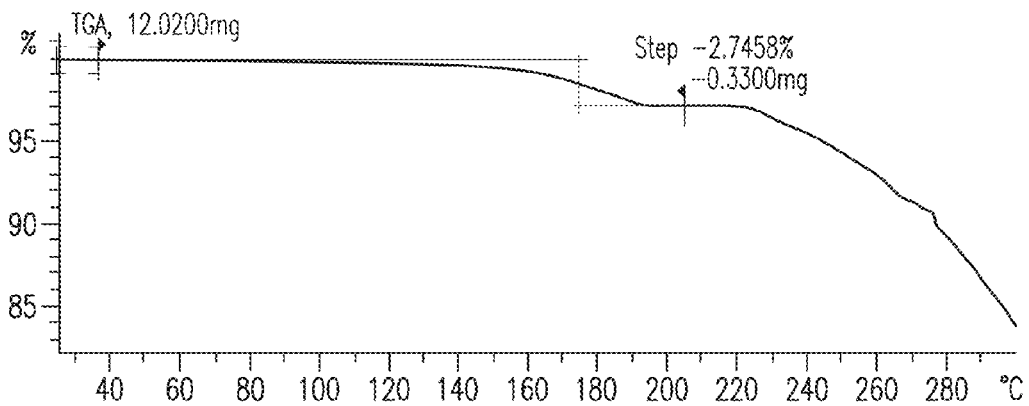

FIG. 2A, FIG. 2B, and FIG. 2C provide representative thermal gravimetric analysis (TGA) thermograms of a solid form comprising Form 1 of a sulfuric acid salt of Compound 1.

Figure 3A:
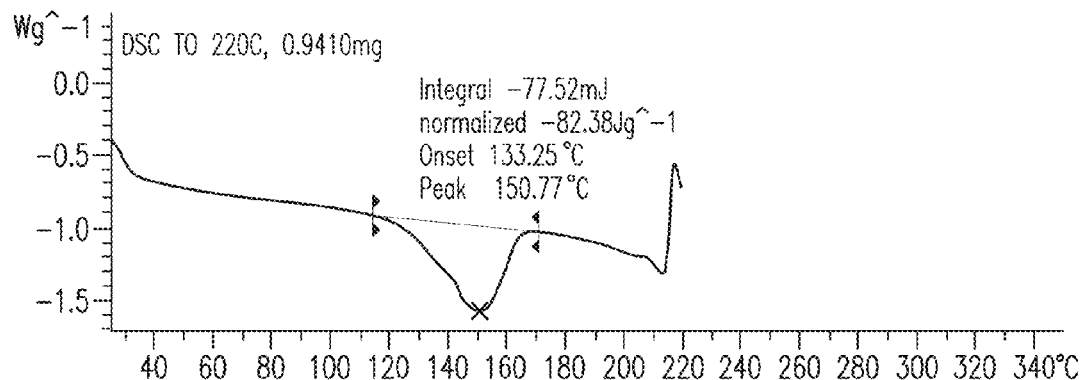
Figure 3B:
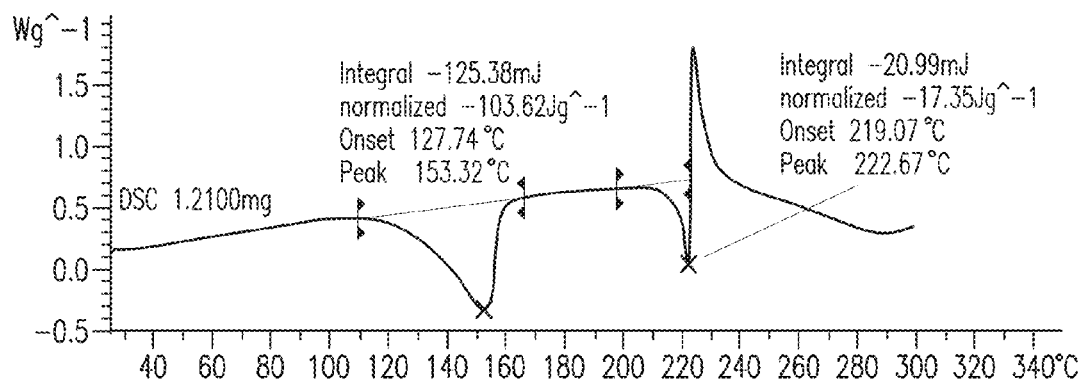
Figure 3C:
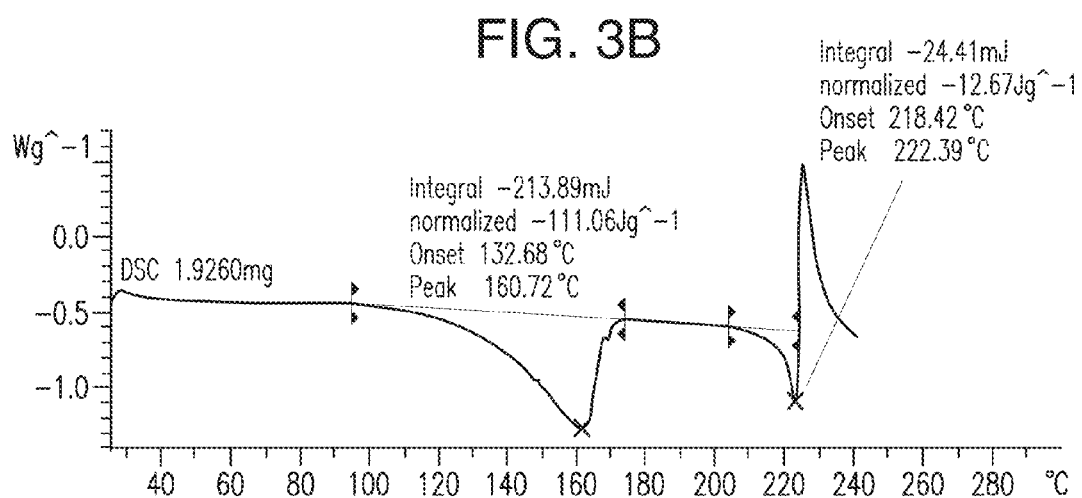

FIG. 3A, FIG. 3B, and FIG. 3C provide representative differential scanning calorimetry (DSC) thermograms of a solid form comprising Form 1 of a sulfuric acid salt of Compound 1.

Figure 4:
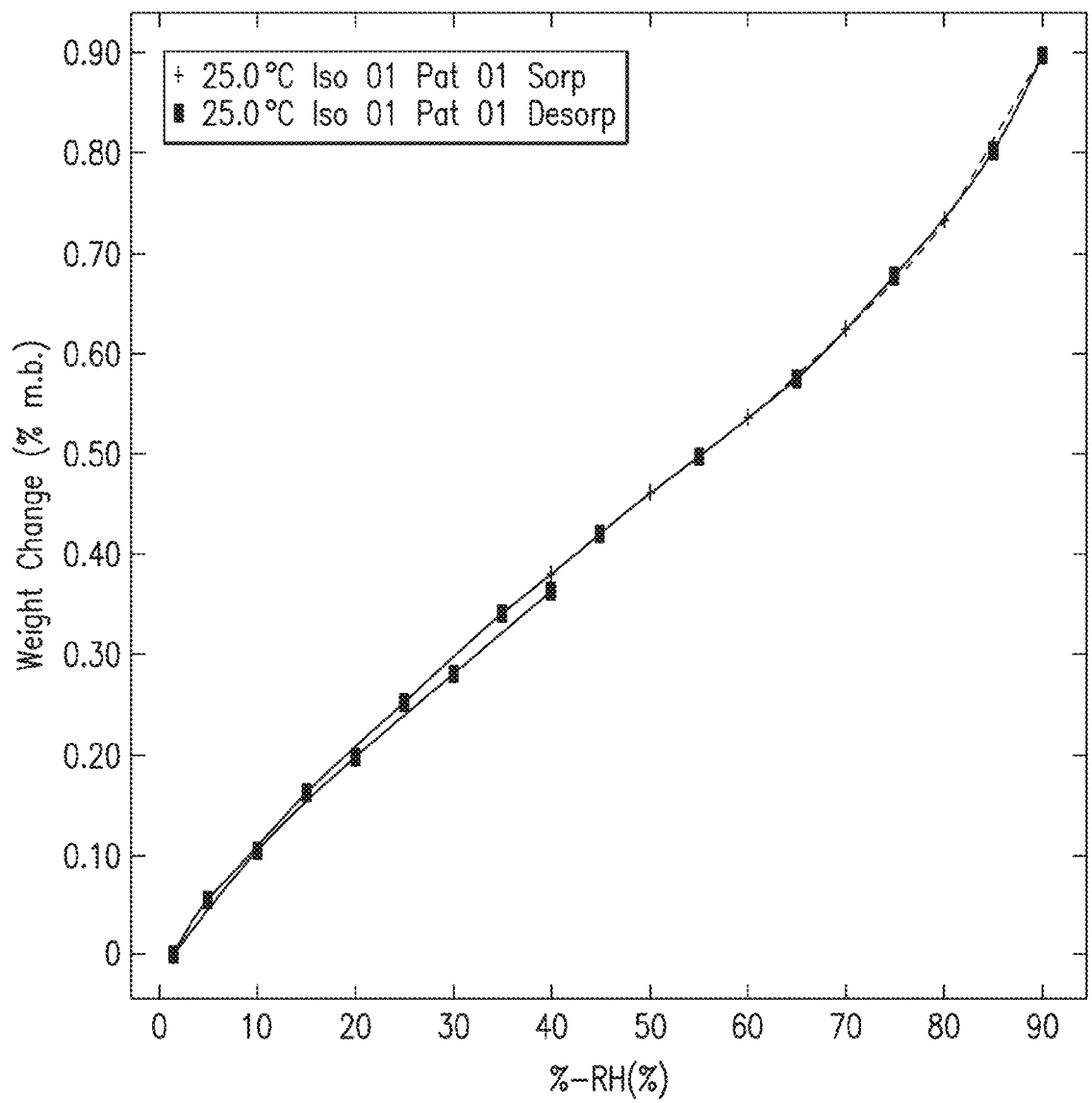

FIG. 4 provides a representative gravimetric vapor sorption (GVS) plot of a solid form comprising Form 1 of a sulfuric acid salt of Compound 1.

Figure 5A:
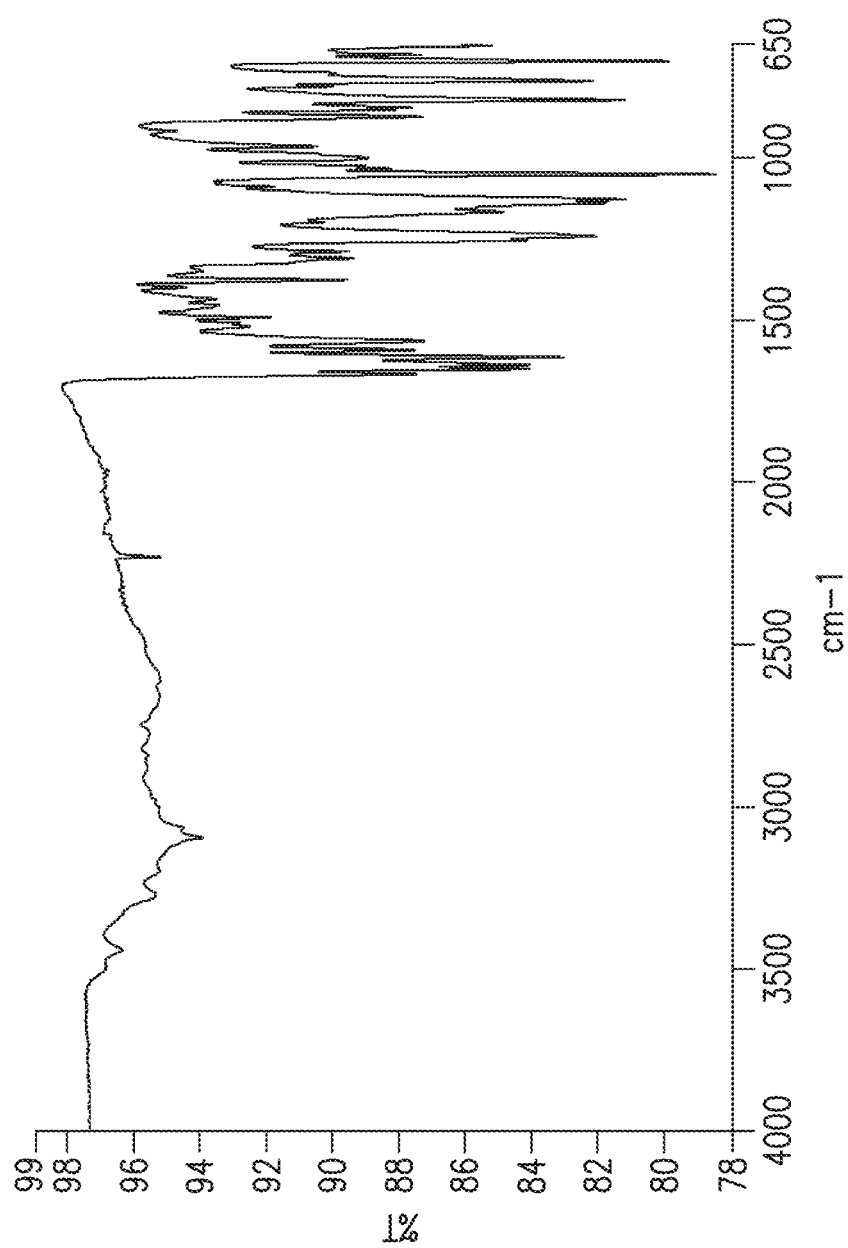
Figure 5B:
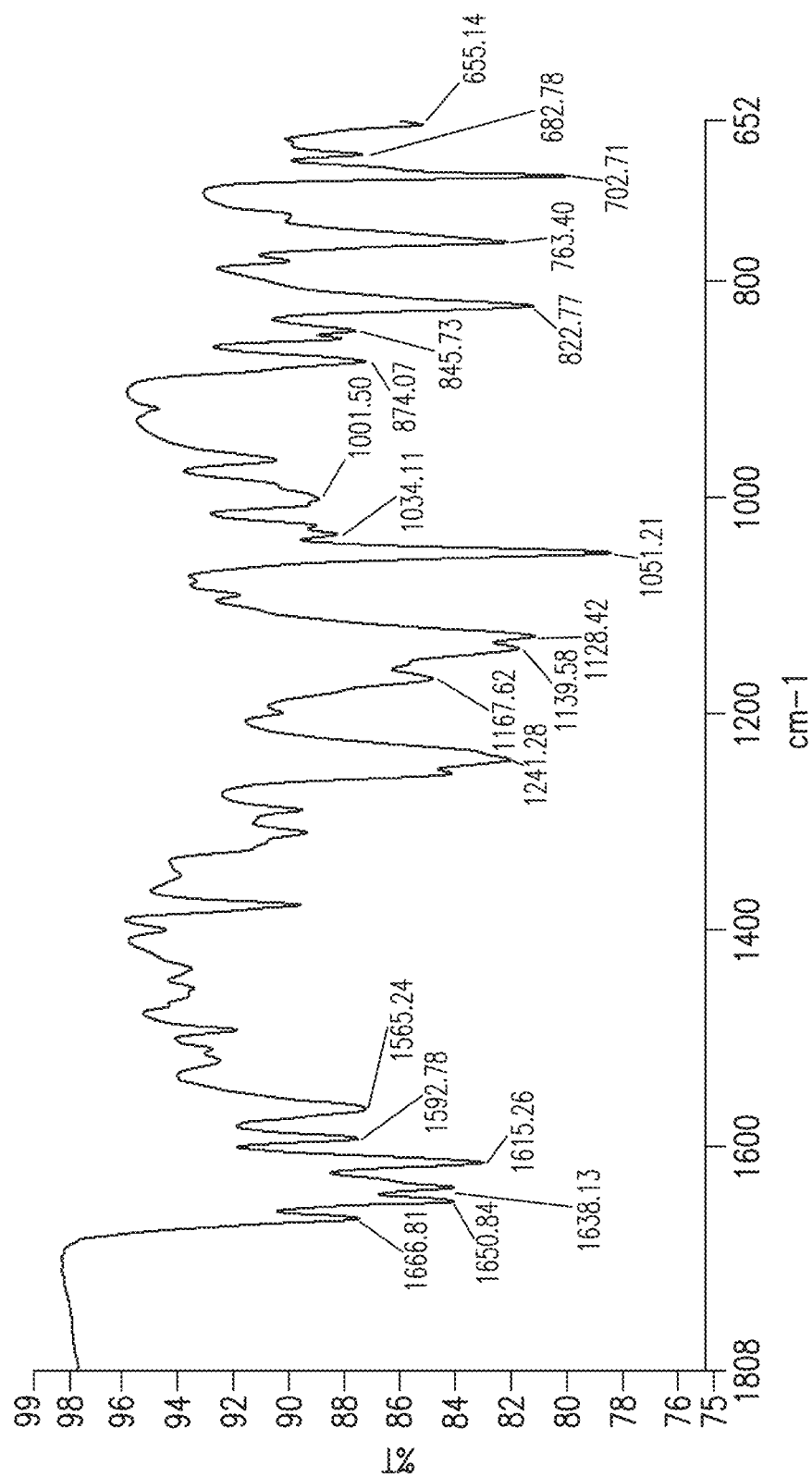

FIG. 5A and FIG. 5B provide representative FT-IR spectra of a solid form comprising Form 1 of a sulfuric acid salt of Compound 1.

Figure 6:
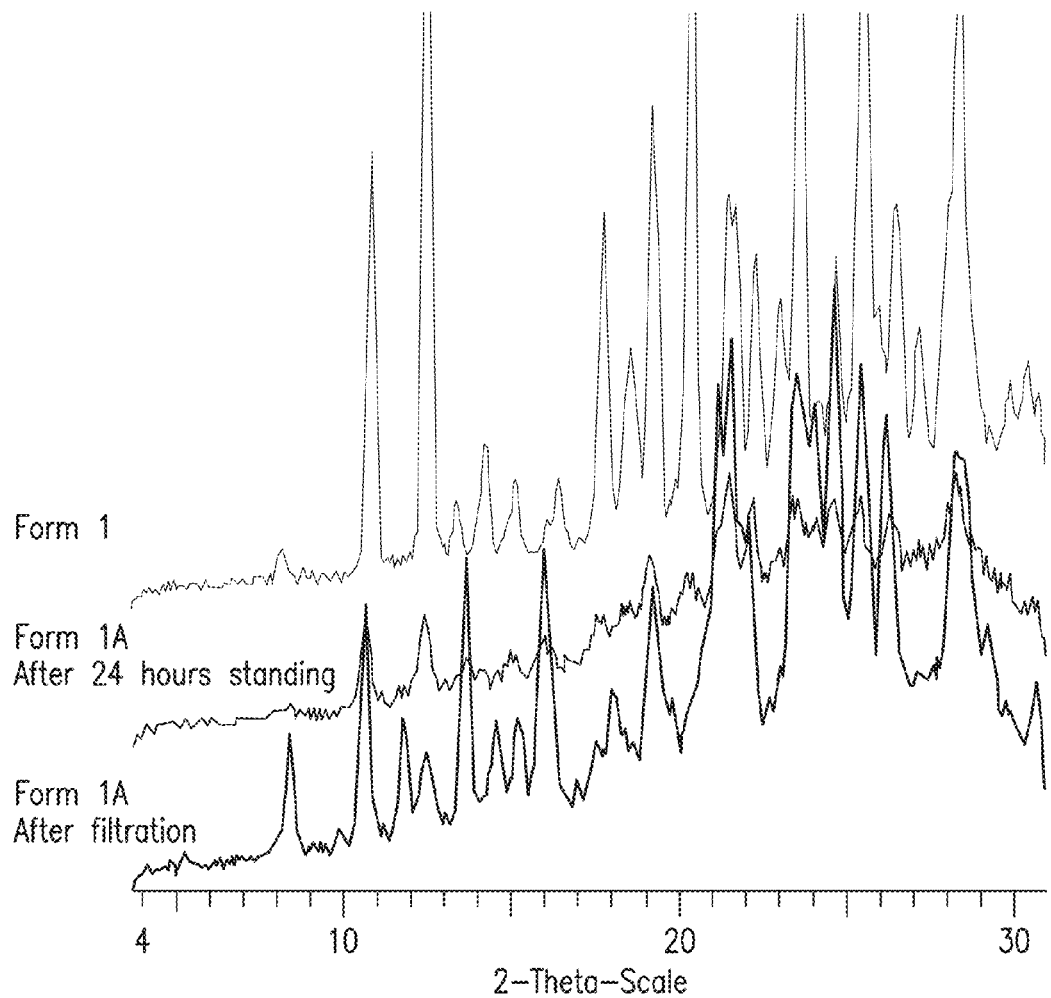

FIG. 6 provides a representative overlay plot of the XRPD patterns of Form 1A and Form 1 of a sulfuric acid salt of Compound 1.

Figure 7:
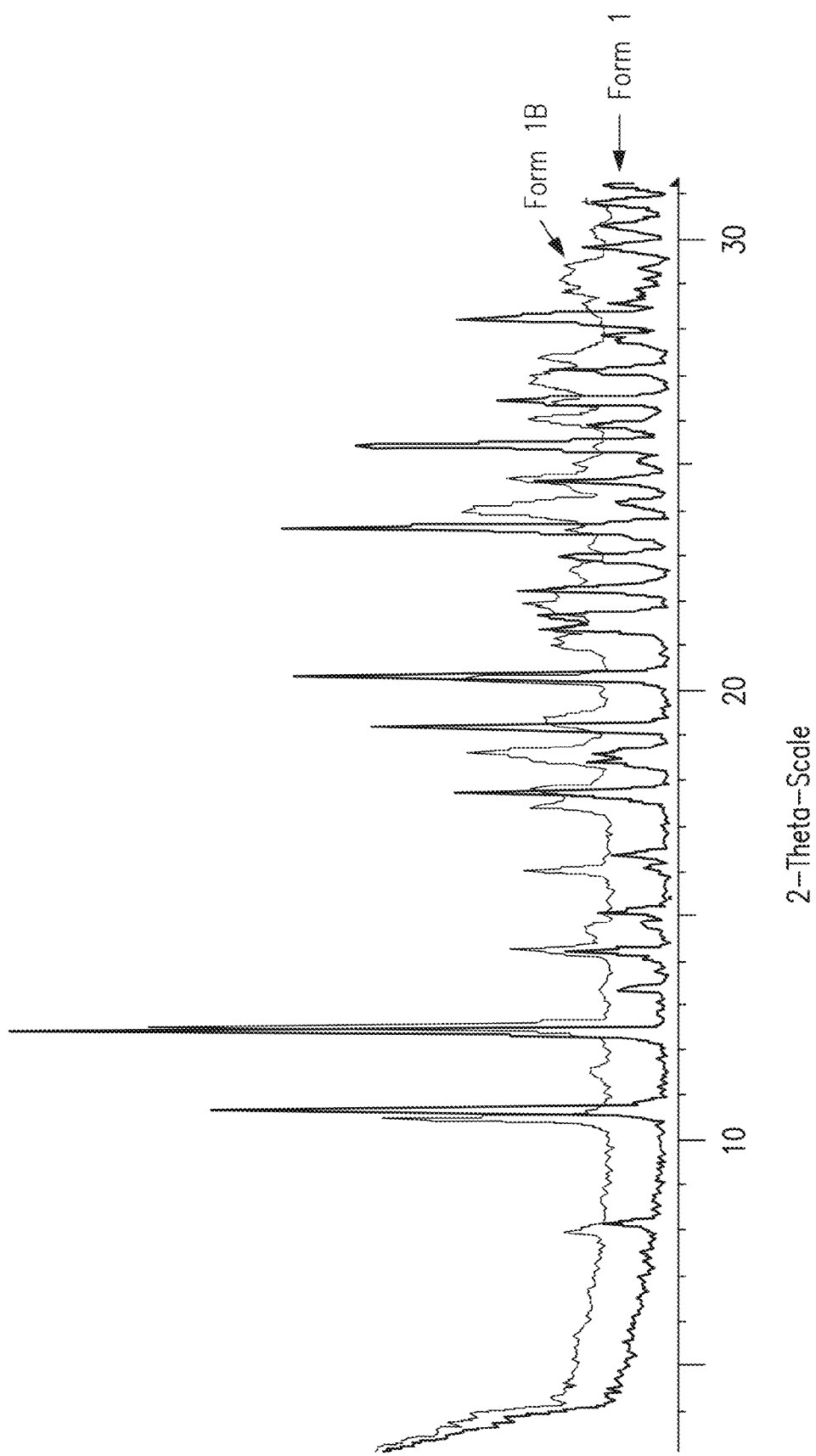

FIG. 7 provides a representative overlay plot of the XRPD patterns of Form 1B and Form 1 of a sulfuric acid salt of Compound 1.

Figure 8A:
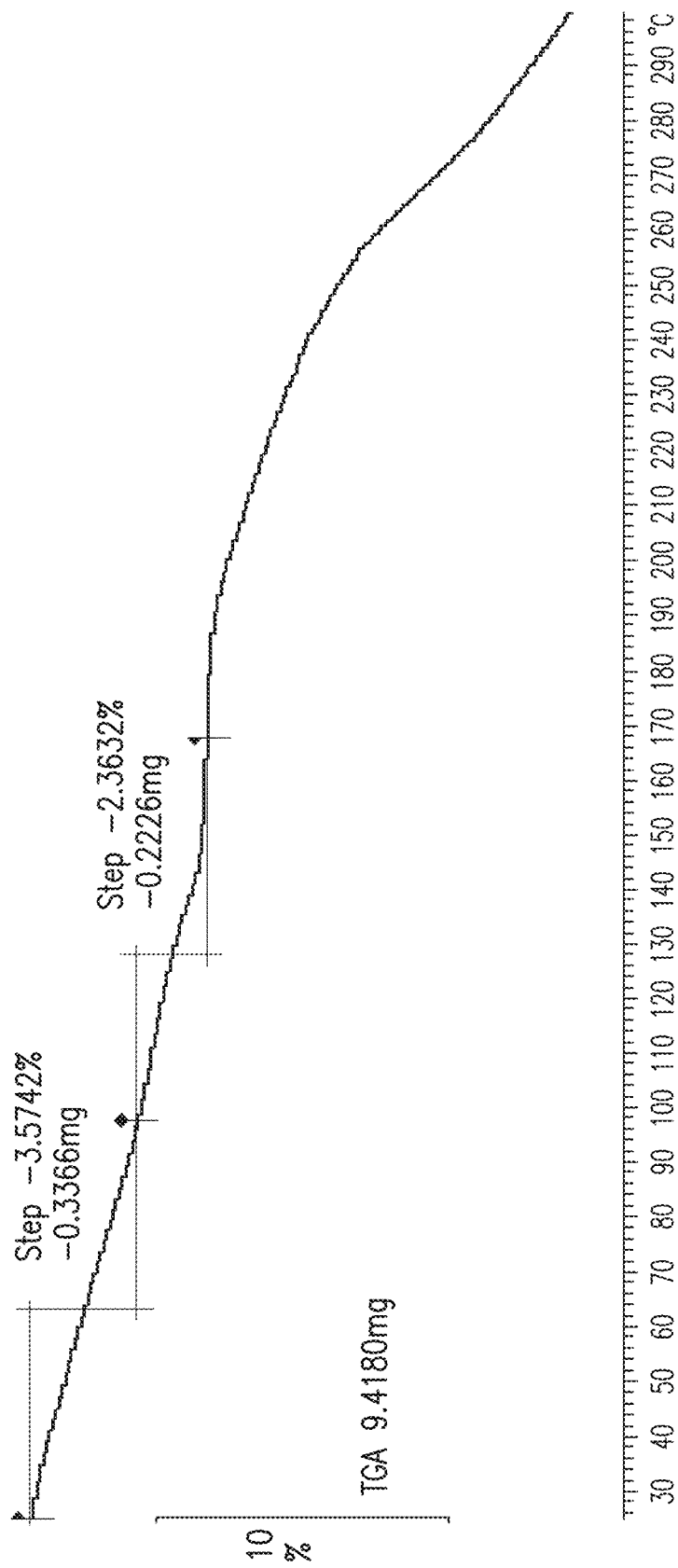

FIG. 8A provides a representative TGA thermogram of a solid form comprising Form 1B of a sulfuric acid salt of Compound 1.

Figure 8B:
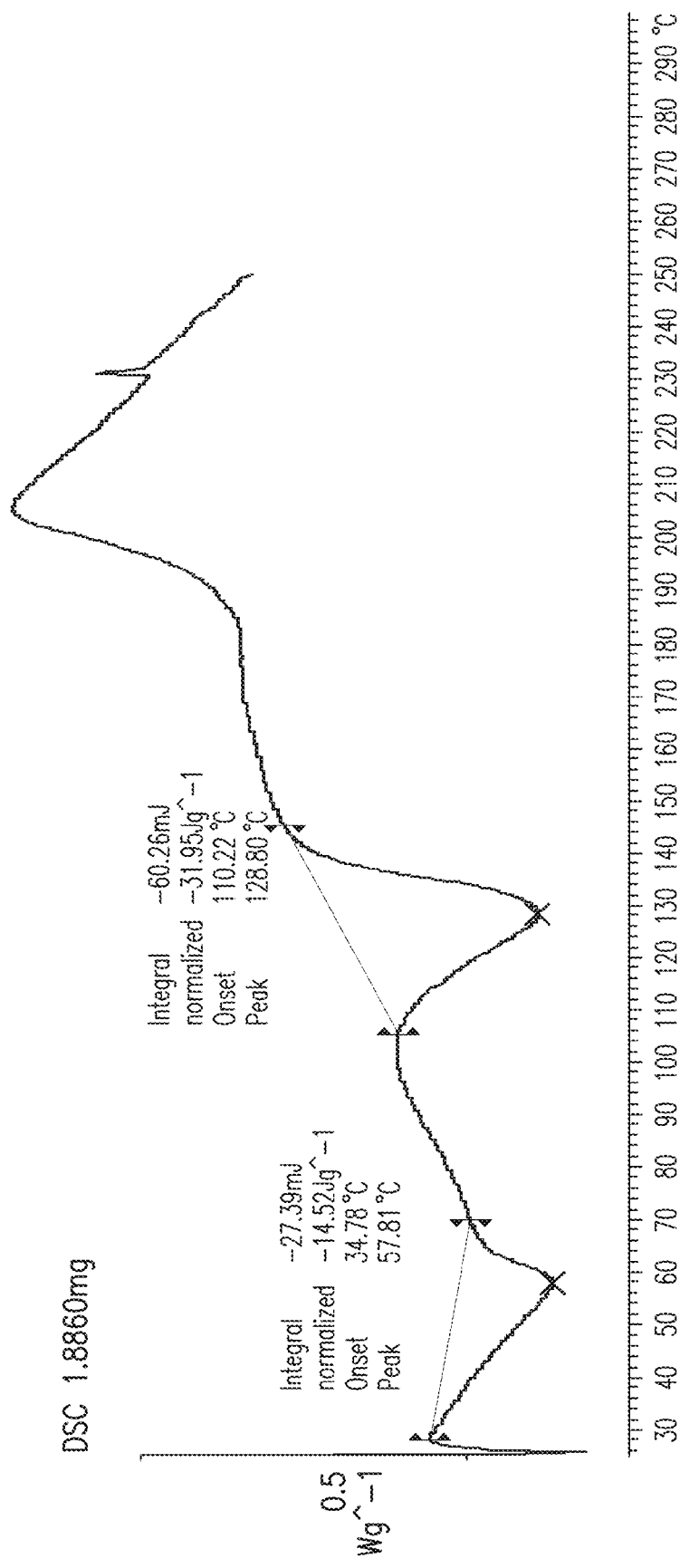

FIG. 8B provides a representative DSC thermogram of a solid form comprising Form 1B of a sulfuric acid salt of Compound 1.

Figure 9:
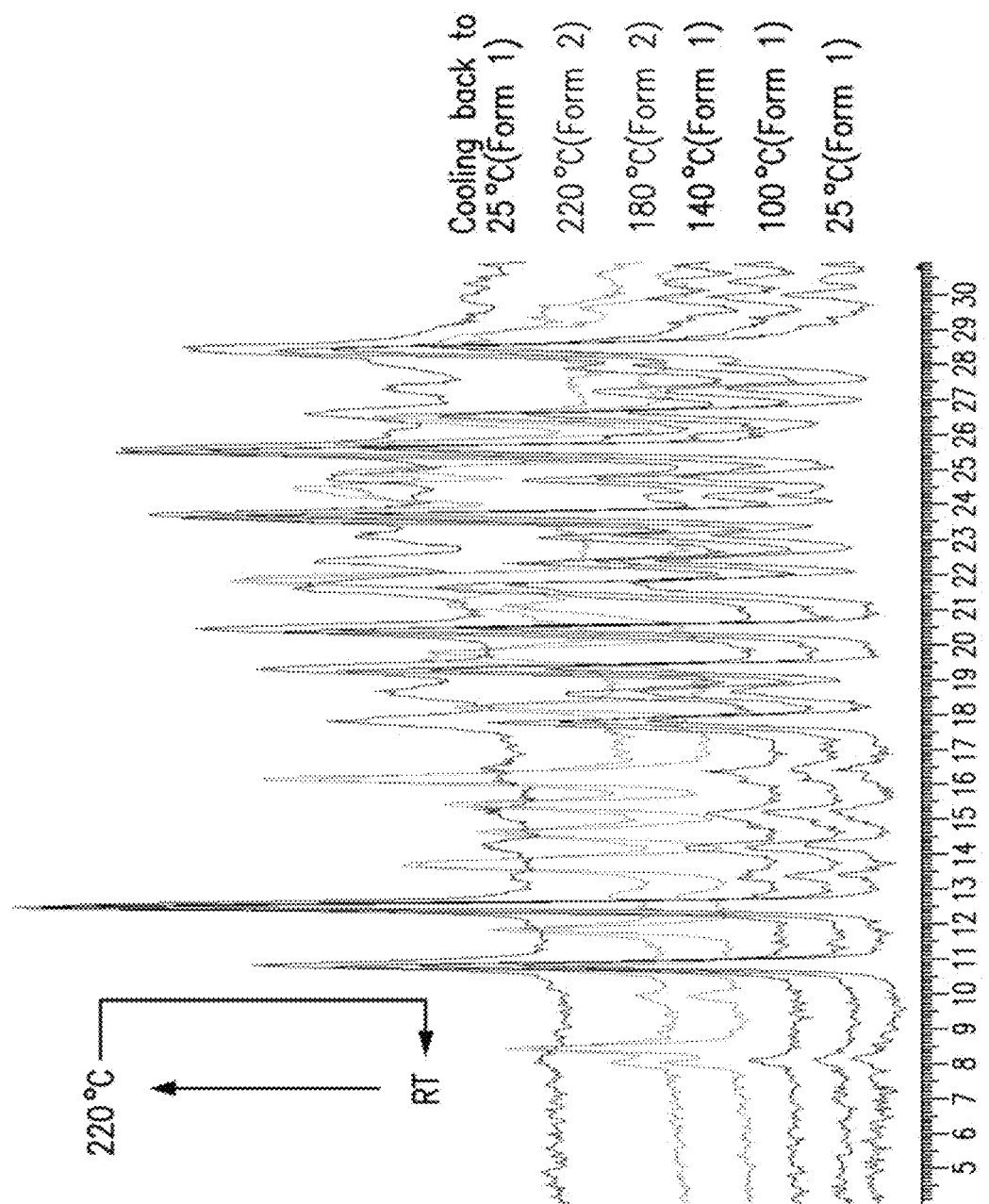

FIG. 9 provides a representative overlay plot of the XRPD patterns of Form 1 and Form 2 of a sulfuric acid salt of Compound 1.

Figure 10:
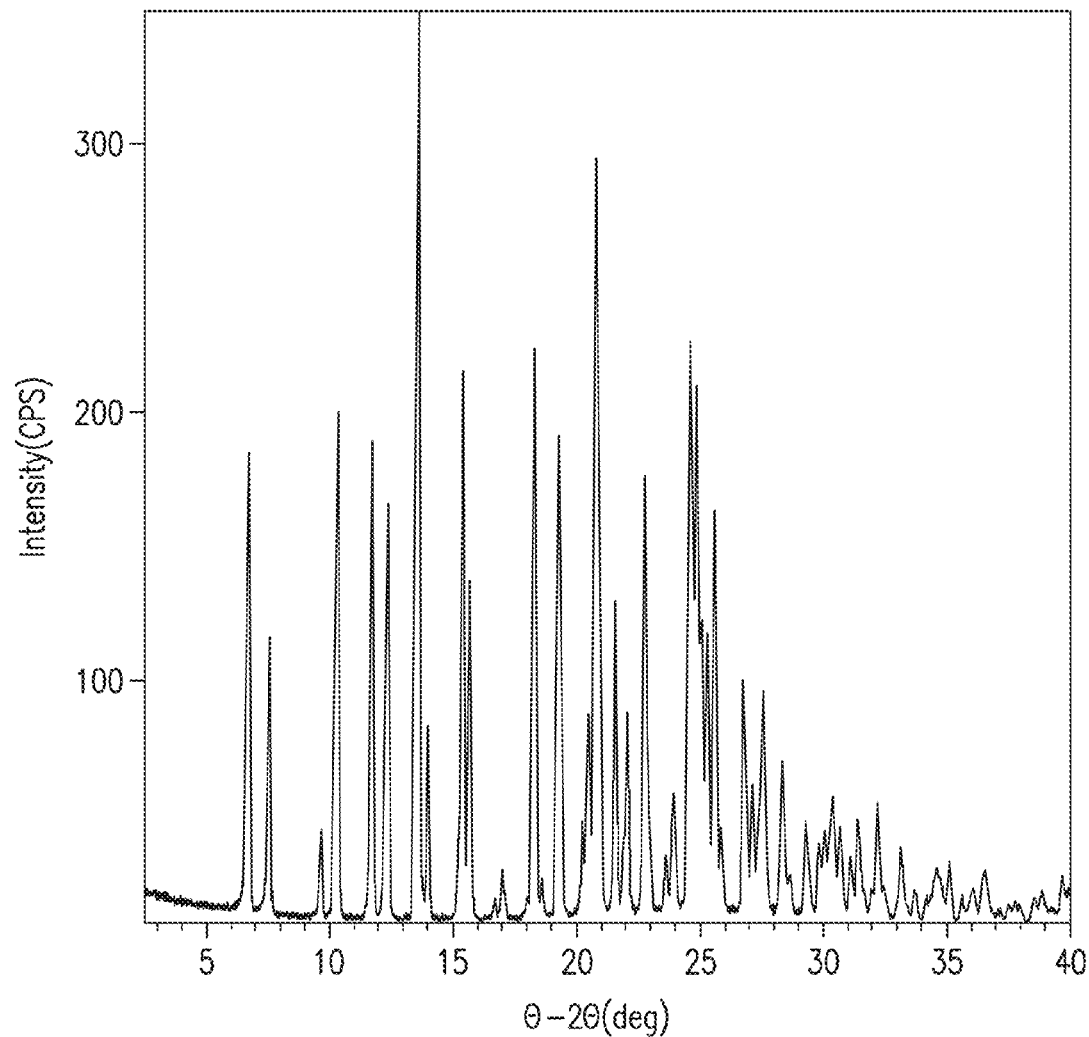

FIG. 10 provides a representative XRPD pattern of a solid form comprising Form 3 of a sulfuric acid salt of Compound 1.

Figure 11A:
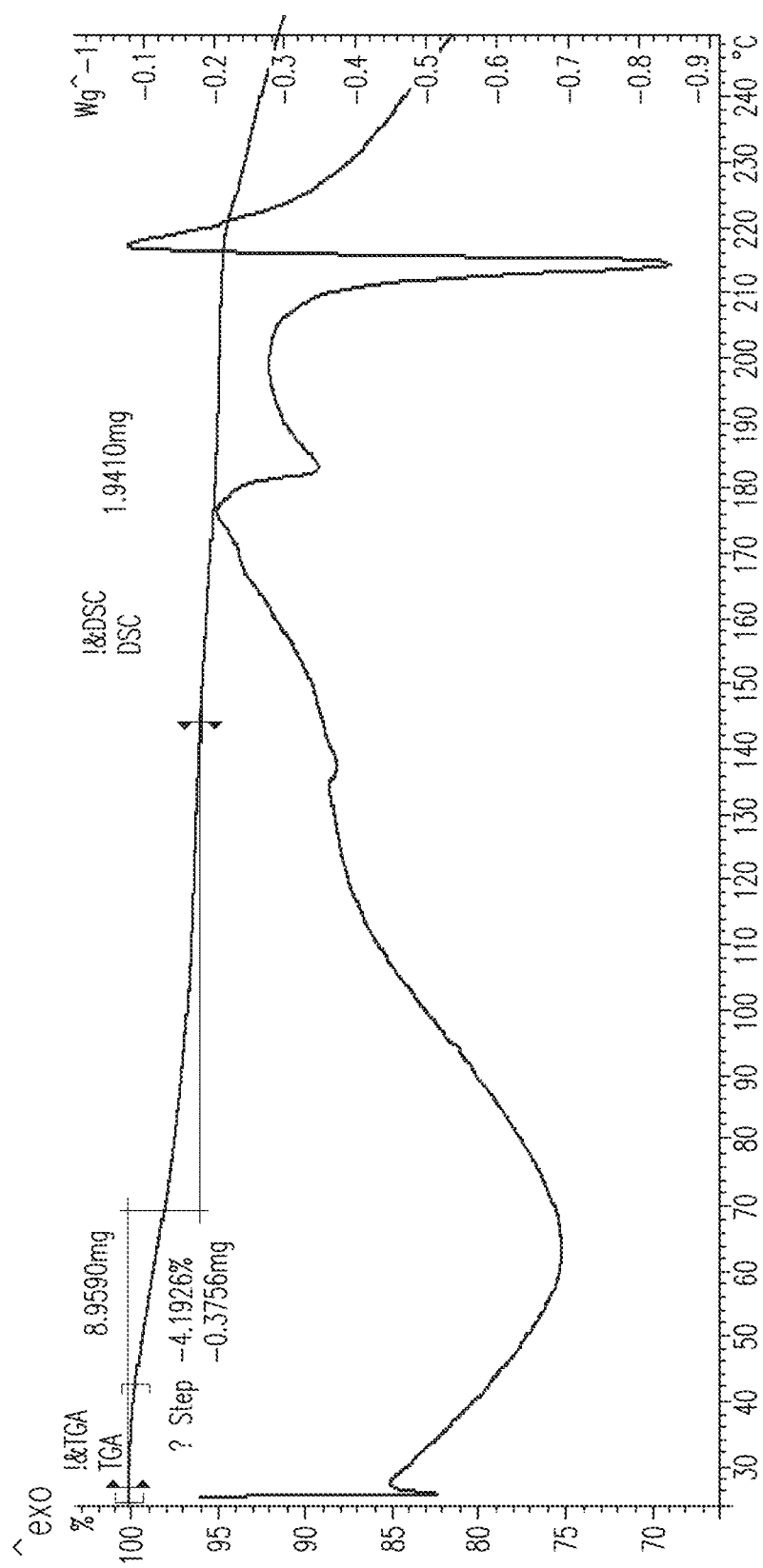
Figure 11B:
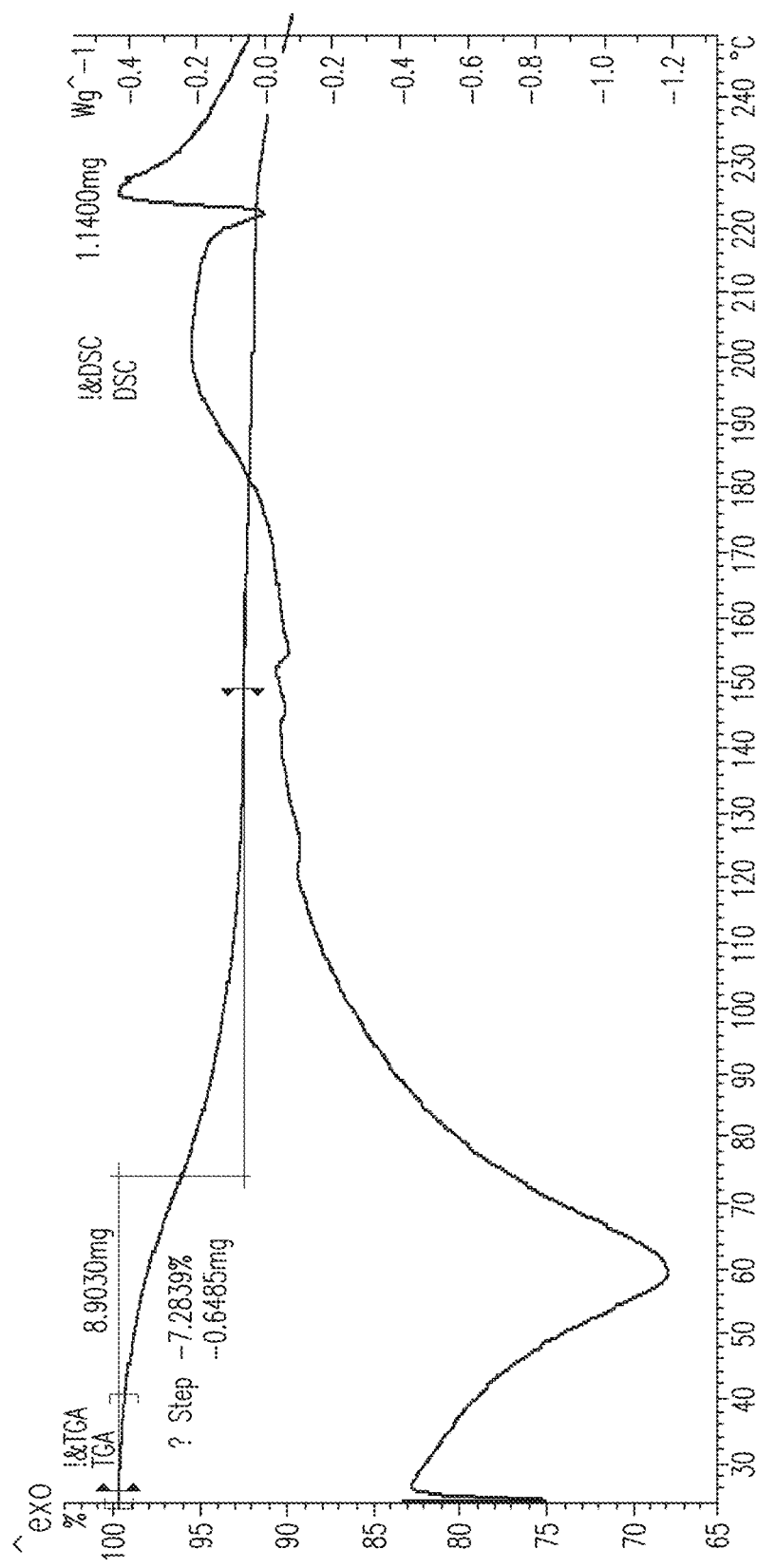

FIG. 11A and FIG. 11B provide representative TGA and DSC thermograms of a solid form comprising Form 3 of a sulfuric acid salt of Compound 1.

Figure 12C:
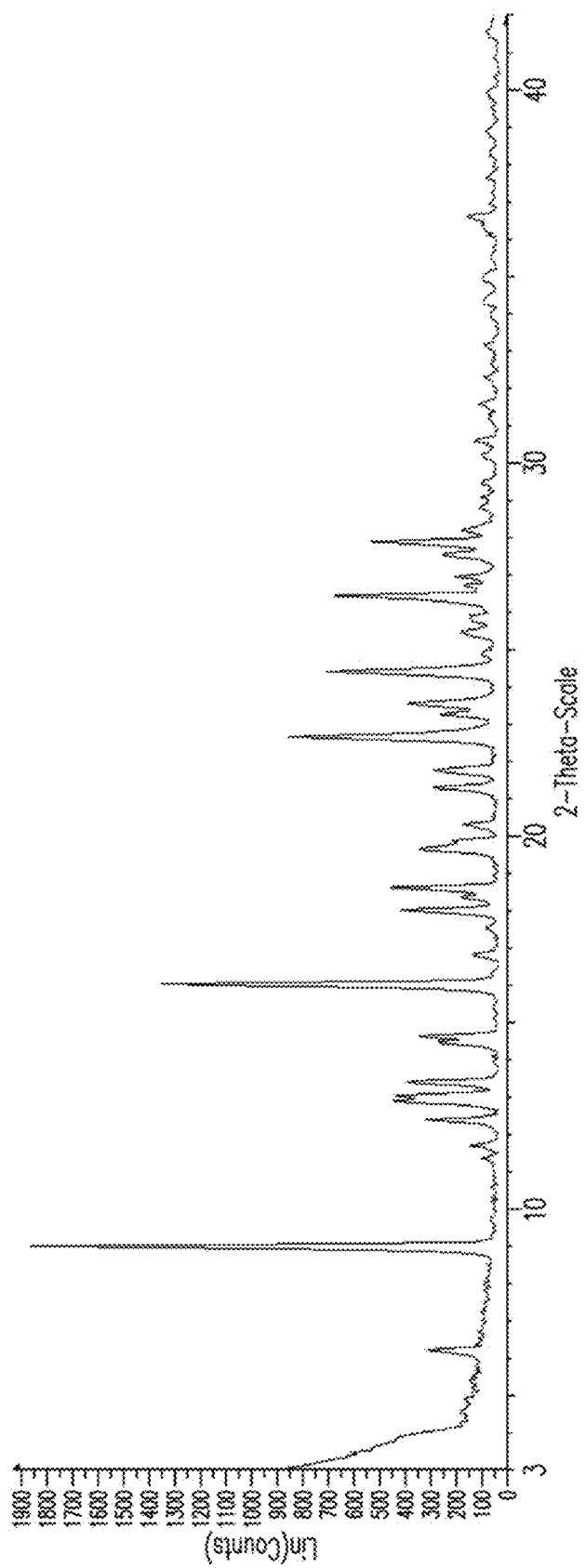

FIG. 12A, FIG. 12B, and FIG. 12C provide representative XRPD patterns of a solid form comprising Form 1 of a maleic acid salt of Compound 1.

Figure 13A:
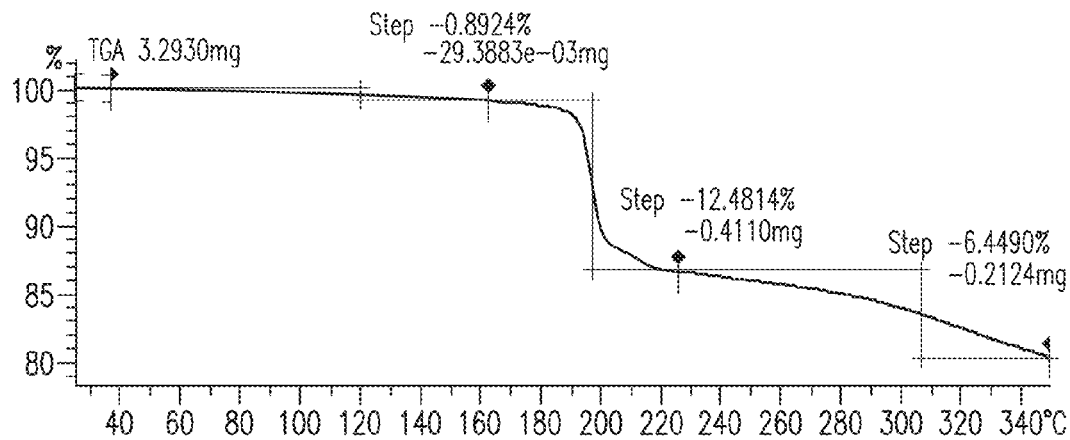
Figure 13B:
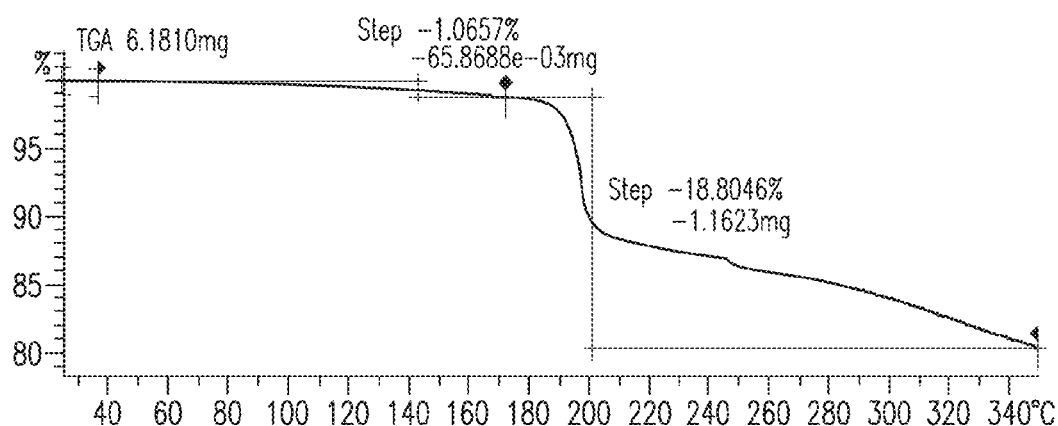
Figure 13C:
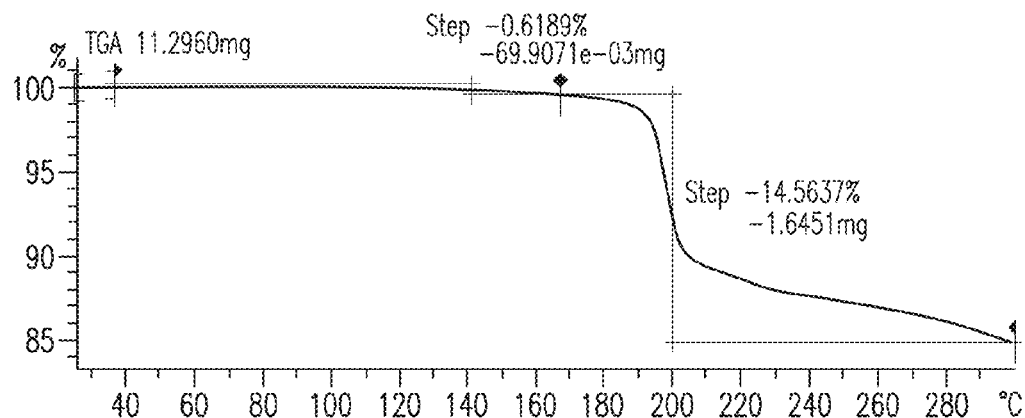

FIG. 13A, FIG. 13B, and FIG. 13C provide representative TGA thermograms of a solid form comprising Form 1 of a maleic acid salt of Compound 1.

Figure 14A:
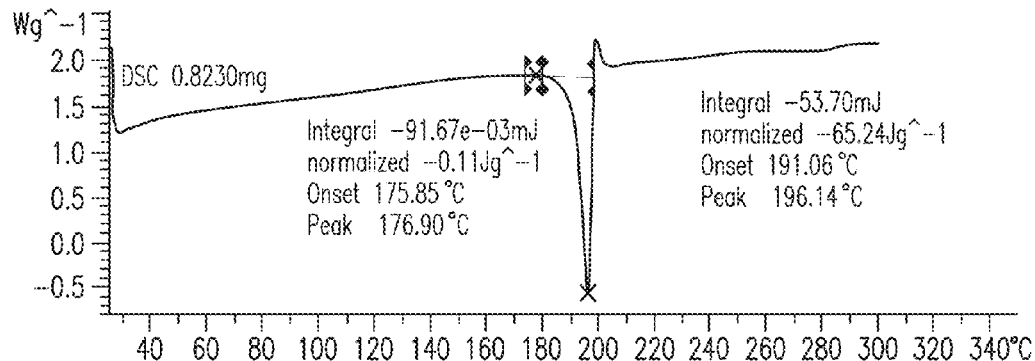
Figure 14B:
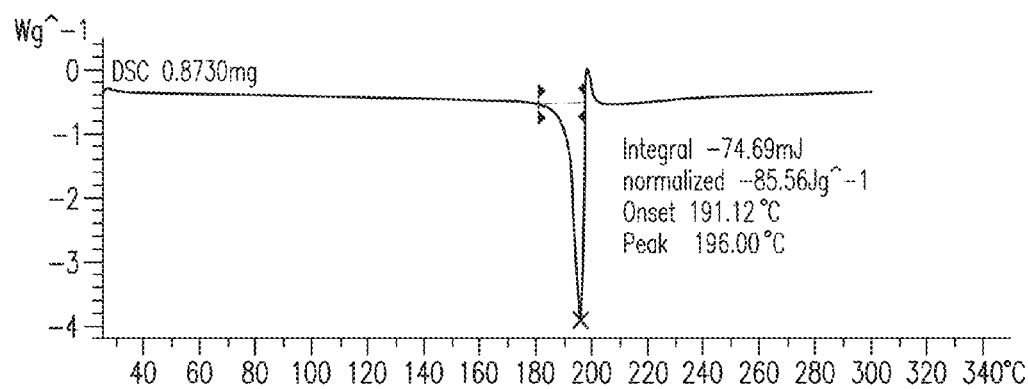
Figure 14C:
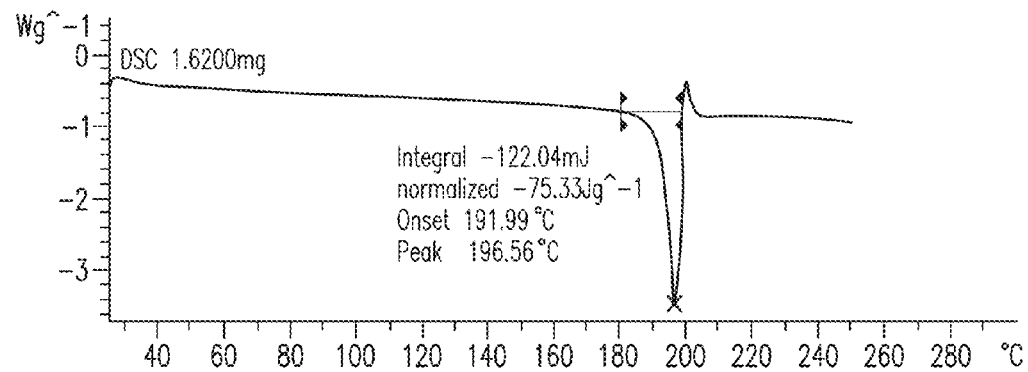

FIG. 14A, FIG. 14B, and FIG. 14C provide representative DSC thermograms of a solid form comprising Form 1 of a maleic acid salt of Compound 1.

Figure 15:
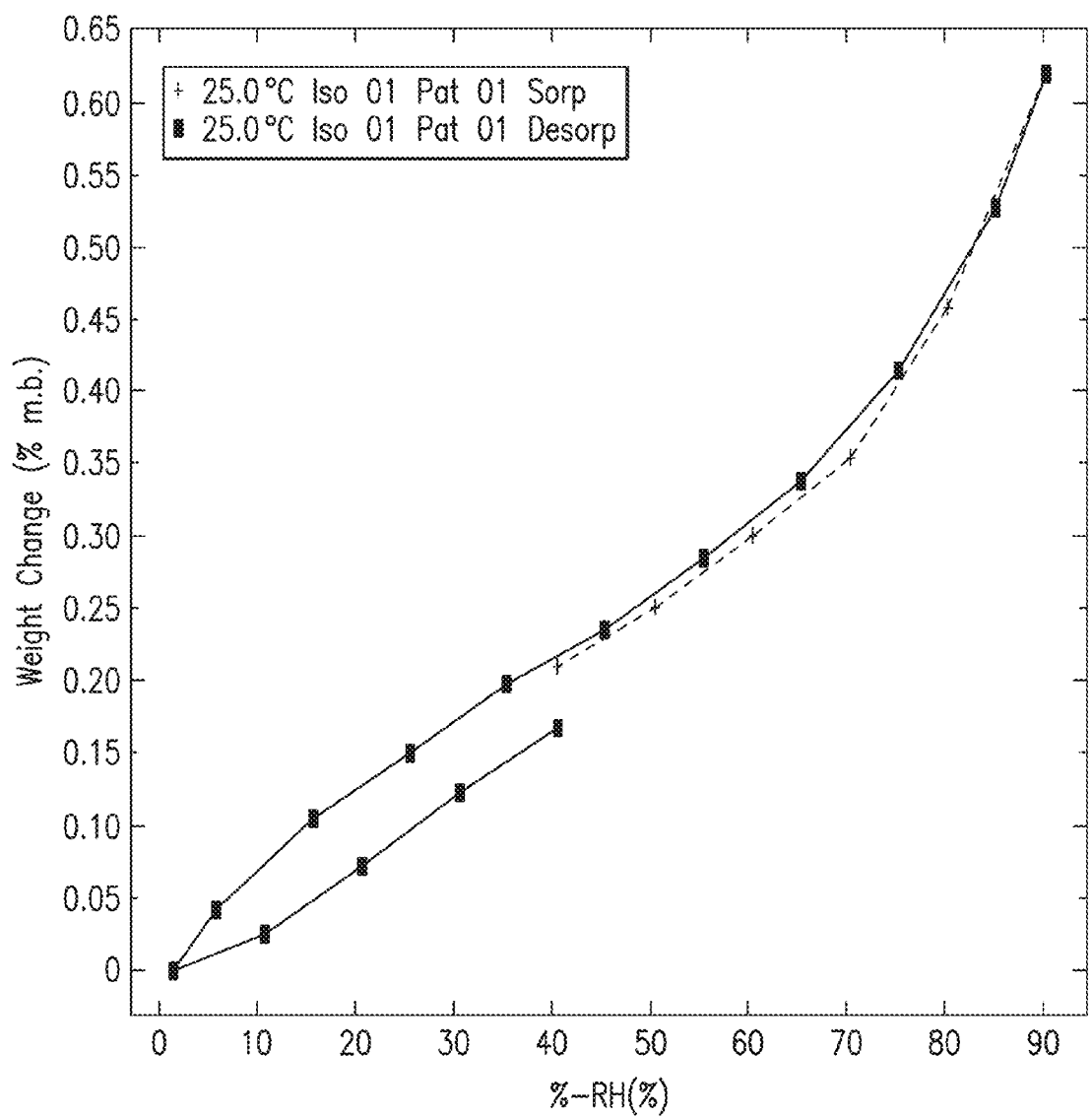

FIG. 15 provides a representative GVS plot of a solid form comprising Form 1 of a maleic acid salt of Compound 1.

Figure 16A:
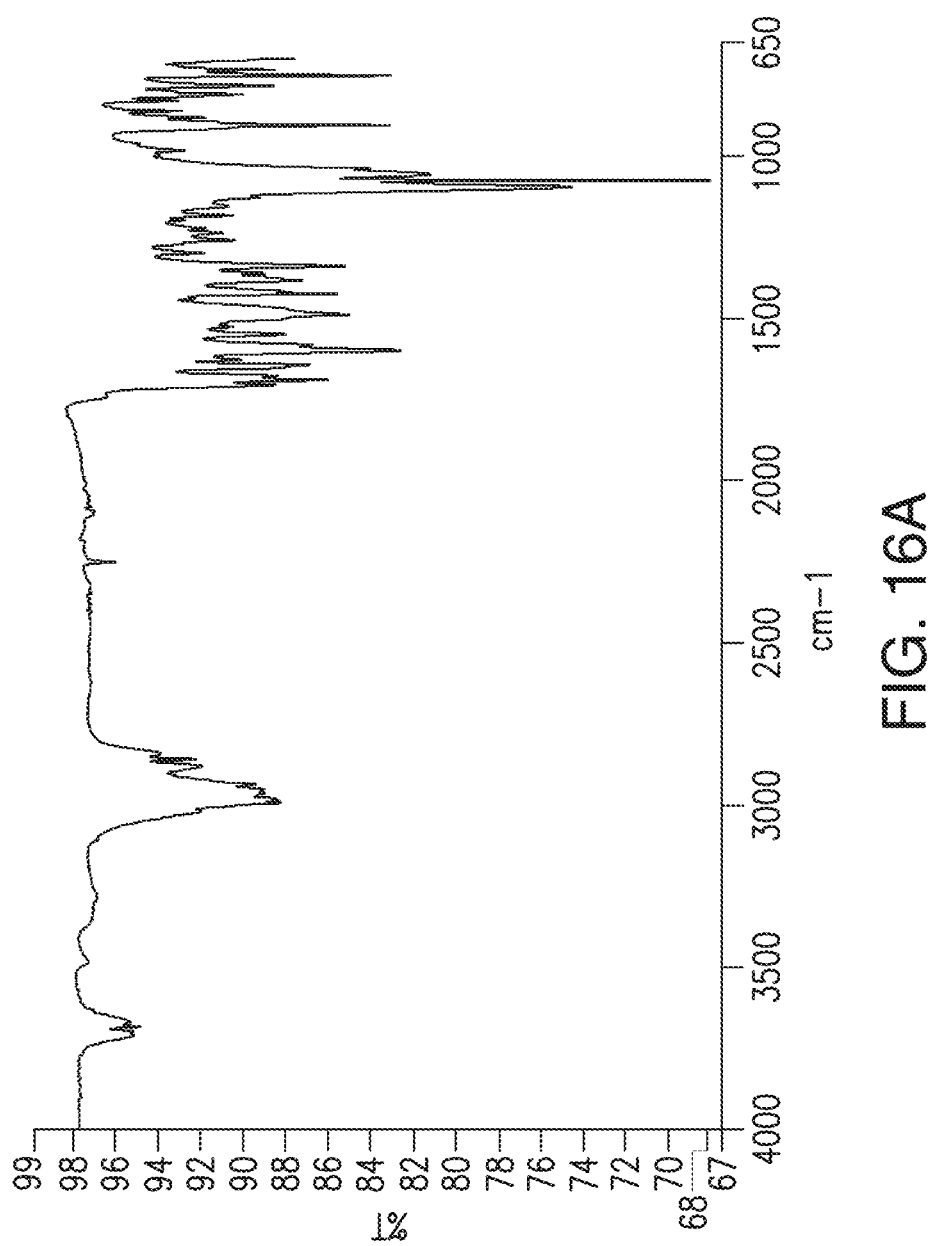
Figure 16B:
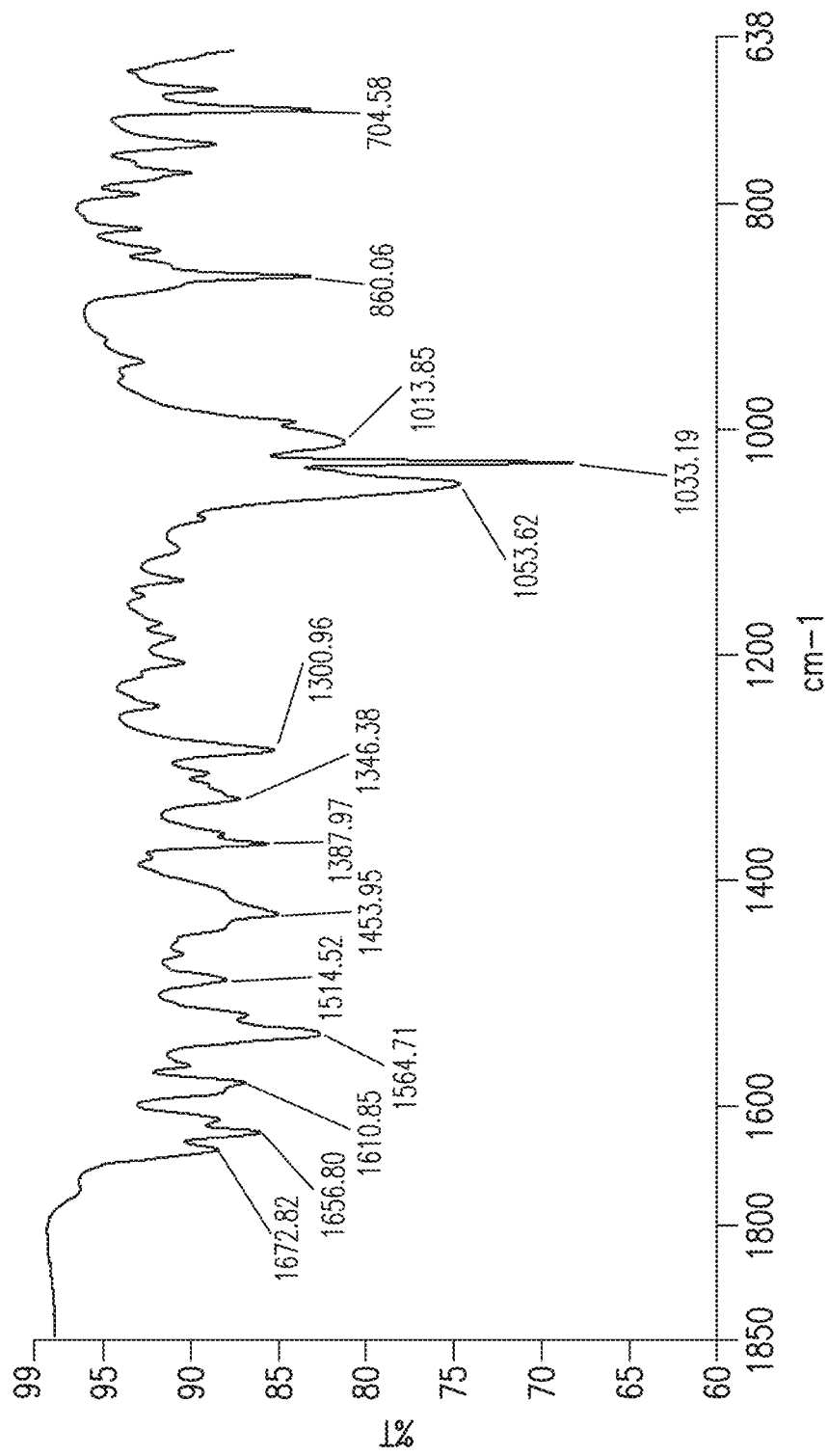

FIG. 16A and FIG. 16B provide representative FT-IR spectra of a solid form comprising Form 1 of a maleic acid salt of Compound 1.

Figure 17A:
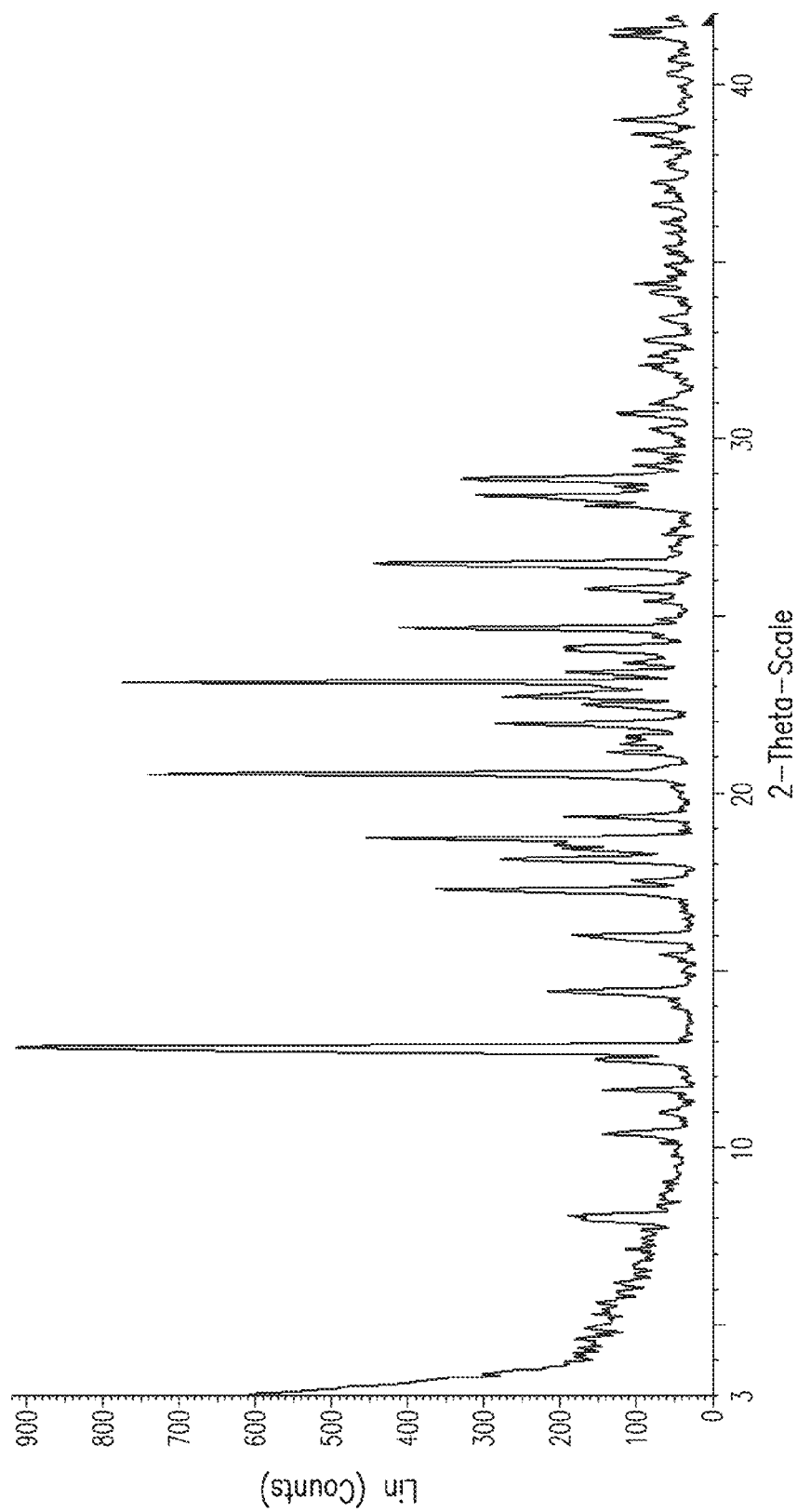
Figure 17B:
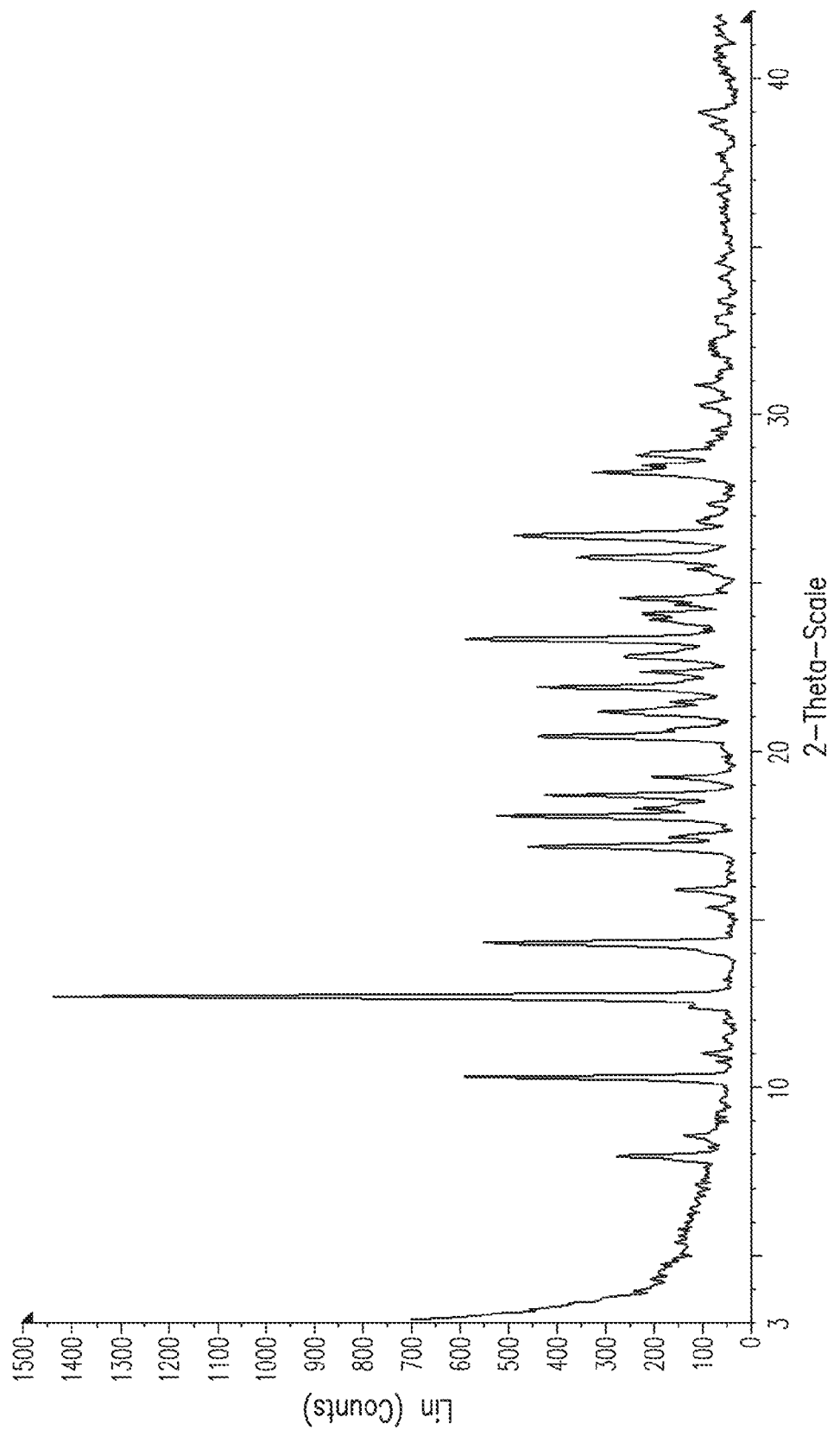

FIG. 17A and FIG. 17B provide representative XRPD patterns of a solid form comprising Form 1 of an 1,2-ethanedisulfonic acid salt of Compound 1.

Figure 18A:
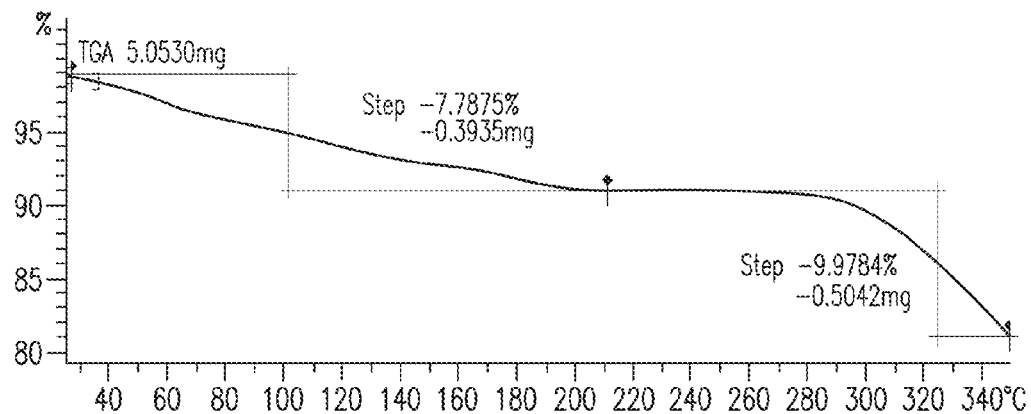
Figure 18B:
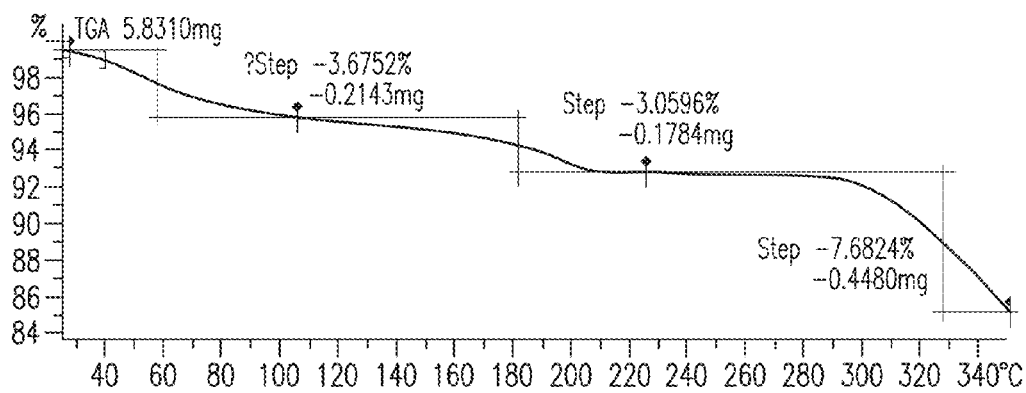

FIG. 18A and FIG. 18B provide representative TGA thermograms of a solid form comprising Form 1 of an 1,2-ethanedisulfonic acid salt of Compound 1.

Figure 19A:
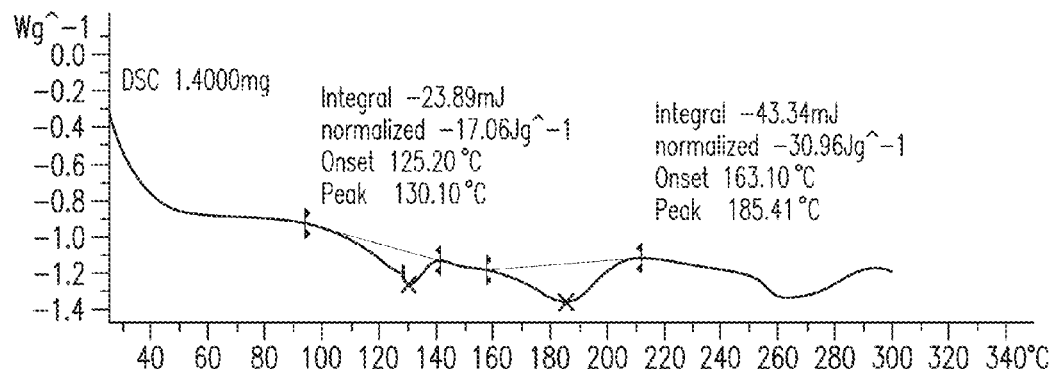
Figure 19B:
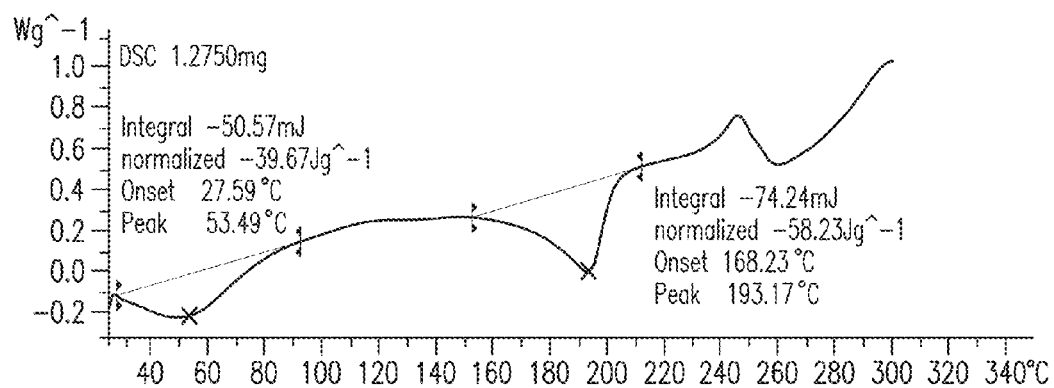

FIG. 19A and FIG. 19B provide representative DSC thermograms of a solid form comprising Form 1 of an 1,2-ethanedisulfonic acid salt of Compound 1.

Figure 20:
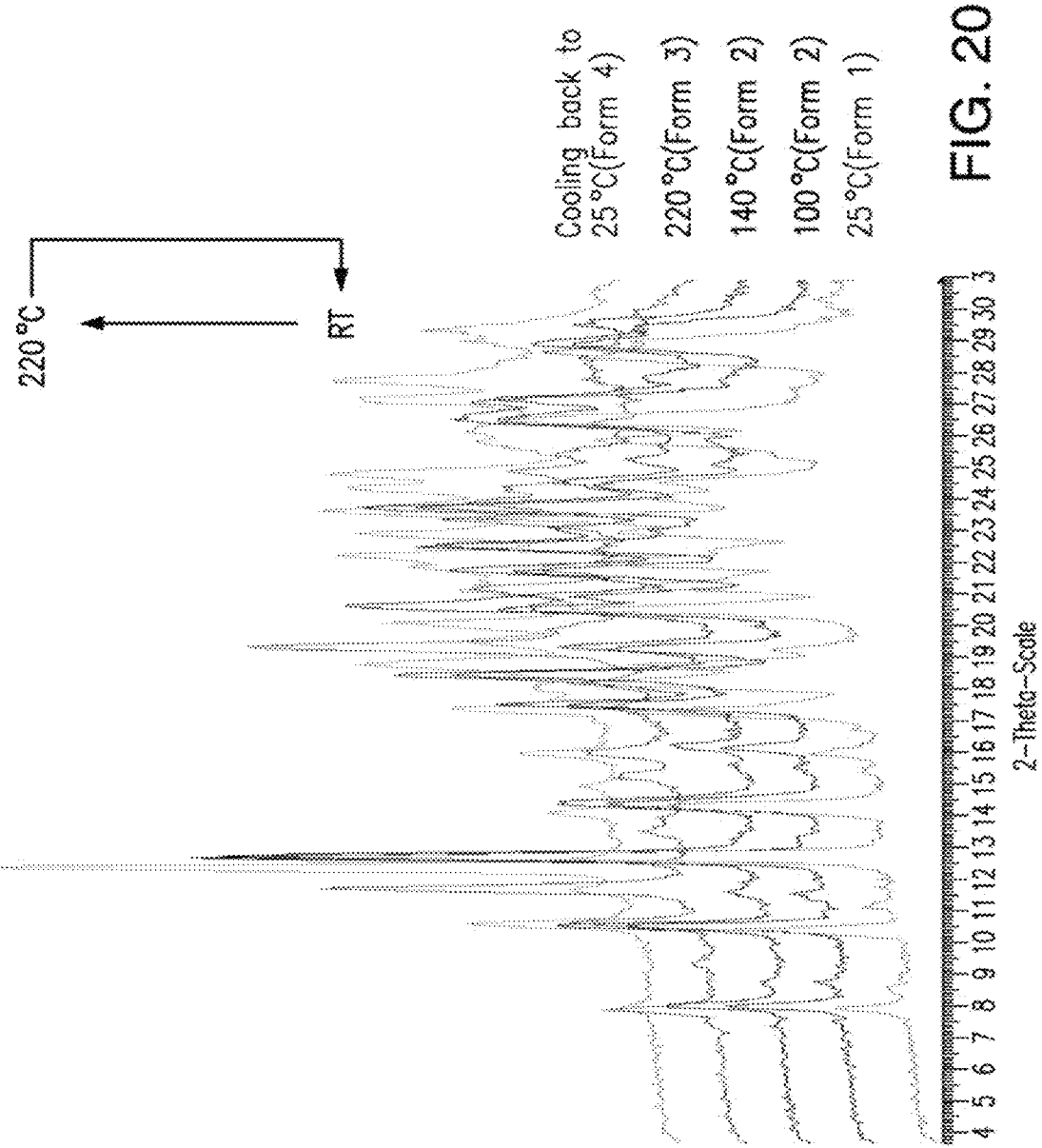

FIG. 20 provides a representative overlay plot of the XRPD patterns of Form 1, Form 2, Form 3, and Form 4 of an 1,2-ethanedisulfonic acid salt of Compound 1.

Figure 21A:
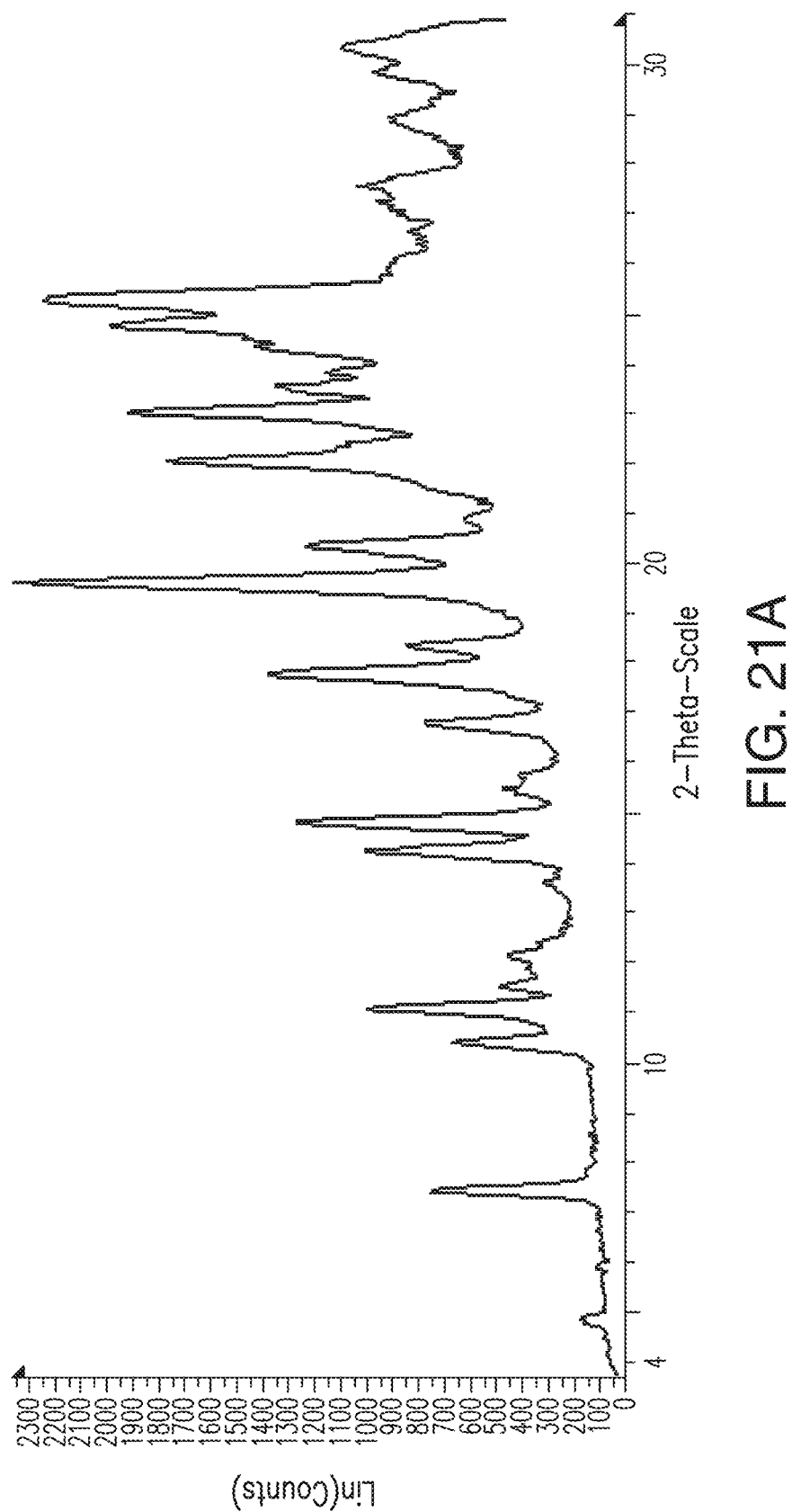

FIG. 21A provides a representative XRPD pattern of a solid form comprising Form 1 of a hydrochloride salt of Compound 1.

Figure 21B:
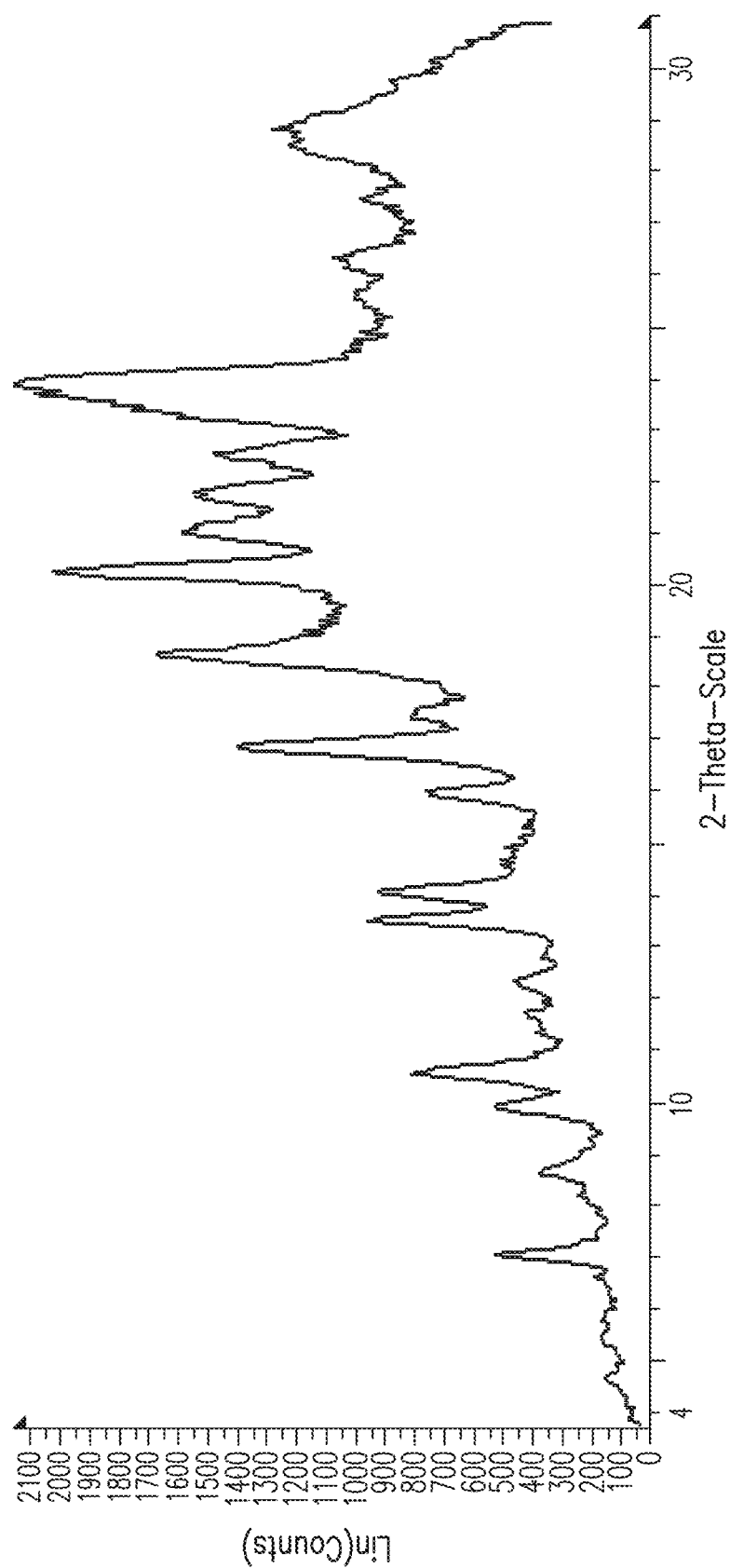

FIG. 21B provides a representative XRPD pattern of a solid form comprising Form 2 of a hydrochloride salt of Compound 1.

Figure 22:
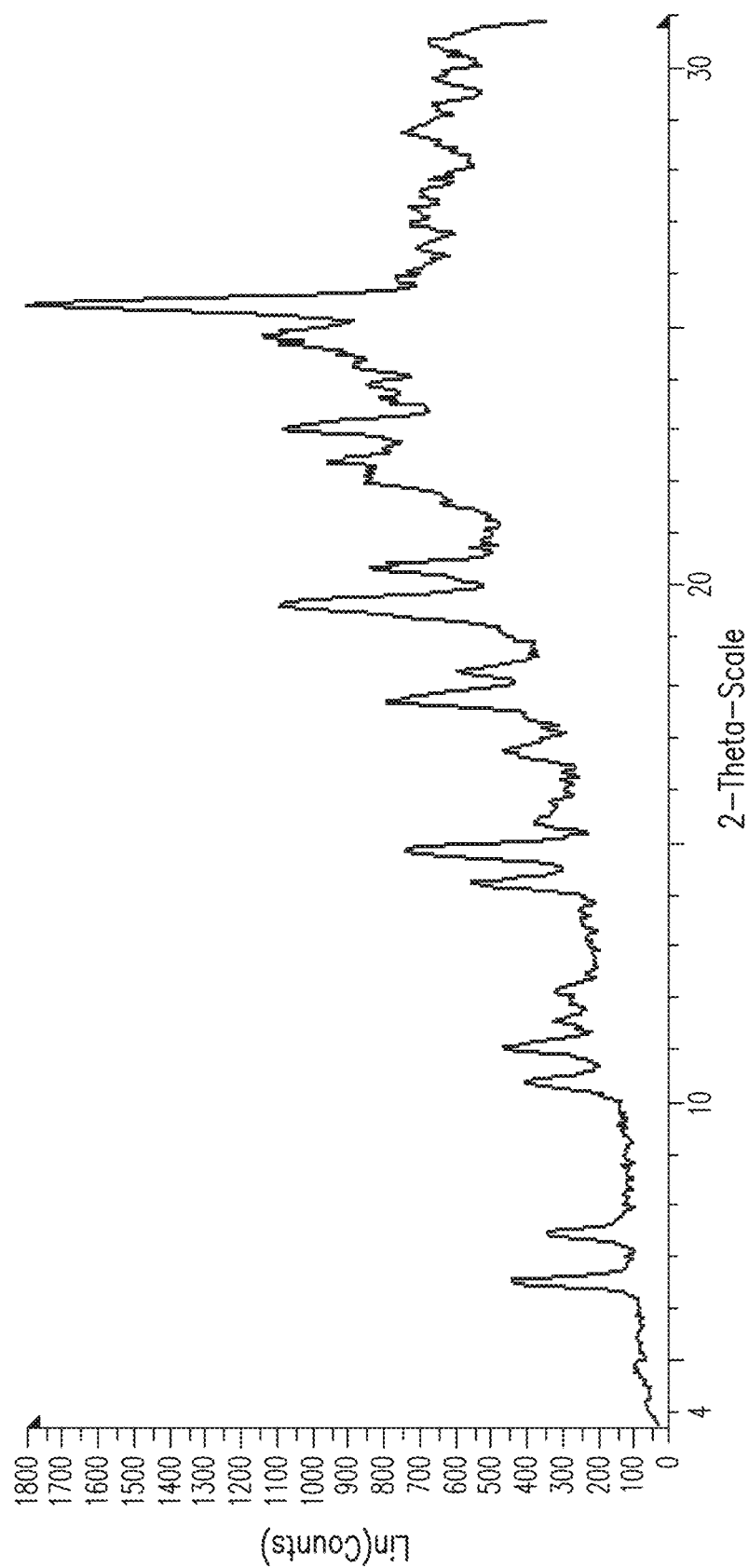

FIG. 22 provides a representative XRPD pattern of a solid form comprising Form 1 of an isethionate salt of Compound 1.

Figure 23:
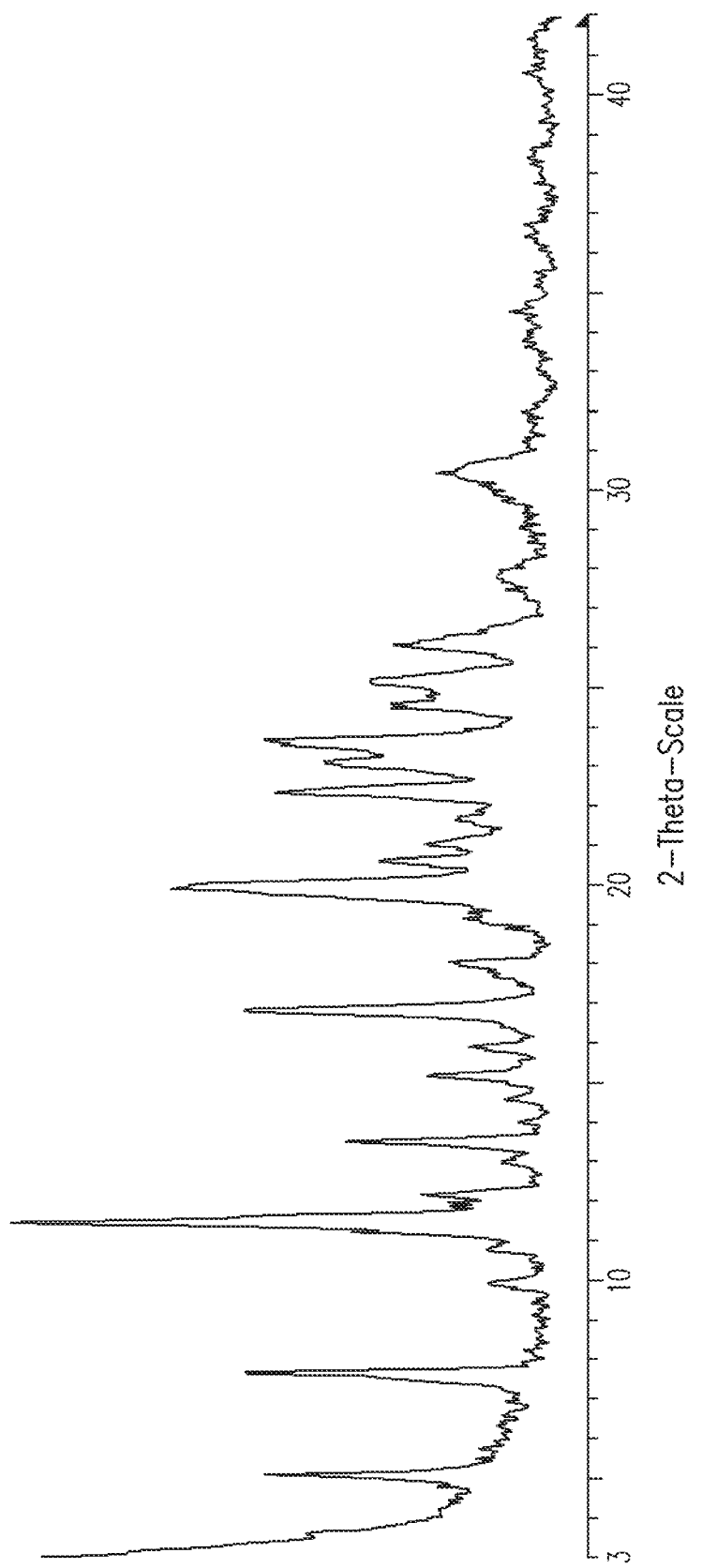

FIG. 23 provides a representative XRPD pattern of a solid form comprising Form 1 of a free base of Compound 1.

Figure 24:
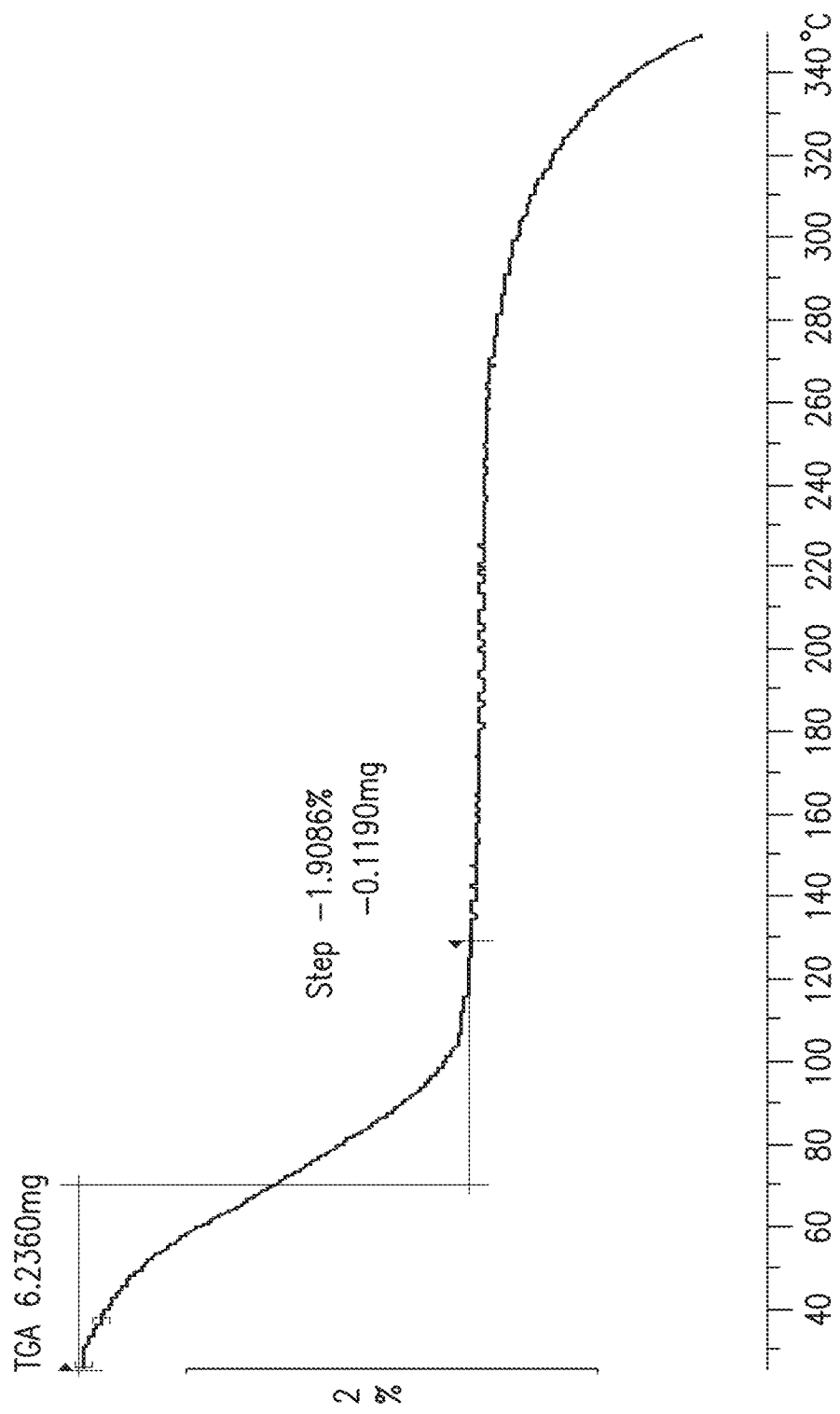

FIG. 24 provides a representative TGA thermogram of a solid form comprising Form 1 of a free base of Compound 1.

Figure 25:
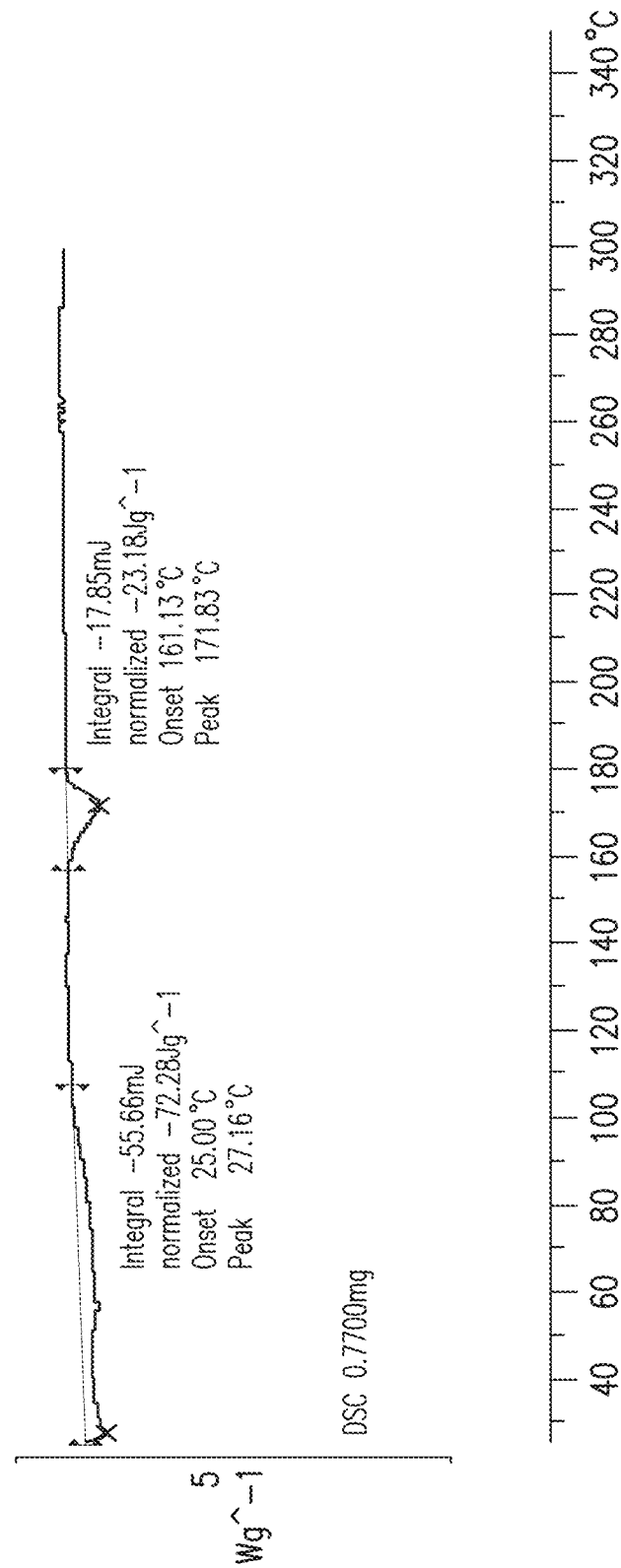

FIG. 25 provides a representative DSC thermogram of a solid form comprising Form 1 of a free base of Compound 1.

Figure 26:
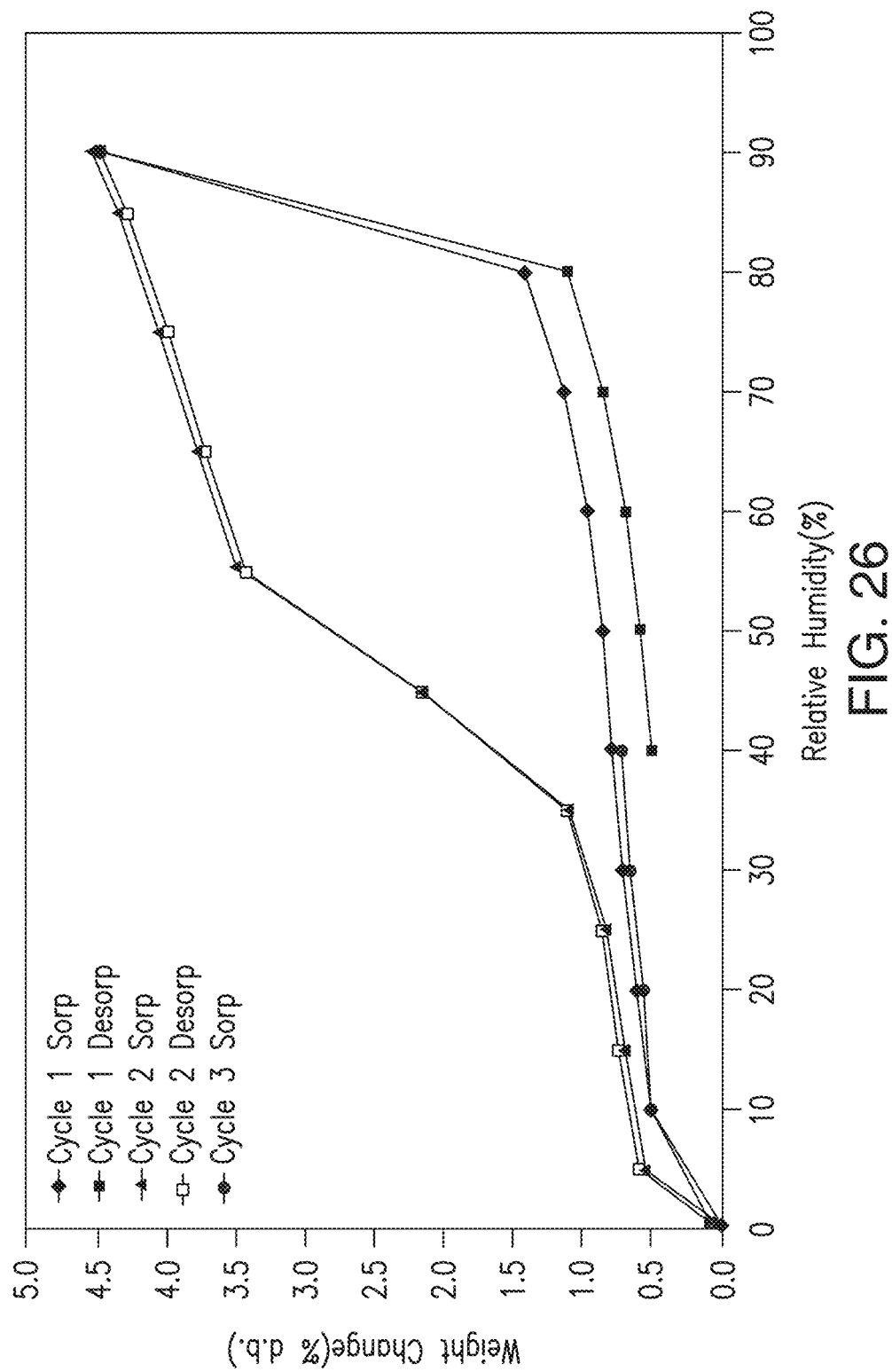

FIG. 26 provides a representative GVS plot of a solid form comprising Form 1 of a free base of Compound 1.

Figure 27:
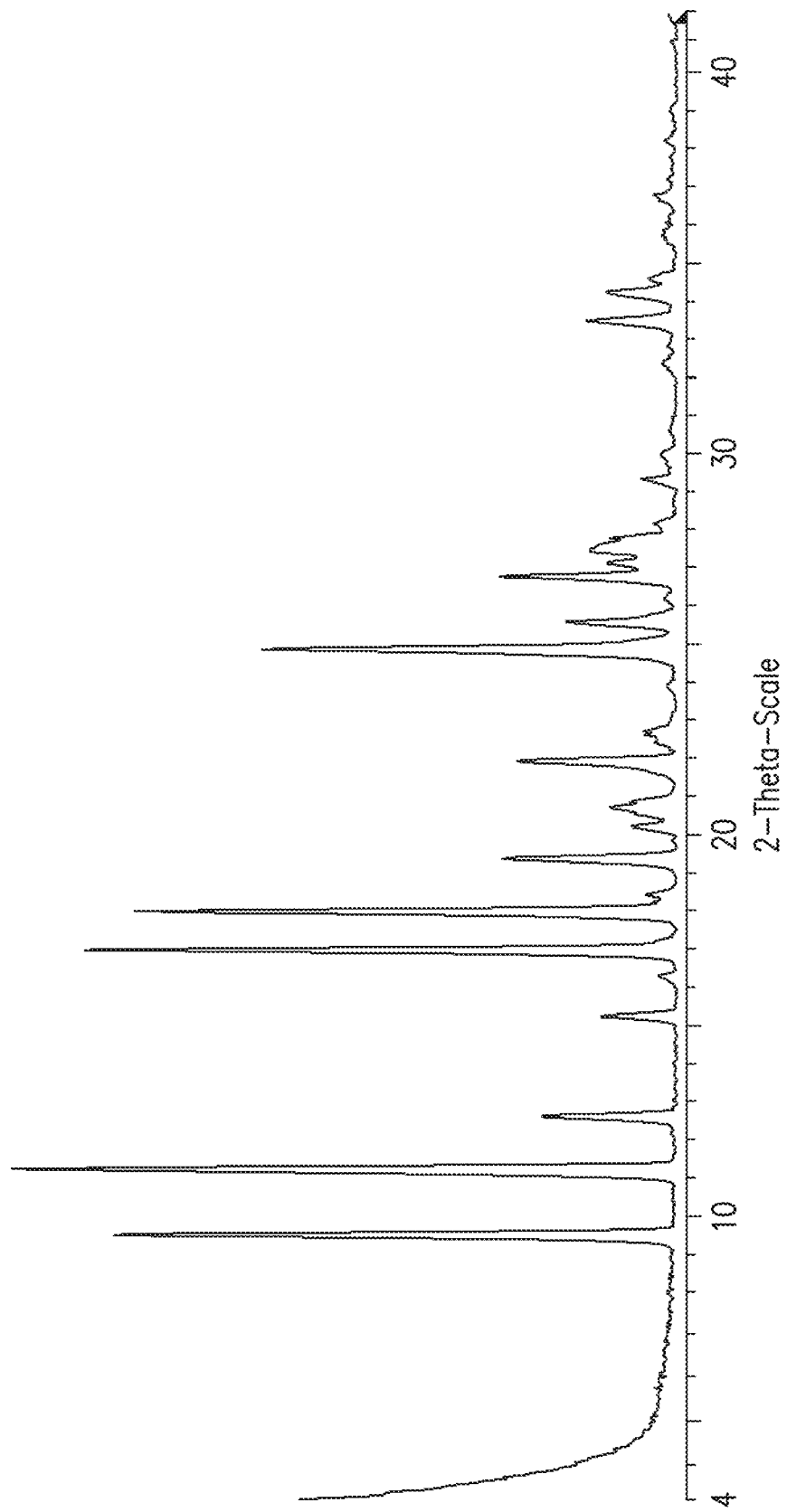

FIG. 27 provides a representative XRPD pattern of a solid form comprising Form 2 of a free base of Compound 1.

Figure 28:
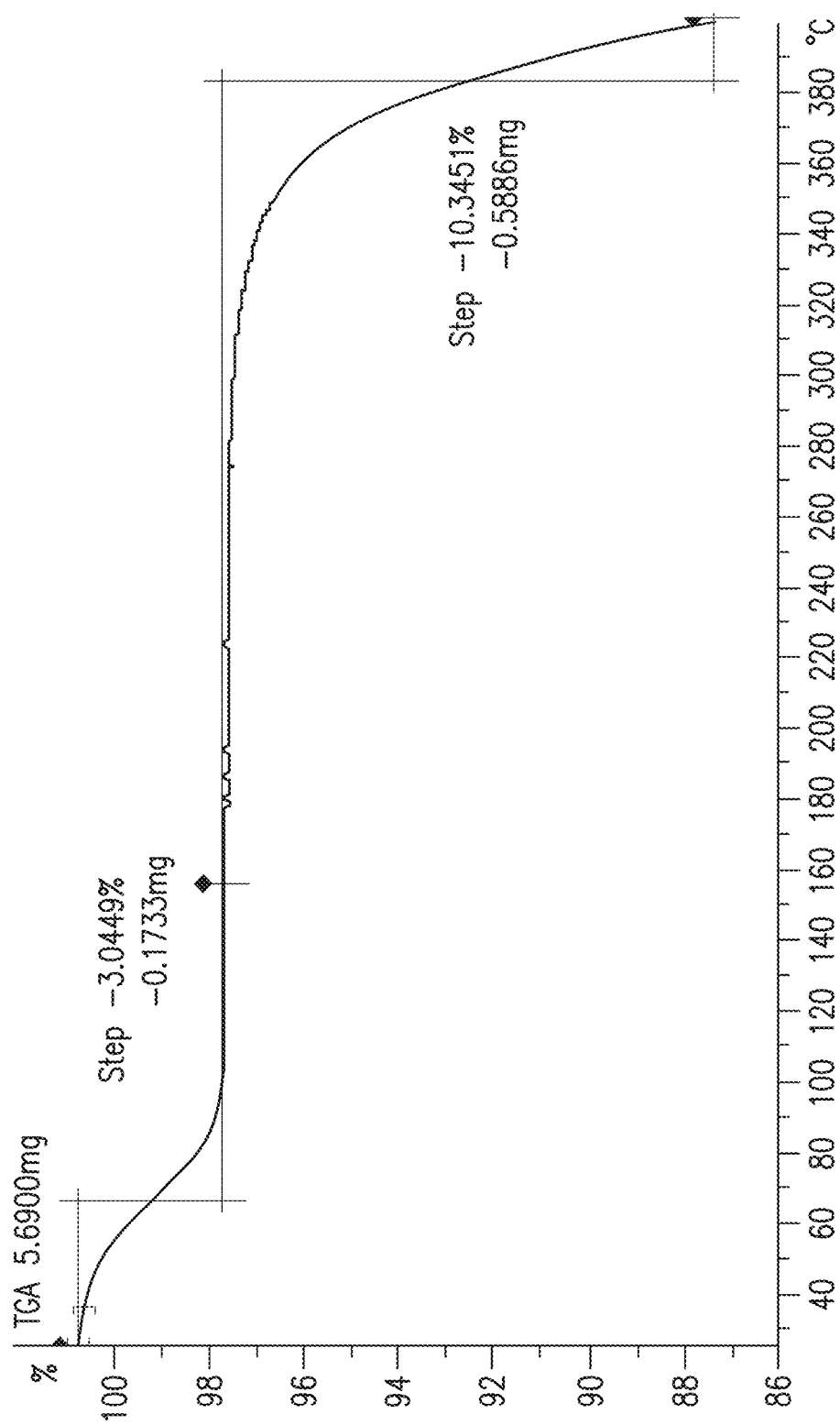

FIG. 28 provides a representative TGA thermogram of a solid form comprising Form 2 of a free base of Compound 1.

Figure 29:
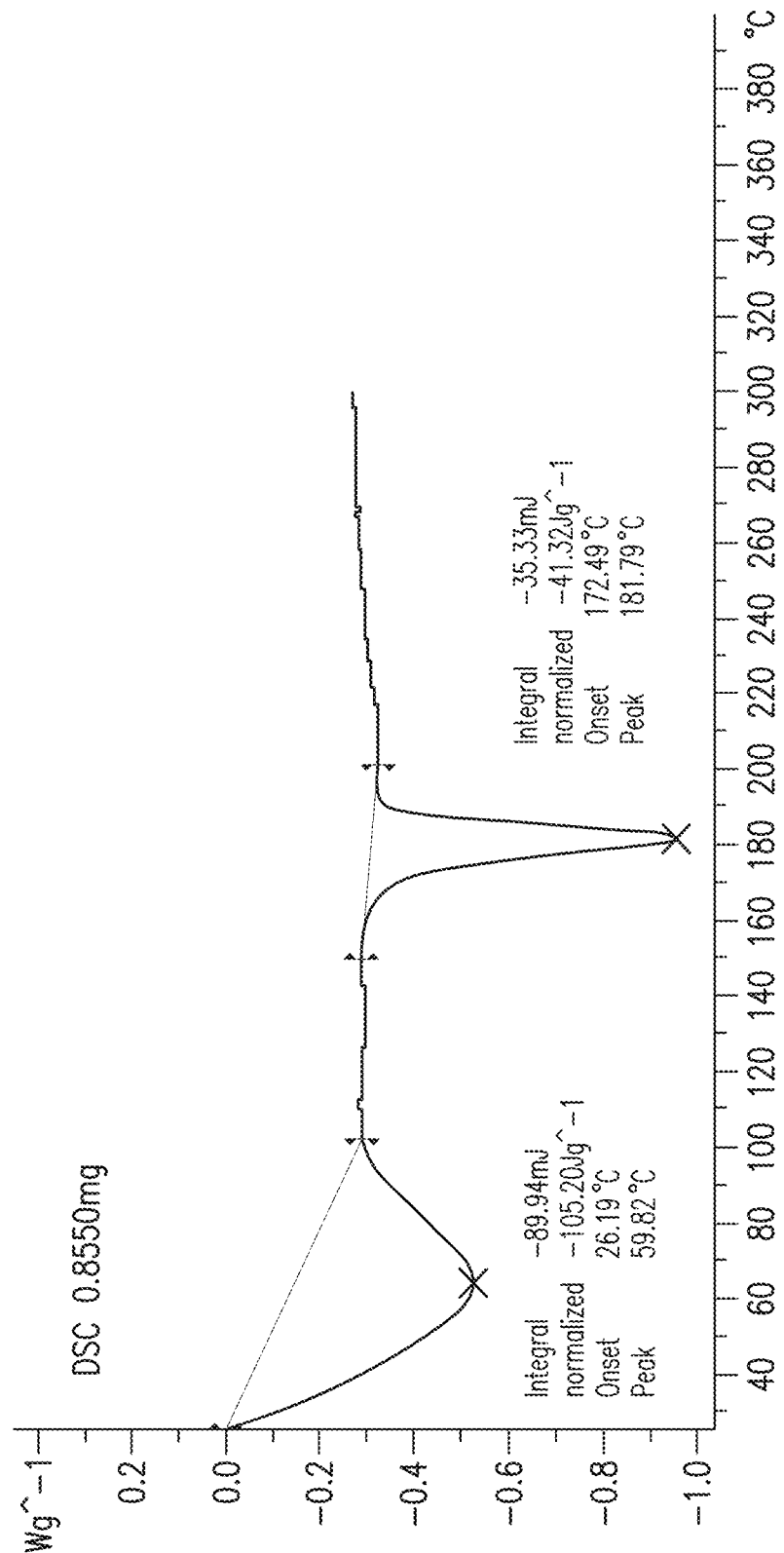

FIG. 29 provides a representative DSC thermogram of a solid form comprising Form 2 of a free base of Compound 1.

Figure 30:
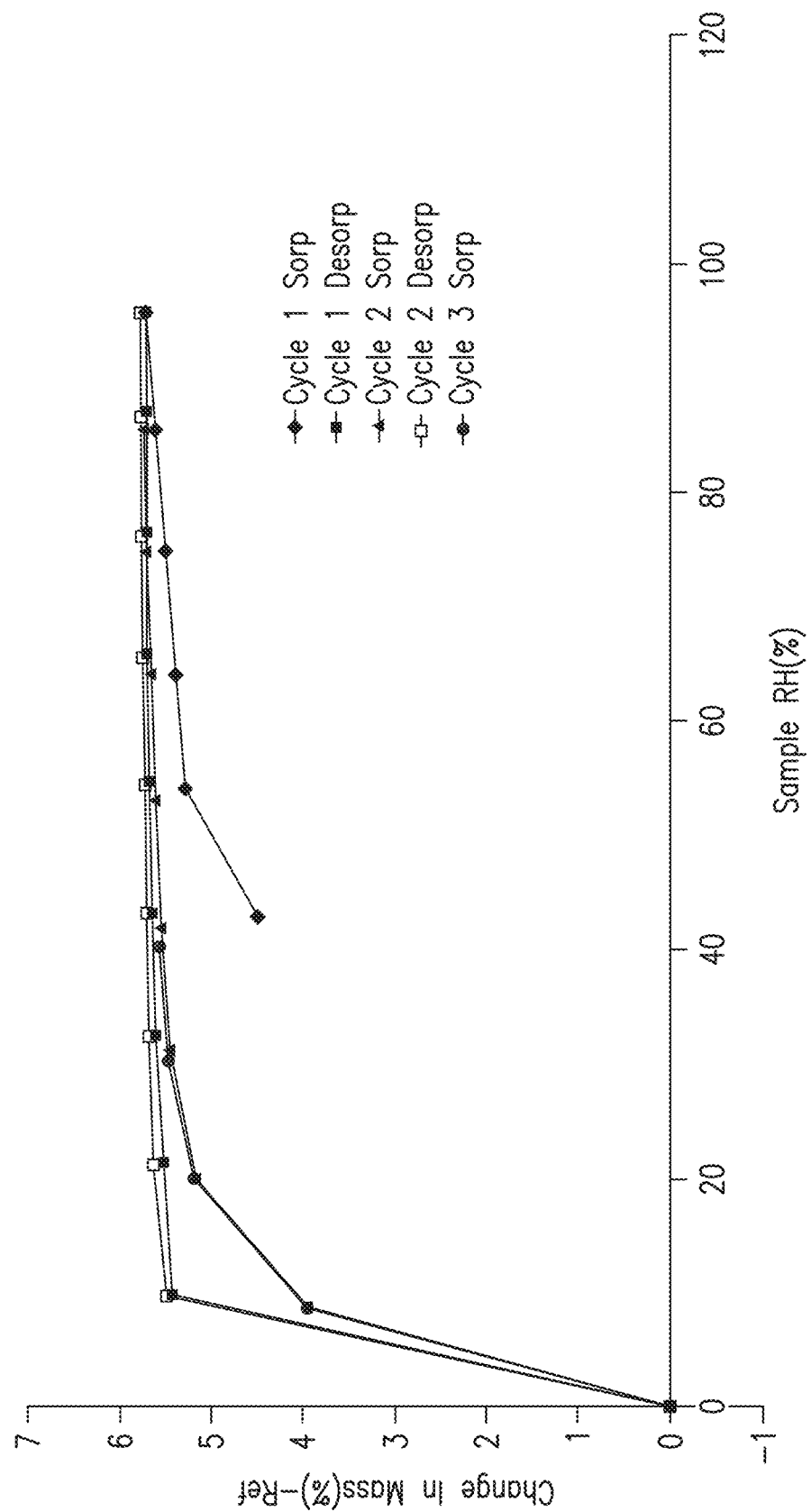

FIG. 30 provides a representative GVS plot of a solid form comprising Form 2 of a free base of Compound 1.

Figure 31:
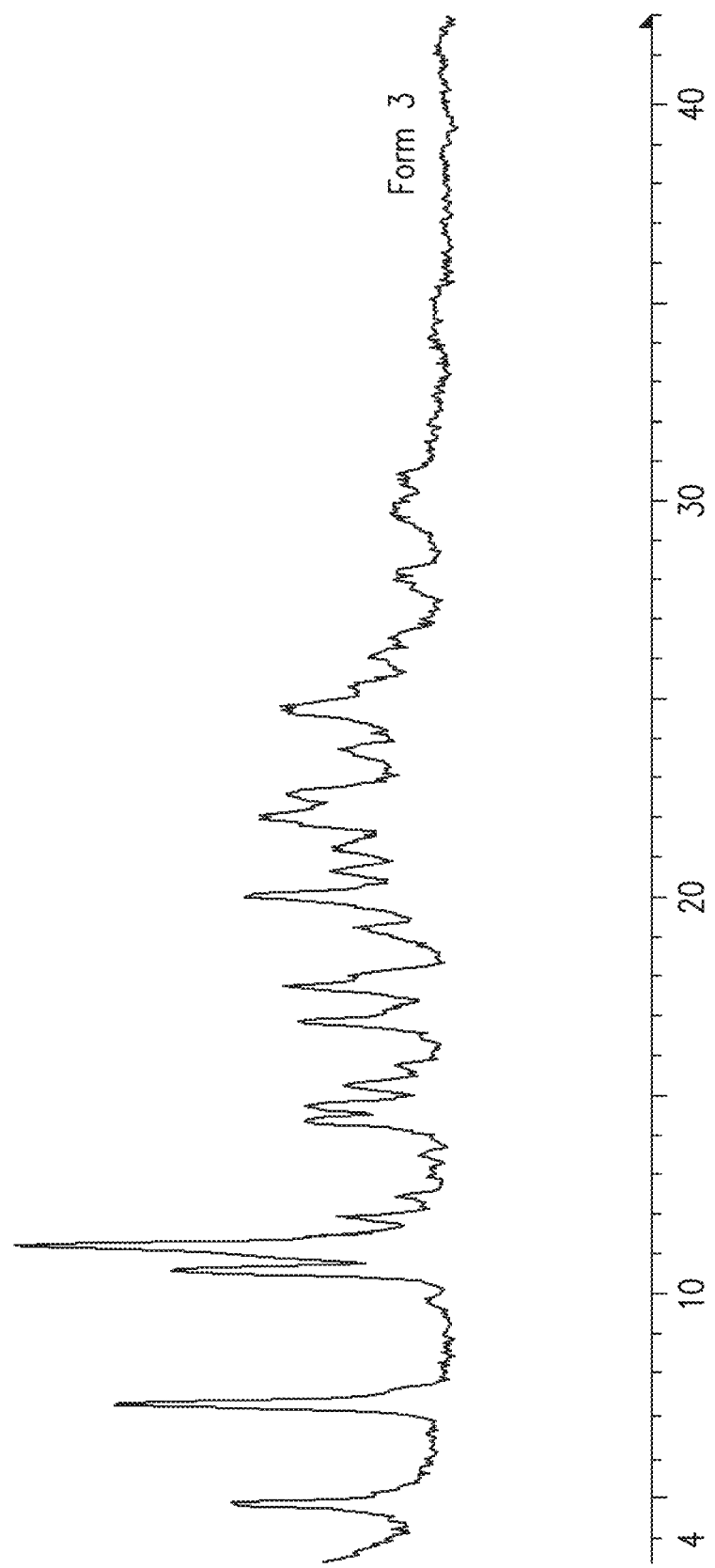

FIG. 31 provides a representative XRPD pattern of a solid form comprising Form 3 of a free base of Compound 1.

Figure 32:
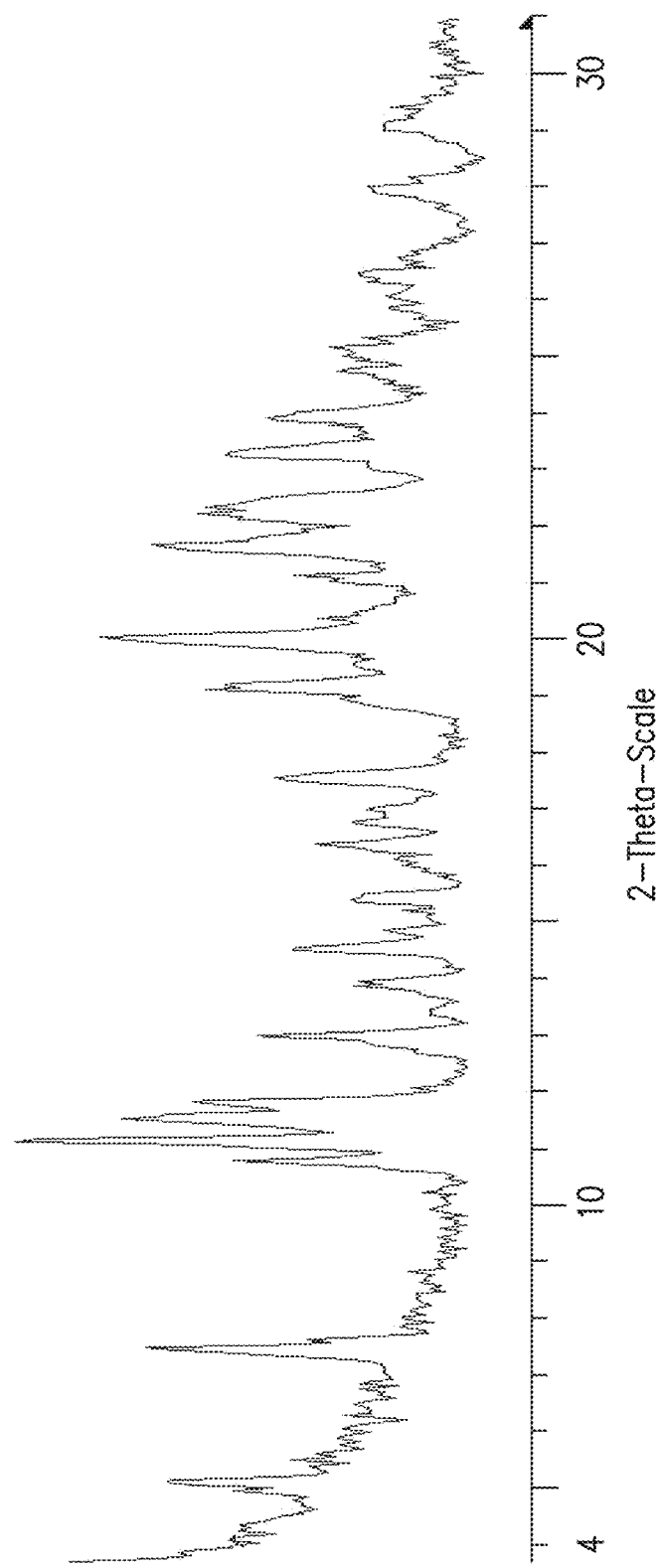

FIG. 32 provides a representative XRPD pattern of a solid form comprising Form 4 of a free base of Compound 1.

Figure 33:
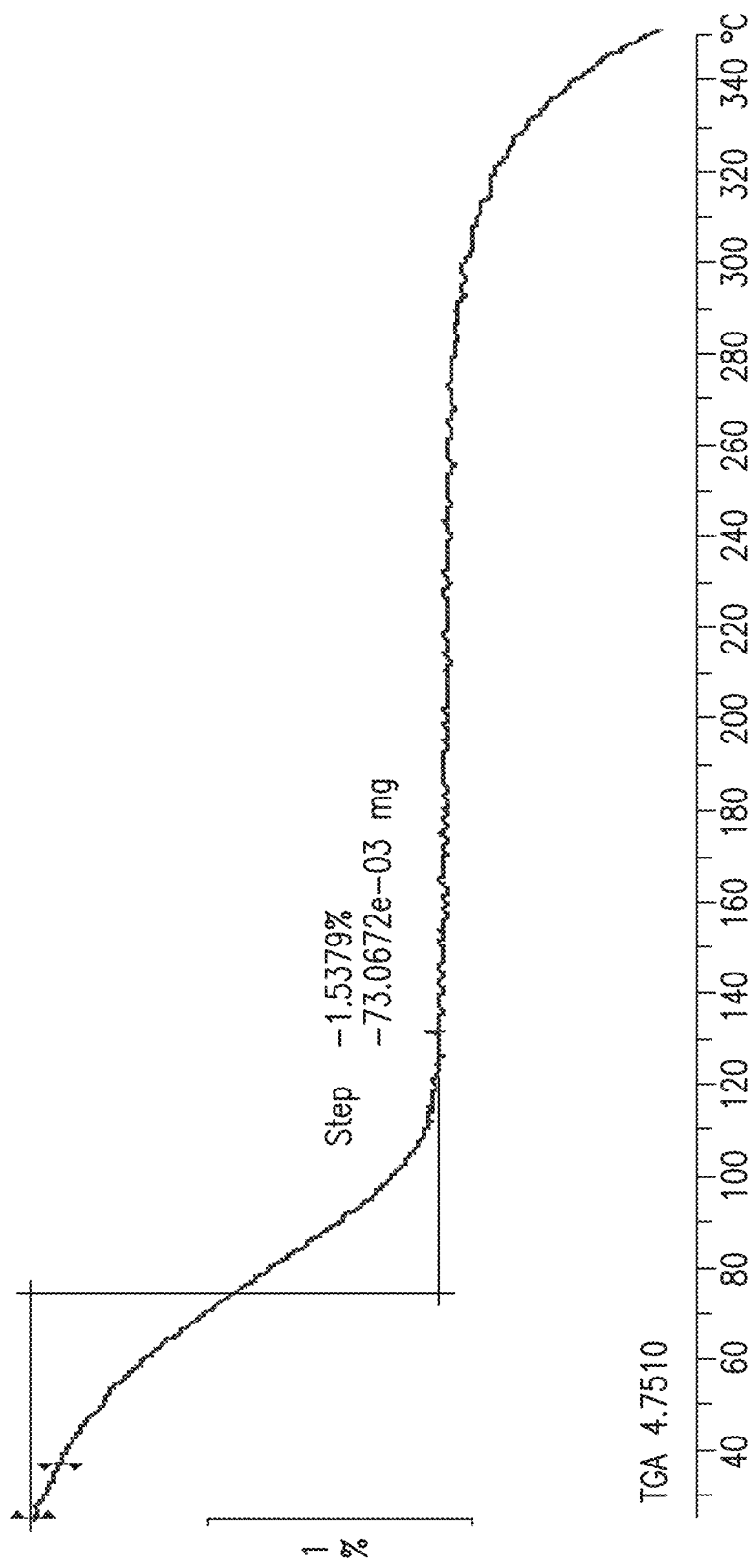

FIG. 33 provides a representative TGA thermogram of a solid form comprising Form 4 of a free base of Compound 1.

Figure 34:
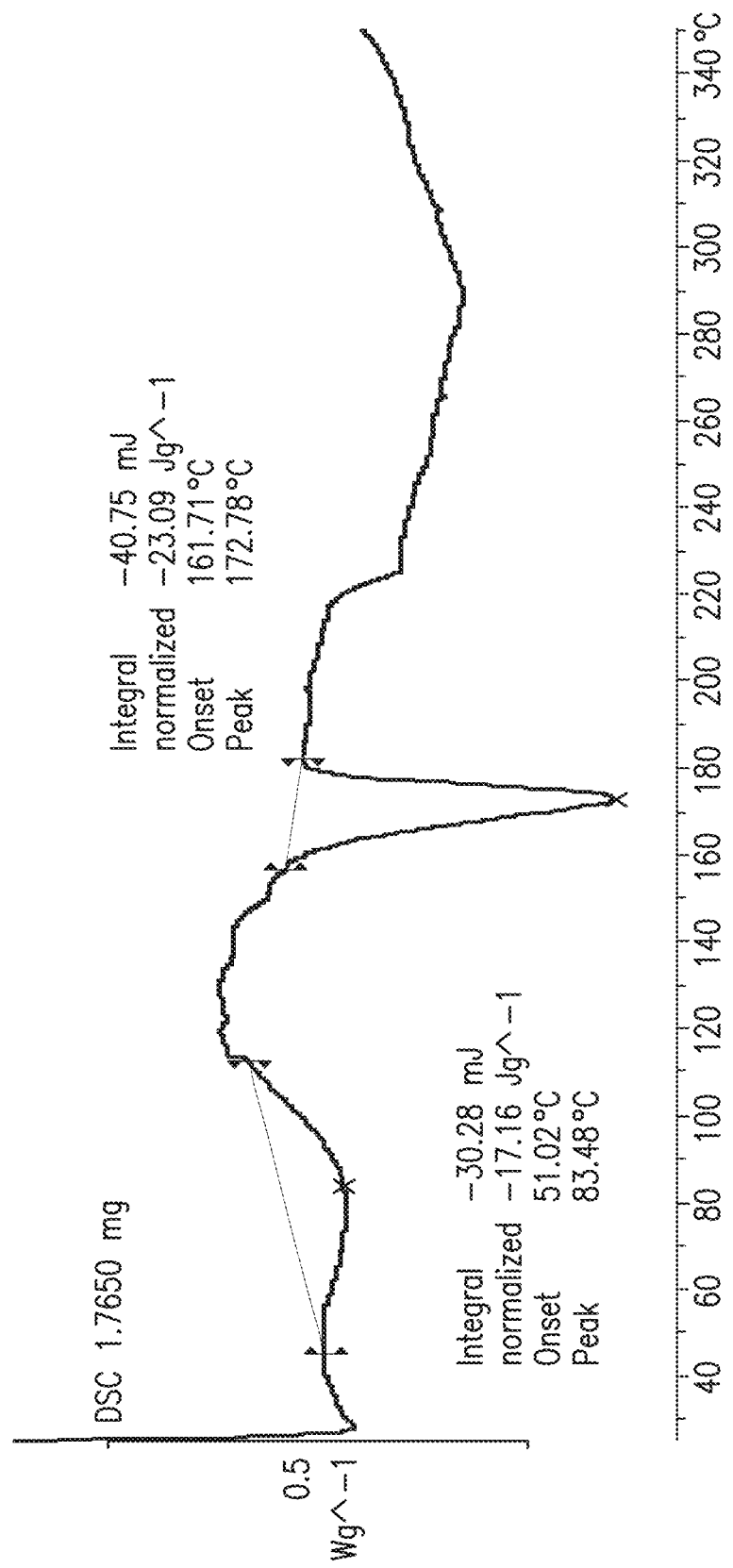

FIG. 34 provides a representative DSC thermogram of a solid form comprising Form 4 of a free base of Compound 1.

Figure 35:
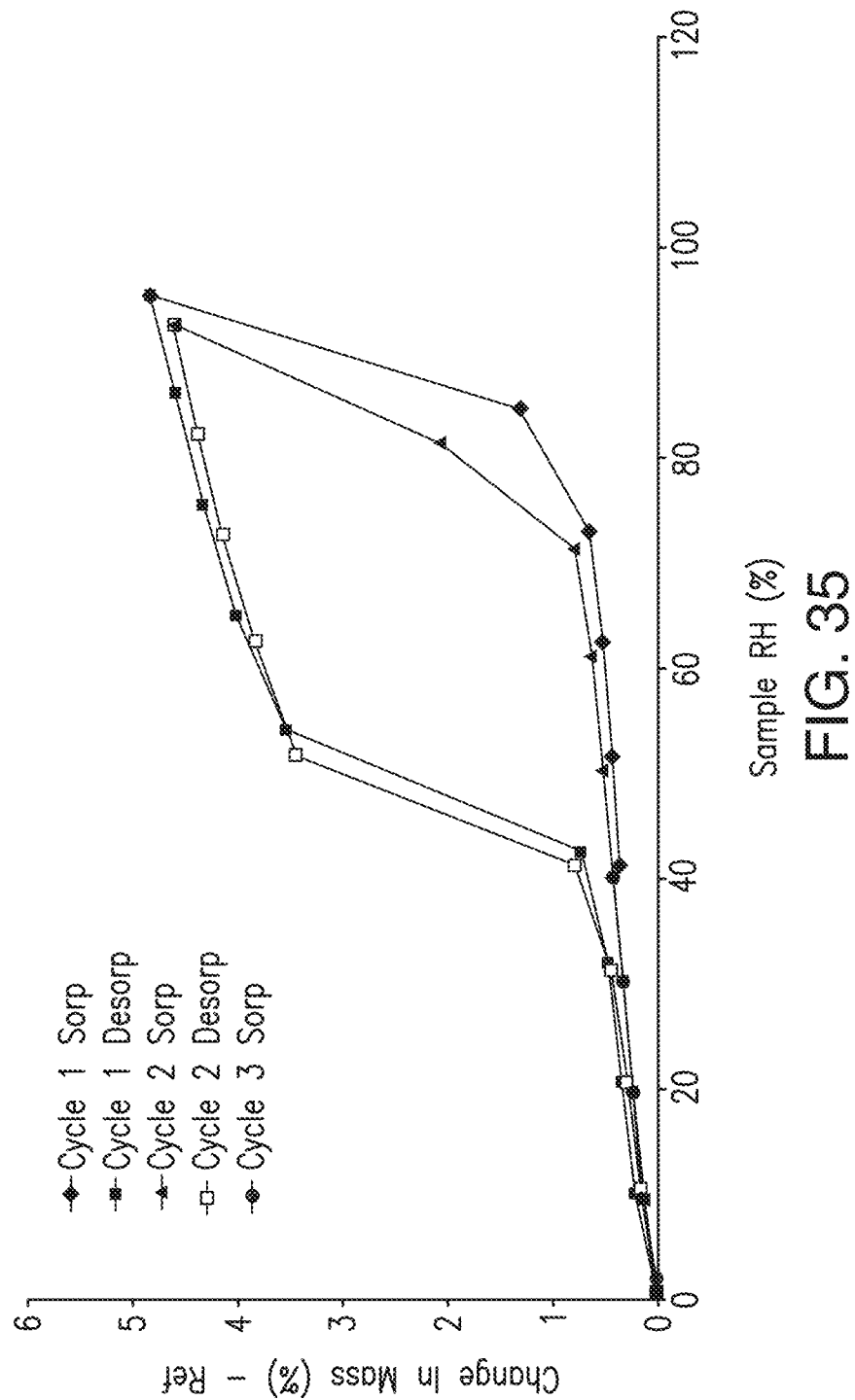

FIG. 35 provides a representative GVS plot of a solid form comprising Form 4 of a free base of Compound 1.

Figure 36:
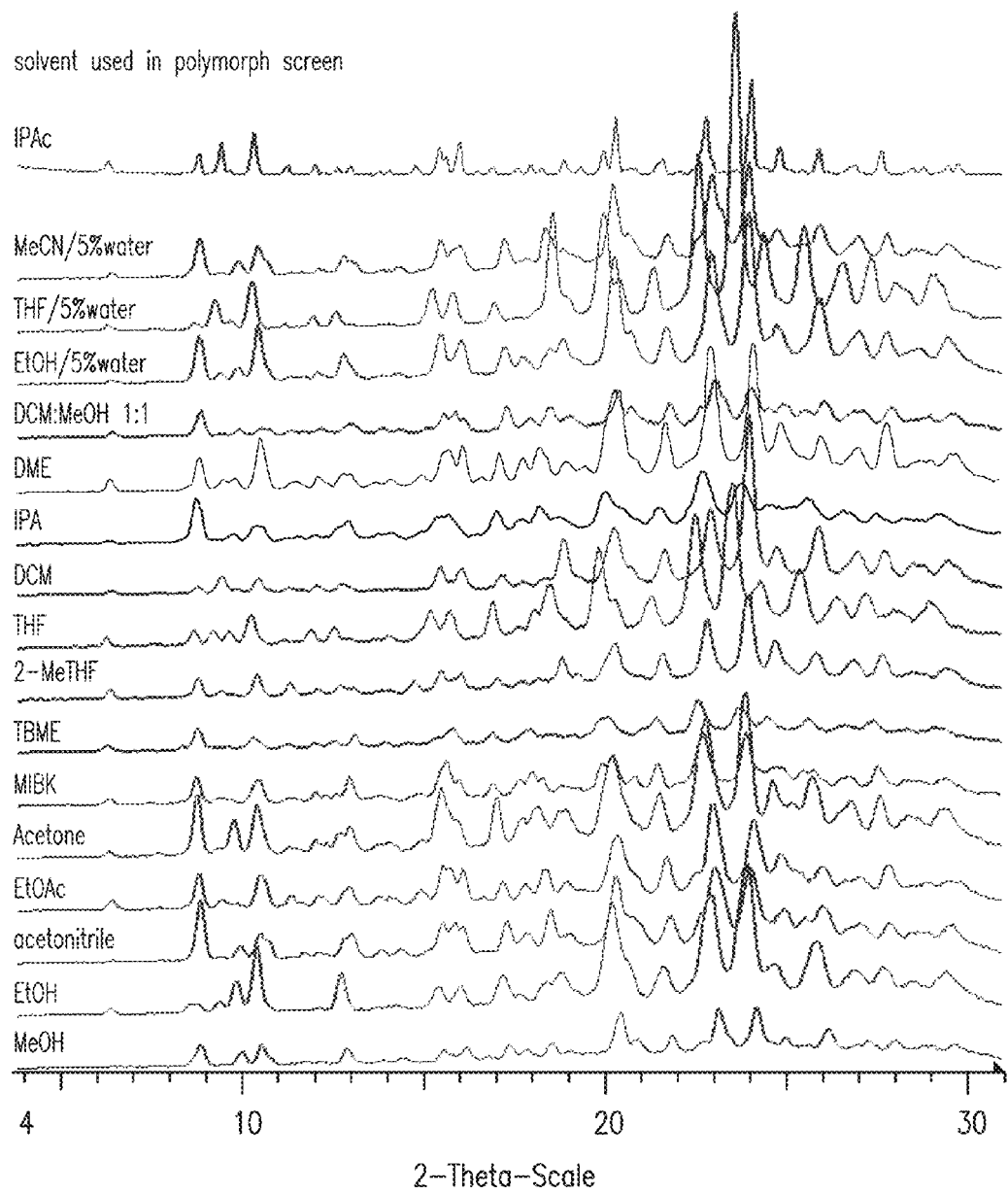
Figure 37:
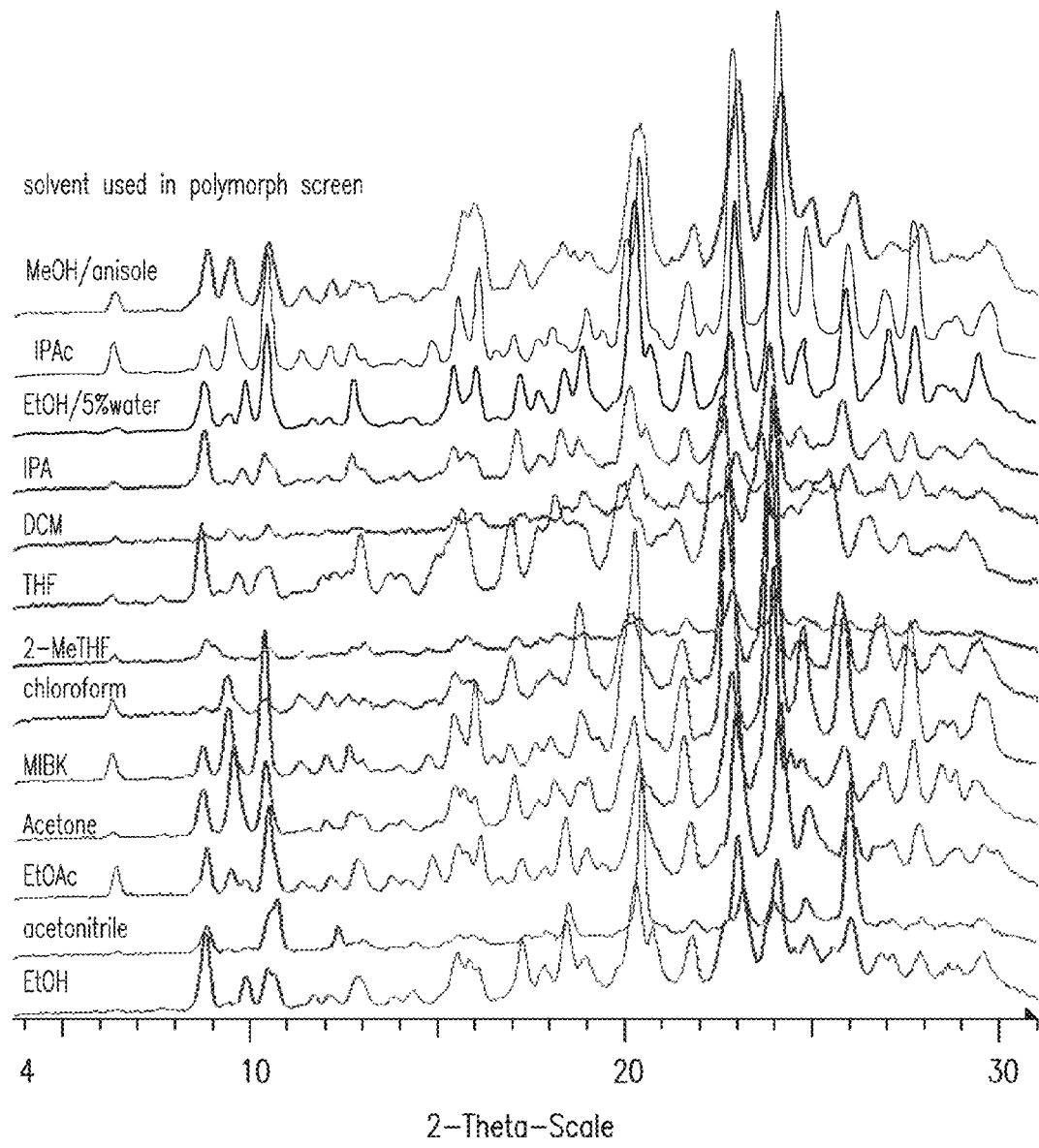

FIG. 36 and FIG. 37 provide representative overlay plots of the XRPD patterns of Form 5 of a free base of Compound 1.

Figure 38:
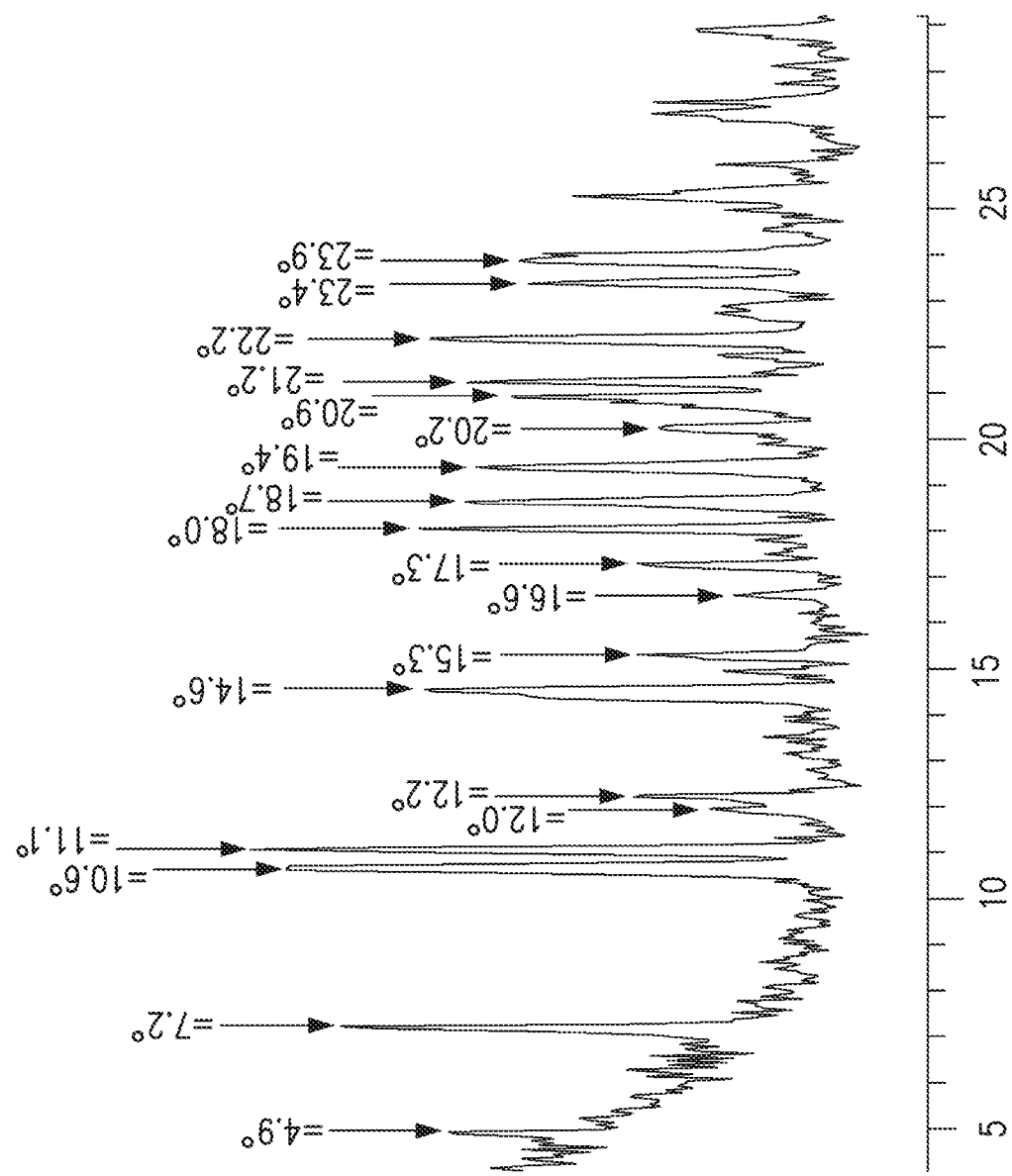

FIG. 38 provides a representative XRPD pattern of a solid form comprising Form 6 of a free base of Compound 1.

Figure 39:
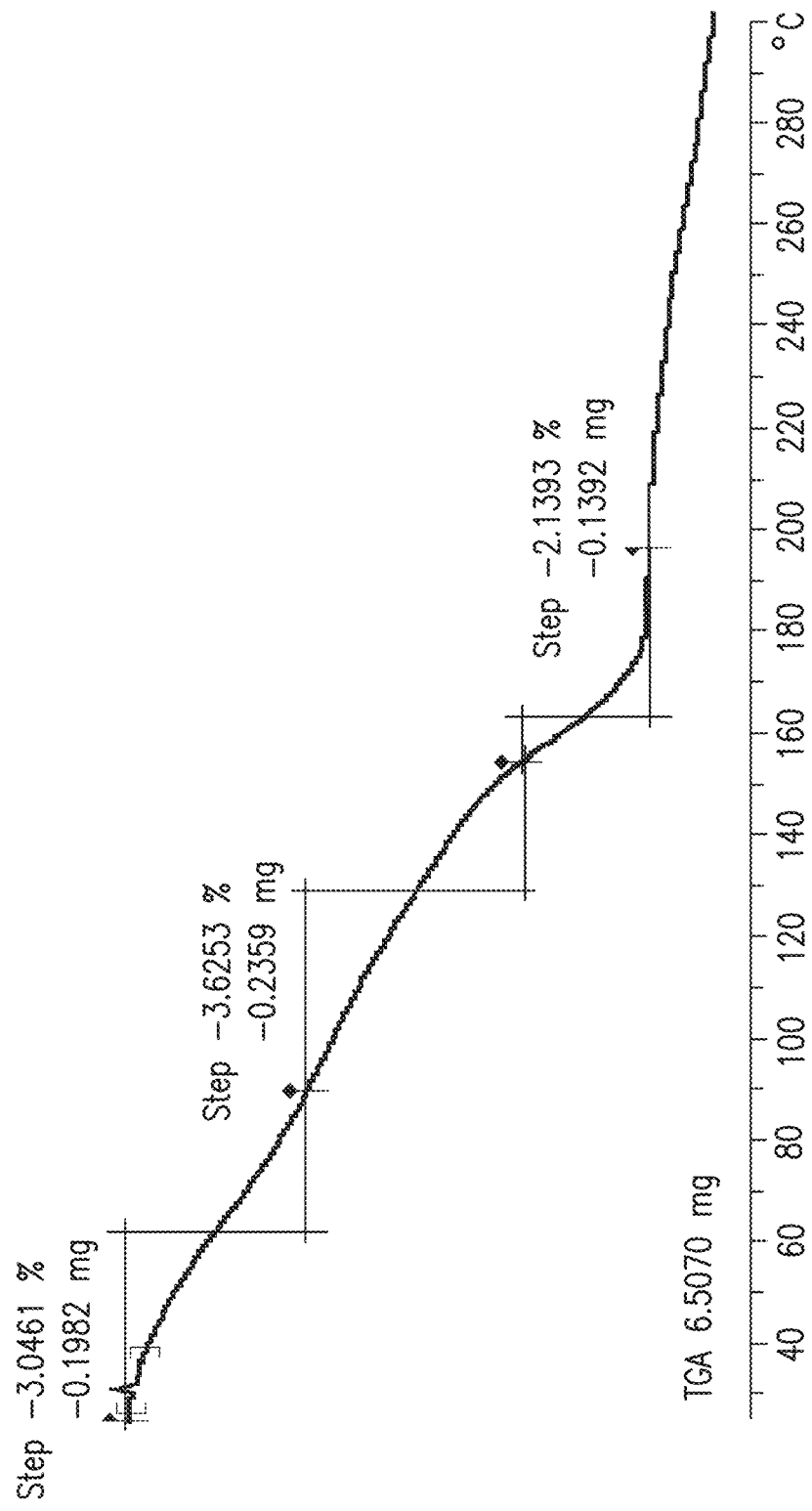

FIG. 39 provides a representative TGA thermogram of a solid form comprising Form 6 of a free base of Compound 1.

Figure 40:
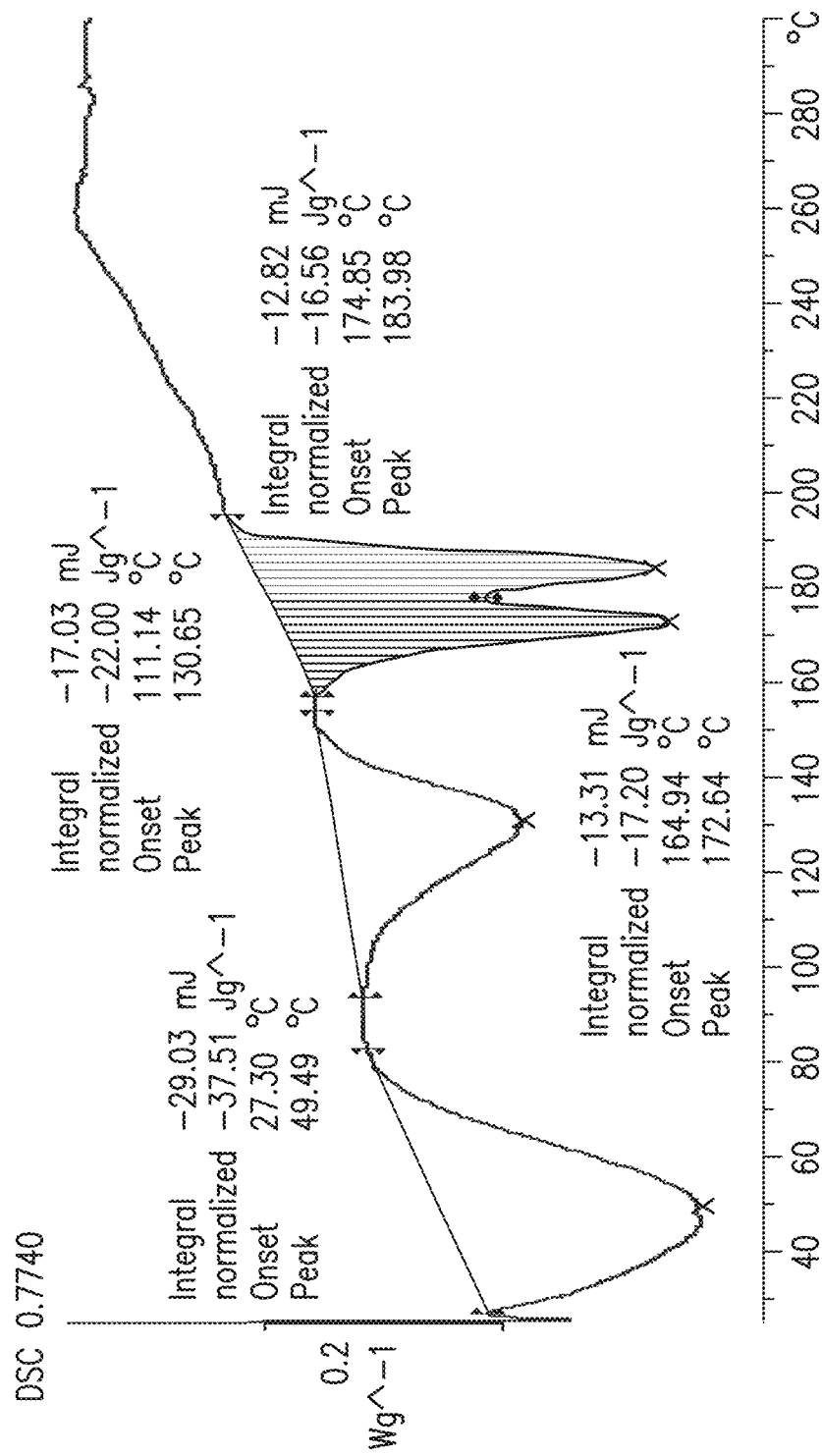

FIG. 40 provides a representative DSC thermogram of a solid form comprising Form 6 of a free base of Compound 1.

Figure 41:
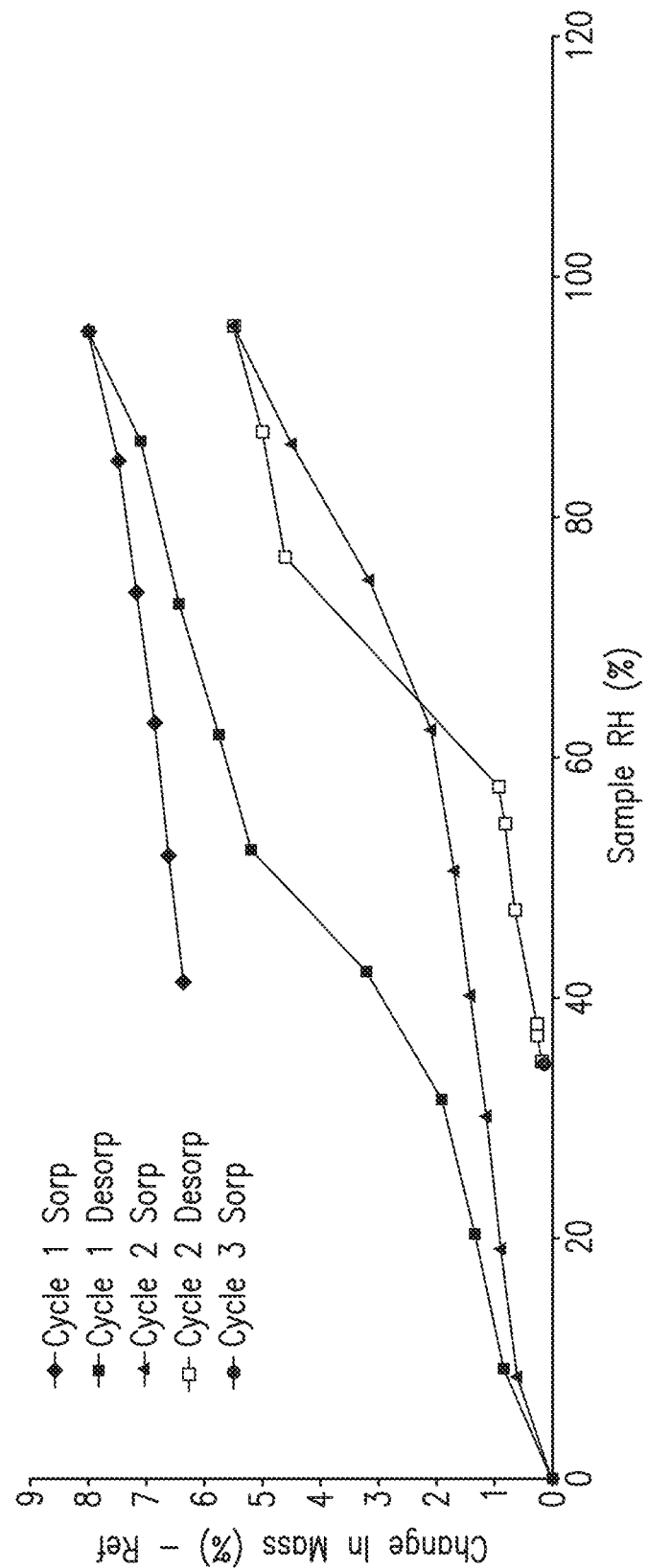

FIG. 41 provides a representative GVS plot of a solid form comprising Form 6 of a free base of Compound 1.

Figure 42:
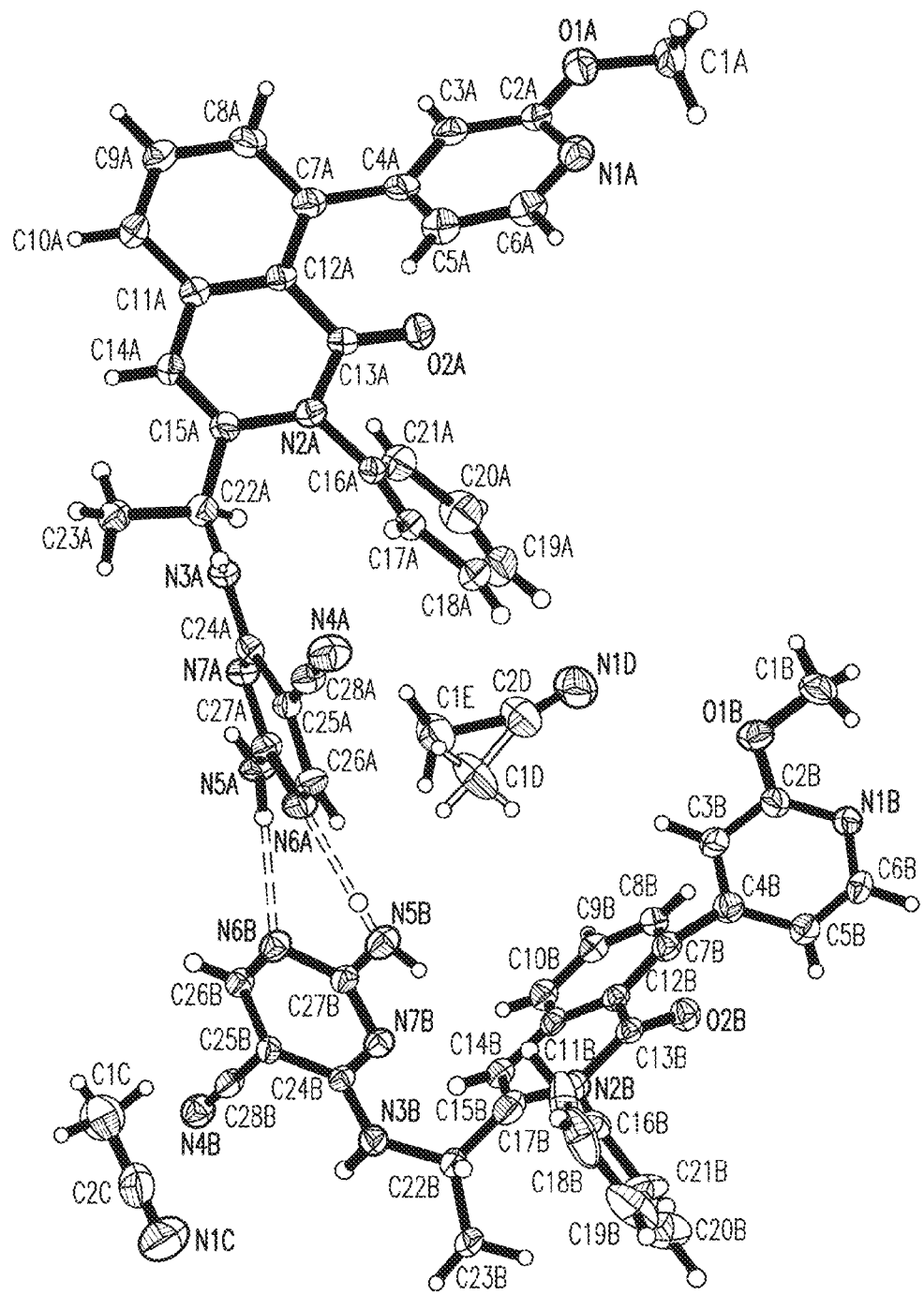

FIG. 42 provides a view of a molecule of Compound 1 in a single crystal of an acetonitrile solvate (Form 5) of Compound 1.

Figure 43:
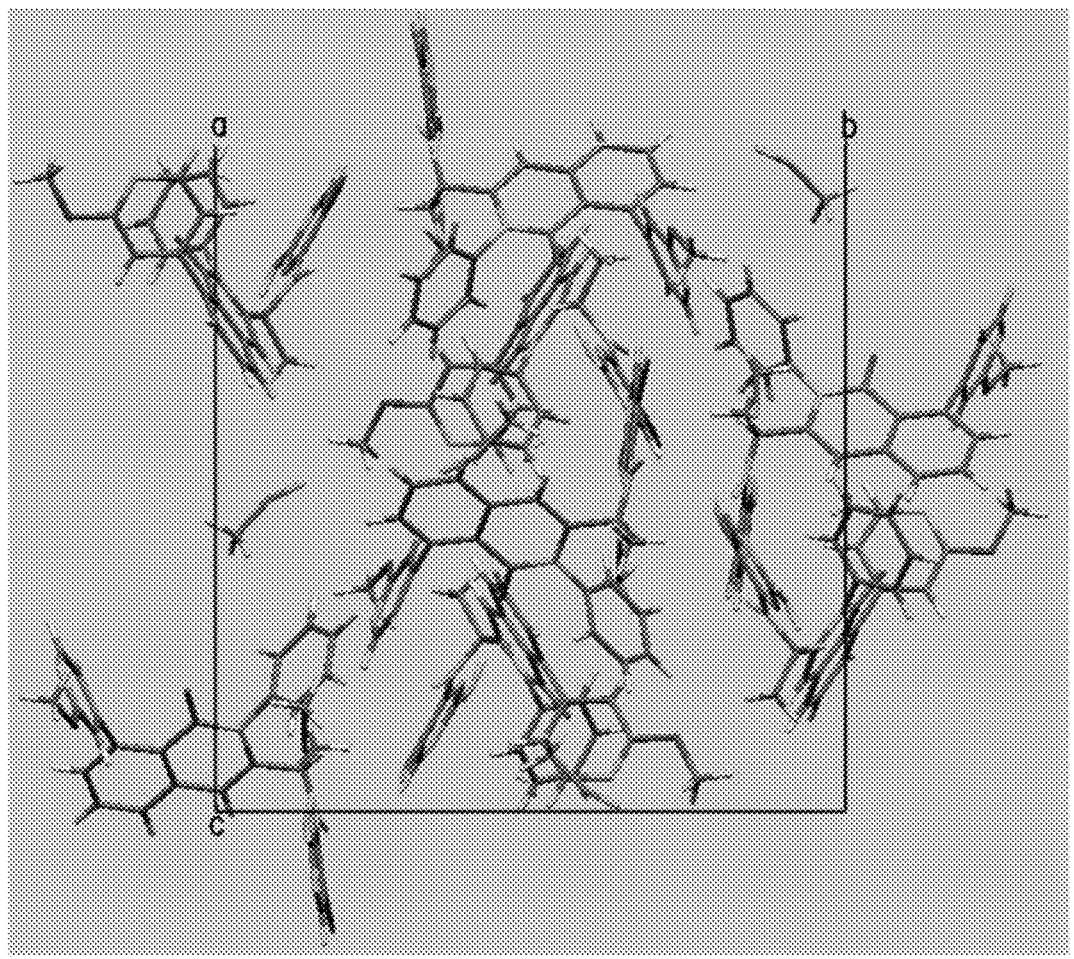

FIG. 43 provides a view of part of the crystal packing of the acetonitrile solvate (Form 5).

Figure 44:
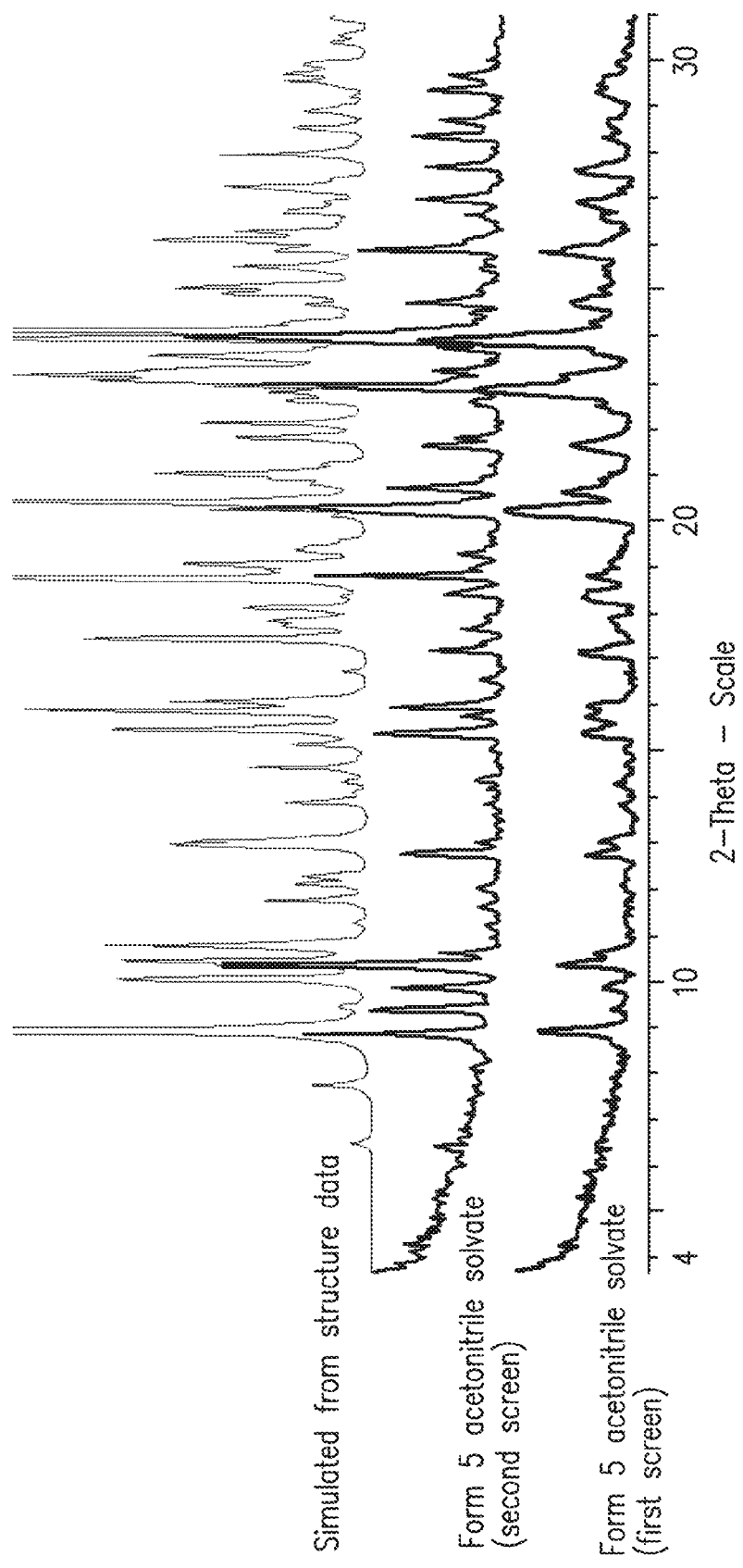

FIG. 44 provides an overlay of the experimental and calculated XRPD patterns of an acetonitrile solvate (Form 5) of Compound 1.

Figure 45A:
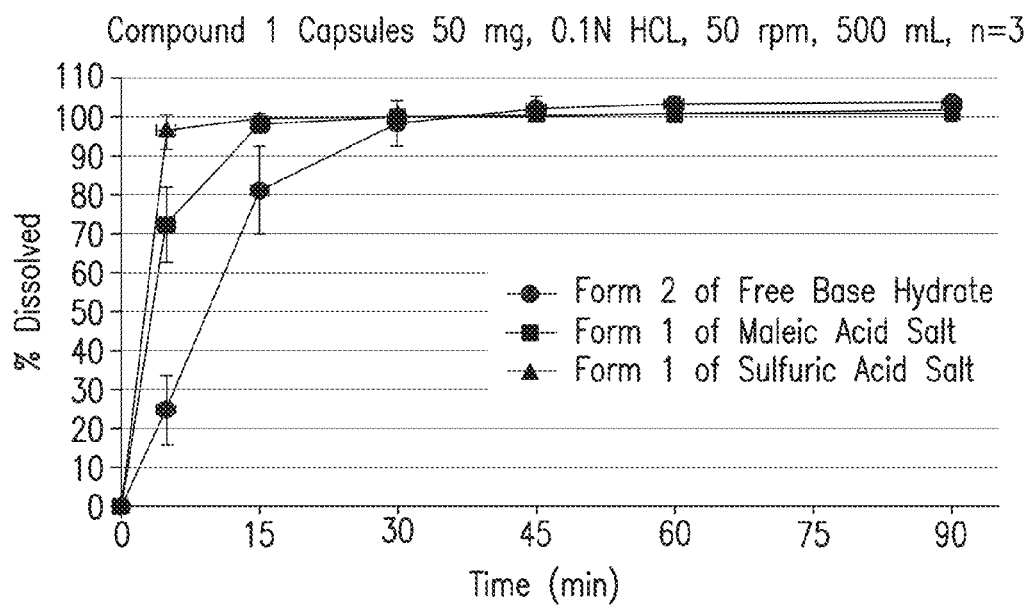
Figure 45B:
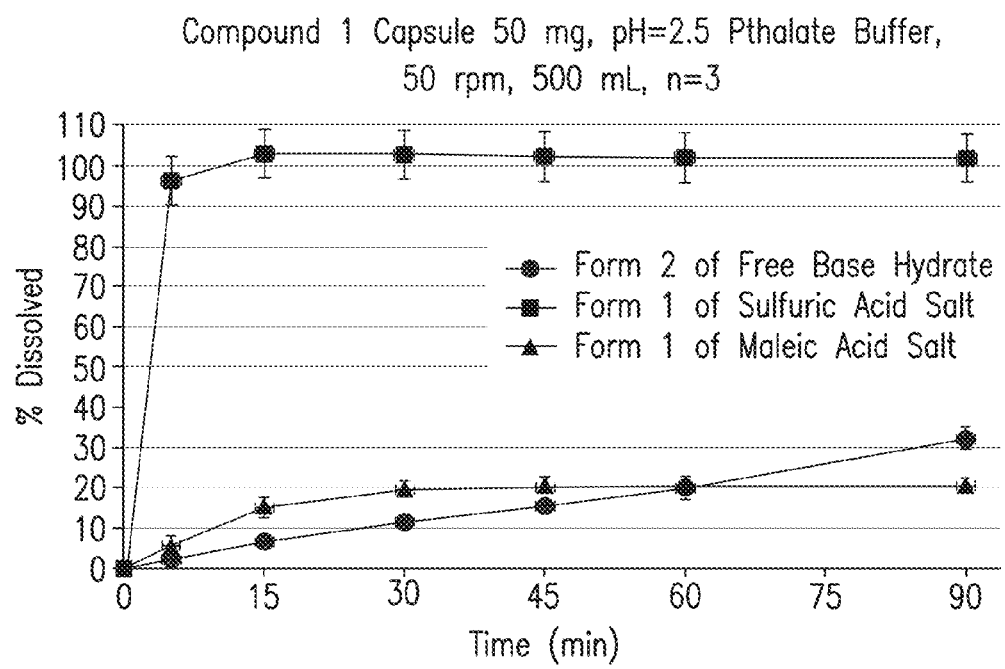

FIG. 45A and FIG. 45B provide representative comparison of dissolution rates of free base hydrate, Form 1 of bis-sulfuric acid monohydrate salt, and Form 1 of mono-maleic acid salt of Compound 1

Figure 46:
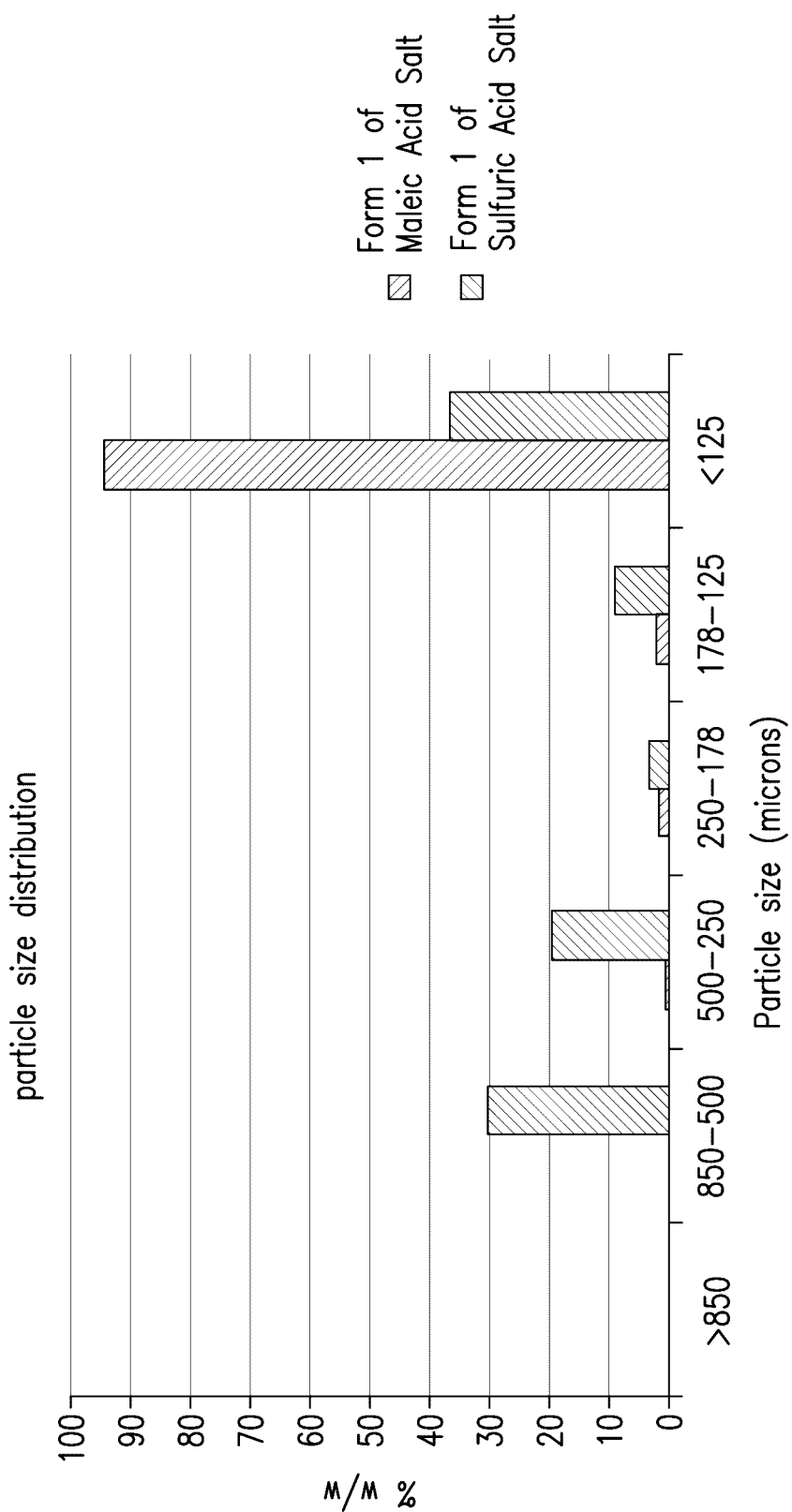

FIG. 46 provides representative comparison of particle size distribution of Form 1 of bis-sulfuric acid monohydrate salt, and Form 1 of mono-maleic acid salt of Compound 1

5. DETAILED DESCRIPTION

5.1 Definitions

Unless defined otherwise, all technical and scientific terms used herein have the same meaning as is commonly understood by one of skill in the art.

As used in the specification and claims, the singular form "a", "an" and "the" includes plural references unless the context clearly dictates otherwise.

When ranges are used herein for physical properties, such as molecular weight, or chemical properties, such as chemical formulae, all combinations and subcombinations of ranges and specific embodiments therein are intended to be included. As used herein, the terms "about" and "approximately" when used in combination with a numeric value or range of values mean that the value or range of values may deviate to an extent deemed reasonable to one of ordinary skill in the art, e.g., within experimental variability (or within statistical experimental error), and thus the numeric value or range of values can vary from, for example, between 1% and 15%, between 1% and 10%, between 1% and 5%, between 0.5% and 5%, and between 0.5% and 1%, of the stated numeric value or range of values. As disclosed herein, every instance where a numeric value or range of values preceded by the term "about" also includes the embodiment of the given value(s). For example, "about 3° C." discloses the embodiment of the temperature being "3° C.". The terms "about" and "approximately" are used completely interchangeable throughout the disclosure. The term "between" includes the endpoint numbers on both limits of the range. For example, the range described by "between 3 and 5" is inclusive of the numbers "3" and "5". As used herein, a tilde (i.e., "~") preceding a numerical value or range of values indicates "about" or "approximately."

As used herein, and unless otherwise specified, "agent" or "biologically active agent" or "second active agent" refers to a biological, pharmaceutical, or chemical compound or other moiety. Non-limiting examples include simple or complex organic or inorganic molecules, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present disclosure.

As used herein, and unless otherwise specified, the term "agonist" refers to a compound having the ability to initiate or enhance a biological function of a target protein, whether by enhancing or initiating the activity or expression of the target protein. Accordingly, the term "agonist" is defined in the context of the biological role of the target protein. While agonists provided herein can specifically interact with (e.g., bind to) the target, compounds that initiate or enhance a biological activity of the target protein by interacting with other members of the signal transduction pathway of which the target protein is a member are also specifically included within this definition.

As used herein, and unless otherwise specified, the terms "antagonist" and "inhibitor" are used interchangeably, and they refer to a compound having the ability to inhibit a biological function of a target protein, whether by inhibiting the activity or expression of the target protein. Accordingly, the terms "antagonist" and "inhibitors" are defined in the context of the biological role of the target protein. While antagonists provided herein can specifically interact with (e.g., bind to) the target, compounds that inhibit a biological activity of the target protein by interacting with other members of the signal transduction pathway of which the target protein is a member are also specifically included within this definition. In one embodiment, a biological activity inhibited by an antagonist is associated with the development, growth, or spread of a tumor, or an undesired immune response, e.g., as manifested in autoimmune disease.

As used herein, and unless otherwise specified, an "anti-cancer agent", "anti-tumor agent" or "chemotherapeutic agent" refers to any agent useful in the treatment of a neoplastic condition. One class of anti-cancer agents comprises chemotherapeutic agents. As used herein, and unless otherwise specified, "chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

As used herein, and unless otherwise specified, the term "cell proliferation" refers to a phenomenon by which the cell number has changed as a result of division. In one embodiment, this term also encompasses cell growth by which the cell morphology has changed (e.g., increased in size) consistent with a proliferative signal.

As used herein, and unless otherwise specified, the term "co-administration," "administered in combination with," and their grammatical equivalents, encompasses administration of two or more agents to an animal either simultaneously or sequentially. In one embodiment, both agents and/or their metabolites are present in the animal at the same time. In one embodiment, co-administration includes simultaneous administration in separate compositions, administration at different times in separate compositions, or administration in a composition in which both agents are present.

As used herein, and unless otherwise specified, the term "effective amount" or "therapeutically effective amount" refers to an amount of a compound described herein that is sufficient to effect an intended application or effect, including, but not limited to, disease treatment, as defined herein. The therapeutically effective amount can vary depending upon the intended application (in vitro or in vivo), or the subject and disease condition being treated, e.g., the weight and age of the subject, the severity of the disease condition, the manner of administration, and the like, which can be determined by one of ordinary skill in the art. The term can also apply to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, and unless otherwise specified, the terms "treatment", "treating", "palliating" and "ameliorating" are used interchangeably herein, and refer to an approach for obtaining beneficial or desired results, including, but not limited to, a therapeutic benefit and/or a prophylactic benefit. In one embodiment, therapeutic benefit means eradication or amelioration of the underlying disorder being treated. In one embodiment, a therapeutic benefit is achieved with the eradication or amelioration of one or more of the physiological symptoms associated with the underlying disorder, such that an improvement is observed in the patient, notwithstanding that the patient can still be afflicted with the underlying disorder. For prophylactic benefit, the compositions can be administered to a patient at risk of developing a particular disease, or to a patient reporting one or more of the physiological symptoms of a disease, even though a diagnosis of this disease can or cannot have been made.

As used herein, and unless otherwise specified, a "therapeutic effect" encompasses a therapeutic benefit and/or a prophylactic benefit as described herein. A prophylactic effect includes delaying or eliminating the appearance of a disease or condition, delaying or eliminating the onset of symptoms of a disease or condition, slowing, halting, or reversing the progression of a disease or condition, or any combination thereof.

As used herein, and unless otherwise specified, "signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator can augment (agonist) or suppress (antagonist) the activity of a signaling molecule.

As used herein, and unless otherwise specified, the term "selective inhibition" or "selectively inhibit" as applied to a biologically active agent refers to the agent's ability to selectively reduce the target signaling activity as compared to off-target signaling activity, via direct or interact interaction with the target.

As used herein, and unless otherwise specified, the term "in vivo" refers to an event that takes place in a subject's body.

As used herein, and unless otherwise specified, the term "in vitro" refers to an event that takes places outside of a subject's body. For example, an in vitro assay encompasses any assay run outside of a subject assay. In vitro assays encompass cell-based assays in which cells alive or dead are employed. In one embodiment, in vitro assays also encompass a cell-free assay in which no intact cells are employed.

"Subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

As used herein, and unless otherwise specified, "radiation therapy" means exposing a patient, using routine methods and compositions known to the practitioner, to radiation emitters such as alpha-particle emitting radionuclides (e.g., actinium and thorium radionuclides), low linear energy transfer (LET) radiation emitters (e.g., beta emitters), conversion electron emitters (e.g., strontium-89 and samarium-153-EDTMP), or high-energy radiation, including without limitation, x-rays, gamma rays, and neutrons.

As used herein, the term "combining" refers to bringing one or more chemical entities into association with another one or more chemical entities. Combining includes the processes of adding one or more compounds to a solid, liquid or gaseous mixture of one or more compounds (the same or other chemical entities), or a liquid solution or multiphasic liquid mixture. The act of combining includes the process or processes of one or more compounds reacting (e.g., bond formation or cleavage; salt formation, solvate formation, chelation, or other non-bond altering association) with one or more compounds (the same or other chemical entities). The act of combining can include alteration of one or more compounds, such as by isomerization (e.g., tautomerization, resolution of one isomer from another, or racemization).

As used herein, the term "recovering" includes, but is not limited to, the action of obtaining one or more compounds by collection during and/or after a process step as disclosed herein, and the action of obtaining one or more compounds by separation of one or more compounds from one or more other chemical entities during and/or after a process step as disclosed herein. The term "collection" refers to any action(s) known in the art for this purpose, including, but not limited to, filtration, decanting a mother liquor from a solid to obtain one or more compounds, and evaporation of liquid media in a solution or other mixture to afford a solid, oil, or other residue that includes one or more compounds. The solid can be crystalline, acrystalline, partially crystalline, amorphous, containing one or more polymorphs, a powder, granular, of varying particle sizes, of uniform particle size, among other characteristics known in the art. An oil can vary in color and viscosity, and include one or more solid forms as a heterogeneous mixture, among other characteristics known in the art. The term "separation" refers to any action(s) known in the art for this purpose, including, but not limited to, isolating one or more compounds from a solution or mixture using, for example, seeded or seedless crystallization or other precipitation techniques (e.g., adding an anti-solvent to a solution to induce compound precipitation; heating a solution, then cooling to induce compound precipitation; scratching the surface of a solution with an implement to induce compound precipitation), and distillation techniques. Recovering one or more compounds can involve preparation of a salt, solvate, hydrate, chelate or other complexes of the same, then collecting or separating as described above.

As used herein, a "pharmaceutically acceptable form" of a disclosed Formula (I) includes, but is not limited to, pharmaceutically acceptable salts, hydrates, solvates, chelates, non-covalent complexes, isomers, prodrugs, and isotopically labeled derivatives thereof, and mixtures thereof. Hence, the terms "chemical entity" and "chemical entities" also encompass pharmaceutically acceptable salts, hydrates, solvates, chelates, non-covalent complexes, isomers, prodrugs, and isotopically labeled derivatives, and mixtures thereof. In some embodiments, a pharmaceutically acceptable form of a disclosed Formula (I) includes a salt, a solvate, or a hydrate thereof.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19. Pharmaceutically acceptable salts of the compounds provided herein include those derived from suitable inorganic and organic acids and bases. Inorganic acids from which salts can be derived include, but are not limited to, hydrochloric acid, hydrobromic acid, sulfuric acid, nitric acid, phosphoric acid, and the like. Organic acids from which salts can be derived include, but are not limited to, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Pharmaceutically acceptable salts derived from appropriate bases include alkali metal, alkaline earth metal, ammonium and $N^+(C_{1-4}alkyl)_4$-salts. Inorganic bases from which salts can be derived include, but are not limited to, sodium, potassium, lithium, ammonium, calcium, magnesium, iron, zinc, copper, manganese, aluminum, and the like. Organic bases from which salts can be derived include, but are not limited to, primary, secondary, and tertiary amines, substituted amines, including naturally occurring substituted amines, cyclic amines, basic ion exchange resins, and the like, examples include, but are not limited to, isopropylamine, trimethylamine, diethylamine, triethylamine, tripropylamine, and ethanolamine. In some embodiments, the pharmaceutically acceptable base addition salt is ammonium, potassium, sodium, calcium, or magnesium salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts. Bis salts (i.e., two counterions) and higher salts (e.g., three or more counterions) are encompassed within the meaning of pharmaceutically acceptable salts.

In addition, if a compound of the present disclosure is obtained as an acid addition salt, the free base can be obtained by basifying a solution of the acid salt. Conversely, if a product is a free base, an acid addition salt, particularly a pharmaceutically acceptable addition salt, can be produced by dissolving the free base in a suitable organic solvent and treating the solution with an acid, in accordance with conventional procedures for preparing acid addition salts from base compounds. Those skilled in the art will recognize various synthetic methodologies that can be used to prepare non-toxic pharmaceutically acceptable addition salts.

In certain embodiments, the pharmaceutically acceptable form is a "solvate" (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or one to about 2, 3 or 4, solvent or water molecules. In some embodiments, the solvate can be a channel solvate. It will be understood that the term "compound" as used herein encompasses the compound and solvates of the compound, as well as mixtures thereof.

As used herein, and unless otherwise specified, "prodrug" is meant to indicate a compound that can be converted under physiological conditions or by solvolysis to a biologically active compound described herein. Thus, the term "prodrug" refers to a precursor of a biologically active compound that is pharmaceutically acceptable. A prodrug can be inactive when administered to a subject, but is converted in vivo to an active compound, for example, by hydrolysis. In some embodiments, the prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active Formula (I) in vivo when such prodrug is administered to a mammalian subject. Prodrugs of an active compound, as described herein, can be prepared by modifying functional groups present in the active Formula (I) in such a way that the modifications are cleaved, either in routine manipulation or in vivo, to the parent active compound. Prodrugs include compounds wherein a hydroxy, amino or mercapto group is bonded to any group that, when the prodrug of the active Formula (I) is administered to a mammalian subject, cleaves to form a free hydroxy, free amino or free mercapto group, respectively.

Examples of prodrugs include, but are not limited to, acetate, formate, and benzoate derivatives of an alcohol; or acetamide, formamide, and benzamide derivatives of an amine functional group in the active compound, and the like. Other examples of prodrugs include compounds that comprise —NO, —$NO_2$, —ONO, or —$ONO_2$ moieties. Prodrugs can typically be prepared using well-known methods, such as those described in Burger's Medicinal Chemistry and Drug Discovery, 172-178, 949-982 (Manfred E. Wolff ed., 5th ed., 1995), and Design of Prodrugs (H. Bundgaard ed., Elsevier, New York, 1985).

For example, if a disclosed compound or a pharmaceutically acceptable form of the compound contains a carboxylic acid functional group, a prodrug can comprise a pharmaceutically acceptable ester formed by the replacement of the hydrogen atom of the acid group with a group such as ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

Similarly, if a disclosed compound or a pharmaceutically acceptable form of the compound contains an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-(($C_1$-$C_6$)alkanoyloxy)ethyl($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate).

If a disclosed compound or a pharmaceutically acceptable form of the Formula (I) incorporates an amine functional group, a prodrug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, a natural α-aminoacyl or natural α-aminoacyl-natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl, carboxy($C_1$-$C_6$)alkyl, amino($C_1$-$C_4$)alkyl or mono-N— or di-N,N—($C_1$-$C_6$)alkylaminoalkyl, —C(Y$^4$)Y$^5$ wherein Y$^4$ is H or methyl and Y$^5$ is mono-N— or di-N,N—($C_1$-$C_6$)alkylamino, morpholino, piperidin-1-yl or pyrrolidin-1-yl.

In certain embodiments, the pharmaceutically acceptable form is an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this disclosure.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

"Enantiomers" are a pair of stereoisomers that are non-superimposable mirror images of each other. A mixture of a pair of enantiomers in any proportion can be known as a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a Formula (I) is an enantiomer, the stereochemistry at each chirogenic carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, optically substantially pure forms and intermediate mixtures. Optically active (R)- and (S)-isomers can be prepared, for example, using chiral synthons or chiral reagents, or resolved using conventional techniques.

As used herein, and unless otherwise specified, the term "stereomerically pure" means a composition or substance that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other stereoisomers (e.g., diastereoisomers or enantiomers, or syn or anti isomers, or cis or trans isomers) of the compound. A typical stereomerically pure compound comprises greater than about 80 percent by weight of one stereoisomer of the compound and less than about 20 percent by weight of other stereoisomers of the compound, greater than about 90 percent by weight of one stereoisomer of the compound and less than about 10 percent by weight of the other stereoisomers of the compound, greater than about 95 percent by weight of one stereoisomer of the compound and less than about 5 percent by weight of the other stereoisomers of the compound, or greater than about 97 percent by weight of one stereoisomer of the compound and less than about 3 percent by weight of the other stereoisomers of the compound.

As used herein, and unless otherwise specified, the term "enantiomerically pure" means a stereomerically pure composition of a compound having one or more chiral center(s).

As used herein, and unless otherwise specified, the terms "enantiomeric excess" and "diastereomeric excess" are used interchangeably herein. In some embodiments, compounds with a single stereocenter can be referred to as being present in "enantiomeric excess," and those with at least two stereocenters can be referred to as being present in "diastereomeric excess." For example, the term "enantiomeric excess" is well known in the art and is defined as:

$$ee_a = \left(\frac{conc. \text{ of } a - conc. \text{ of } b}{conc. \text{ of } a + conc. \text{ of } b}\right) \times 100$$

Thus, the term "enantiomeric excess" is related to the term "optical purity" in that both are measures of the same phenomenon. The value of ee will be a number from 0 to 100, zero being racemic and 100 being enantiomerically pure. A compound which in the past might have been called 98% optically pure is now more precisely characterized by 96% ee. A 90% ee reflects the presence of 95% of one enantiomer and 5% of the other(s) in the material in question.

Some compositions described herein contain an enantiomeric excess of at least about 50%, 75%, 90%, 95%, or 99% of the S enantiomer. In other words, the compositions contain an enantiomeric excess of the S enantiomer over the R enantiomer. In other embodiments, some compositions described herein contain an enantiomeric excess of at least about 50%, 75%, 90%, 95%, or 99% of the R enantiomer. In other words, the compositions contain an enantiomeric excess of the R enantiomer over the S enantiomer.

For instance, an isomer/enantiomer can, in some embodiments, be provided substantially free of the corresponding enantiomer, and can also be referred to as "optically enriched," "enantiomerically enriched," "enantiomerically pure" and "non-racemic," as used interchangeably herein. These terms refer to compositions in which the percent by weight of one enantiomer is greater than the amount of that one enantiomer in a control mixture of the racemic composition (e.g., greater than about 1:1 by weight). For example, an enantiomerically enriched preparation of the S enantiomer, means a preparation of the compound having greater than about 50% by weight of the S enantiomer relative to the R enantiomer, such as at least about 75% by weight, further such as at least about 80% by weight. In some embodiments, the enrichment can be much greater than about 80% by weight, providing a "substantially enantiomerically enriched," "substantially enantiomerically pure" or a "substantially non-racemic" preparation, which refers to preparations of compositions which have at least about 85% by weight of one enantiomer relative to other enantiomer, such as at least about 90% by weight, and further such as at least 95% by weight. In certain embodiments, the compound provided herein is made up of at least about 90% by weight of one enantiomer. In other embodiments, the Formula (I) is made up of at least about 95%, 98%, or 99% by weight of one enantiomer.

Enantiomers can be isolated from racemic mixtures by any method known to those skilled in the art, including chiral high pressure liquid chromatography (HPLC), the formation and crystallization of chiral salts, or prepared by asymmetric syntheses. See, for example, *Enantiomers, Racemates and Resolutions* (Jacques, Ed., Wiley Interscience, New York, 1981); Wilen et al., *Tetrahedron* 33:2725 (1977); *Stereochemistry of Carbon Compounds* (E. L. Eliel, Ed., McGraw-Hill, NY, 1962); and *Tables of Resolving*

*Agents and Optical Resolutions* p. 268 (E. L. Eliel, Ed., Univ. of Notre Dame Press, Notre Dame, Ind. 1972).

In certain embodiments, the pharmaceutically acceptable form is a tautomer. As used herein, the term "tautomer" is a type of isomer that includes two or more interconvertable compounds resulting from at least one formal migration of a hydrogen atom and at least one change in valency (e.g., a single bond to a double bond, a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-to-enol; amide-to-imide; lactam-to-lactim; enamine-to-imine; and enamine-to-(a different) enamine tautomerizations. An example of keto-enol tautomerization is the interconversion of pentane-2,4-dione and 4-hydroxypent-3-en-2-one tautomers. Another example of tautomerization is phenol-keto tautomerization. Another example of phenol-keto tautomerization is the interconversion of pyridin-4-ol and pyridin-4(1H)-one tautomers.

As used herein, and unless otherwise specified, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon, or the replacement of a nitrogen by $^{13}$N- or $^{15}$N-enriched nitrogen, or the replacement of an oxygen by $^{14}$O-, $^{15}$O-, $^{17}$O-, or $^{18}$O-enriched oxygen, or the replacement of a chlorine by $^{35}$Cl-, $^{36}$Cl-, or $^{37}$Cl-enriched chlorine, are within the scope of this disclosure.

In one embodiment, the compounds of the present disclosure can also contain unnatural proportions of atomic isotopes at one or more of atoms that constitute such compounds. For example, the compounds can be radiolabeled with radioactive isotopes, such as, for example, tritium ($^{3}$H), iodine-125 ($^{125}$I), or carbon-14 ($^{14}$C). Certain isotopically-labeled disclosed compounds (e.g., those labeled with $^{3}$H and $^{14}$C) are useful in compound and/or substrate tissue distribution assays. Tritiated (i.e., $^{3}$H) and carbon-14 (i.e., $^{14}$C) isotopes can allow for ease of preparation and detectability. Further, substitution with heavier isotopes such as deuterium (i.e., $^{2}$H) can afford certain therapeutic advantages resulting from greater metabolic stability (e.g., increased in vivo half-life or reduced dosage requirements). Isotopically labeled disclosed compounds can generally be prepared by substituting an isotopically labeled reagent for a non-isotopically labeled reagent. In some embodiments, provided herein are compounds that can also contain unnatural proportions of atomic isotopes at one or more of atoms that constitute such compounds. All isotopic variations of compounds of the present disclosure, whether radioactive or not, are encompassed within the scope of the present disclosure.

As used herein, and unless otherwise specified, the terms "solvent," "organic solvent," or "inert solvent" each mean a solvent inert under the conditions of the reaction being described in conjunction therewith, including, without limitation, benzene, toluene, acetonitrile, ethyl acetate, isopropyl acetate, hexanes, heptanes, dioxane, tetrahydrofuran ("THF"), dimethylformamide ("DMF"), dimethylacetamide ("DMA"), chloroform, methylene chloride (dichloromethane), diethyl ether, methanol, butanol, methyl t-butyl ether ("MTBE", or "TBME"), 2-butanone ("MEK"), N-methylpyrrolidone ("NMP"), pyridine, and the like. Unless specified to the contrary, the solvents used in reactions described herein are inert organic solvents. Unless specified to the contrary, for each gram of a limiting reagent, one cc (or mL) of solvent constitutes a volume equivalent.

As used herein, and unless otherwise specified, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is known in the art. Except insofar as any conventional media or agent is incompatible with the active ingredient, its use in the therapeutic compositions of the present disclosure is contemplated. Supplementary active ingredients can also be incorporated into the compositions.

As used herein and unless otherwise specified, the term "solid form" and related terms refer to a physical form which is not predominantly in a liquid or a gaseous state. Solid forms may be crystalline, amorphous or mixtures thereof. In particular embodiments, solid forms may be liquid crystals.

In some embodiments, a solid form provided herein is a single component or multiple component solid form. A "single-component" solid form comprising a compound of a formula consists essentially of the compound of the formula. A "multiple-component" solid form comprising a compound of a formula comprises a significant quantity of one or more additional species, such as ions and/or molecules, within the solid form. For example, a crystalline multiple-component solid form comprising a compound of a formula further comprises one or more species non-covalently bonded at regular positions in the crystal lattice. A multiple component solid form provided herein may be a co-crystal.

As used herein and unless otherwise specified, the term "crystalline" and related terms, when used to describe a substance, modification, material, component or product mean that the substance, modification, material, component or product is substantially crystalline as determined by X-ray diffraction. See, e.g., *Remington: The Science and Practice of Pharmacy*, 21$^{st}$ edition, Lippincott, Williams and Wilkins, Baltimore, Md. (2005); *The United States Pharmacopeia*, 23$^{th}$ edition, 1843-1844 (1995).

As used herein and unless otherwise specified, the term "crystal forms" and related terms refer to solid forms that are crystalline. Crystal forms include single-component crystal forms and multiple-component crystal forms, and include, but are not limited to, polymorphs, solvates, hydrates, and other molecular complexes, as well as salts, solvates of salts, hydrates of salts, other molecular complexes of salts, and polymorphs thereof. In certain embodiments, a crystal form of a substance may be substantially free of amorphous forms and/or other crystal forms. In certain embodiments, a crystal form of a substance may contain less than about 1%, 2%, 3%, 4%, 5%, 6%, 7%, 8%, 9%, 10%, 15%, 20%, 25%, 30%, 35%, 40%, 45% or 50% of one or more amorphous forms and/or other crystal forms on a weight basis. In certain embodiments, a crystal form of a substance may be physically and/or chemically pure. In certain embodiments, a crystal form of a substance may be about 99%, 98%, 97%, 96%, 95%, 94%, 93%, 92%, 91% or 90% physically and/or chemically pure.

As used herein and unless otherwise specified, the terms "polymorphs," "polymorphic forms" and related terms herein, refer to two or more crystal forms that consist essentially of the same molecule, molecules or ions. Like different crystal forms, different polymorphs may have different physical properties such as, for example, melting temperatures, heats of fusion, solubilities, dissolution rates and/or vibrational spectra, as a result of the arrangement or conformation of the molecules and/or ions in the crystal lattice. The differences in physical properties may affect pharmaceutical parameters such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to a thermodynamically more stable polymorph) or both (e.g., tablets of one polymorph are more susceptible to breakdown at high humidity). As a result of solubility/dissolution differences, in the extreme case, some solid-state transitions may result in lack of potency or, at the other extreme, toxicity. In addition, the physical properties may be important in processing (for example, one polymorph might be more likely to form solvates or might be difficult to filter and wash free of impurities, and particle shape and size distribution might be different between polymorphs).

As used herein and unless otherwise specified, the term "solvate" and "solvated," refer to a crystal form of a substance which contains solvent. The term "hydrate" and "hydrated" refer to a solvate wherein the solvent comprises water. "Polymorphs of solvates" refers to the existence of more than one crystal form for a particular solvate composition. Similarly, "polymorphs of hydrates" refers to the existence of more than one crystal form for a particular hydrate composition. The term "desolvated solvate," as used herein, refers to a crystal form of a substance which may be prepared by removing the solvent from a solvate.

As used herein and unless otherwise specified, the term "amorphous," "amorphous form," and related terms used herein, mean that the substance, component or product in question is not substantially crystalline as determined by X-ray diffraction. In particular, the term "amorphous form" describes a disordered solid form, i.e., a solid form lacking long range crystalline order. In certain embodiments, an amorphous form of a substance may be substantially free of other amorphous forms and/or crystal forms. In other embodiments, an amorphous form of a substance may contain less than about 1%, 2%, 3%, 4%, 5%, 10%, 15%, 20%, 25%, 30%, 35%, 40%, 45% or 50% of one or more other amorphous forms and/or crystal forms on a weight basis. In certain embodiments, an amorphous form of a substance may be physically and/or chemically pure. In certain embodiments, an amorphous form of a substance may be about 99%, 98%, 97%, 96%, 95%, 94%, 93%, 92%, 91% or 90% physically and/or chemically pure.

Techniques for characterizing crystal forms and amorphous forms include, but are not limited to, thermal gravimetric analysis (TGA), differential scanning calorimetry (DSC), X-ray powder diffractometry (XRPD), gravimetric vapor sorption (GVS), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility measurements, dissolution measurements, elemental analysis and Karl Fischer analysis. Characteristic unit cell parameters may be determined using one or more techniques such as, but not limited to, X-ray diffraction and neutron diffraction, including single-crystal diffraction and powder diffraction. Techniques useful for analyzing powder diffraction data include profile refinement, such as Rietveld refinement, which may be used, e.g., to analyze diffraction peaks associated with a single phase in a sample comprising more than one solid phase. Other methods useful for analyzing powder diffraction data include unit cell indexing, which allows one of skill in the art to determine unit cell parameters from a sample comprising crystalline powder.

In some embodiments, the solid forms, e.g., crystal or amorphous forms, described herein are substantially pure, i.e., substantially free of other solid forms and/or of other chemical compounds, containing less than about 25%, 20%, 15%, 10%, 9%, 8%, 7%, 6%, 5%, 4%, 3%, 2%, 1%, 0.75%, 0.5%, 0.25% or 0.1% percent by weight of one or more other solid forms and/or of other chemical compounds.

Solid forms may exhibit distinct physical characterization data that are unique to a particular solid form, such as the crystal forms described herein. These characterization data may be obtained by various techniques known to those skilled in the art, including for example X-ray powder diffraction, differential scanning calorimetry, thermal gravimetric analysis, and nuclear magnetic resonance spectroscopy. The data provided by these techniques may be used to identify a particular solid form. One skilled in the art can determine whether a solid form is one of the forms described herein by performing one of these characterization techniques and determining whether the resulting data "matches" the reference data provided herein, which is identified as being characteristic of a particular solid form. Characterization data that "matches" those of a reference solid form is understood by those skilled in the art to correspond to the same solid form as the reference solid form. In analyzing whether data "match," a person of ordinary skill in the art understands that particular characterization data points may vary to a reasonable extent while still describing a given solid form, due to, for example, experimental error and routine sample-to-sample analysis.

The solid forms provided herein may be crystalline, amorphous, or an intermediate form. The crystal forms described herein, therefore, may have varying degrees of crystallinity or lattice order. The solid forms described herein are not limited by any particular degree of crystallinity or lattice order, and may be 0-100% crystalline. Methods of determining the degree of crystallinity are known to those of ordinary skill in the, such as those described in Suryanarayanan, R., *X-Ray Power Diffractometry*, Physical Characterization of Pharmaceutical Salts, H. G. Brittain, Editor, Mercel Dekkter, Murray Hill, N.J., 1995, pp. 187-199, which is incorporated herein by reference in its entirety. In some embodiments, the solid forms described herein are about 0, 5, 10, 15, 20, 25, 30, 35, 40, 45, 50, 55, 60, 65, 70, 75, 80, 85, 90, 95 or 100% crystalline.

Definitions of specific functional groups and chemical terms are described in more detail below. For purposes of this invention, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, Comprehensive *Organic Transformations*, VCH Publishers, Inc., New York, 1989; Carruthers, *Some Modern Methods of Organic Synthesis*, 3rd Edition, Cambridge University Press, Cambridge, 1987.

The term "alkyl," as used herein, refers to saturated, straight- or branched-chain optionally substituted hydrocarbon radicals derived from an aliphatic moiety containing between one and six carbon atoms (e.g., $C_{1-6}$ alkyl) by removal of a single hydrogen atom. In some embodiments, the alkyl group employed in the invention contains 1-5 carbon atoms. In another embodiment, the alkyl group employed contains 1-4 carbon atoms. In still other embodiments, the alkyl group contains 1-3 carbon atoms. In yet another embodiments, the alkyl group contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain optionally substituted aliphatic moiety having at least one carbon-carbon double bond by the removal of a single hydrogen atom. In certain embodiments, the alkenyl group employed in the invention contains 2-6 carbon atoms (e.g., $C_{2-6}$ alkenyl). In certain embodiments, the alkenyl group employed in the invention contains 2-5 carbon atoms. In some embodiments, the alkenyl group employed in the invention contains 2-4 carbon atoms. In another embodiment, the alkenyl group employed contains 2-3 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain optionally substituted aliphatic moiety having at least one carbon-carbon triple bond by the removal of a single hydrogen atom. In certain embodiments, the alkynyl group employed in the invention contains 2-6 carbon atoms (e.g., $C_{2-6}$ alkynyl). In certain embodiments, the alkynyl group employed in the invention contains 2-5 carbon atoms. In some embodiments, the alkynyl group employed in the invention contains 2-4 carbon atoms. In another embodiment, the alkynyl group employed contains 2-3 carbon atoms. Representative alkynyl groups include, but are not limited to, ethynyl, 2-propynyl (propargyl), 1-propynyl, and the like.

The term "aryl" used alone or as part of a larger moiety as in "aralkyl", "aralkoxy", or "aryloxyalkyl", refers to monocyclic and bicyclic optionally substituted ring systems having a total of five to twelve ring members, wherein at least one ring in the system is aromatic and wherein each ring in the system contains three to seven ring members. In some embodiments, "aryl" refers to monocyclic and bicyclic optionally substituted ring systems having a total of six to twelve ring members (e.g., $C_{6-12}$ aryl), wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic ring is fused to one or more non-aromatic rings, such as indanyl, phthalimidyl, naphthimidyl, phenantriidinyl, or tetrahydronaphthyl, and the like.

The terms "heteroaryl" used alone or as part of a larger moiety, e.g., "heteroaralkyl", or "heteroaralkoxy", refer to optionally substituted groups having 5 to 10 ring atoms, preferably 5, 6, or 9 ring atoms; having 6, 10, or 14 π electrons shared in a cyclic array; and having, in addition to carbon atoms, from one to five heteroatoms. In some embodiments, the term "heteroaryl" refers to optionally substituted groups as defined above having 6 to 10 ring atoms (e.g., $C_{6-12}$ heteroaryl). The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH═CHPh, which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)

R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched)alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$, —NO$_2$, —SiR$^\bullet$$_3$, —C(O)SR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O) R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

5.2 Salts, Solid Forms, and Solid Forms of Salts

Potential pharmaceutical solids include crystalline solids and amorphous solids. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (see, e.g., S. R. Vippagunta et al., *Adv. Drug. Deliv. Rev.*, (2001) 48:3-26; L. Yu, *Adv. Drug. Deliv. Rev.*, (2001) 48:27-42). A change in solid form may affect a variety of physical and chemical properties, which may provide benefits or drawbacks in processing, formulation, stability and bioavailability, among other important pharmaceutical characteristics.

Whether crystalline or amorphous, potential solid forms of a pharmaceutical compound may include single-component and multiple-component solids. Single-component solids consist essentially of the pharmaceutical compound in the absence of other compounds. Variety among single-component crystalline materials may potentially arise from the phenomenon of polymorphism, wherein multiple three-dimensional arrangements exist for a particular pharmaceutical compound (see, e.g., S. R. Byrn et al., *Solid State Chemistry of Drugs*, (1999) SSCI, West Lafayette).

Additional diversity among the potential solid forms of a pharmaceutical compound may arise from the possibility of multiple-component solids. Crystalline solids comprising two or more ionic species are termed salts (see, e.g., *Handbook of Pharmaceutical Salts: Properties, Selection and Use*, P. H. Stahl and C. G. Wermuth, Eds., (2002), Wiley, Weinheim). Additional types of multiple-component solids that may potentially offer other property improvements for a pharmaceutical compound or salt thereof include, e.g., hydrates, solvates, co-crystals and clathrates, among others (see, e.g., S. R. Byrn et al., *Solid State Chemistry of Drugs*, (1999) SSCI, West Lafayette). Moreover, multiple-component crystal forms may potentially be susceptible to polymorphism, wherein a given multiple-component composition may exist in more than one three-dimensional crystalline arrangement. The discovery of solid forms is of great importance in the development of a safe, effective, stable and marketable pharmaceutical compound.

The solid forms provided herein are useful as active pharmaceutical ingredients for the preparation of formulations for use in animals or humans. Thus, embodiments herein encompass the use of these solid forms as a final drug product. Certain embodiments provide solid forms useful in making final dosage forms with improved properties, e.g., powder flow properties, compaction properties, tableting properties, stability properties, and excipient compatibility properties, among others, that are needed for manufacturing, processing, formulation and/or storage of final drug products. Certain embodiments herein provide pharmaceutical compositions comprising a single-component crystal form, a multiple-component crystal form, a single-component amorphous form and/or a multiple-component amorphous form comprising the compound of formula (I) and a pharmaceutically acceptable diluent, excipient or carrier.

Solid form and related terms refer to a physical form which is not predominantly in a liquid or a gaseous state. Solid forms may be crystalline, amorphous or mixtures thereof. A "single-component" solid form comprising a particular compound consists essentially of that compound. A "multiple-component" solid form comprising a particular compound comprises that compound and a significant quantity of one or more additional species, such as ions and/or molecules, within the solid form. The solid forms provided herein may be crystalline, amorphous, or an intermediate form. The crystal forms described herein, therefore, may have varying degrees of crystallinity or lattice order. The solid forms described herein are not limited to any particular degree of crystallinity or lattice order, and may be 0-100% crystalline. Methods of determining the degree of crystallinity are known to those of ordinary skill in the, such as those described in Suryanarayanan, R., *X-Ray Power Diffractometry*, Physical Characterization of Pharmaceutical Salts, H. G. Brittain, Editor, Mercel Dekkter, Murray Hill, N.J., 1995, pp. 187-199, which is incorporated herein by reference in its entirety. In some embodiments, the solid forms described herein are about 0, 5, 10, 15, 20, 25, 30, 35, 40, 45, 50, 55, 60, 65, 70, 75, 80, 85, 90, 95 or 100% crystalline.

Solid forms may exhibit distinct physical characterization data that are unique to a particular solid form, such as the crystal forms described herein. These characterization data may be obtained by various techniques known to those skilled in the art, including for example X-ray powder diffraction, differential scanning calorimetry, thermal gravimetric analysis, and nuclear magnetic resonance spectroscopy. The data provided by these techniques may be used to identify a particular solid form. One skilled in the art can determine whether a solid form is one of the forms described herein by performing one of these characterization techniques and determining whether the resulting data is "substantially similar" to the reference data provided herein, which is identified as being characteristic of a particular solid form. Characterization data that is "substantially similar" to those of a reference solid form is understood by those skilled in the art to correspond to the same solid form as the reference solid form. In analyzing whether data is "substantially similar," a person of ordinary skill in the art understands that particular characterization data points may vary to a reasonable extent while still describing a given solid form, due to, for example, experimental error and routine sample-to-sample analysis.

In some embodiments, provided herein are solid forms of a compound of formula (I):

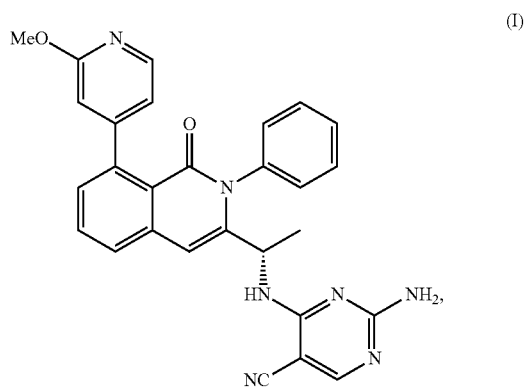 [SMILES: COc1cc(-c2cccc3cc([C@H](C)Nc4nc(N)ncc4C#N)n(-c4ccccc4)c(=O)c23)ccn1]

or a salt, solvate (e.g., hydrate), or solvate of a salt thereof, or a mixture thereof. In one embodiment, the solid form of a compound of formula (I) can be a crystalline form, a partially crystalline form, an amorphous form, or a mixture of crystalline form(s) and/or amorphous form(s). In one embodiment, provided herein is a solid form comprising a crystalline form of a compound of formula (I), or a salt, solvate (e.g., hydrate), or solvate of a salt thereof, or a mixture thereof.

The compound of formula (I) has a chemical name of (S)-2-amino-((1-(8-(2-methoxypyridin-4-yl)-1-oxo-2-phenyl-1,2-dihydroisoquinolin-3-yl)ethyl)amino)pyrimidine-5-carbonitrile. The compound of formula (I) is provided in the class of molecules described in US2013/0053362, the entirety of which is incorporated herein by reference.

In some embodiments, the Formula (I) is a racemic mixture of (S)- and (R)-isomers. In other embodiments, provided herein is a mixture of compounds wherein individual compounds of the mixture exist predominately in an (S)- or (R)-isomeric configuration. For example, the compound mixture has an (S)-enantiomeric excess of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5% or more. In some other embodiments, the compound mixture has an (R)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

As used herein and unless otherwise specified, the term "Formula (I)" includes (S)-2-amino-4-((1-(8-(2-methoxy-pyridin-4-yl)-1-oxo-2-phenyl-1,2-dihydroisoquinolin-3-yl) ethyl)amino)pyrimidine-5-carbonitrile in its imide tautomer shown below as (1-1) and in its lactim tautomer shown below as (1-2):

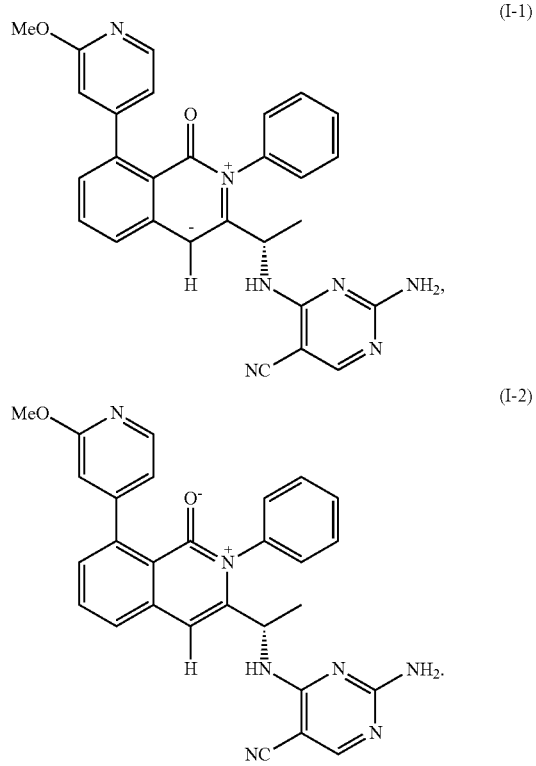

In some embodiments, provided herein are salts of the compound of formula (I), or a solvate (e.g., hydrate) thereof. In some embodiments, the salt is a salt of H—X, wherein X is F, Cl, Br, I, RSO$_3$, or RCO$_2$, wherein R is alkyl, aryl, substituted alkyl, or substituted aryl. In one embodiment, the salt is a pharmaceutically acceptable salt. In some embodiments, provided herein is a salt of the compound of formula (I), wherein the salt is a hydrobromic acid salt, a hydrochloric acid salt, a sulfuric acid salt, an 1,2-ethane disulfonic acid salt, a p-toluene sulfonic acid salt, a methane sulfonic acid salt, an oxalic acid salt, a 2-hydroxy ethanesulfonic acid salt (i.e., an isethionate salt), a L-aspartic acid salt, a maleic acid salt, a phosphoric acid salt, or an ethane sulfonic acid salt.

The compound of formula (I) has at least two basic nitrogen atoms with a pKa value of about 3.5 and about 4.2, respectively. Without being limited by any particular theory, in some embodiments, the acids are associated with the basic nitrogen of the pyrimidine ring of the compound of formula (I); in other embodiments, the acids are associated with the basic nitrogen of the pyridine ring of the compound of formula (I); and yet in other embodiments, the acids are associated with both of the basic nitrogen of the pyrimidine ring and the basic nitrogen of the pyridine ring of the compound of formula (I).

Also provided herein are solid forms of a salt of the compound of formula (I), or a solvate (e.g., hydrate) thereof. In one embodiment, the solid form provided herein is Form 1, Form 1A, Form 1B, Form 2, Form 3, or an amorphous form of a sulfuric acid salt of Compound 1, or a mixture thereof. In one embodiment, the solid form provided herein is Form 1, or an amorphous form of a maleic acid salt of Compound 1, or a mixture thereof. In one embodiment, the solid form provided herein is Form 1, Form 2, Form 3, Form 4, or an amorphous form of an 1,2-ethanedisulfonic acid salt of Compound 1, or a mixture thereof. In one embodiment, the solid form provided herein is Form 1, Form 2, or an amorphous form of a hydrochloride salt of Compound 1, or a mixture thereof. In one embodiment, the solid form provided herein is Form 1, or an amorphous form of an isethionate salt of Compound 1, or a mixture thereof.

Also provided herein are solid forms of a free base of the compound of formula (I), or a solvate (e.g., hydrate) thereof. In one embodiment, the solid form provided herein is Form 1, Form 2, Form 3, Form 4, Form 5, Form 6, or an amorphous form of a free base of Compound 1, or a mixture thereof.

In some embodiment, a solid form provided herein is a solvate of a free base or salt of Compound 1. In one embodiment, the solvate is a hydrate.

In some embodiments, provided herein is a pharmaceutical composition comprising a solid form of a compound of formula (I):

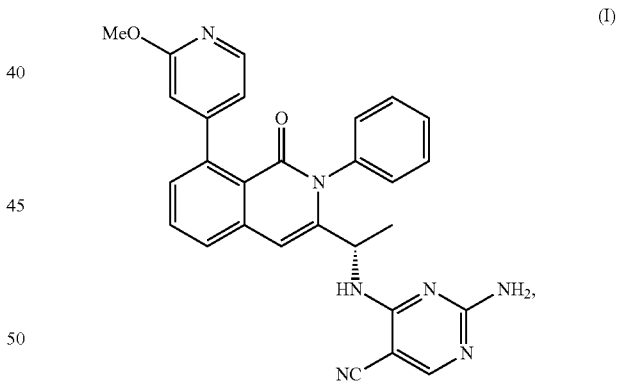

or a salt, solvate (e.g., hydrate), or solvate of a salt thereof, or a mixture thereof, and one or more pharmaceutically acceptable excipients. In some embodiments, provided herein is a pharmaceutical composition comprising a therapeutically effective amount of a solid form of a compound of formula (I), or a salt, solvate (e.g., hydrate), or solvate of a salt thereof, or a mixture thereof, and one or more pharmaceutically acceptable excipients.

In one embodiment, as depicted in Scheme 1 below, Compound 1 is prepared in two steps from (S)-3-(1-amino-ethyl)-8-chloro-2-phenylisoquinolin-1(2H)-one in two steps. The preparation of Compound 1 has also been reported in US2013/0053362.

Scheme 1

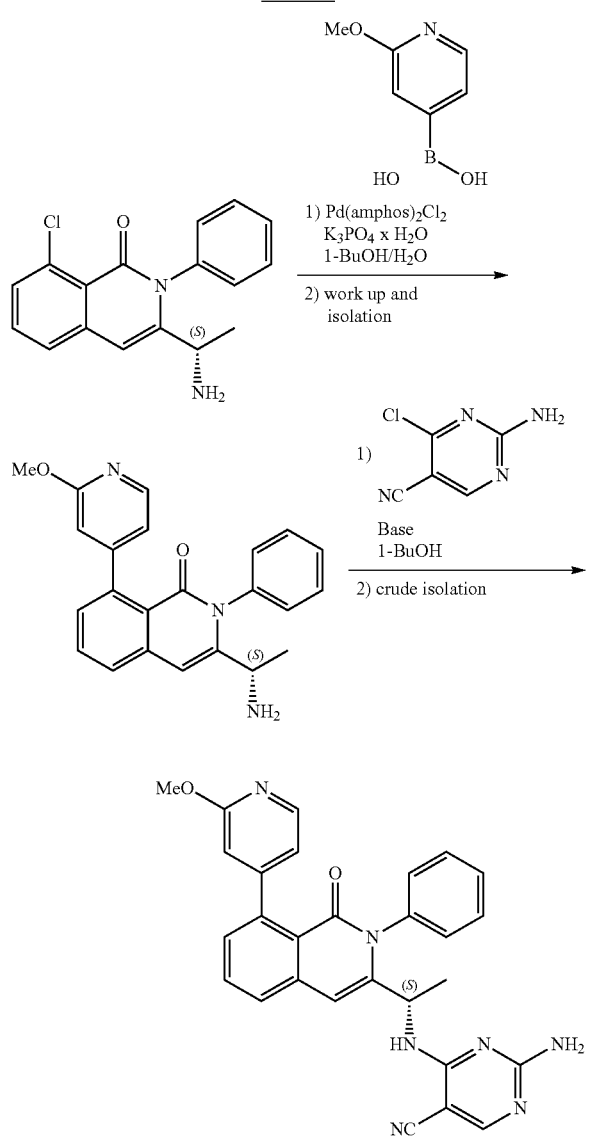

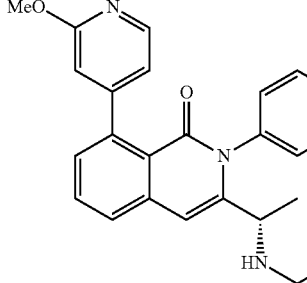

In one embodiment, solid forms provided herein are useful in the production of medicinal preparations and can be obtained by means of a crystallization process to produce crystalline and semi-crystalline forms or a solidification process to obtain the amorphous form. In certain embodiments, the crystallization is carried out by either generating a compound of Formula (I), or a salt thereof, in a reaction mixture and recovering a solid form from the reaction mixture, or by dissolving a compound of Formula (I), or a salt thereof, in a solvent, optionally with heat, followed by crystallizing/solidifying the product by cooling and/or by the addition of an anti-solvent for a period of time. The crystallization or solidification can be followed by drying carried out under controlled conditions until a certain solvent or water content is reached in the end solid form.

In some embodiments, provided herein is a method of preparing a solid form of a compound of formula (I):

or a salt, solvate (e.g., hydrate), or solvate of a salt thereof, or a mixture thereof. In one embodiment, the method comprises recovering a solid form as a first solid form after synthesis of a compound of Formula (I), or a salt thereof. In another embodiment, the method comprises recovering a solid form as a transition from a prior solid form of a compound of Formula (I), or a salt thereof, (e.g., first recovering a first solid form of a compound of Formula (I), or a salt, solvate (e.g., hydrate), or solvate of a salt thereof, and converting the recovered first solid form to a second solid form under suitable conditions). Transitions from one solid form to another are within the scope of the disclosure. In one embodiment, such transition processes can be used as a manufacturing method for obtaining a solid form for the production of medicinal preparations.

In some embodiments, provided herein are methods for preparing a solid form of a salt of Compound 1, or a solvate thereof; comprising (a) contacting Compound 1 with an acid in a solvent system or exposing a material comprising a salt of Compound 1 to a solvent system; and (b) producing and/or recovering the solid form of the salt of Compound 1 from the mixture resulted from step (a).

In some embodiments, provided herein are methods for preparing a solid form of a salt of Compound 1, or a solvate thereof; comprising (a) contacting Compound 1 with an acid in a solvent system; and (b) producing and/or recovering the solid form of the salt of Compound 1 from the mixture resulted from step (a).

In one embodiment, provided herein are methods for preparing a solid form of a salt of Compound 1, or a solvate thereof; comprising (a) mixing (1) a mixture of Compound 1 in a first solvent and (ii) a mixture of an acid in a second solvent; and (b) producing and/or recovering the solid form of the salt of Compound 1 from the mixture resulted from step (a). The first solvent and the second solvent can be different or the same. In one embodiment, the first solvent is anisole. In another embodiment, the first solvent is anisole/MeOH. In one embodiment, the first solvent is anisole/MeOH (ca. 6/4 v/v). In one embodiment, the second solvent is a solvent that dissolves the acid. In one embodiment, the second solvent is a solvent that dissolves the acid at RT in no more than 100 volumes. In one embodiment, the second solvent is THF. In one embodiment, Compound 1 used in step (a) is an amorphous form of Compound 1. In another embodiment, Compound 1 used in step (a) is a crystalline form of Compound 1, e.g., Form 1, Form 2, Form 3, Form 4, Form 5, or Form 6 of a free base of Compound 1, or a mixture thereof. In one embodiment, Compound 1 used in step (a) is substantially pure. In another embodiment, Compound 1 used in step (a) is a crude material after synthesis of Compound 1, wherein the crude material is optionally treated with activated carbon.

In some embodiments, provided herein are methods for preparing a solid form of a salt of Compound 1, or a solvate thereof; comprising (a) exposing a material comprising a salt of Compound 1 to a solvent system; and (b) producing and/or recovering the solid form of the salt of Compound 1 from the mixture resulted from step (a).

In some embodiments, provided herein are methods for preparing a solid form of a free base of Compound 1, or a solvate thereof; comprising (a) exposing a material comprising a salt or free base of Compound 1 to a solvent system; and (b) producing and/or recovering the solid form of the free base of Compound 1 from the mixture resulted from step (a).

In certain embodiments, step (b) comprises one or more of the following steps: (i) cooling a solution containing a salt or free base of Compound 1; (ii) adding an anti-solvent, with or without a cooling step, to cause precipitation of a solid material comprising a salt or free base of Compound 1; (iii) evaporating (e.g., slow evaporation or fast evaporation) a solution containing a salt or free base of Compound 1; (iv) slurrying a material comprising a salt or free base of Compound 1 in a solvent system; and (v) subjecting a material comprising a salt or free base of Compound 1 to maturation in a solvent system.

5.2.1 Sulfuric Acid Salt of Compound 1

In some embodiments, provided herein is a sulfuric acid salt of Compound 1. It is contemplated that a sulfuric acid salt of Compound 1 can exist in a variety of solid forms. Such solid forms include crystalline solids, such as polymorphs, solvates and hydrates of crystalline sulfuric acid salt of Compound 1, as well as amorphous solids, or mixtures thereof. All such solid forms of sulfuric acid salt of Compound 1 are contemplated under the present invention.

As used here, and unless otherwise specified, the term "a sulfuric acid salt" refers to a salt comprising at least one counterion derived from sulfuric acid ($H_2SO_4$). A counterion derived from sulfuric acid include, but are not limited to, $HSO_4^-$ (e.g., hydrogen sulfate, hydrosulfate, or bisulfate) and $SO_4^{2-}$ (e.g., sulfate). The molar ratio of the cation to the coutnerion derived from sulfuric acid in a sulfuric acid salt can be any ratio known in the art. Exemplary molar ratios include, but are not limited to, about 1:2 (i.e., bis-sulfuric acid salt), about 1:1 (i.e., mono-sulfuric acid salt), and about 2:1 (i.e., hemi-sulfuric acid salt). The term "a sulfuric acid salt" includes all forms of the salt, including, but not limited to, an amorphous form, a crystalline form, an anhydrous form, a solvate form (e.g., a hydrate form), of the salt, or a combination or mixture thereof.

In one embodiment, provided herein is a solid form comprising a sulfuric acid salt of Compound 1, or a solvate (e.g., hydrate) thereof. In one embodiment, provided herein is a solid form comprising a solvate of a sulfuric acid salt of Compound 1. In one embodiment, provided herein is a solid form comprising a hydrate of a sulfuric acid salt of Compound 1. In one embodiment, provided herein is a solid form comprising a crystalline form of a sulfuric acid salt of Compound 1, or a solvate (e.g., hydrate) thereof. In one embodiment, provided herein is a solid form comprising a crystalline form of a solvate of a sulfuric acid salt of Compound 1. In one embodiment, provided herein is a solid form comprising a crystalline form of a hydrate of a sulfuric acid salt of Compound 1. In one embodiment, the sulfuric acid salt of Compound 1 is a sulfate salt. In another embodiment, the sulfuric acid salt of Compound 1 is a bisulfate (i.e., hydrosulfate) salt.

In some embodiments, the molar ratio of Compound 1 to sulfuric acid in the solid form ranges from about 2:1 to about 1:2. In one embodiment, the molar ratio is about 1:2 (i.e., bis-sulfuric acid salt). In another embodiment, the molar ratio is about 1:1 (i.e., mono-sulfuric acid salt). In yet another embodiment, the molar ratio is about 2:1 (i.e., hemi-sulfuric acid salt).

In some embodiments, the molar ratio of Compound 1 to the solvent/water in the solid form ranges from about 2:1 to about 1:2. In one embodiment, the molar ratio is about 1:2 (i.e., bis-solvate/hydrate). In another embodiment, the molar ratio is about 1:1 (i.e., mono-solvate/hydrate). In yet another embodiment, the molar ratio is about 2:1 (i.e., hemi-solvate/hydrate).

In one embodiment, the hydrate of the sulfuric acid salt of Compound 1 is a monohydrate of a bis-sulfuric acid salt of Compound 1.

Form 1 of Sulfuric Acid Salt of Compound 1

In some embodiments, provided herein is Form 1 of the sulfuric acid salt of Compound 1. In one embodiment, Form 1 of the sulfuric acid salt of Compound 1 is a crystalline bis-sulfuric acid monohydrate salt of Compound 1. In some embodiments, Form 1 of the sulfuric acid salt of Compound 1 is substantially free of amorphous sulfuric acid salt of Compound 1. In some embodiments, Form 1 of the sulfuric acid salt of Compound 1 is substantially free of other crystalline forms (i.e., polymorphs) of the sulfuric acid salt of Compound 1. In some embodiments, Form 1 of the sulfuric acid salt of Compound 1 is substantially free of other salts of Compound 1. In some embodiments, Form 1 of the sulfuric acid salt of Compound 1 is substantially free of the free base of Compound 1. In some embodiments, Form 1 of the sulfuric acid salt of Compound 1 is provided as substantially pure Form 1 of the sulfuric acid salt of Compound 1. In one embodiment, Form 1 of the sulfuric acid salt of Compound 1 is a sulfate salt. In another embodiment, Form 1 of the sulfuric acid salt of Compound 1 is a bisulfate (i.e., hydrosulfate) salt.

Representative XRPD patterns of Form 1 of the sulfuric acid salt of Compound 1 are provided in FIG. 1A, FIG. 1B, and FIG. 1C.

In some embodiments, provided herein is a solid form comprising a sulfuric acid salt of Compound 1 characterized by XRPD peaks located at 1, 2, 3, 4, 5, 6, 7, 8, 9, 10, 11, 12, 13, 14, 15, or all of the following or approximately the following positions 8.1, 10.7, 10.9, 12.4, 13.3, 14.0, 14.2, 14.8, 15.1, 16.0, 16.3, 17.6, 17.7, 18.4, 18.6, 18.7, 19.2, 20.4, 21.4, 21.7, 22.2, 23.0, 23.4, 23.6, 24.2, and 24.7 degrees 2θ, plus or minus 0.10. In some embodiments, provided herein is a solid form comprising a sulfuric acid salt of Compound 1 characterized by XRPD peaks located at 1, 2, 3, 4, 5, 6, 7, 8, 9, 10, 11, 12, or all of the following or approximately the following positions 10.7, 12.4, 14.2, 17.7, 18.4, 19.2, 20.4, 21.4, 21.7, 22.2, 23.0, 23.6, and 24.7 degrees 2θ, plus or minus 0.10. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by 11 of the peaks. In some embodiments, the solid form is characterized by 13 of the peaks. In some embodiments, the solid form is characterized by all of the peaks.

In some embodiments, provided herein is a solid form comprising a sulfuric acid salt of Compound 1 having an XRPD pattern comprising peaks at approximately 10.7, 12.4, and 23.6 degrees 2θ. In certain embodiments, the solid form further comprises peaks at approximately 19.2 and 20.4 degrees 2θ. In certain embodiments, the solid form further comprises peaks at approximately 17.7 and 22.2 degrees 2θ. In one embodiment, the solid form comprises peaks at approximately 10.7, 12.4, 14.2, 17.7, 18.4, 19.2, 20.4, 21.4, 21.7, 22.2, 23.0, 23.6, and 24.7 degrees 2θ.

In some embodiments, the XRPD peaks above (degrees 2θ peaks) are when analyzed using copper Kα radiation.

In some embodiments, provided herein is a solid form comprising a sulfuric acid salt of Compound 1, wherein the solid form is characterized by an XRPD diffraction pattern which matches the XRPD pattern presented in FIG. 1A, FIG. 1B, or FIG. 1C.

A representative thermal gravimetric analysis (TGA) curve of the sulfuric acid salt of Compound 1 is provided in FIG. 2A, which exhibits a weight loss of about 2.70% of the total sample weight upon heating from about 30 to about 220° C. Without being limited by any particular theory, the weight loss corresponds to loss of about 1 equivalent of water.

Another representative thermal gravimetric analysis (TGA) curve of the sulfuric acid salt of Compound 1 is provided in FIG. 2B, which exhibits a weight loss of about 2.76% of the total sample weight upon heating from about 30 to about 220° C. Without being limited by any particular theory, the weight loss corresponds to loss of about 1 equivalent of water.

Yet another representative thermal gravimetric analysis (TGA) curve of the sulfuric acid salt of Compound 1 is provided in FIG. 2C, which exhibits a weight loss of about 2.75% of the total sample weight upon heating from about 30 to about 220° C. Without being limited by any particular theory, the weight loss corresponds to loss of about 1 equivalent of water.

In some embodiments, provided herein is a solid form comprising a sulfuric acid salt of Compound 1, wherein the solid form is characterized by a TGA thermogram which matches the TGA thermogram presented in FIG. 2A, FIG. 2B, or FIG. 2C.

A representative differential scanning calorimetry (DSC) thermogram of the sulfuric acid salt of Compound 1 is presented in FIG. 3A. In some embodiments, provided herein is a solid form comprising a sulfuric acid salt of Compound 1 that exhibits a thermal event, as characterized by DSC, with a peak temperature of about 151° C. and/or an onset temperature of about 133° C. Without being limited by any particular theory, the thermal event with a peak temperature of about 151° C. and/or an onset temperature of about 133° C. corresponds to dehydration of the solid form.

Another representative differential scanning calorimetry (DSC) thermogram of the sulfuric acid salt of Compound 1 is presented in FIG. 3B. In some embodiments, provided herein is a solid form comprising a sulfuric acid salt of Compound 1 that exhibits a thermal event, as characterized by DSC, with a peak temperature of about 153° C. and/or an onset temperature of about 128° C., or with a peak temperature of about 223° C. and/or an onset temperature of about 219° C. In some embodiments, provided herein is a solid form comprising a sulfuric acid salt of Compound 1 that exhibits thermal events, as characterized by DSC, with a peak temperature of about 153° C. and/or an onset temperature of about 128° C., and with a peak temperature of about 223° C. and/or an onset temperature of about 219° C. Without being limited by any particular theory, the thermal event with a peak temperature of about 153° C. and/or an onset temperature of about 128° C. corresponds to dehydration of the solid form. Without being limited by any particular theory, the thermal event with a peak temperature of about 223° C. and/or an onset temperature of about 219° C. corresponds to melt/dissociation of the solid form.

Yet another representative differential scanning calorimetry (DSC) thermogram of the sulfuric acid salt of Compound 1 is presented in FIG. 3C. In some embodiments, provided herein is a solid form comprising a sulfuric acid salt of Compound 1 that exhibits a thermal event, as characterized by DSC, with a peak temperature of about 161° C. and/or an onset temperature of about 133° C., or with a peak temperature of about 222° C. and/or an onset temperature of about 218° C. In some embodiments, provided herein is a solid form comprising a sulfuric acid salt of Compound 1 that exhibits thermal events, as characterized by DSC, with a peak temperature of about 161° C. and/or an onset temperature of about 133° C., and with a peak temperature of about 222° C. and/or an onset temperature of about 218° C. Without being limited by any particular theory, the thermal event with a peak temperature of about 161° C. and/or an onset temperature of about 133° C. corresponds to dehydration of the solid form. Without being limited by any particular theory, the thermal event with a peak temperature of about 222° C. and/or an onset temperature of about 218° C. corresponds to melt/dissociation of the solid form.

In some embodiments, provided herein is a solid form comprising a sulfuric acid salt of Compound 1, wherein the solid form is characterized by a DSC thermogram which matches the DSC thermogram presented in FIG. 3A, FIG. 3B, or FIG. 3C.

A representative gravimetric vapor sorption (GVS) isotherm of the sulfuric acid salt of Compound 1 is presented in FIG. 4. In one embodiment, provided herein is a solid form comprising a sulfuric acid salt of Compound 1, wherein the solid form is characterized by a GVS isotherm which matches the GVS isotherm presented in FIG. 4.

Representative FT-IR spectra of the sulfuric acid salt of Compound 1 are presented in FIG. 5A and FIG. 5B. In one embodiment, provided herein is a solid form comprising a sulfuric acid salt of Compound 1, wherein the solid form is characterized by an FT-IR spectrum which matches the FT-IR spectrum presented in FIG. 5A or FIG. 5B.

In one embodiment, provided herein is a method for preparing Form 1 of the sulfuric acid salt of Compound 1 comprising (a) contacting Compound 1 with sulfuric acid in a solvent system or exposing a material comprising a sulfuric acid salt of Compound 1 to a solvent system; and (b) producing and/or recovering Form 1 of the sulfuric acid salt of Compound 1 from the mixture resulted from step (a). In one embodiment, provided herein is a method for preparing Form 1 of the sulfuric acid salt of Compound 1 comprising (a) mixing (1) a mixture of Compound 1 in a first solvent and (ii) a mixture of sulfuric acid in a second solvent; and (b) producing and/or recovering Form 1 of the sulfuric acid salt of Compound 1 from the mixture resulted from step (a).

In one embodiment, step (a) is conducted at a temperature ranging from about 20° C. to about 100° C., from about 30° C. to about 80° C., or from about 40° C. to about 60° C. In one embodiment, step (a) is conducted at about 50° C.

In one embodiment, the molar ratio of Compound 1 to sulfuric acid in step (a) ranges from about 1:1.5 to about 1:3. In one embodiment, the molar ratio ranges from about 1:1.8 to about 1:2.5. In one embodiment, the molar ratio ranges from about 1:1.9 to about 1:2.4. In one embodiment, the molar ratio ranges from about 1:2 to about 1:2.2. In one embodiment, the molar ratio is about 1:2.2.

In one embodiment, the material comprising a sulfuric acid salt of Compound 1 in step (a) comprises at least one non-Form 1 form of a sulfuric acid salt of Compound 1. In one embodiment, the non-Form 1 form of a sulfuric acid salt of Compound 1 is Form 1A, Form 1B, Form 2, Form 3, or an amorphous form of a sulfuric acid salt of Compound 1. In another embodiment, the material comprising a sulfuric acid salt of Compound 1 in step (a) comprises Form 1 of a sulfuric acid salt of Compound 1 and one or more impurities.

The solvent system (e.g., the solvent system resulted from the mixing of the first solvent and the second solvent) may be a mono-solvent system or a multi-solvent system, i.e., a binary, tertiary, or greater solvent system. In certain embodiments, step (a) and/or step (b) are conducted in a non-anhydrous condition. Where the conditions are non-anhydrous, water can be present in trace amounts, or in amounts less than about 1% by volume of solvent, or present as water vapor. In certain embodiments, the solvent system is a non-anhydrous solvent system. In certain embodiments, water can be present as a co-solvent (or anti-solvent), for example, in an amount ranging from about 1% to about 50%. For example, water can be present in about 5%, about 10%, about 15%, about 20%, about 25%, about 30%, about 35%, about 40%, about 45%, and about 50% by volume of solvent. In certain embodiments, water can be present in amounts equal to or greater than about 50% by volume of solvent. For example, water can be present in about 55%, about 60%, about 65%, about 70%, about 75%, about 80%, about 85%, about 90%, about 95%, and up to 100% by volume of solvent. In certain embodiments, liquid water is present in a multi-solvent system, for example, in an amount ranging from about 10% to about 50% by volume of the solvent system. In certain embodiments, liquid water is present in a multi-solvent system, in an amount equal to or greater than about 50% by volume of the solvent system. In certain embodiments, water can be present as water vapor or ambient humidity.

In one embodiment, the non-water solvent is a water-miscible solvent. For example, liquid water can be present in an amount of about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or about 100% by volume of the solvent system. In one embodiment, liquid water is present in an amount of between about 10% and about 50% by volume of the solvent system.

In one embodiment, the solvent system (e.g., the solvent system resulted from the mixing of the first solvent and the second solvent) comprises water and a water-miscible solvent, e.g., $C_1$-$C_4$ alcohol, acetone, acetonitrile, among others. In one embodiment, the water-miscible solvent is an alcohol, e.g., $C_1$-$C_4$ alcohol. In one embodiment, the water-miscible solvent is a $C_2$-$C_4$ alcohol. In one embodiment, the water-miscible solvent is ethanol, 1-propanol, 2-propanol, 1-butanol, 2-butanol, t-butanol, or ethylene glycol. In one embodiment, the ratio of water and water-miscible solvent in a solvent system provided herein is about 50:1, about 40:1, about 30:1, about 20:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, about 1:20, about 1:30, about 1:40, or about 1:50 v/v. In one embodiment, the ratio of water and water-miscible solvent in a solvent system provided herein is from about 50:1 to about 1:1, from about 40:1 to about 1:1, from about 30:1 to about 1:1, from about 20:1 to about 1:1, from about 10:1 to about 1:1, from about 9:1 to about 1:1, from about 8:1 to about 1:1, from about 7:1 to about 1:1, from about 6:1 to about 1:1, from about 5:1 to about 1:1, from about 4:1 to about 1:1, from about 3:1 to about 3:1, from about 2:1 to about 1:2, from about 1:1 to about 1:4, from about 1:1 to about 1:5, from about 1:1 to about 1:6, from about 1:1 to about 1:7, from about 1:1 to about 1:8, from about 1:1 to about 1:9, from about 1:1 to about 1:10, from about 1:1 to about 1:20, from about 1:1 to about 1:30, from about 1:1 to about 1:40, or from about 1:1 to about 1:50 v/v. In one embodiment, the solvent system comprises water, an alcohol, and a non-alcohol solvent.

In certain embodiments, step (b) comprises one or more of the following steps: (i) cooling a solution containing a sulfuric acid salt of Compound 1; (ii) adding an anti-solvent, with or without a cooling step, to cause precipitation of a solid material comprising a sulfuric acid salt of Compound 1; (iii) evaporating (e.g., slow evaporation or fast evaporation) a solution containing a sulfuric acid salt of Compound 1; (iv) slurrying a material comprising a sulfuric acid salt of Compound 1 in a solvent system; and (v) subjecting a material comprising a sulfuric acid salt of Compound 1 to maturation in a solvent system. In one embodiment, step (b) further comprises seeding with a Form 1 of a sulfuric acid salt of Compound 1. In one embodiment, step (b) further comprises a sonication step.

As used herein, and unless otherwise specified, the term "maturation" refers to a process of crystallization, wherein a material comprising an amorphous solid form, a gel-like form, an oily form, or other low crystalline forms of a compound is kept at a certain temperature or within a certain temperature range for a certain period of time, with or without stirring, to allow the said amorphous solid form, gel-like form, oily form, or other low crystalline forms of the compound to crystallize. A maturation process is normally conducted in a solvent system. A maturation process may involve subjecting the material to one or more heating cycle(s).

In one embodiment, provided herein is a method for preparing Form 1 of the sulfuric acid salt of Compound 1 comprising (1) contacting Compound 1 with sulfuric acid in a solvent system; (2) cooling the resulted mixture; and (3) optionally subjecting the mixture to maturation. In one embodiment, provided herein is a method for preparing Form 1 of the sulfuric acid salt of Compound 1 comprising (1) mixing (i) a mixture of Compound 1 in a first solvent and (ii) a mixture of sulfuric acid in a second solvent; (2) cooling the resulted mixture; and (3) optionally subjecting the mixture to maturation. In one embodiment, the first solvent is anisole/EtOH. In another embodiment, the first solvent is EtOH. In another embodiment, the first solvent is acetone. In one embodiment, the second solvent is water. In another embodiment, the first solvent is anisole/EtOH and the second solvent is water. In another embodiment, the first solvent is EtOH and the second solvent is water. In another embodiment, the first solvent is acetone and the second solvent is water.

In one embodiment, the solvent system (e.g., the solvent system resulted from the mixing of the first solvent and the second solvent) is a non-anhydrous solvent system. In one embodiment, the solvent system comprises water and an alcohol. In one embodiment, the solvent system comprises water and a $C_2$-$C_4$ alcohol. In one embodiment, the solvent system comprises water and EtOH. In one embodiment, the amount of water in the solvent system ranges from about 1% to about 20%, from about 2% to about 17.5%, from about 3% to about 15%, from about 4% to about 12.5%, or from about 5% to about 10%, by volume of solvent. In one embodiment, the amount of EtOH in the solvent system ranges from about 20% to about 99%, from about 20% to about 90%, from about 20% to about 80%, from about 25% to about 70%, from about 25% to about 60%, from about 25% to about 50%, or from about 30% to about 40%, by volume of solvent. In one embodiment, the solvent system is a water/EtOH mixture. In one embodiment, the solvent system is a water/EtOH mixture, wherein the amount of water in the solvent system ranges from about 3% to about 15% by volume of solvent. In another embodiment, the solvent system is a water/EtOH/anisole mixture. In one embodiment, the solvent system is a water/EtOH/anisole mixture, wherein the amount of water in the solvent system ranges from about 3% to about 5% by volume of solvent, and the amount of EtOH in the solvent system ranges from about 30% to about 40% by volume of solvent.

In one embodiment, the cooling temperature ranges from about −20° C. to about 5° C. In one embodiment, the cooling temperature is about 5° C. In one embodiment, the cooling time is at least 4 hours, at least 8 hours, or at least 24 hours.

In one embodiment, the maturation is conducted within a temperature range from about 0° C. to about 70° C., from about 10° C. to about 60° C., or from about 20° C. (room temperature) to about 50° C. In one embodiment, the maturation is conducted within a temperature range from about 20° C. (room temperature) to about 50° C. In one embodiment, the maturation is conducted for at least 4 hours, at least 8 hours, at least 24 hours, at least 48 hours, or at least 72 hours. In another embodiment, the maturation is conducted for about 4 hours, about 8 hours, about 24 hours, about 48 hours, or about 72 hours.

In one embodiment, Form 1 of a sulfuric acid salt of Compound 1 is prepared by evaporation of a solution of a sulfuric acid salt of Compound 1 in MIBK, followed by maturation in 1-BuOH.

In one embodiment, Form 1 of a sulfuric acid salt of Compound 1 is prepared by evaporation of a solution of a sulfuric acid salt of Compound 1 in 2-MeTHF, followed by maturation in acetone.

In one embodiment, Form 1 of a sulfuric acid salt of Compound 1 is prepared by cooling a solution of a sulfuric acid salt of Compound 1 in acetone/water. In one embodiment, the volume ratio of acetone to water is about 9:1. In one embodiment, the cooling temperature is about 5° C. In one embodiment, the solution is optionally seeded with Form 1 of a sulfuric acid salt of Compound 1.

In one embodiment, Form 1 of a sulfuric acid salt of Compound 1 is prepared by slow evaporation of a solution of a sulfuric acid salt of Compound 1 in EtOH/THF (ca. 5/1 v/v).

In one embodiment, Form 1 of a sulfuric acid salt of Compound 1 is prepared by cooling a solution of a sulfuric acid salt of Compound 1 in MEK/THF (ca. 5/1 v/v), followed by maturation.

In one embodiment, Form 1 of a sulfuric acid salt of Compound 1 is prepared by hydration of Form 2 of a sulfuric acid salt of Compound 1.

In one embodiment, Form 1 of the sulfuric acid salt of Compound 1 is stable after storage at 40° C./75% RH for up to 1 week.

In one embodiment, Form 1 of the sulfuric acid salt of Compound 1 is stable after maturation between RT to 50° C. for 5 days in ethanol, 2-propanol, 1-propanol, 1-butanol, 2-butanone, MIBK, acetone, ethyl acetate, anisole, anisole/methanol (50/50 v/v), toluene, isopropylacetate, TBME, 2-methyl-1-propanol, THF, 2-propanol/water (90/10 v/v), or anisole/TBME (50/50 v/v). In another embodiment, Form 1 of the sulfuric acid salt of Compound 1 is stable after maturation between RT to 50° C. for 5 days in MeOH.

All of the combinations of the above embodiments are encompassed by this invention.

Form 1A of Sulfuric Acid Salt of Compound 1

In some embodiments, provided herein is Form 1A of the sulfuric acid salt of Compound 1. In one embodiment, Form 1A of the sulfuric acid salt of Compound 1 is prepared by subjecting an amorphous sulfuric acid salt of Compound 1 to maturation in acetonitrile. In one embodiment, the crystallinity of Form 1A of the sulfuric acid salt of Compound 1 decreases after standing at RT for 24 hours. An overlay plot of representative XRPD patterns of Form 1A and Form 1 of the sulfuric acid salt of Compound 1 is provided in FIG. 6. In one embodiment, provided herein is a solid form comprising a sulfuric acid salt of Compound 1, wherein the solid form is characterized by an XRPD diffraction pattern which matches the XRPD pattern presented in FIG. 6 (bottom pattern).

Form 1B of Sulfuric Acid Salt of Compound 1

In some embodiments, provided herein is Form 1B of the sulfuric acid salt of Compound 1. In one embodiment, Form 1B of the sulfuric acid salt of Compound 1 is prepared by slow evaporation of a solution of a sulfuric acid salt of Compound 1 in an anisole/MeOH/THF mixture solvent. An overlay plot of representative XRPD patterns of Form 1B and Form 1 of the sulfuric acid salt of Compound 1 is provided in FIG. 7. In one embodiment, provided herein is a solid form comprising a sulfuric acid salt of Compound 1, wherein the solid form is characterized by an XRPD diffraction pattern which matches the XRPD pattern presented in FIG. 7 (top pattern).

A representative thermal gravimetric analysis (TGA) curve of the sulfuric acid salt of Compound 1 is provided in FIG. 8A, which exhibits a weight loss of about 3.57% of the total sample weight upon heating from about 30 to about 100° C., and a weight loss of about 2.36% of the total sample weight upon heating from about 100 to about 170° C. Without being limited by any particular theory, the weight loss corresponds to loss of solvent. In some embodiments, provided herein is a solid form comprising a sulfuric acid salt of Compound 1, wherein the solid form is characterized by a TGA thermogram which matches the TGA thermogram presented in FIG. 8A.

A representative differential scanning calorimetry (DSC) thermogram of the sulfuric acid salt of Compound 1 is presented in FIG. 8B. In some embodiments, provided herein is a solid form comprising a sulfuric acid salt of Compound 1 that exhibits a thermal event, as characterized by DSC, with a peak temperature of about 58° C. and/or an onset temperature of about 35° C., or with a peak temperature of about 129° C. and/or an onset temperature of about 110° C. In some embodiments, provided herein is a solid form comprising a sulfuric acid salt of Compound 1 that exhibits thermal events, as characterized by DSC, with a peak temperature of about 58° C. and/or an onset temperature of about 35° C., and with a peak temperature of about 129° C. and/or an onset temperature of about 110° C. In some embodiments, provided herein is a solid form comprising a sulfuric acid salt of Compound 1, wherein the solid form is characterized by a DSC thermogram which matches the DSC thermogram presented in FIG. 8B.

Form 2 of Sulfuric Acid Salt of Compound 1

In some embodiments, provided herein is Form 2 of the sulfuric acid salt of Compound 1. In one embodiment, Form 2 of the sulfuric acid salt of Compound 1 is a crystalline anhydrous bis-sulfuric acid salt of Compound 1.

In one embodiment, Form 2 of the sulfuric acid salt of Compound 1 is prepared by dehydration of Form 1 of the sulfuric acid salt of Compound 1. In one embodiment, Form 2 of the sulfuric acid salt of Compound 1 is prepared by dehydration of Form 1 of the sulfuric acid salt of Compound 1 at approximately 180° C. In some embodiments, Form 2 of the sulfuric acid of Compound 1 is unstable at ambient conditions. In one embodiment, Form 2 of the sulfuric acid of Compound 1 converts to Form 1 of the sulfuric acid of Compound 1 by hydration.

An overlay plot of representative XRPD patterns of Form 2 and Form 1 of the sulfuric acid salt of Compound 1 is provided in FIG. 9. In one embodiment, provided herein is a solid form comprising a sulfuric acid salt of Compound 1, wherein the solid form is characterized by an XRPD diffraction pattern which matches the XRPD pattern presented in FIG. 9 (the second and/or the third pattern from the top).

Form 3 of Sulfuric Acid Salt of Compound 1

In some embodiments, provided herein is Form 3 of the sulfuric acid salt of Compound 1. In one embodiment, Form 3 of the sulfuric acid salt of Compound 1 is a crystalline bis-sulfuric acid salt of Compound 1. In some embodiments, Form 3 of the sulfuric acid salt of Compound 1 is substantially free of amorphous sulfuric acid salt of Compound 1. In some embodiments, Form 3 of the sulfuric acid salt of Compound 1 is substantially free of other crystalline forms (i.e., polymorphs) of the sulfuric acid salt of Compound 1. In some embodiments, Form 3 of the sulfuric acid salt of Compound 1 is substantially free of other salts of Compound 1. In some embodiments, Form 3 of the sulfuric acid salt of Compound 1 is substantially free of the free base of Compound 1. In some embodiments, Form 3 of the sulfuric acid salt of Compound 1 is provided as substantially pure Form 3 of the sulfuric acid salt of Compound 1.

A representative XRPD pattern of Form 3 of the sulfuric acid salt of Compound 1 is provided in FIG. 10.

In some embodiments, provided herein is a solid form comprising a sulfuric acid salt of Compound 1 characterized by XRPD peaks located at 1, 2, 3, 4, 5, 6, 7, 8, 9, 10, 11, 12, 13, 14, 15, or all of the following or approximately the following positions 6.8, 7.7, 9.7, 10.4, 11.8, 12.4, 13.7, 14.1, 15.5, 15.8, 18.3, 19.3, 20.9, 21.7, 22.1, 22.8, 24.0, 24.6, 24.9, 25.3, 25.7, 26.8, 27.1, 27.6, and 28.4 degrees 2θ, plus or minus 0.10. In some embodiments, provided herein is a solid form comprising a sulfuric acid salt of Compound 1 characterized by XRPD peaks located at 1, 2, 3, 4, 5, 6, 7, 8, 9, 10, 11, 12, 13, 14, 15, or all of the following or approximately the following positions 6.8, 10.4, 11.8, 12.4, 13.7, 15.5, 15.8, 18.3, 19.3, 20.9, 21.7, 22.8, 24.6, 24.9, 25.3, and 25.7 degrees 2θ, plus or minus 0.10. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by 11 of the peaks. In some embodiments, the solid form is characterized by 13 of the peaks. In some embodiments, the solid form is characterized by all of the peaks.

In some embodiments, provided herein is a solid form comprising a sulfuric acid salt of Compound 1 having an XRPD pattern comprising peaks at approximately 13.7, 15.5, and 20.9 degrees 2θ. In certain embodiments, the solid form further comprises peaks at approximately 24.6 and 24.9 degrees 2θ. In certain embodiments, the solid form further comprises peaks at approximately 11.8 and 18.3 degrees 2θ. In one embodiment, the solid form comprises peaks at approximately 6.8, 10.4, 11.8, 12.4, 13.7, 15.5, 15.8, 18.3, 19.3, 20.9, 21.7, 22.8, 24.6, 24.9, 25.3, and 25.7 degrees 2θ.

In some embodiments, the XRPD peaks above (degrees 2θ peaks) are when analyzed using copper Kα radiation.

In some embodiments, provided herein is a solid form comprising a sulfuric acid salt of Compound 1, wherein the solid form is characterized by an XRPD diffraction pattern which matches the XRPD pattern presented in FIG. 10.

A representative thermal gravimetric analysis (TGA) curve of the sulfuric acid salt of Compound 1 is provided in FIG. 11A, which exhibits a weight loss of about 4.19% of the total sample weight upon heating from about 30 to about 150° C.

Another representative thermal gravimetric analysis (TGA) curve of the sulfuric acid salt of Compound 1 is provided in FIG. 11B, which exhibits a weight loss of about 7.28% of the total sample weight upon heating from about 30 to about 220° C.

In some embodiments, provided herein is a solid form comprising a sulfuric acid salt of Compound 1, wherein the solid form is characterized by a TGA thermogram which matches the TGA thermogram presented in FIG. 11A or FIG. 11B.

A representative differential scanning calorimetry (DSC) thermogram of the sulfuric acid salt of Compound 1 is presented in FIG. 11A. Another representative differential scanning calorimetry (DSC) thermogram of the sulfuric acid salt of Compound 1 is presented in FIG. 11B. In some embodiments, provided herein is a solid form comprising a sulfuric acid salt of Compound 1, wherein the solid form is characterized by a DSC thermogram which matches the DSC thermogram presented in FIG. 11A or FIG. 11B.

In one embodiment, provided herein is a method for preparing Form 3 of the sulfuric acid salt of Compound 1 comprising (a) contacting Compound 1 with sulfuric acid in a solvent system or exposing a material comprising a sulfuric acid salt of Compound 1 to a solvent system; and (b) producing and/or recovering Form 3 of the sulfuric acid salt of Compound 1 from the mixture resulted from step (a). In one embodiment, provided herein is a method for preparing Form 3 of the sulfuric acid salt of Compound 1 comprising (a) mixing (1) a mixture of Compound 1 in a first solvent and (ii) a mixture of sulfuric acid in a second solvent; and (b) producing and/or recovering Form 3 of the sulfuric acid salt of Compound 1 from the mixture resulted from step (a).

In one embodiment, step (a) is conducted at a temperature ranging from about 20° C. to about 100° C., from about 30° C. to about 80° C., or from about 40° C. to about 60° C. In one embodiment, step (a) is conducted at about 50° C.

In one embodiment, the molar ratio of Compound 1 to sulfuric acid in step (a) ranges from about 1:1.5 to about 1:3. In one embodiment, the molar ratio ranges from about 1:1.8 to about 1:2.5. In one embodiment, the molar ratio ranges from about 1:1.9 to about 1:2.4. In one embodiment, the molar ratio ranges from about 1:2 to about 1:2.2. In one embodiment, the molar ratio is about 1:2.2.

The solvent system (e.g., the solvent system resulted from the mixing of the first solvent and the second solvent) may be a mono-solvent system or a multi-solvent system, i.e., a binary, tertiary, or greater solvent system. In certain embodiments, step (a) and/or step (b) are conducted in a non-anhydrous condition. Where the conditions are non-anhydrous, water can be present in trace amounts, or in amounts less than about 1% by volume of solvent, or present as water vapor. In certain embodiments, the solvent system is a non-anhydrous solvent system. In certain embodiments, water can be present as a co-solvent (or anti-solvent), for example, in an amount ranging from about 1% to about 50%. For example, water can be present in about 5%, about 10%, about 15%, about 20%, about 25%, about 30%, about 35%, about 40%, about 45%, and about 50% by volume of solvent. In certain embodiments, water can be present in amounts equal to or greater than about 50% by volume of solvent. For example, water can be present in about 55%, about 60%, about 65%, about 70%, about 75%, about 80%, about 85%, about 90%, about 95%, and up to 100% by volume of solvent. In certain embodiments, liquid water is present in a multi-solvent system, for example, in an amount ranging from about 10% to about 50% by volume of the solvent system. In certain embodiments, liquid water is present in a multi-solvent system, in an amount equal to or greater than about 50% by volume of the solvent system. In certain embodiments, water can be present as water vapor or ambient humidity.

In one embodiment, the non-water solvent is a water-miscible solvent. For example, liquid water can be present in an amount of about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or about 100% by volume of the solvent system. In one embodiment, liquid water is present in an amount of between about 10% and about 50% by volume of the solvent system.

In one embodiment, the solvent system (e.g., the solvent system resulted from the mixing of the first solvent and the second solvent) comprises water and a water-miscible solvent, e.g., $C_1$-$C_4$ alcohol, acetone, acetonitrile, among others. In one embodiment, the water-miscible solvent is an alcohol, e.g., $C_1$-$C_4$ alcohol. In one embodiment, the water-miscible solvent is a $C_2$-$C_4$ alcohol. In one embodiment, the water-miscible solvent is ethanol, 1-propanol, 2-propanol, 1-butanol, 2-butanol, t-butanol, or ethylene glycol. In one embodiment, the ratio of water and water-miscible solvent in a solvent system provided herein is about 50:1, about 40:1, about 30:1, about 20:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, about 1:20, about 1:30, about 1:40, or about 1:50 v/v. In one embodiment, the ratio of water and water-miscible solvent in a solvent system provided herein is from about 50:1 to about 1:1, from about 40:1 to about 1:1, from about 30:1 to about 1:1, from about 20:1 to about 1:1, from about 10:1 to about 1:1, from about 9:1 to about 1:1, from about 8:1 to about 1:1, from about 7:1 to about 1:1, from about 6:1 to about 1:1, from about 5:1 to about 1:1, from about 4:1 to about 1:1, from about 3:1 to about 3:1, from about 2:1 to about 1:2, from about 1:1 to about 1:4, from about 1:1 to about 1:5, from about 1:1 to about 1:6, from about 1:1 to about 1:7, from about 1:1 to about 1:8, from about 1:1 to about 1:9, from about 1:1 to about 1:10, from about 1:1 to about 1:20, from about 1:1 to about 1:30, from about 1:1 to about 1:40, or from about 1:1 to about 1:50 v/v. In one embodiment, the solvent system comprises water, an alcohol, and a non-alcohol solvent.

In certain embodiments, step (b) comprises one or more of the following steps: (i) cooling a solution containing a sulfuric acid salt of Compound 1; and (ii) adding an anti-solvent, with or without a cooling step, to cause precipitation of a solid material comprising a sulfuric acid salt of Compound 1.

In one embodiment, provided herein is a method for preparing Form 3 of the sulfuric acid salt of Compound 1 comprising (1) contacting Compound 1 with sulfuric acid in a solvent system; and (2) adding an anti-solvent and/or cooling the resulted mixture. In one embodiment, provided herein is a method for preparing Form 3 of the sulfuric acid salt of Compound 1 comprising (1) mixing (i) a mixture of Compound 1 in a first solvent and (ii) a mixture of sulfuric acid in a second solvent; and (2) adding an anti-solvent and/or cooling the resulted mixture. In one embodiment, the first solvent is EtOH. In one embodiment, the second solvent is water. In one embodiment, the first solvent is EtOH and the second solvent is water. In one embodiment, the method does not comprise a maturation step. In one embodiment, the anti-solvent is EtOH.

In one embodiment, the solvent system (e.g., the solvent system resulted from the mixing of the first solvent and the second solvent) is a non-anhydrous solvent system. In one embodiment, the solvent system comprises water and an alcohol. In one embodiment, the solvent system comprises water and a $C_2$-$C_4$ alcohol. In one embodiment, the solvent system comprises water and EtOH. In one embodiment, the amount of water in the solvent system ranges from about 1% to about 20%, from about 2% to about 17.5%, from about 3% to about 15%, from about 4% to about 12.5%, or from about 5% to about 10%, by volume of solvent. In one embodiment, the amount of EtOH in the solvent system ranges from about 20% to about 99%, from about 20% to about 90%, from about 20% to about 80%, from about 25% to about 70%, from about 25% to about 60%, from about 25% to about 50%, or from about 30% to about 40%, by volume of solvent. In one embodiment, the solvent system is a water/EtOH mixture. In one embodiment, the solvent system is a water/EtOH mixture, wherein the amount of water in the solvent system ranges from about 3% to about 15% by volume of solvent.

In one embodiment, the cooling temperature ranges from about −20° C. to about 5° C. In one embodiment, the cooling temperature is about 5° C. In one embodiment, the cooling time is at least 4 hours, at least 8 hours, or at least 24 hours.

In one embodiment, Form 3 of the sulfuric acid salt of Compound 1 converts to Form 1 of the sulfuric acid salt of Compound 1 after maturation in 10% water/EtOH between RT and 50° C. for 3 days. In one embodiment, Form 3 of the sulfuric acid salt of Compound 1 converts to Form 1 of the sulfuric acid salt of Compound 1 after maturation in anisole between RT and 50° C. for 3 days.

Amorphous Sulfuric Acid Salt of Compound 1

In some embodiments, provided herein is an amorphous sulfuric acid salt of Compound 1. In one embodiment, the amorphous sulfuric acid salt of Compound 1 is prepared by evaporation of a solution of a sulfuric acid salt of Compound 1 in a solvent. In one embodiment, the solvent is MeOH. In one embodiment, the amorphous sulfuric acid salt of Compound 1 contains about 0.3 equivalent of MeOH.

In one embodiment, the amorphous sulfuric acid salt of Compound 1 remains as amorphous sulfuric acid salt of Compound 1 after maturation between RT to 50° C. for 24 or 48 hours in toluene, DCM, THF, EtOAc, BuOAc, TBME, dioxane, IPA, or DIPE.

5.2.2 Maleic Acid Salt of Compound 1

In some embodiments, provided herein is a maleic acid salt of Compound 1. It is contemplated that a maleic acid salt of Compound 1 can exist in a variety of solid forms. Such solid forms include crystalline solids, such as polymorphs, solvates and hydrates of crystalline maleic acid salt of Compound 1, as well as amorphous solids, or mixtures thereof. All such solid forms of maleic acid salt of Compound 1 are contemplated under the present invention.

As used here, and unless otherwise specified, the term "a maleic acid salt" refers to a salt comprising at least one counterion derived from maleic acid (cis-HOOC—CH═CH—COOH). A counterion derived from maleic acid include, but are not limited to, cis-HOOC—CH═CH—COO⁻ and cis-⁻OOC—CH═CH—COO⁻. The molar ratio of the cation to the coutnerion derived from maleic acid in a maleic acid salt can be any ratio known in the art. Exemplary molar ratios include, but are not limited to, about 1:2 (i.e., bis-maleic acid salt), about 1:1 (i.e., mono-maleic acid salt), and about 2:1 (i.e., hemi-maleic acid salt). The term "a maleic acid salt" includes all forms of the salt, including, but not limited to, an amorphous form, a crystalline form, an anhydrous form, a solvate form (e.g., a hydrate form), of the salt, or a combination or mixture thereof.

In one embodiment, provided herein is a solid form comprising a maleic acid salt of Compound 1, or a solvate (e.g., hydrate) thereof. In one embodiment, provided herein is a solid form comprising an anhydrous maleic acid salt of Compound 1. In one embodiment, provided herein is a solid form comprising a crystalline form of an anhydrous maleic acid salt of Compound 1. In one embodiment, the anhydrous maleic acid salt of Compound 1 is an anhydrous mono-maleic acid salt.

In some embodiments, the molar ratio of Compound 1 to maleic acid in the solid form ranges from about 2:1 to about 1:2. In one embodiment, the molar ratio is about 1:2 (i.e., bis-maleic acid salt). In another embodiment, the molar ratio is about 1:1 (i.e., mono-maleic acid salt). In yet another embodiment, the molar ratio is about 2:1 (i.e., hemi-maleic acid salt).

In some embodiments, the molar ratio of Compound 1 to the solvent/water in the solid form ranges from about 2:1 to about 1:2. In one embodiment, the molar ratio is about 1:2 (i.e., bis-solvate/hydrate). In another embodiment, the molar ratio is about 1:1 (i.e., mono-solvate/hydrate). In yet another embodiment, the molar ratio is about 2:1 (i.e., hemi-solvate/hydrate).

Form 1 of Maleic Acid Salt of Compound 1

In some embodiments, provided herein is Form 1 of the maleic acid salt of Compound 1. In one embodiment, Form 1 of the maleic acid salt of Compound 1 is a crystalline anhydrous mono-maleic acid salt of Compound 1. In some embodiments, Form 1 of the maleic acid salt of Compound 1 is substantially free of amorphous maleic acid salt of Compound 1. In some embodiments, Form 1 of the maleic acid salt of Compound 1 is substantially free of other crystalline forms (i.e., polymorphs) of the maleic acid salt of Compound 1. In some embodiments, Form 1 of the maleic acid salt of Compound 1 is substantially free of other salts of Compound 1. In some embodiments, Form 1 of the maleic acid salt of Compound 1 is substantially free of the free base of Compound 1. In some embodiments, Form 1 of the maleic acid salt of Compound 1 is provided as substantially pure Form 1 of the maleic acid salt of Compound 1.

Representative XRPD patterns of Form 1 of the maleic acid salt of Compound 1 are provided in FIG. 12A, FIG. 12B, and FIG. 12C.

In some embodiments, provided herein is a solid form comprising a maleic acid salt of Compound 1 characterized by XRPD peaks located at 1, 2, 3, 4, 5, 6, 7, 8, 9, 10, 11, 12, 13, 14, 15, or all of the following or approximately the following positions: 6.2, 9.0, 11.3, 11.7, 12.4, 12.9, 13.0, 13.4, 14.4, 14.6, 16.0, 16.8, 17.5, 18.0, 18.3, 18.6, 19.6, 19.8, 20.3, 21.3, 21.7, 22.6, 23.2, 23.5, and 24.4 degrees 2θ, plus or minus 0.10. In some embodiments, provided herein is a solid form comprising a maleic acid salt of Compound 1 characterized by XRPD peaks located at 1, 2, 3, 4, 5, 6, 7, 8, 9, 10, 11, 12, 13, or all of the following or approximately the following positions: 6.2, 9.0, 12.4, 12.9, 13.0, 13.4, 14.6, 16.0, 18.0, 18.6, 19.6, 22.6, 23.5, and 24.4 degrees 2θ, plus or minus 0.10. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by 11 of the peaks. In some embodiments, the solid form is characterized by 13 of the peaks. In some embodiments, the solid form is characterized by all of the peaks.

In some embodiments, provided herein is a solid form comprising a maleic acid salt of Compound 1 having an XRPD pattern comprising peaks at approximately 9.0, 16.0, and 22.6 degrees 2θ. In certain embodiments, the solid form further comprises peaks at approximately 18.6 and 24.4 degrees 2θ. In certain embodiments, the solid form further comprises peaks at approximately 12.9 and 13.0 degrees 2θ. In one embodiment, the solid form comprises peaks at approximately 6.2, 9.0, 12.4, 12.9, 13.0, 13.4, 14.6, 16.0, 18.0, 18.6, 19.6, 22.6, 23.5, and 24.4 degrees 2θ.

In some embodiments, the XRPD peaks above (degrees 2θ peaks) are when analyzed using copper Kα radiation.

In some embodiments, provided herein is a solid form comprising a maleic acid salt of Compound 1, wherein the solid form is characterized by an XRPD diffraction pattern which matches the XRPD pattern presented in FIG. 12A, FIG. 12B, or FIG. 12C.

A representative thermal gravimetric analysis (TGA) curve of the maleic acid salt of Compound 1 is provided in FIG. 13A, which exhibits no substantial weight loss upon heating from about 30 to about 170° C., and which exhibits a weight loss of about 12.48% of the total sample weight upon heating from about 170 to about 220° C. Without being limited by any particular theory, the weight loss corresponds to dissociation of the solid form.

Another representative thermal gravimetric analysis (TGA) curve of the maleic acid salt of Compound 1 is provided in FIG. 13B, which exhibits no substantial weight loss upon heating from about 30 to about 170° C.

Yet another representative thermal gravimetric analysis (TGA) curve of the maleic acid salt of Compound 1 is provided in FIG. 13C, which exhibits no substantial weight loss upon heating from about 30 to about 170° C.

In some embodiments, provided herein is a solid form comprising a maleic acid salt of Compound 1, wherein the solid form is characterized by a TGA thermogram which matches the TGA thermogram presented in FIG. 13A, FIG. 13B, or FIG. 13C.

A representative differential scanning calorimetry (DSC) thermogram of the maleic acid salt of Compound 1 is presented in FIG. 14A. In some embodiments, provided herein is a solid form comprising a maleic acid salt of Compound 1 that exhibits a thermal event, as characterized by DSC, with a peak temperature of about 196° C. and/or an onset temperature of about 191° C. Without being limited by any particular theory, the thermal event with a peak temperature of about 196° C. and/or an onset temperature of about 191° C. corresponds to melt/dissociation of the solid form.

Another representative differential scanning calorimetry (DSC) thermogram of the maleic acid salt of Compound 1 is presented in FIG. 14B. In some embodiments, provided herein is a solid form comprising a maleic acid salt of Compound 1 that exhibits a thermal event, as characterized by DSC, with a peak temperature of about 196° C. and/or an onset temperature of about 191° C. Without being limited by any particular theory, the thermal event with a peak temperature of about 196° C. and/or an onset temperature of about 191° C. corresponds to melt/dissociation of the solid form.

Yet another representative differential scanning calorimetry (DSC) thermogram of the maleic acid salt of Compound 1 is presented in FIG. 14C. In some embodiments, provided herein is a solid form comprising a maleic acid salt of Compound 1 that exhibits a thermal event, as characterized by DSC, with a peak temperature of about 197° C. and/or an onset temperature of about 192° C. Without being limited by any particular theory, the thermal event with a peak temperature of about 197° C. and/or an onset temperature of about 192° C. corresponds to melt/dissociation of the solid form.

In some embodiments, provided herein is a solid form comprising a maleic acid salt of Compound 1, wherein the solid form is characterized by a DSC thermogram which matches the DSC thermogram presented in FIG. 14A, FIG. 14B, or FIG. 14C.

A representative gravimetric vapor sorption (GVS) isotherm of the maleic acid salt of Compound 1 is presented in FIG. 15. In one embodiment, provided herein is a solid form comprising a maleic acid salt of Compound 1, wherein the solid form is characterized by a GVS isotherm which matches the GVS isotherm presented in FIG. 15.

Representative FT-IR spectra of the maleic acid salt of Compound 1 are presented in FIG. 16A and FIG. 16B. In one embodiment, provided herein is a solid form comprising a maleic acid salt of Compound 1, wherein the solid form is characterized by an FT-IR spectrum which matches the FT-IR spectrum presented in FIG. 16A or FIG. 16B.

In one embodiment, provided herein is a method for preparing Form 1 of the maleic acid salt of Compound 1 comprising (a) contacting Compound 1 with maleic acid in a solvent system or exposing a material comprising a maleic acid salt of Compound 1 to a solvent system; and (b) producing and/or recovering Form 1 of the maleic acid salt of Compound 1 from the mixture resulted from step (a). In one embodiment, provided herein is a method for preparing Form 1 of the maleic acid salt of Compound 1 comprising (a) mixing (1) a mixture of Compound 1 in a first solvent and (ii) a mixture of maleic acid in a second solvent; and (b) producing and/or recovering Form 1 of the maleic acid salt of Compound 1 from the mixture resulted from step (a).

In one embodiment, step (a) is conducted at a temperature ranging from about 20° C. to about 100° C., from about 30° C. to about 80° C., or from about 40° C. to about 60° C. In one embodiment, step (a) is conducted at about 50° C.

In one embodiment, the molar ratio of maleic acid to Compound 1 in step (a) ranges from about 0.4:1 to about 3:1. In one embodiment, the molar ratio ranges from about 0.4:1 to about 0.6:1, from about 1:1 to about 1.3:1, or from about 2:1 to about 2.4:1. In one embodiment, the molar ratio ranges from about 0.4:1 to about 0.6:1. In one embodiment, the molar ratio is about 0.5:1. In one embodiment, the molar ratio ranges from about 1:1 to about 1.3:1. In one embodiment, the molar ratio is about 1.1:1. In one embodiment, the molar ratio ranges from about 2:1 to about 2.4:1. In one embodiment, the molar ratio is about 2.2:1.

In one embodiment, the material comprising a maleic acid salt of Compound 1 in step (a) comprises at least one non-Form 1 form of a maleic acid salt of Compound 1. In one embodiment, the non-Form 1 form of a maleic acid salt of Compound 1 is an amorphous form of a maleic acid salt of Compound 1. In another embodiment, the material comprising a maleic acid salt of Compound 1 in step (a) comprises Form 1 of a maleic acid salt of Compound 1 and one or more impurities.

In certain embodiments, step (b) comprises one or more of the following steps: (i) cooling a solution containing a maleic acid salt of Compound 1; (ii) adding an anti-solvent, with or without a cooling step, to cause precipitation of a solid material comprising a maleic acid salt of Compound 1; (iii) evaporating (e.g., slow evaporation or fast evaporation) a solution containing a maleic acid salt of Compound 1; (iv) slurrying a material comprising a maleic acid salt of Compound 1 in a solvent system; and (v) subjecting a material comprising a maleic acid salt of Compound 1 to maturation in a solvent system. In one embodiment, step (b) further comprises seeding with a Form 1 of a maleic acid salt of Compound 1. In one embodiment, step (b) further comprises a sonication step.

In one embodiment, provided herein is a method for preparing Form 1 of the maleic acid salt of Compound 1 comprising (1) contacting Compound 1 with maleic acid in a solvent system; (2) cooling the resulted mixture; and (3) optionally subjecting the mixture to maturation. In one embodiment, provided herein is a method for preparing Form 1 of the maleic acid salt of Compound 1 comprising (1) mixing (i) a mixture of Compound 1 in a first solvent and (ii) a mixture of maleic acid in a second solvent; (2) cooling the resulted mixture; and (3) optionally subjecting the mixture to maturation. In one embodiment, the first solvent is anisole. In another embodiment, the first solvent is MIBK. In one embodiment, the second solvent is THF. In another embodiment, the second solvent is IPA. In another embodiment, the second solvent is EtOH. In one embodiment, the first solvent is MIBK and the second solvent is THF. In another embodiment, the first solvent is anisole and the second solvent is THF. In another embodiment, the first solvent is anisole and the second solvent is EtOH. In another embodiment, the first solvent is anisole and the second solvent is IPA.

In one embodiment, the cooling temperature ranges from about −20° C. to about 5° C. In one embodiment, the cooling temperature is about 5° C. In one embodiment, the cooling time is at least 4 hours, at least 8 hours, or at least 24 hours.

In one embodiment, the maturation is conducted within a temperature range from about 0° C. to about 70° C., from about 10° C. to about 60° C., or from about 20° C. (room temperature) to about 50° C. In one embodiment, the maturation is conducted within a temperature range from about 20° C. (room temperature) to about 50° C. In one embodiment, the maturation is conducted for at least 4 hours, at least 8 hours, at least 24 hours, at least 48 hours, or at least 72 hours. In another embodiment, the maturation is conducted for about 4 hours, about 8 hours, about 24 hours, about 48 hours, or about 72 hours.

In one embodiment, Form 1 of a maleic acid salt of Compound 1 is prepared by evaporation of a solution of a maleic acid salt of Compound 1 in MeOH/THF, followed by maturation in TBME.

In one embodiment, Form 1 of a maleic acid salt of Compound 1 is prepared by cooling a solution of a maleic acid salt of Compound 1 in MIBK/THF. In one embodiment, the volume ratio of MIBK to THF is about 9:1. In one embodiment, Form 1 of a maleic acid salt of Compound 1 is prepared by cooling a solution of a maleic acid salt of Compound 1 in 2-butanone/MEK. In one embodiment, Form 1 of a maleic acid salt of Compound 1 is prepared by cooling a solution of a maleic acid salt of Compound 1 in ethyl acetate. In one embodiment, Form 1 of a maleic acid salt of Compound 1 is prepared by cooling a solution of a maleic acid salt of Compound 1 in MEK. In one embodiment, Form 1 of a maleic acid salt of Compound 1 is prepared by cooling a solution of a maleic acid salt of Compound 1 in anisole/THF. In one embodiment, the cooling temperature is about 5° C. In one embodiment, the solution is optionally seeded with Form 1 of a maleic acid salt of Compound 1.

In one embodiment, Form 1 of a maleic acid salt of Compound 1 is prepared by maturation of an amorphous maleic acid salt of Compound 1 in 1-butanol. In one embodiment, Form 1 of a maleic acid salt of Compound 1 is prepared by maturation of an amorphous maleic acid salt of Compound 1 in 2-butanone. In one embodiment, Form 1 of a maleic acid salt of Compound 1 is prepared by maturation of an amorphous maleic acid salt of Compound 1 in MIBK. In one embodiment, Form 1 of a maleic acid salt of Compound 1 is prepared by maturation of an amorphous maleic acid salt of Compound 1 in ethyl acetate. In one embodiment, Form 1 of a maleic acid salt of Compound 1 is prepared by maturation of an amorphous maleic acid salt of Compound 1 in anisole. In one embodiment, Form 1 of a maleic acid salt of Compound 1 is prepared by maturation of an amorphous maleic acid salt of Compound 1 in toluene. In one embodiment, Form 1 of a maleic acid salt of Compound 1 is prepared by maturation of an amorphous maleic acid salt of Compound 1 in isopropylacetate. In one embodiment, Form 1 of a maleic acid salt of Compound 1 is prepared by maturation of an amorphous maleic acid salt of Compound 1 in 2-methyl-1-propanol. In one embodiment, Form 1 of a maleic acid salt of Compound 1 is prepared by maturation of an amorphous maleic acid salt of Compound 1 in 2-MeTHF. In one embodiment, Form 1 of a maleic acid salt of Compound 1 is prepared by maturation of an amorphous maleic acid salt of Compound 1 in acetonitrile. In one embodiment, the maturation is conducted between RT and about 50° C. for about 3 days.

In one embodiment, Form 1 of the maleic acid salt of Compound 1 is stable after storage at 40° C./75% RH for up to 1 week.

In one embodiment, Form 1 of the maleic acid salt of Compound 1 is stable after maturation between RT to 50° C. for 3 days in 1-butanol, MIBK, ethyl acetate, anisole, anisole/methanol (50/50 v/v), toluene, isopropylacetate, TBME, 2-methyl-1-propanol, or anisole/TBME (50/50 v/v).

In one embodiment, Form 1 of the maleic acid salt of Compound 1 converts to Form 2 of the free base of Compound 1 after maturation between RT to 50° C. for 3 days in 2-propanol/water (90/10 v/v) or acetic acid/water (25/75 v/v).

In one embodiment, Form 1 of the maleic acid salt of Compound 1 converts to Form 5 of the free base of Compound 1 after maturation between RT to 50° C. for 3 days in ethanol, 2-propanol, 1-propanol, acetone, THF, or EtOH/water (90/10 v/v).

In one embodiment, Form 1 of the maleic acid salt of Compound 1 converts to an amorphous compound of formula (I) after maturation between RT to 50° C. for 3 days in 2-butanone or MeOH.

All of the combinations of the above embodiments are encompassed by this invention.

Amorphous Maleic Acid Salt of Compound 1

In some embodiments, provided herein is an amorphous maleic acid salt of Compound 1. In one embodiment, the amorphous maleic acid salt of Compound 1 is prepared by evaporation of a solution of a maleic acid salt of Compound 1 in a solvent. In one embodiment, the solvent is MeOH. In one embodiment, the amorphous maleic acid salt of Compound 1 contains about 0.9 equivalent of maleic acid and/or about 0.6 equivalent of MeOH.

In one embodiment, the amorphous maleic acid salt of Compound 1 converts to Form 1 of the maleic acid salt of Compound 1 after maturation between RT to 50° C. for 3 days in 1-butanol, 2-butanone, MIBK, ethyl acetate, anisole, toluene, isopropylacetate, 2-methyl-1-propanol, 2-MeTHF, or acetonitrile.

5.2.3 1,2-Ethanedisulfonic Acid Salt of Compound 1

In some embodiments, provided herein is an 1,2-ethanedisulfonic acid salt of Compound 1. It is contemplated that an 1,2-ethanedisulfonic acid salt of Compound 1 can exist in a variety of solid forms. Such solid forms include crystalline solids, such as polymorphs, solvates and hydrates of crystalline 1,2-ethanedisulfonic acid salt of Compound 1, as well as amorphous solids, or mixtures thereof. All such solid forms of 1,2-ethanedisulfonic acid salt of Compound 1 are contemplated under the present invention.

As used here, and unless otherwise specified, the term "a 1,2-ethanedisulfonic acid salt" refers to a salt comprising at least one counterion derived from 1,2-ethanedisulfonic acid ($HO_3S$—$CH_2CH_2$—$SO_3H$). A counterion derived from 1,2-ethanedisulfonic acid include, but are not limited to, $HO_3S$—$CH_2CH_2$—$SO_3^-$ and $^-O_3S$—$CH_2CH_2$—$SO_3^-$. The molar ratio of the cation to the coutnerion derived from 1,2-ethanedisulfonic acid in a 1,2-ethanedisulfonic acid salt can be any ratio known in the art. Exemplary molar ratios include, but are not limited to, about 1:2 (i.e., bis-1,2-ethanedisulfonic acid salt), about 1:1 (i.e., mono-1,2-ethanedisulfonic acid salt), and about 2:1 (i.e., hemi-1,2-ethanedisulfonic acid salt). The term "a 1,2-ethanedisulfonic acid salt" includes all forms of the salt, including, but not limited to, an amorphous form, a crystalline form, an anhydrous form, a solvate form (e.g., a hydrate form), of the salt, or a combination or mixture thereof.

In one embodiment, provided herein is a solid form comprising an 1,2-ethanedisulfonic acid salt of Compound 1, or a solvate (e.g., hydrate) thereof. In one embodiment, provided herein is a solid form comprising a solvate of an 1,2-ethanedisulfonic acid salt of Compound 1. In one embodiment, provided herein is a solid form comprising a hydrate of an 1,2-ethanedisulfonic acid salt of Compound 1. In one embodiment, provided herein is a solid form comprising a crystalline form of an 1,2-ethanedisulfonic acid salt of Compound 1, or a solvate (e.g., hydrate) thereof. In one embodiment, provided herein is a solid form comprising a crystalline form of a solvate of an 1,2-ethanedisulfonic acid salt of Compound 1. In one embodiment, provided herein is a solid form comprising a crystalline form of a hydrate of an 1,2-ethanedisulfonic acid salt of Compound 1.

In some embodiments, the molar ratio of Compound 1 to 1-2-ethane disulfonic acid in the solid form ranges from about 2:1 to about 1:2. In one embodiment, the molar ratio is about 1:2 (i.e., bis-1,2-ethanedisulfonic acid salt). In another embodiment, the molar ratio is about 1:1 (i.e., mono-1,2-ethanedisulfonic acid salt). In yet another embodiment, the molar ratio is about 2:1 (i.e., hemi-1,2-ethanedisulfonic acid salt).

In some embodiments, the molar ratio of Compound 1 to the solvent/water in the solid form ranges from about 2:1 to about 1:2. In one embodiment, the molar ratio is about 1:2 (i.e., bis-solvate/hydrate). In another embodiment, the molar ratio is about 1:1 (i.e., mono-solvate/hydrate). In yet another embodiment, the molar ratio is about 2:1 (i.e., hemi-solvate/hydrate).

In one embodiment, the hydrate of the 1,2-ethanedisulfonic acid salt of Compound 1 is a hydrate of a mono-1,2-ethanedisulfonic acid salt of Compound 1. In one embodiment, the hydrate of the 1,2-ethanedisulfonic acid salt of Compound 1 is a monohydrate of a mono-1,2-ethanedisulfonic acid salt of Compound 1.

Form 1 of 1,2-Ethanedisulfonic Acid Salt of Compound 1

In some embodiments, provided herein is Form 1 of the 1,2-ethanedisulfonic acid salt of Compound 1. In one embodiment, Form 1 of the 1,2-ethanedisulfonic acid salt of Compound 1 is a crystalline hydrate of mono-1,2-ethanedisulfonic acid salt of Compound 1. In some embodiments, Form 1 of the 1,2-ethanedisulfonic acid salt of Compound 1 is substantially free of amorphous 1,2-ethanedisulfonic acid salt of Compound 1. In some embodiments, Form 1 of the 1,2-ethanedisulfonic acid salt of Compound 1 is substantially free of other crystalline forms (i.e., polymorphs) of the 1,2-ethanedisulfonic acid salt of Compound 1. In some embodiments, Form 1 of the 1,2-ethanedisulfonic acid salt of Compound 1 is substantially free of other salts of Compound 1. In some embodiments, Form 1 of the 1,2-ethanedisulfonic acid salt of Compound 1 is substantially free of the free base of Compound 1. In some embodiments, Form 1 of the 1,2-ethanedisulfonic acid salt of Compound 1 is provided as substantially pure Form 1 of the 1,2-ethanedisulfonic acid salt of Compound 1.

Representative XRPD patterns of Form 1 of the 1,2-ethanedisulfonic acid salt of Compound 1 are provided in FIG. 17A and FIG. 17B.

In some embodiments, provided herein is a solid form comprising an 1,2-ethanedisulfonic acid salt of Compound 1 characterized by XRPD peaks located at 1, 2, 3, 4, 5, 6, 7, 8, 9, 10, 11, 12, 13, 14, 15, or all of the following or approximately the following positions: 7.9, 8.5, 10.3, 10.7, 11.0, 12.4, 12.7, 14.0, 14.3, 15.3, 15.9, 17.2, 17.4, 18.1, 18.3, 18.4, 18.7, 19.2, 20.5, 20.6, 21.2, 21.5, 21.9, 22.4, 22.8, and 23.3 degrees 2θ, plus or minus 0.10. In some embodiments, provided herein is a solid form comprising an 1,2-ethanedisulfonic acid salt of Compound 1 characterized by XRPD peaks located at 1, 2, 3, 4, 5, 6, 7, 8, 9, 10, 11, 12, 13, 14, or all of the following or approximately the following positions: 7.9, 10.3, 12.7, 14.3, 17.2, 18.1, 18.3, 18.7, 19.2, 20.5, 21.2, 21.9, 22.4, 22.8, and 23.3 degrees 2θ, plus or minus 0.10. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by 11 of the peaks. In some embodiments, the solid form is characterized by 13 of the peaks. In some embodiments, the solid form is characterized by all of the peaks.

In some embodiments, provided herein is a solid form comprising an 1,2-ethanedisulfonic acid salt of Compound 1 having an XRPD pattern comprising peaks at approximately 10.3, 12.7, and 23.3 degrees 2θ. In certain embodiments, the solid form further comprises peaks at approximately 14.3 and 18.1 degrees 2θ. In certain embodiments, the solid form further comprises peaks at approximately 17.2 and 21.9 degrees 2θ. In one embodiment, the solid form comprises peaks at approximately 7.9, 10.3, 12.7, 14.3, 17.2, 18.1, 18.3, 18.7, 19.2, 20.5, 21.2, 21.9, 22.4, 22.8, and 23.3 degrees 2θ.

In some embodiments, the XRPD peaks above (degrees 2θ peaks) are when analyzed using copper Kα radiation.

In some embodiments, provided herein is a solid form comprising an 1,2-ethanedisulfonic acid salt of Compound 1, wherein the solid form is characterized by an XRPD diffraction pattern which matches the XRPD pattern presented in FIG. 17A or FIG. 17B.

A representative thermal gravimetric analysis (TGA) curve of the 1,2-ethanedisulfonic acid salt of Compound 1 is provided in FIG. 18A, which exhibits a weight loss of about 7.79% of the total sample weight upon heating from about 30 to about 220° C. Without being limited by any particular theory, the weight loss corresponds to loss of water and/or solvent.

Another representative thermal gravimetric analysis (TGA) curve of the 1,2-ethanedisulfonic acid salt of Compound 1 is provided in FIG. 18B, which exhibits a weight loss of about 3.67% of the total sample weight upon heating from about 30 to about 110° C. and a weight loss of about 3.06% of the total sample weight upon heating from about 110° C. to about 220° C. Without being limited by any particular theory, the weight losses correspond to loss of water and/or solvate.

In some embodiments, provided herein is a solid form comprising an 1,2-ethanedisulfonic acid salt of Compound 1, wherein the solid form is characterized by a TGA thermogram which matches the TGA thermogram presented in FIG. 18A or FIG. 18B.

A representative differential scanning calorimetry (DSC) thermogram of the 1,2-ethanedisulfonic acid salt of Compound 1 is presented in FIG. 19A. In some embodiments, provided herein is a solid form comprising an 1,2-ethanedisulfonic acid salt of Compound 1 that exhibits a thermal event, as characterized by DSC, with a peak temperature of about 130° C. and/or an onset temperature of about 125° C., or with a peak temperature of about 185° C. and/or an onset temperature of about 163° C. In some embodiments, provided herein is a solid form comprising an 1,2-ethanedisulfonic acid salt of Compound 1 that exhibits thermal events, as characterized by DSC, with a peak temperature of about 130° C. and/or an onset temperature of about 125° C., and with a peak temperature of about 185° C. and/or an onset temperature of about 163° C. Without being limited by any particular theory, the thermal events correspond to loss of water and/or solvent.

Another representative differential scanning calorimetry (DSC) thermogram of the 1,2-ethanedisulfonic acid salt of Compound 1 is presented in FIG. 19B. In some embodiments, provided herein is a solid form comprising an 1,2-ethanedisulfonic acid salt of Compound 1 that exhibits a thermal event, as characterized by DSC, with a peak temperature of about 53° C. and/or an onset temperature of about 28° C., or with a peak temperature of about 193° C. and/or an onset temperature of about 168° C. In some embodiments, provided herein is a solid form comprising an 1,2-ethanedisulfonic acid salt of Compound 1 that exhibits thermal events, as characterized by DSC, with a peak temperature of about 53° C. and/or an onset temperature of about 28° C., and with a peak temperature of about 193° C. and/or an onset temperature of about 168° C. Without being limited by any particular theory, the thermal events correspond to loss of water and/or solvent.

In some embodiments, provided herein is a solid form comprising an 1,2-ethanedisulfonic acid salt of Compound 1, wherein the solid form is characterized by a DSC thermogram which matches the DSC thermogram presented in FIG. 19A or FIG. 19B.

In one embodiment, provided herein is a method for preparing Form 1 of the 1,2-ethanedisulfonic acid salt of Compound 1 comprising (a) contacting Compound 1 with 1,2-ethanedisulforic acid in a solvent system or exposing a material comprising an 1,2-ethanedisulfonic acid salt of Compound 1 to a solvent system; and (b) producing and/or recovering Form 1 of the 1,2-ethanedisulfonic acid salt of Compound 1 from the mixture resulted from step (a). In one embodiment, provided herein is a method for preparing Form 1 of the 1,2-ethanedisulfonic acid salt of Compound 1 comprising (a) mixing (1) a mixture of Compound 1 in a first solvent and (ii) a mixture of 1,2-ethanedisulfonic acid in a second solvent; and (b) producing and/or recovering Form 1 of the 1,2-ethanedisulfonic acid salt of Compound 1 from the mixture resulted from step (a).

In one embodiment, step (a) is conducted at a temperature ranging from about 20° C. to about 100° C., from about 30° C. to about 80° C., or from about 40° C. to about 60° C. In one embodiment, step (a) is conducted at about 50° C.

In one embodiment, the molar ratio of 1,2-ethanedisulforic acid to Compound 1 in step (a) ranges from about 0.4:1 to about 3:1. In one embodiment, the molar ratio ranges from about 0.4:1 to about 0.6:1, from about 1:1 to about 1.3:1, or from about 2:1 to about 2.4:1. In one embodiment, the molar ratio ranges from about 0.4:1 to about 0.6:1. In one embodiment, the molar ratio is about 0.5:1. In one embodiment, the molar ratio ranges from about 1:1 to about 1.3:1. In one embodiment, the molar ratio is about 1.1:1. In one embodiment, the molar ratio ranges from about 2:1 to about 2.4:1. In one embodiment, the molar ratio is about 2.2:1.

In one embodiment, the material comprising an 1,2-ethanedisulfonic acid salt of Compound 1 in step (a) comprises at least one non-Form 1 form of an 1,2-ethanedisulfonic acid salt of Compound 1. In one embodiment, the non-Form 1 form of an 1,2-ethanedisulfonic acid salt of Compound 1 is an amorphous form of an 1,2-ethanedisulfonic acid salt of Compound 1. In another embodiment, the material comprising an 1,2-ethanedisulfonic acid salt of Compound 1 in step (a) comprises Form 1 of an 1,2-ethanedisulfonic acid salt of Compound 1 and one or more impurities.

In certain embodiments, step (b) comprises one or more of the following steps: (i) cooling a solution containing an 1,2-ethanedisulfonic acid salt of Compound 1; (ii) adding an anti-solvent, with or without a cooling step, to cause precipitation of a solid material comprising an 1,2-ethanedisulfonic acid salt of Compound 1; (iii) evaporating (e.g., slow evaporation or fast evaporation) a solution containing an 1,2-ethanedisulfonic acid salt of Compound 1; (iv) slurrying a material comprising an 1,2-ethanedisulfonic acid salt of Compound 1 in a solvent system; and (v) subjecting a material comprising an 1,2-ethanedisulfonic acid salt of Compound 1 to maturation in a solvent system. In one embodiment, step (b) further comprises seeding with a Form 1 of an 1,2-ethanedisulfonic acid salt of Compound 1. In one embodiment, step (b) further comprises a sonication step.

In one embodiment, provided herein is a method for preparing Form 1 of the 1,2-ethanedisulfonic acid salt of Compound 1 comprising (1) contacting Compound 1 with 1,2-ethanedisulfonic acid in a solvent system; (2) cooling the resulted mixture; and (3) optionally subjecting the mixture to maturation. In one embodiment, provided herein is a method for preparing Form 1 of the 1,2-ethanedisulfonic acid salt of Compound 1 comprising (1) mixing (i) a mixture of Compound 1 in a first solvent and (ii) a mixture of 1,2-ethanedisulfonic acid in a second solvent; (2) cooling the resulted mixture; and (3) optionally subjecting the mixture to maturation. In one embodiment, the first solvent is EtOH. In one embodiment, the second solvent is THF. In one embodiment, the first solvent is EtOH and the second solvent is THF.

In one embodiment, the cooling temperature ranges from about −20° C. to about 5° C. In one embodiment, the cooling temperature is about 5° C. In one embodiment, the cooling time is at least 4 hours, at least 8 hours, or at least 24 hours.

In one embodiment, the maturation is conducted within a temperature range from about 0° C. to about 70° C., from about 10° C. to about 60° C., or from about 20° C. (room temperature) to about 50° C. In one embodiment, the maturation is conducted within a temperature range from about 20° C. (room temperature) to about 50° C. In one embodiment, the maturation is conducted for at least 4 hours, at least 8 hours, at least 24 hours, at least 48 hours, or at least 72 hours. In another embodiment, the maturation is conducted for about 4 hours, about 8 hours, about 24 hours, about 48 hours, or about 72 hours.

In one embodiment, Form 1 of an 1,2-ethanedisulfonic acid salt of Compound 1 is prepared by cooling a solution of an 1,2-ethanedisulfonic acid salt of Compound 1 in MeOH/THF. In one embodiment, Form 1 of an 1,2-ethanedisulfonic acid salt of Compound 1 is prepared by cooling a solution of an 1,2-ethanedisulfonic acid salt of Compound 1 in EtOH/THF. In one embodiment, the volume ratio of EtOH to THF is about 18:1. In one embodiment, the cooling temperature is about 5° C. In one embodiment, the solution is optionally seeded with Form 1 of an 1,2-ethanedisulfonic acid salt of Compound 1.

In one embodiment, Form 1 of an 1,2-ethanedisulfonic acid salt of Compound 1 is prepared by evaporation of a solution of an 1,2-ethanedisulfonic acid salt of Compound 1 in MIBK, followed by maturation in 1-BuOH.

In one embodiment, Form 1 of the 1,2-ethanedisulfonic acid salt of Compound 1 is stable after storage at 40° C./75% RH for up to 1 week.

All of the combinations of the above embodiments are encompassed by this invention.

Form 2, Form 3, and Form 4 of 1,2-Ethanedisulfonic Acid Salt of Compound 1

In some embodiments, provided herein is Form 2 of the 1,2-ethanedisulfonic acid salt of Compound 1. In one embodiment, Form 2 of the 1,2-ethanedisulfonic acid salt of Compound 1 is prepared by heating Form 1 of the 1,2-ethanedisulfonic acid salt of Compound 1 to about 100-140° C.

In some embodiments, provided herein is Form 3 of the 1,2-ethanedisulfonic acid salt of Compound 1. In one embodiment, Form 3 of the 1,2-ethanedisulfonic acid salt of Compound 1 is prepared by heating Form 1 of the 1,2-ethanedisulfonic acid salt of Compound 1 to about 220° C.

In some embodiments, provided herein is Form 4 of the 1,2-ethanedisulfonic acid salt of Compound 1. In one embodiment, Form 4 of the 1,2-ethanedisulfonic acid salt of Compound 1 is prepared by heating Form 1 of the 1,2-ethanedisulfonic acid salt of Compound 1 to about 220° C. followed by cooling back to about 25° C.

An overlay plot of representative XRPD patterns of Form 1, Form 2, Form 3, and Form 4 of the 1,2-ethanedisulfonic acid salt of Compound 1 is provided in FIG. 20. In one embodiment, provided herein is a solid form comprising an 1,2-ethanedisulfonic acid salt of Compound 1, wherein the solid form is characterized by an XRPD diffraction pattern which matches one of the XRPD pattern presented in FIG. 20.

5.2.4 Hydrochloride Salt of Compound 1

In some embodiments, provided herein is a hydrochloride salt of Compound 1. It is contemplated that a hydrochloride salt of Compound 1 can exist in a variety of solid forms. Such solid forms include crystalline solids, such as polymorphs, solvates and hydrates of crystalline hydrochloride salt of Compound 1, as well as amorphous solids, or mixtures thereof. All such solid forms of hydrochloride salt of Compound 1 are contemplated under the present invention.

In one embodiment, provided herein is a solid form comprising a hydrochloride salt of Compound 1, or a solvate (e.g., hydrate) thereof. In one embodiment, provided herein is a solid form comprising a solvate of a hydrochloride salt of Compound 1. In one embodiment, provided herein is a solid form comprising a hydrate of a hydrochloride salt of Compound 1. In one embodiment, provided herein is a solid form comprising a crystalline form of a hydrochloride salt of Compound 1, or a solvate (e.g., hydrate) thereof. In one embodiment, provided herein is a solid form comprising a crystalline form of a solvate of a hydrochloride salt of Compound 1. In one embodiment, provided herein is a solid form comprising a crystalline form of a hydrate of a hydrochloride salt of Compound 1.

In some embodiments, the molar ratio of Compound 1 to hydrochloric acid in the solid form ranges from about 2:1 to about 1:2. In one embodiment, the molar ratio is about 1:2 (i.e., bis-hydrochloride salt). In another embodiment, the molar ratio is about 1:1 (i.e., mono-hydrochloride salt). In yet another embodiment, the molar ratio is about 2:1 (i.e., hemi-hydrochloride salt).

In some embodiments, the molar ratio of Compound 1 to the solvent/water in the solid form ranges from about 2:1 to about 1:2. In one embodiment, the molar ratio is about 1:2 (i.e., bis-solvate/hydrate). In another embodiment, the molar ratio is about 1:1 (i.e., mono-solvate/hydrate). In yet another embodiment, the molar ratio is about 2:1 (i.e., hemi-solvate/hydrate).

Form 1 of Hydrochloride Salt of Compound 1

In some embodiments, provided herein is Form 1 of the hydrochloride salt of Compound 1. A representative XRPD pattern of Form 1 of the hydrochloride salt of Compound 1 is provided in FIG. 21A. In one embodiment, provided herein is a solid form comprising a hydrochloride salt of Compound 1, wherein the solid form is characterized by an XRPD diffraction pattern which matches the XRPD pattern presented in FIG. 21A.

In one embodiment, provided herein is a method for preparing Form 1 of the hydrochloride salt of Compound 1 comprising (1) contacting Compound 1 with hydrochloric acid in a solvent system; (2) cooling the resulted mixture; and (3) optionally subjecting the mixture to maturation. In one embodiment, provided herein is a method for preparing Form 1 of the hydrochloride salt of Compound 1 comprising (1) mixing (i) a mixture of Compound 1 in a first solvent and (ii) a mixture of hydrochloric acid in a second solvent; (2) cooling the resulted mixture; and (3) optionally subjecting the mixture to maturation. In one embodiment, the first solvent is MeOH. In one embodiment, the second solvent is THF. In one embodiment, the first solvent is MeOH and the second solvent is THF.

In one embodiment, the cooling temperature ranges from about −20° C. to about 5° C. In one embodiment, the cooling temperature is about 5° C. In one embodiment, the cooling time is at least 4 hours, at least 8 hours, or at least 24 hours.

In one embodiment, the maturation is conducted within a temperature range from about 0° C. to about 70° C., from about 10° C. to about 60° C., or from about 20° C. (room temperature) to about 50° C. In one embodiment, the maturation is conducted within a temperature range from about 20° C. (room temperature) to about 50° C. In one embodiment, the maturation is conducted for at least 4 hours, at least 8 hours, at least 24 hours, at least 48 hours, or at least 72 hours. In another embodiment, the maturation is conducted for about 4 hours, about 8 hours, about 24 hours, about 48 hours, or about 72 hours.

In one embodiment, Form 1 of a hydrochloride salt of Compound 1 is prepared by slow evaporation of a solution of a hydrochloride salt of Compound 1 in MeOH. In one embodiment, Form 1 of a hydrochloride salt of Compound 1 is prepared by slow evaporation of a solution of a hydrochloride salt of Compound 1 in MeOH/THF. In one embodiment, Form 1 of a hydrochloride salt of Compound 1 is prepared by slow evaporation of a solution of a hydrochloride salt of Compound 1 in MeOH/THF/water.

In one embodiment, Form 1 of a hydrochloride salt of Compound 1 is prepared by cooling a solution of a hydrochloride salt of Compound 1 in anisole. In one embodiment, Form 1 of a hydrochloride salt of Compound 1 is prepared by cooling a solution of a hydrochloride salt of Compound 1 in water. In one embodiment, the cooling occurs at about 5° C. for about 24 hours. In one embodiment, Form 1 of the hydrochloride salt of Compound 1 prepared by the method provided herein has a low crystallinity.

In one embodiment, Form 1 of the hydrochloride salt of Compound 1 deliquesces after storage at 40° C./75% RH for up to 1 week.

Form 2 of Hydrochloride Salt of Compound 1

In some embodiments, provided herein is Form 2 of the hydrochloride salt of Compound 1. A representative XRPD pattern of Form 2 of the hydrochloride salt of Compound 1 is provided in FIG. 21B. In one embodiment, provided herein is a solid form comprising a hydrochloride salt of Compound 1, wherein the solid form is characterized by an XRPD diffraction pattern which matches the XRPD pattern presented in FIG. 21B.

In one embodiment, provided herein is a method for preparing Form 2 of the hydrochloride salt of Compound 1 comprising (1) contacting Compound 1 with hydrochloric acid in a solvent system; (2) cooling the resulted mixture; and (3) optionally subjecting the mixture to maturation. In one embodiment, provided herein is a method for preparing Form 2 of the hydrochloride salt of Compound 1 comprising (1) mixing (i) a mixture of Compound 1 in a first solvent and (ii) a mixture of hydrochloric acid in a second solvent; (2) cooling the resulted mixture; and (3) optionally subjecting the mixture to maturation. In one embodiment, the first solvent is 2-MeTHF. In one embodiment, the second solvent is THF. In one embodiment, the first solvent is 2-MeTHF and the second solvent is THF.

In one embodiment, the cooling temperature ranges from about −20° C. to about 5° C. In one embodiment, the cooling temperature is about 5° C. In one embodiment, the cooling time is at least 4 hours, at least 8 hours, or at least 24 hours.

In one embodiment, the maturation is conducted within a temperature range from about 0° C. to about 70° C., from about 10° C. to about 60° C., or from about 20° C. (room temperature) to about 50° C. In one embodiment, the maturation is conducted within a temperature range from about 20° C. (room temperature) to about 50° C. In one embodiment, the maturation is conducted for at least 4 hours, at least 8 hours, at least 24 hours, at least 48 hours, or at least 72 hours. In another embodiment, the maturation is conducted for about 4 hours, about 8 hours, about 24 hours, about 48 hours, or about 72 hours.

In one embodiment, Form 2 of a hydrochloride salt of Compound 1 is prepared by cooling a solution of a hydrochloride salt of Compound 1 in 2-MeTHF. In one embodiment, the cooling occurs at about 5° C. for about 24 hours.

In one embodiment, Form 2 of the hydrochloride salt of Compound 1 is a mono-hydrochloride salt.

5.2.5 Isethionate Salt of Compound 1

In some embodiments, provided herein is an isethionate salt of Compound 1. It is contemplated that an isethionate salt of Compound 1 can exist in a variety of solid forms. Such solid forms include crystalline solids, such as polymorphs, solvates and hydrates of crystalline isethionate salt of Compound 1, as well as amorphous solids, or mixtures thereof. All such solid forms of isethionate salt of Compound 1 are contemplated under the present invention.

In one embodiment, provided herein is a solid form comprising an isethionate salt of Compound 1, or a solvate (e.g., hydrate) thereof. In one embodiment, provided herein is a solid form comprising a solvate of an isethionate salt of Compound 1. In one embodiment, provided herein is a solid form comprising a hydrate of an isethionate salt of Compound 1. In one embodiment, provided herein is a solid form comprising a crystalline form of an isethionate salt of Compound 1, or a solvate (e.g., hydrate) thereof. In one embodiment, provided herein is a solid form comprising a crystalline form of a solvate of an isethionate salt of Compound 1. In one embodiment, provided herein is a solid form comprising a crystalline form of a hydrate of an isethionate salt of Compound 1.

In some embodiments, the molar ratio of Compound 1 to 2-hydroxyethanesulfonic acid in the solid form ranges from about 2:1 to about 1:2. In one embodiment, the molar ratio is about 1:2 (i.e., bis-isethionate salt). In another embodiment, the molar ratio is about 1:1 (i.e., mono-isethionate salt). In yet another embodiment, the molar ratio is about 2:1 (i.e., hemi-isethionate salt).

In some embodiments, the molar ratio of Compound 1 to the solvent/water in the solid form ranges from about 2:1 to about 1:2. In one embodiment, the molar ratio is about 1:2 (i.e., bis-solvate/hydrate). In another embodiment, the molar ratio is about 1:1 (i.e., mono-solvate/hydrate). In yet another embodiment, the molar ratio is about 2:1 (i.e., hemi-solvate/hydrate).

Form 1 of Isethionate Salt of Compound 1

In some embodiments, provided herein is Form 1 of the isethionate salt of Compound 1. A representative XRPD pattern of Form 1 of the isethionate salt of Compound 1 is provided in FIG. 22. In one embodiment, provided herein is a solid form comprising an isethionate salt of Compound 1, wherein the solid form is characterized by an XRPD diffraction pattern which matches the XRPD pattern presented in FIG. 22.

In one embodiment, provided herein is a method for preparing Form 1 of the isethionate salt of Compound 1 comprising (1) contacting Compound 1 with 2-hydroxyethanesulfonic acid in a solvent system; (2) cooling the resulted mixture; and (3) optionally subjecting the mixture to maturation. In one embodiment, provided herein is a method for preparing Form 1 of the isethionate salt of Compound 1 comprising (1) mixing (i) a mixture of Compound 1 in a first solvent and (ii) a mixture of 2-hydroxyethanesulfonic acid in a second solvent; (2) cooling the resulted mixture; and (3) optionally subjecting the mixture to maturation.

In one embodiment, the cooling temperature ranges from about −20° C. to about 5° C. In one embodiment, the cooling temperature is about 5° C. In one embodiment, the cooling time is at least 4 hours, at least 8 hours, or at least 24 hours.

In one embodiment, the maturation is conducted within a temperature range from about 0° C. to about 70° C., from about 10° C. to about 60° C., or from about 20° C. (room temperature) to about 50° C. In one embodiment, the maturation is conducted within a temperature range from about 20° C. (room temperature) to about 50° C. In one embodiment, the maturation is conducted for at least 4 hours, at least 8 hours, at least 24 hours, at least 48 hours, or at least 72 hours. In another embodiment, the maturation is conducted for about 4 hours, about 8 hours, about 24 hours, about 48 hours, or about 72 hours.

In one embodiment, Form 1 of an isethionate salt of Compound 1 is prepared by slow evaporation of a solution of an isethionate salt of Compound 1 in MeOH.

In one embodiment, Form 1 of the isethionate salt of Compound 1 deliquesces after storage at 40° C./75% RH for up to 1 week.

5.2.6 Free Base of Compound 1

In some embodiments, provided herein is a free base of Compound 1. It is contemplated that a free base of Compound 1 can exist in a variety of solid forms. Such solid forms include crystalline solids, such as polymorphs, solvates and hydrates of crystalline free base of Compound 1, as well as amorphous solids, or mixtures thereof. All such solid forms of free base of Compound 1 are contemplated under the present invention.

In one embodiment, provided herein is a solid form comprising a free base of Compound 1, or a solvate (e.g., hydrate) thereof. In one embodiment, provided herein is a solid form comprising a solvate of a free base of Compound 1. In one embodiment, provided herein is a solid form comprising a hydrate of a free base of Compound 1. In one embodiment, provided herein is a solid form comprising a crystalline form of a free base of Compound 1, or a solvate (e.g., hydrate) thereof. In one embodiment, provided herein is a solid form comprising a crystalline form of a solvate of a free base of Compound 1. In one embodiment, provided herein is a solid form comprising a crystalline form of a hydrate of a free base of Compound 1.

In some embodiments, the molar ratio of Compound 1 to the solvent/water in the solid form ranges from about 2:1 to about 1:2. In one embodiment, the molar ratio is about 1:2 (i.e., bis-solvate/hydrate). In another embodiment, the molar ratio is about 1:1 (i.e., mono-solvate/hydrate). In yet another embodiment, the molar ratio is about 2:1 (i.e., hemi-solvate/hydrate).

Form 1 of Free Base of Compound 1

In some embodiments, provided herein is Form 1 of the free base of Compound 1. In one embodiment, Form 1 of the free base of Compound 1 is a crystalline semi-hydrate of Compound 1. In some embodiments, Form 1 of the free base of Compound 1 is substantially free of amorphous free base of Compound 1. In some embodiments, Form 1 of the free base of Compound 1 is substantially free of other crystalline forms (i.e., polymorphs) of the free base of Compound 1. In some embodiments, Form 1 of the free base of Compound 1 is substantially free of salts of Compound 1. In some embodiments, Form 1 of the free base of Compound 1 is provided as substantially pure Form 1 of the free base of Compound 1.

In one embodiment, Form 1 of the free base of Compound 1 is a hydrate, wherein the molar ratio of Compound 1 to the water ranges from about 1:0.5 to about 1:0.6 (i.e., semi-hydrate). In one embodiment, the molar ratio of Compound 1 to the water is about 1:0.6.

A representative XRPD patterns of Form 1 of the free base of Compound 1 is provided in FIG. 23.

In some embodiments, provided herein is a solid form comprising a free base of Compound 1 characterized by XRPD peaks located at 1, 2, 3, 4, 5, 6, 7, 8, 9, 10, 11, 12, 13, 14, 15, or all of the following or approximately the following positions: 5.0, 7.6, 9.9, 10.7, 11.4, 12.2, 13.0, 13.5, 14.0, 14.5, 15.1, 15.9, 16.4, 16.8, 17.7, 18.1, 19.1, 19.9, 20.6, 21.1, 21.7, 22.4, 23.1, 23.7, 24.6, and 25.2 degrees 2θ, plus or minus 0.10. In some embodiments, provided herein is a solid form comprising a free base of Compound 1 characterized by XRPD peaks located at 1, 2, 3, 4, 5, 6, 7, 8, 9, 10, 11, 12, 13, 14, or all of the following or approximately the following positions: 5.0, 7.6, 11.4, 12.2, 13.5, 15.1, 16.8, 19.9, 20.6, 21.1, 22.4, 23.1, 23.7, 24.6, and 25.2 degrees 2θ, plus or minus 0.10. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by 11 of the peaks. In some embodiments, the solid form is characterized by 13 of the peaks. In some embodiments, the solid form is characterized by all of the peaks.

In some embodiments, provided herein is a solid form comprising a free base of Compound 1 having an XRPD pattern comprising peaks at approximately 11.4, 16.8, and 19.9 degrees 2θ. In certain embodiments, the solid form further comprises peaks at approximately 5.0 and 7.6 degrees 2θ. In certain embodiments, the solid form further comprises peaks at approximately 22.4 and 23.7 degrees 2θ. In one embodiment, the solid form comprises peaks at approximately 5.0, 7.6, 11.4, 12.2, 13.5, 15.1, 16.8, 19.9, 20.6, 21.1, 22.4, 23.1, 23.7, 24.6, and 25.2 degrees 2θ.

In some embodiments, the XRPD peaks above (degrees 2θ peaks) are when analyzed using copper Kα radiation.

In some embodiments, provided herein is a solid form comprising a free base of Compound 1, wherein the solid form is characterized by an XRPD diffraction pattern which matches the XRPD pattern presented in FIG. 23.

A representative thermal gravimetric analysis (TGA) curve of the free base of Compound 1 is provided in FIG. 24, which exhibits a weight loss of about 1.91% of the total sample weight upon heating from about 30 to about 130° C. Without being limited by any particular theory, the weight loss corresponds to loss of water. In some embodiments, provided herein is a solid form comprising a free base of Compound 1, wherein the solid form is characterized by a TGA thermogram which matches the TGA thermogram presented in FIG. 24.

A representative differential scanning calorimetry (DSC) thermogram of the free base of Compound 1 is presented in FIG. 25. In some embodiments, provided herein is a solid form comprising a free base of Compound 1 that exhibits a thermal event, as characterized by DSC, with a peak temperature of about 27° C. and/or an onset temperature of about 25° C., or with a peak temperature of about 172° C. and/or an onset temperature of about 161° C. In some embodiments, provided herein is a solid form comprising a free base of Compound 1 that exhibits thermal events, as characterized by DSC, with a peak temperature of about 27° C. and/or an onset temperature of about 25° C., and with a peak temperature of about 172° C. and/or an onset temperature of about 161° C. Without being limited by any particular theory, the thermal events correspond to loss of water. In some embodiments, provided herein is a solid form comprising a free base of Compound 1, wherein the solid form is characterized by a DSC thermogram which matches the DSC thermogram presented in FIG. 25.

A representative gravimetric vapor sorption (GVS) isotherm of Compound 1 is presented in FIG. 26. In one embodiment, provided herein is a solid form comprising a free base of Compound 1, wherein the solid form is characterized by a GVS isotherm which matches the GVS isotherm presented in FIG. 26.

In one embodiment, Form 1 of the free base of Compound 1 is prepared by adding an anti-solvent to a solution of Compound 1 in a solvent system. In one embodiment, the solvent system is a mixture of acetic acid and water. In one embodiment, the solvent system is acetic acid/water (1/1 v/v). In one embodiment, the anti-solvent is NH$_4$OH. In one embodiment, Form 1 of the free base of Compound 1 is prepared by adding NH$_4$OH to a solution of Compound 1 in a mixture of acetic acid and water. In one embodiment, Form 1 of the free base of Compound 1 is prepared by adding NH$_4$OH to a solution of Compound 1 in a mixture of acetic acid and water, wherein pH of the resulted mixture is about neutral. In one embodiment, preparation of Form 1 of the free base of Compound 1 does not involve a maturation step.

In one embodiment, Form 1 of the free base of Compound 1 converts to Form 4 of the free base of Compound 1 by dehydration. In one embodiment, the dehydration occurs from about 40 to about 75° C. In one embodiment, Form 1 of the free base of Compound 1 converts to Form 3 of the free base of Compound 1 by hydration. In one embodiment, the hydration occurs in a range of about 80-90% RH. In one embodiment, Form 1 of the free base of Compound 1 is stable after storage at 40° C./75% RH for 1 week. In another embodiment, Form 1 of the free base of Compound 1 converts to Form 3 of the free base of Compound 1 after storage at 25° C./93% RH for 1 week.

In one embodiment, Form 1 of the free base of Compound 1 converts to Form 6 of the free base of Compound 1 after maturation in acetic acid/water (1:1) for 72 hours.

All of the combinations of the above embodiments are encompassed by this invention.

Form 2 of Free Base of Compound 1

In some embodiments, provided herein is Form 2 of the free base of Compound 1. In one embodiment, Form 2 of the free base of Compound 1 is a crystalline mono-hydrate of Compound 1. In some embodiments, Form 2 of the free base of Compound 1 is substantially free of amorphous free base of Compound 1. In some embodiments, Form 2 of the free base of Compound 1 is substantially free of other crystalline forms (i.e., polymorphs) of the free base of Compound 1. In some embodiments, Form 2 of the free base of Compound 1 is substantially free of salts of Compound 1. In some embodiments, Form 2 of the free base of Compound 1 is provided as substantially pure Form 2 of the free base of Compound 1.

In one embodiment, Form 2 of the free base of Compound 1 is a hydrate, wherein the molar ratio of Compound 1 to the water ranges from about 1:0.5 to about 1:0.8. In one embodiment, the molar ratio of Compound 1 to the water is about 1:0.8.

A representative XRPD patterns of Form 2 of the free base of Compound 1 is provided in FIG. 27.

In some embodiments, provided herein is a solid form comprising a free base of Compound 1 characterized by XRPD peaks located at 1, 2, 3, 4, 5, 6, 7, 8, 9, 10, 11, 12, 13, 14, 15, or all of the following or approximately the following positions: 9.1, 10.9, 12.3, 15.0, 16.1, 16.8, 17.8, 18.1, 18.3, 19.3, 20.1, 20.5, 20.7, 20.8, 21.5, 21.9, 22.4, 22.7, 23.9, 24.9, 25.6, 26.2, 26.8, 27.2, and 27.5 degrees 2θ, plus or minus 0.10. In some embodiments, provided herein is a solid form comprising a free base of Compound 1 characterized by XRPD peaks located at 1, 2, 3, 4, 5, 6, 7, 8, 9, 10, 11, 12, 13, or all of the following or approximately the following positions: 9.1, 10.9, 12.3, 15.0, 16.8, 17.8, 19.3, 20.7, 21.9, 24.9, 25.6, 26.8, 27.2, and 27.5 degrees 2θ, plus or minus 0.10. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by 11 of the peaks. In some embodiments, the solid form is characterized by 13 of the peaks. In some embodiments, the solid form is characterized by all of the peaks.

In some embodiments, provided herein is a solid form comprising a free base of Compound 1 having an XRPD pattern comprising peaks at approximately 9.1, 10.9, and 16.8 degrees 2θ. In certain embodiments, the solid form further comprises peaks at approximately 17.8 and 24.9 degrees 2θ. In certain embodiments, the solid form further comprises peaks at approximately 19.3 and 26.8 degrees 2θ. In one embodiment, the solid form comprises peaks at approximately 9.1, 10.9, 12.3, 15.0, 16.8, 17.8, 19.3, 20.7, 21.9, 24.9, 25.6, 26.8, 27.2, and 27.5 degrees 2θ.

In some embodiments, the XRPD peaks above (degrees 2θ peaks) are when analyzed using copper Kα radiation.

In some embodiments, provided herein is a solid form comprising a free base of Compound 1, wherein the solid form is characterized by an XRPD diffraction pattern which matches the XRPD pattern presented in FIG. 27.

A representative thermal gravimetric analysis (TGA) curve of the free base of Compound 1 is provided in FIG. 28, which exhibits a weight loss of about 3.04% of the total sample weight upon heating from about 30 to about 130° C. Without being limited by any particular theory, the weight loss corresponds to loss of water. In some embodiments, provided herein is a solid form comprising a free base of Compound 1, wherein the solid form is characterized by a TGA thermogram which matches the TGA thermogram presented in FIG. 28.

A representative differential scanning calorimetry (DSC) thermogram of the free base of Compound 1 is presented in FIG. 29. In some embodiments, provided herein is a solid form comprising a free base of Compound 1 that exhibits a thermal event, as characterized by DSC, with a peak temperature of about 60° C. and/or an onset temperature of about 26° C., or with a peak temperature of about 182° C. and/or an onset temperature of about 172° C. In some embodiments, provided herein is a solid form comprising a free base of Compound 1 that exhibits thermal events, as characterized by DSC, with a peak temperature of about 60° C. and/or an onset temperature of about 26° C., and with a peak temperature of about 182° C. and/or an onset temperature of about 172° C. In some embodiments, provided herein is a solid form comprising a free base of Compound 1, wherein the solid form is characterized by a DSC thermogram which matches the DSC thermogram presented in FIG. 29.

A representative gravimetric vapour sorption (GVS) isotherm of Compound 1 is presented in FIG. 30. In one embodiment, provided herein is a solid form comprising a free base of Compound 1, wherein the solid form is characterized by a GVS isotherm which matches the GVS isotherm presented in FIG. 30.

In one embodiment, Form 2 of the free base of Compound 1 is prepared by adding an anti-solvent to a solution of Compound 1 in a solvent system, followed by maturation. In one embodiment, the solvent system is a mixture of acetic acid and water. In one embodiment, the solvent system is acetic acid/water (1/1 v/v). In one embodiment, the anti-solvent is NH$_4$OH. In one embodiment, Form 2 of the free base of Compound 1 is prepared by adding NH$_4$OH to a solution of Compound 1 in a mixture of acetic acid and water, followed by maturation. In one embodiment, Form 2 of the free base of Compound 1 is prepared by adding NH$_4$OH to a solution of Compound 1 in a mixture of acetic acid and water, wherein pH of the resulted mixture is about neutral, followed by maturation. In one embodiment, the maturation is conducted at about 90° C. for about 5 to about 24, or about 10 to about 15 hours.

In one embodiment, Form 2 of the free base of Compound 1 is stable after storage at 40° C./75% RH for 1 week or after storage at 25° C./93% RH for 1 week. In one embodiment, without being limited by any particular theory, Form 2 of the free base of Compound 1 is a channel hydrate. In a channel hydrate, water can easily move in and out of the crystal lattice.

In one embodiment, Form 2 of the free base of Compound 1 converts to Form 5 of the free base of Compound 1 after maturation in a solvent. In one embodiment, solvent is EtOH, acetonitrile, EtOAc, Acetone, MIBK, IPA, EtOH/5% water, IPAc, or 1-butanol, or a mixture thereof. In one embodiment, the maturation is performed between RT and 50° C. for 5 days. In one embodiment, Form 2 of the free base of Compound 1 is stable after maturation in EtOH/water (1:1) between RT to 50° C. for 5 days.

In one embodiment, Form 2 of the free base of Compound 1 is stable after maturation in acetic acid/water (1:1) for 72 hours. In another embodiment, Form 2 of the free base of Compound 1 is stable after maturation in water at 25° C. for about 40 hours. In yet another embodiment, Form 2 of the free base of Compound 1 is stable after maturation in water at 90° C. for about 40 hours. In yet another embodiment, Form 2 of the free base of Compound 1 is stable after maturation in acetic acid/water (1:3) at 25° C. for about 40 hours. In yet another embodiment, Form 2 of the free base of Compound 1 partially converts to Form 6 of the free base of Compound 1 after maturation in water at 90° C. for about 40 hours.

In one embodiment, Form 2 of a free base of Compound 1 is prepared by maturation of Form 1 of a maleic acid salt of Compound 1 in 2-propanol/water (90/10 v/v). In one embodiment, Form 2 of a free base of Compound 1 is prepared by maturation of Form 1 of a maleic acid salt of Compound 1 in acetic acid/water (25/75 v/v). In one embodiment, the maturation is performed between RT to about 50° C. for about 24 to about 72 hours.

In one embodiment, Form 2 of a free base of Compound 1 is prepared by cooling a solution of a maleic acid salt of Compound 1 in 2-butanone/water. In one embodiment, Form 2 of a free base of Compound 1 is prepared by cooling a solution of a maleic acid salt of Compound 1 in 1-butanol/water. In one embodiment, Form 2 of a free base of Compound 1 is prepared by cooling a solution of a maleic acid salt of Compound 1 in ethyl acetate/water. In one embodiment, Form 2 of a free base of Compound 1 is prepared by cooling a solution of a maleic acid salt of Compound 1 in anisole/water. In one embodiment, the cooling temperature ranges from about −20° C. to about 5° C. In one embodiment, the cooling temperature is about 5° C. In one embodiment, the cooling time is at least 4 hours, at least 8 hours, or at least 24 hours.

Form 3 of Free Base of Compound 1

In some embodiments, provided herein is Form 3 of the free base of Compound 1. In one embodiment, Form 3 of the free base of Compound 1 is a crystalline hydrate of Compound 1. In some embodiments, Form 3 of the free base of Compound 1 is substantially free of amorphous free base of Compound 1. In some embodiments, Form 3 of the free base of Compound 1 is substantially free of other crystalline forms (i.e., polymorphs) of the free base of Compound 1. In some embodiments, Form 3 of the free base of Compound 1 is substantially free of salts of Compound 1. In some embodiments, Form 3 of the free base of Compound 1 is provided as substantially pure Form 3 of the free base of Compound 1.

A representative XRPD patterns of Form 3 of the free base of Compound 1 is provided in FIG. 31.

In some embodiments, provided herein is a solid form comprising a free base of Compound 1 characterized by XRPD peaks located at 1, 2, 3, 4, 5, 6, 7, 8, 9, 10, 11, 12, or all of the following or approximately the following positions: 4.9, 7.3, 10.6, 11.3, 12.0, 14.4, 14.9, 15.2, 16.9, 17.7, 20.0, 21.9, and 24.6 degrees 2θ, plus or minus 0.10. In some embodiments, provided herein is a solid form comprising a free base of Compound 1 characterized by XRPD peaks located at 1, 2, 3, 4, 5, 6, 7, 8, 9, 10, or all of the following or approximately the following positions: 4.9, 7.3, 10.6, 11.3, 14.4, 14.9, 16.9, 17.7, 20.0, 21.9, and 24.6 degrees 2θ, plus or minus 0.10. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by 11 of the peaks. In some embodiments, the solid form is characterized by all of the peaks.

In some embodiments, provided herein is a solid form comprising a free base of Compound 1 having an XRPD pattern comprising peaks at approximately 7.3, 10.6, and 11.3 degrees 2θ. In certain embodiments, the solid form further comprises peaks at approximately 4.9 and 20.0 degrees 2θ. In certain embodiments, the solid form further comprises peaks at approximately 21.9 and 24.6 degrees 2θ. In one embodiment, the solid form comprises peaks at approximately 4.9, 7.3, 10.6, 11.3, 14.4, 14.9, 16.9, 17.7, 20.0, 21.9, and 24.6 degrees 2θ.

In some embodiments, the XRPD peaks above (degrees 2θ peaks) are when analyzed using copper Kα radiation.

In some embodiments, provided herein is a solid form comprising a free base of Compound 1, wherein the solid form is characterized by an XRPD diffraction pattern which matches the XRPD pattern presented in FIG. 31.

In one embodiment, Form 3 of a free base of Compound 1 is prepared by hydration of Form 1 of a free base of Compound 1. In one embodiment, Form 3 of a free base of Compound 1 is prepared by subjecting Form 1 of a free base of Compound 1 to a condition of 25° C./93% RH for about a week.

In one embodiment, Form 3 of a free base of Compound 1 is prepared by hydration of Form 6 of a free base of Compound 1. In one embodiment, Form 3 of a free base of Compound 1 is prepared by subjecting Form 6 of a free base of Compound 1 to a condition of 40° C./75% RH for about a week.

In one embodiment, Form 3 of a free base of Compound 1 is prepared by evaporation of a solution of a free base of Compound 1 in dioxane, followed by maturation. In one embodiment, the maturation is conducted between RT and 50° C. for about 48 hours. In one embodiment, the solid form prepared by the method contains both Form 3 and Form 5 of a free base of Compound 1.

All of the combinations of the above embodiments are encompassed by this invention.

Form 4 of Free Base of Compound 1

In some embodiments, provided herein is Form 4 of the free base of Compound 1. In one embodiment, Form 4 of the free base of Compound 1 is a crystalline anhydrous Compound 1. In some embodiments, Form 4 of the free base of Compound 1 is substantially free of amorphous free base of Compound 1. In some embodiments, Form 4 of the free base of Compound 1 is substantially free of other crystalline forms (i.e., polymorphs) of the free base of Compound 1. In some embodiments, Form 4 of the free base of Compound 1 is substantially free of salts of Compound 1. In some embodiments, Form 4 of the free base of Compound 1 is provided as substantially pure Form 4 of the free base of Compound 1.

A representative XRPD patterns of Form 4 of the free base of Compound 1 is provided in FIG. 32.

In some embodiments, provided herein is a solid form comprising a free base of Compound 1 characterized by XRPD peaks located at 1, 2, 3, 4, 5, 6, 7, 8, 9, 10, 11, 12, 13, 14, 15, or all of the following or approximately the following positions: 5.0, 7.4, 10.7, 11.1, 11.5, 11.8, 13.0, 13.8, 14.5, 15.4, 16.4, 16.7, 17.5, 19.1, 20.0, 21.7, 22.2, 22.4, 23.2, and 23.9 degrees 2θ, plus or minus 0.10. In some embodiments, provided herein is a solid form comprising a free base of Compound 1 characterized by XRPD peaks located at 1, 2, 3, 4, 5, 6, 7, 8, 9, 10, 11, 12, 13, 14, 15, or all of the following or approximately the following positions: 5.0, 7.4, 10.7, 11.1, 11.5, 11.8, 13.0, 14.5, 17.5, 19.1, 20.0, 21.7, 22.2, 22.4, 23.2, and 23.9 degrees 2θ, plus or minus 0.10. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by 11 of the peaks. In some embodiments, the solid form is characterized by 13 of the peaks. In some embodiments, the solid form is characterized by all of the peaks.

In some embodiments, provided herein is a solid form comprising a free base of Compound 1 having an XRPD pattern comprising peaks at approximately 11.1, 11.5, and 20.0 degrees 2θ. In certain embodiments, the solid form further comprises peaks at approximately 7.4 and 21.7 degrees 2θ. In certain embodiments, the solid form further comprises peaks at approximately 5.0 and 11.8 degrees 2θ. In one embodiment, the solid form comprises peaks at approximately 5.0, 7.4, 10.7, 11.1, 11.5, 11.8, 13.0, 14.5, 17.5, 19.1, 20.0, 21.7, 22.2, 22.4, 23.2, and 23.9 degrees 2θ.

In some embodiments, the XRPD peaks above (degrees 2θ peaks) are when analyzed using copper Kα radiation.

In some embodiments, provided herein is a solid form comprising a free base of Compound 1, wherein the solid form is characterized by an XRPD diffraction pattern which matches the XRPD pattern presented in FIG. 32.

A representative thermal gravimetric analysis (TGA) curve of the free base of Compound 1 is provided in FIG. 33, which exhibits a weight loss of about 1.54% of the total sample weight upon heating from about 30 to about 130° C. Without being limited by any particular theory, the weight loss corresponds to loss of about 0.4 equivalent of water. In some embodiments, provided herein is a solid form comprising a free base of Compound 1, wherein the solid form is characterized by a TGA thermogram which matches the TGA thermogram presented in FIG. 33.

A representative differential scanning calorimetry (DSC) thermogram of the free base of Compound 1 is presented in FIG. 34. In some embodiments, provided herein is a solid form comprising a free base of Compound 1 that exhibits a thermal event, as characterized by DSC, with a peak temperature of about 83° C. and/or an onset temperature of about 51° C., or with a peak temperature of about 173° C. and/or an onset temperature of about 162° C. In some embodiments, provided herein is a solid form comprising a free base of Compound 1 that exhibits thermal events, as characterized by DSC, with a peak temperature of about 83° C. and/or an onset temperature of about 51° C., and with a peak temperature of about 173° C. and/or an onset temperature of about 162° C. In some embodiments, provided herein is a solid form comprising a free base of Compound 1, wherein the solid form is characterized by a DSC thermogram which matches the DSC thermogram presented in FIG. 34.

A representative gravimetric vapour sorption (GVS) isotherm of Compound 1 is presented in FIG. 35. In one embodiment, provided herein is a solid form comprising a free base of Compound 1, wherein the solid form is characterized by a GVS isotherm which matches the GVS isotherm presented in FIG. 35.

In one embodiment, Form 4 of a free base of Compound 1 is prepared by dehydration of Form 1 of a free base of Compound 1. In one embodiment, Form 4 of a free base of Compound 1 is prepared by heating Form 1 of a free base of Compound 1 to about or over 80° C.

In one embodiment, Form 4 of a free base of Compound 1 is prepared by de-solvation of Form 6 of a free base of Compound 1. In one embodiment, Form 4 of a free base of Compound 1 is prepared by heating Form 6 of a free base of Compound 1 to about or over 100° C.

In one embodiment, Form 4 of a free base of Compound 1 is prepared by maturation of an amorphous free base of Compound 1 in water. In one embodiment, the maturation is performed between RT to about 50° C. for about 24 to about 72 hours.

All of the combinations of the above embodiments are encompassed by this invention.

Form 5 of Free Base of Compound 1

In some embodiments, provided herein is Form 5 of the free base of Compound 1. In one embodiment, Form 5 of the free base of Compound 1 is a crystalline solvate of Compound 1. In one embodiment, Form 5 of the free base of Compound 1 is a crystalline IPAc solvate of Compound 1. In another embodiment, Form 5 of the free base of Compound 1 is a crystalline acetonitrile solvate of Compound 1. In some embodiments, Form 5 of the free base of Compound 1 is substantially free of amorphous free base of Compound 1. In some embodiments, Form 5 of the free base of Compound 1 is substantially free of other crystalline forms (i.e., polymorphs) of the free base of Compound 1. In some embodiments, Form 5 of the free base of Compound 1 is substantially free of salts of Compound 1. In some embodiments, Form 5 of the free base of Compound 1 is provided as substantially pure Form 5 of the free base of Compound 1.

In one embodiment, the molar ratio of Compound 1 to the solvent in the solid form ranges from about 2:1 to about 1:2. In one embodiment, the molar ratio is about 1:2 (i.e., bis-solvate). In another embodiment, the molar ratio is about 1:1 (i.e., mono-solvate). In yet another embodiment, the molar ratio is about 2:1 (i.e., hemi-solvate).

In one embodiment, the solvent is MeOH. In one embodiment, the solvent is EtOH. In one embodiment, the solvent is acetonitrile. In one embodiment, the solvent is ethyl acetate. In one embodiment, the solvent is acetone. In one embodiment, the solvent is MIBK. In one embodiment, the solvent is TBME. In one embodiment, the solvent is 2-MeTHF. In one embodiment, the solvent is THF. In one embodiment, the solvent is DCM. In one embodiment, the solvent is IPA. In one embodiment, the solvent is DME. In one embodiment, the solvent is DCM and/or MeOH. In one embodiment, the solvent is EtOH and/or water. In one embodiment, the solvent is THF and/or water. In one embodiment, the solvent is acetonitrile and/or water. In one embodiment, the solvent is IPAc. In one embodiment, without being limited by any particular theory, Form 5 of the free base of Compound 1 is one or more isostructural solvates.

Representative XRPD patterns of Form 5 of the free base of Compound 1 are provided in FIG. 36 and FIG. 37.

In some embodiments, provided herein is a solid form comprising a free base of Compound 1 characterized by XRPD peaks located at 1, 2, 3, 4, 5, 6, 7, 8, 9, 10, 11, 12, 13, 14, 15, or all of the following or approximately the following positions: 6.5, 9.0, 9.4, 10.0, 10.5, 10.7, 11.3, 11.7, 12.1, 12.9, 13.1, 14.0, 14.5, 15.5, 15.8, 16.0, 16.6, 17.3, 17.5, 17.7, 18.0, 18.5, 18.9, 19.1, and 19.4 degrees 2θ, plus or minus 0.10. In some embodiments, provided herein is a solid form comprising a free base of Compound 1 characterized by XRPD peaks located at 1, 2, 3, 4, 5, 6, 7, 8, 9, 10, 11, 12, 13, 14, or all of the following or approximately the following positions: 6.5, 9.0, 9.4, 10.0, 10.5, 10.7, 12.9, 15.5, 15.8, 16.0, 17.3, 17.7, 18.5, 18.9, and 19.4 degrees 2θ, plus or minus 0.10. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by 11 of the peaks. In some embodiments, the solid form is characterized by 13 of the peaks. In some embodiments, the solid form is characterized by all of the peaks.

In some embodiments, provided herein is a solid form comprising a free base of Compound 1 having an XRPD pattern comprising peaks at approximately 9.0, 10.5, and 18.9 degrees 2θ. In certain embodiments, the solid form further comprises peaks at approximately 9.4 and 15.5 degrees 2θ. In certain embodiments, the solid form further comprises peaks at approximately 10.0 and 16.0 degrees 2θ. In one embodiment, the solid form comprises peaks at approximately 6.5, 9.0, 9.4, 10.0, 10.5, 10.7, 12.9, 15.5, 15.8, 16.0, 17.3, 17.7, 18.5, 18.9, and 19.4 degrees 2θ.

In some embodiments, the XRPD peaks above (degrees 2θ peaks) are when analyzed using copper Kα radiation.

In some embodiments, provided herein is a solid form comprising a free base of Compound 1, wherein the solid form is characterized by an XRPD diffraction pattern which matches one or more of the XRPD patterns presented in FIG. 36 or FIG. 37.

In one embodiment, Form 5 of a free base of Compound 1 is prepared by maturation of an amorphous free base of Compound 1 in MeOH. In one embodiment, Form 5 of a free base of Compound 1 is prepared by maturation of an amorphous free base of Compound 1 in EtOH. In one embodiment, Form 5 of a free base of Compound 1 is prepared by maturation of an amorphous free base of Compound 1 in acetonitrile. In one embodiment, Form 5 of a free base of Compound 1 is prepared by maturation of an amorphous free base of Compound 1 in ethyl acetate. In one embodiment, Form 5 of a free base of Compound 1 is prepared by maturation of an amorphous free base of Compound 1 in acetone. In one embodiment, Form 5 of a free base of Compound 1 is prepared by maturation of an amorphous free base of Compound 1 in MIBK. In one embodiment, Form 5 of a free base of Compound 1 is prepared by maturation of an amorphous free base of Compound 1 in TBME. In one embodiment, Form 5 of a free base of Compound 1 is prepared by maturation of an amorphous free base of Compound 1 in 2-MeTHF. In one embodiment, Form 5 of a free base of Compound 1 is prepared by maturation of an amorphous free base of Compound 1 in THF. In one embodiment, Form 5 of a free base of Compound 1 is prepared by maturation of an amorphous free base of Compound 1 in DCM. In one embodiment, Form 5 of a free base of Compound 1 is prepared by maturation of an amorphous free base of Compound 1 in IPA. In one embodiment, Form 5 of a free base of Compound 1 is prepared by maturation of an amorphous free base of Compound 1 in DME. In one embodiment, Form 5 of a free base of Compound 1 is prepared by maturation of an amorphous free base of Compound 1 in DCM/MeOH (1:1). In one embodiment, Form 5 of a free base of Compound 1 is prepared by maturation of an amorphous free base of Compound 1 in EtOH/5% water. In one embodiment, Form 5 of a free base of Compound 1 is prepared by maturation of an amorphous free base of Compound 1 in THF/5% water. In one embodiment, Form 5 of a free base of Compound 1 is prepared by maturation of an amorphous free base of Compound 1 in acetonitrile/5% water. In one embodiment, Form 5 of a free base of Compound 1 is prepared by maturation of an amorphous free base of Compound 1 in IPAc. In one embodiment, the maturation is performed between RT to about 50° C. for about 24 to about 72 hours.

In one embodiment, Form 5 of a free base of Compound 1 is prepared by maturation of Form 2 of a free base of Compound 1 in EtOH. In one embodiment, Form 5 of a free base of Compound 1 is prepared by maturation of Form 2 of a free base of Compound 1 in acetonitrile. In one embodiment, Form 5 of a free base of Compound 1 is prepared by maturation of Form 2 of a free base of Compound 1 in ethyl acetate. In one embodiment, Form 5 of a free base of Compound 1 is prepared by maturation of Form 2 of a free base of Compound 1 in acetone. In one embodiment, Form 5 of a free base of Compound 1 is prepared by maturation of Form 2 of a free base of Compound 1 in MIBK. In one embodiment, Form 5 of a free base of Compound 1 is prepared by maturation of Form 2 of a free base of Compound 1 in IPA. In one embodiment, Form 5 of a free base of Compound 1 is prepared by maturation of Form 2 of a free base of Compound 1 in EtOH/5% water. In one embodiment, Form 5 of a free base of Compound 1 is prepared by maturation of Form 2 of a free base of Compound 1 in acetonitrile/5% water. In one embodiment, Form 5 of a free base of Compound 1 is prepared by maturation of Form 2 of a free base of Compound 1 in IPAc. In one embodiment, Form 5 of a free base of Compound 1 is prepared by maturation of Form 2 of a free base of Compound 1 in 1-butanol. In one embodiment, the maturation is performed between RT to about 50° C. for about 24 to about 72 hours.

In one embodiment, Form 5 of a free base of Compound 1 is prepared by cooling a solution of Form 2 of a free base of Compound 1 in chloroform, followed by maturation. In one embodiment, Form 5 of a free base of Compound 1 is prepared by cooling a solution of Form 2 of a free base of Compound 1 in THF. In one embodiment, Form 5 of a free base of Compound 1 is prepared by cooling a solution of Form 2 of a free base of Compound 1 in DCM. In one embodiment, Form 5 of a free base of Compound 1 is prepared by cooling a solution of Form 2 of a free base of Compound 1 in DCM/MeOH (1:1). In one embodiment, Form 5 of a free base of Compound 1 is prepared by cooling a solution of Form 2 of a free base of Compound 1 in MeOH/anisole. In one embodiment, the cooling temperature ranges from about −20° C. to about 5° C.

In one embodiment, Form 5 of a free base of Compound 1 is prepared by slow evaporation of a solution of Form 2 of a free base of Compound 1 in 2-MeTHF, followed by maturation.

In one embodiment, Form 5 of a free base of Compound 1 is prepared by maturation of Form 1 of a maleic acid salt of Compound 1 in EtOH. In one embodiment, Form 5 of a free base of Compound 1 is prepared by maturation of Form 1 of a maleic acid salt of Compound 1 in 2-propanol. In one embodiment, Form 5 of a free base of Compound 1 is prepared by maturation of Form 1 of a maleic acid salt of Compound 1 in 1-propanol. In one embodiment, Form 5 of a free base of Compound 1 is prepared by maturation of Form 1 of a maleic acid salt of Compound 1 in acetone. In one embodiment, Form 5 of a free base of Compound 1 is prepared by maturation of Form 1 of a maleic acid salt of Compound 1 in THF. In one embodiment, Form 5 of a free base of Compound 1 is prepared by maturation of Form 1 of a maleic acid salt of Compound 1 in EtOH/water (90/10 v/v). In one embodiment, the maturation is performed between RT to about 50° C. for about 24 to about 72 hours.

In one embodiment, Form 5 of a free base of Compound 1 is prepared by cooling a solution of a maleic acid salt of Compound 1 in ethanol. In one embodiment, Form 5 of a free base of Compound 1 is prepared by cooling a solution of a maleic acid salt of Compound 1 in ethanol/water. In one embodiment, Form 5 of a free base of Compound 1 is prepared by cooling a solution of a maleic acid salt of Compound 1 in 2-butanone/water. In one embodiment, Form 5 of a free base of Compound 1 is prepared by cooling a solution of a maleic acid salt of Compound 1 in ethyl acetate/water. In one embodiment, Form 5 of a free base of Compound 1 is prepared by cooling a solution of a maleic acid salt of Compound 1 in anisole/water. In one embodiment, Form 5 of a free base of Compound 1 is prepared by cooling a solution of a maleic acid salt of Compound 1 in anisole/MeOH/water. In one embodiment, Form 5 of a free base of Compound 1 is prepared by cooling a solution of a maleic acid salt of Compound 1 in MEK. In one embodiment, the cooling temperature ranges from about −20° C. to about 5° C. In one embodiment, the cooling temperature is about 5° C. In one embodiment, the cooling time is at least 4 hours, at least 8 hours, or at least 24 hours.

All of the combinations of the above embodiments are encompassed by this invention.

Form 6 of Free Base of Compound 1

In some embodiments, provided herein is Form 6 of the free base of Compound 1. In one embodiment, Form 6 of the free base of Compound 1 is a crystalline acetic acid solvate of Compound 1. In some embodiments, Form 6 of the free base of Compound 1 is substantially free of amorphous free base of Compound 1. In some embodiments, Form 6 of the free base of Compound 1 is substantially free of other crystalline forms (i.e., polymorphs) of the free base of Compound 1. In some embodiments, Form 6 of the free base of Compound 1 is substantially free of salts of Compound 1. In some embodiments, Form 6 of the free base of Compound 1 is provided as substantially pure Form 6 of the free base of Compound 1.

In some embodiment, Form 6 of the free base of Compound 1 is an acetic acid solvate. In one embodiment, Form 6 of the free base of Compound 1 is an acetic acid solvate, wherein the molar ratio of Compound 1 to the acetic acid ranges from about 1:0.4 to about 1:0.6. In one embodiment, the molar ratio of Compound 1 to the acetic acid is about 1:0.5 (i.e., hemi-solvate).

A representative XRPD pattern of Form 6 of the free base of Compound 1 are provided in FIG. 38.

In some embodiments, provided herein is a solid form comprising a free base of Compound 1 characterized by XRPD peaks located at 1, 2, 3, 4, 5, 6, 7, 8, 9, 10, 11, 12, 13, 14, 15, or all of the following or approximately the following positions: 4.9, 7.2, 10.6, 11.1, 12.0, 12.2, 14.6, 15.3, 16.6, 17.3, 18.1, 18.7, 19.4, 20.2, 21.0, 21.2, 22.2, 23.4, and 23.9 degrees 2θ, plus or minus 0.10. In some embodiments, provided herein is a solid form comprising a free base of Compound 1 characterized by XRPD peaks located at 1, 2, 3, 4, 5, 6, 7, 8, 9, 10, 11, 12, or all of the following or approximately the following positions: 4.9, 7.2, 10.6, 11.1, 14.6, 18.1, 18.7, 19.4, 21.0, 21.2, 22.2, 23.4, and 23.9 degrees 2θ, plus or minus 0.10. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by 11 of the peaks. In some embodiments, the solid form is characterized by 13 of the peaks. In some embodiments, the solid form is characterized by all of the peaks.

In some embodiments, provided herein is a solid form comprising a free base of Compound 1 having an XRPD pattern comprising peaks at approximately 7.2, 10.6, and 11.1 degrees 2θ. In certain embodiments, the solid form further comprises peaks at approximately 14.6 and 18.1 degrees 2θ. In certain embodiments, the solid form further comprises peaks at approximately 4.9 and 22.2 degrees 2θ. In one embodiment, the solid form comprises peaks at approximately 4.9, 7.2, 10.6, 11.1, 14.6, 18.1, 18.7, 19.4, 21.0, 21.2, 22.2, 23.4, and 23.9 degrees 2θ.

In some embodiments, the XRPD peaks above (degrees 2θ peaks) are when analyzed using copper Kα radiation.

In some embodiments, provided herein is a solid form comprising a free base of Compound 1, wherein the solid form is characterized by an XRPD diffraction pattern which matches the XRPD pattern presented in FIG. 38.

A representative thermal gravimetric analysis (TGA) curve of the free base of Compound 1 is provided in FIG. 39, which exhibits a weight loss of about 3.05% of the total sample weight upon heating from about 30 to about 60° C., a weight loss of about 3.63% of the total sample weight upon heating from about 60 to about 130° C., and a weight loss of about 2.14% of the total sample weight upon heating from about 130 to about 200° C. Without being limited by any particular theory, the weight losses correspond to loss of about 0.5 equivalent of acetic acid. In some embodiments, provided herein is a solid form comprising a free base of Compound 1, wherein the solid form is characterized by a TGA thermogram which matches the TGA thermogram presented in FIG. 39.

A representative differential scanning calorimetry (DSC) thermogram of the free base of Compound 1 is presented in FIG. 40. In some embodiments, provided herein is a solid form comprising a free base of Compound 1 that exhibits a thermal event, as characterized by DSC, with a peak temperature of about 49° C. and/or an onset temperature of about 27° C., with a peak temperature of about 131° C. and/or an onset temperature of about 111° C., with a peak temperature of about 173° C. and/or an onset temperature of about 165° C., or with a peak temperature of about 184° C. and/or an onset temperature of about 175° C. In some embodiments, provided herein is a solid form comprising a free base of Compound 1 that exhibits thermal events, as characterized by DSC, with a peak temperature of about 49° C. and/or an onset temperature of about 27° C., with a peak temperature of about 131° C. and/or an onset temperature of about 111° C., with a peak temperature of about 173° C. and/or an onset temperature of about 165° C., and with a peak temperature of about 184° C. and/or an onset temperature of about 175° C. Without being limited by any particular theory, the thermal events correspond to loss of about 0.5 equivalent of acetic acid. In some embodiments, provided herein is a solid form comprising a free base of Compound 1, wherein the solid form is characterized by a DSC thermogram which matches the DSC thermogram presented in FIG. 40.

A representative gravimetric vapour sorption (GVS) isotherm of Compound 1 is presented in FIG. 41. In one embodiment, provided herein is a solid form comprising a free base of Compound 1, wherein the solid form is characterized by a GVS isotherm which matches the GVS isotherm presented in FIG. 41.

In one embodiment, Form 6 of the free base of Compound 1 is prepared by maturation of amorphous free base of Compound 1 in acetic acid/water (1:1). In one embodiment, Form 6 of the free base of Compound 1 is prepared by maturation of Form 1 of a free base of Compound 1 in acetic acid/water (1:1). In one embodiment, the maturation is performed between RT to about 50° C. for about 72 hours.

In one embodiment, Form 6 of the free base of Compound 1 converts to Form 4 of the free base of Compound 1 by desolvation. In one embodiment, the desolvation occurs at about 100° C. In another embodiment, the desolvation occurs at 0% RH. In one embodiment, Form 6 of the free base of Compound 1 converts to Form 3 of the free base of Compound 1 after storage at elevated humidity conditions (e.g., 40° C./75% RH for about a week). In one embodiment, without being limited by any particular theories, Form 6 and Form 3 of the free base of Compound 1 are isostructural solvate/hydrate.

All of the combinations of the above embodiments are encompassed by this invention.

Amorphous Free Base of Compound 1

In some embodiments, provided herein is an amorphous free base of Compound 1. In one embodiment, the amorphous free base of Compound 1 is prepared by freeze-drying (e.g., lyophilization) of a solution of a free base of Compound 1. In one embodiment, the amorphous free base of Compound 1 is prepared by freeze-drying (e.g., lyophilization) of a solution of a free base of Compound 1 in a mixed solvent of t-BuOH and water. In one embodiment, amorphous free base of Compound 1 prepared by freeze-drying (e.g., lyophilization) of a solution of a free base of Compound 1 in a mixed solvent of t-BuOH and water is a t-BuOH solvate. In one embodiment, the t-BuOH solvate of the amorphous free base of Compound 1 contains about 10% to about 40%, or about 20% to about 35%, of t-BuOH by molar ratio.

In one embodiment, the amorphous free base of Compound 1 is prepared by evaporation of a solution of a free base of Compound 1 in DMSO.

In one embodiment, amorphous free base of Compound 1 converts to Form 6 of the free base of Compound 1 after maturation in acetic acid/water (1:1) for 72 hours.

Mixture of Solid Forms of Compound 1 or Salts Thereof.

In certain embodiments, provided herein are compositions comprising more than one solid forms of Compound 1, or a salt, solvate (e.g., hydrate), or solvate of a salt thereof. Such solid forms include, but are not limited to, Form 1 of a sulfuric acid salt of Compound 1, Form 1A of a sulfuric acid salt of Compound 1, Form 1B of a sulfuric acid salt of Compound 1, Form 2 of a sulfuric acid salt of Compound 1, Form 3 of a sulfuric acid salt of Compound 1, an amorphous sulfuric acid salt of Compound 1, Form 1 of a maleic acid salt of Compound 1, an amorphous maleic acid salt of Compound 1, Form 1 of an 1,2-ethanedisulfonic acid salt of Compound 1, Form 2 of an 1,2-ethanedisulfonic acid salt of Compound 1, Form 3 of an 1,2-ethanedisulfonic acid salt of Compound 1, Form 4 of an 1,2-ethanedisulfonic acid salt of Compound 1, an amorphous 1,2-ethanedisulfonic acid salt of Compound 1, Form 1 of a hydrochloride salt of Compound 1, Form 2 of a hydrochloride salt of Compound 1, an amorphous hydrochloride salt of Compound 1, Form 1 of an isethionate salt of Compound 1, an amorphous isethionate salt of Compound 1, Form 1 of a free base of Compound 1, Form 2 of a free base of Compound 1, Form 3 of a free base of Compound 1, Form 4 of a free base of Compound 1, Form 5 of a free base of Compound 1, Form 6 of a free base of Compound 1, or an amorphous free base of Compound 1.

In one embodiment, provided herein is a composition comprising Form 1 of a sulfuric acid salt of Compound 1 and at least one other solid form of Compound 1, or a salt, solvate (e.g., hydrate), or solvate of a salt thereof. In one embodiment, the ratio of Form 1 of a sulfuric acid salt of Compound 1 to the total amount of other solid forms in the composition is greater than about 1:1, greater than about 2:1, greater than about 3:1, greater than about 4:1, greater than about 5:1, greater than about 6:1, greater than about 7:1, greater than about 8:1, or greater than about 9:1.

In one embodiment, provided herein is a composition comprising Form 1 of a maleic acid salt of Compound 1 and at least one other solid form of Compound 1, or a salt, solvate (e.g., hydrate), or solvate of a salt thereof. In one embodiment, the ratio of Form 1 of a maleic acid salt of Compound 1 to the total amount of other solid forms in the composition is greater than about 1:1, greater than about 2:1, greater than about 3:1, greater than about 4:1, greater than about 5:1, greater than about 6:1, greater than about 7:1, greater than about 8:1, or greater than about 9:1.

In one embodiment, provided herein is a composition comprising Form 1 of a free base of Compound 1 and at least one other solid form of Compound 1, or a salt, solvate (e.g., hydrate), or solvate of a salt thereof. In one embodiment, the composition comprises Form 1 of a free base of Compound 1 and Form 2 of a free base of Compound 1. In another embodiment, the composition comprises Form 1 of a free base of Compound 1 and Form 3 of a free base of Compound 1. In another embodiment, the composition comprises Form 1 of a free base of Compound 1 and Form 4 of a free base of Compound 1. In another embodiment, the composition comprises Form 1 of a free base of Compound 1 and Form 5 of a free base of Compound 1. In another embodiment, the composition comprises Form 1 of a free base of Compound 1 and Form 6 of a free base of Compound 1. In another embodiment, the composition comprises Form 1 of a free base of Compound 1 and an amorphous free base of Compound 1. In one embodiment, the ratio of Form 1 of a free base of Compound 1 to the total amount of other solid forms in the composition is greater than about 1:1, greater than about 2:1, greater than about 3:1, greater than about 4:1, greater than about 5:1, greater than about 6:1, greater than about 7:1, greater than about 8:1, or greater than about 9:1.

In one embodiment, provided herein is a composition comprising Form 2 of a free base of Compound 1 and at least one other solid form of Compound 1, or a salt, solvate (e.g., hydrate), or solvate of a salt thereof. In one embodiment, the composition comprises Form 2 of a free base of Compound 1 and Form 1 of a free base of Compound 1. In another embodiment, the composition comprises Form 2 of a free base of Compound 1 and Form 3 of a free base of Compound 1. In another embodiment, the composition comprises Form 2 of a free base of Compound 1 and Form 4 of a free base of Compound 1. In another embodiment, the composition comprises Form 2 of a free base of Compound 1 and Form 5 of a free base of Compound 1. In another embodiment, the composition comprises Form 2 of a free base of Compound 1 and Form 6 of a free base of Compound 1. In another embodiment, the composition comprises Form 2 of a free base of Compound 1 and an amorphous free base of Compound 1. In one embodiment, the ratio of Form 2 of a free base of Compound 1 to the total amount of other solid forms in the composition is greater than about 1:1, greater than about 2:1, greater than about 3:1, greater than about 4:1, greater than about 5:1, greater than about 6:1, greater than about 7:1, greater than about 8:1, or greater than about 9:1.

In one embodiment, provided herein is a composition comprising Form 3 of a free base of Compound 1 and at least one other solid form of Compound 1, or a salt, solvate (e.g., hydrate), or solvate of a salt thereof. In one embodiment, the composition comprises Form 3 of a free base of Compound 1 and Form 1 of a free base of Compound 1. In another embodiment, the composition comprises Form 3 of a free base of Compound 1 and Form 2 of a free base of Compound 1. In another embodiment, the composition comprises Form 3 of a free base of Compound 1 and Form 4 of a free base of Compound 1. In another embodiment, the composition comprises Form 3 of a free base of Compound 1 and Form 5 of a free base of Compound 1. In another embodiment, the composition comprises Form 3 of a free base of Compound 1 and Form 6 of a free base of Compound 1. In another embodiment, the composition comprises Form 3 of a free base of Compound 1 and an amorphous free base of Compound 1. In one embodiment, the ratio of Form 3 of a free base of Compound 1 to the total amount of other solid forms in the composition is greater than about 1:1, greater than about 2:1, greater than about 3:1, greater than about 4:1, greater than about 5:1, greater than about 6:1, greater than about 7:1, greater than about 8:1, or greater than about 9:1.

In one embodiment, provided herein is a composition comprising Form 4 of a free base of Compound 1 and at least one other solid form of Compound 1, or a salt, solvate (e.g., hydrate), or solvate of a salt thereof. In one embodiment, the composition comprises Form 4 of a free base of Compound 1 and Form 1 of a free base of Compound 1. In another embodiment, the composition comprises Form 4 of a free base of Compound 1 and Form 2 of a free base of Compound 1. In another embodiment, the composition comprises Form 4 of a free base of Compound 1 and Form 3 of a free base of Compound 1. In another embodiment, the composition comprises Form 4 of a free base of Compound 1 and Form 5 of a free base of Compound 1. In another embodiment, the composition comprises Form 4 of a free base of Compound 1 and Form 6 of a free base of Compound 1. In another embodiment, the composition comprises Form 4 of a free base of Compound 1 and an amorphous free base of Compound 1. In one embodiment, the ratio of Form 4 of a free base of Compound 1 to the total amount of other solid forms in the composition is greater than about 1:1, greater than about 2:1, greater than about 3:1, greater than about 4:1, greater than about 5:1, greater than about 6:1, greater than about 7:1, greater than about 8:1, or greater than about 9:1.

In one embodiment, provided herein is a composition comprising Form 5 of a free base of Compound 1 and at least one other solid form of Compound 1, or a salt, solvate (e.g., hydrate), or solvate of a salt thereof. In one embodiment, the composition comprises Form 5 of a free base of Compound 1 and Form 1 of a free base of Compound 1. In another embodiment, the composition comprises Form 5 of a free base of Compound 1 and Form 2 of a free base of Compound 1. In another embodiment, the composition comprises Form 5 of a free base of Compound 1 and Form 3 of a free base of Compound 1. In another embodiment, the composition comprises Form 5 of a free base of Compound 1 and Form 4 of a free base of Compound 1. In another embodiment, the composition comprises Form 5 of a free base of Compound 1 and Form 6 of a free base of Compound 1. In another embodiment, the composition comprises Form 5 of a free base of Compound 1 and an amorphous free base of Compound 1. In one embodiment, the ratio of Form 5 of a free base of Compound 1 to the total amount of other solid forms in the composition is greater than about 1:1, greater than about 2:1, greater than about 3:1, greater than about 4:1, greater than about 5:1, greater than about 6:1, greater than about 7:1, greater than about 8:1, or greater than about 9:1.

In one embodiment, provided herein is a composition comprising Form 6 of a free base of Compound 1 and at least one other solid form of Compound 1, or a salt, solvate (e.g., hydrate), or solvate of a salt thereof. In one embodiment, the composition comprises Form 6 of a free base of Compound 1 and Form 1 of a free base of Compound 1. In another embodiment, the composition comprises Form 6 of a free base of Compound 1 and Form 2 of a free base of Compound 1. In another embodiment, the composition comprises Form 6 of a free base of Compound 1 and Form 3 of a free base of Compound 1. In another embodiment, the composition comprises Form 6 of a free base of Compound 1 and Form 4 of a free base of Compound 1. In another embodiment, the composition comprises Form 6 of a free base of Compound 1 and Form 5 of a free base of Compound 1. In another embodiment, the composition comprises Form 6 of a free base of Compound 1 and an amorphous free base of Compound 1. In one embodiment, the ratio of Form 6 of a free base of Compound 1 to the total amount of other solid forms in the composition is greater than about 1:1, greater than about 2:1, greater than about 3:1, greater than about 4:1, greater than about 5:1, greater than about 6:1, greater than about 7:1, greater than about 8:1, or greater than about 9:1.

5.2.7 Methods for Analyzing Material

In some embodiments, provided herein are also methods for analyzing a material for the presence or amount of a solid form provided herein, comprising
providing a material comprising a compound of formula (I), or a salt, solvate, or solvate of a salt thereof, or a mixture thereof; and
using a characterization method to determine whether a signatory characteristic associated with the solid form is present in the material by comparing the characteristic obtained from the material with a reference signatory characteristic;
wherein the existence of a characteristic substantially identical to the reference signatory characteristic indicates the presence of the solid form in the material.

In one embodiment, the method further comprises selecting a batch as a result of the determination based upon comparison to the reference standard. In one embodiment, the method further comprises making a determination regarding the quality of the material. In one embodiment, the method further comprises making a determination whether to use the material in the manufacturing of a pharmaceutical composition. In one embodiment, the method further comprises making a determination whether to use the material for treating a PI3K mediated disorder.

In one embodiment, the characterization method is one or more of XRPD, TGA, DSC, GVS, FT-IR, or NMR.

In one embodiment, the method is for analyzing a material for the presence or amount of Form 1 of the sulfuric acid salt of Compound 1. In one embodiment, the characterization method is XRPD. In one embodiment, the characterization method is XRPD, and the signatory characteristic is XRPD peaks located at 1, 2, 3, 4, 5, 6, 7, 8, 9, 10, 11, 12, 13, 14, 15, or all of the following or approximately the following positions 8.1, 10.7, 10.9, 12.4, 13.3, 14.0, 14.2, 14.8, 15.1, 16.0, 16.3, 17.6, 17.7, 18.4, 18.6, 18.7, 19.2, 20.4, 21.4, 21.7, 22.2, 23.0, 23.4, 23.6, 24.2, and 24.7 degrees 2θ, plus or minus 0.10.

In one embodiment, the method is for analyzing a material for the presence or amount of Form 1 of the maleic acid salt of Compound 1. In one embodiment, the characterization method is XRPD. In one embodiment, the characterization method is XRPD, and the signatory characteristic is XRPD peaks located at 1, 2, 3, 4, 5, 6, 7, 8, 9, 10, 11, 12, 13, 14, 15, or all of the following or approximately the following positions: 6.2, 9.0, 11.3, 11.7, 12.4, 12.9, 13.0, 13.4, 14.4, 14.6, 16.0, 16.8, 17.5, 18.0, 18.3, 18.6, 19.6, 19.8, 20.3, 21.3, 21.7, 22.6, 23.2, 23.5, and 24.4 degrees 2θ, plus or minus 0.10.

In one embodiment, the method is for analyzing a material for the presence or amount of Form 1 of the 1,2-ethanedisulfonic acid salt of Compound 1. In one embodiment, the characterization method is XRPD. In one embodiment, the characterization method is XRPD, and the signatory characteristic is XRPD peaks located at 1, 2, 3, 4, 5, 6, 7, 8, 9, 10, 11, 12, 13, 14, 15, or all of the following or approximately the following positions: 7.9, 8.5, 10.3, 10.7, 11.0, 12.4, 12.7, 14.0, 14.3, 15.3, 15.9, 17.2, 17.4, 18.1, 18.3, 18.4, 18.7, 19.2, 20.5, 20.6, 21.2, 21.5, 21.9, 22.4, 22.8, and 23.3 degrees 2θ, plus or minus 0.10.

In one embodiment, the method is for analyzing a material for the presence or amount of Form 1 of the free base of Compound 1. In one embodiment, the characterization method is XRPD. In one embodiment, the characterization method is XRPD, and the signatory characteristic is XRPD peaks located at 1, 2, 3, 4, 5, 6, 7, 8, 9, 10, 11, 12, 13, 14, 15, or all of the following or approximately the following positions: 5.0, 7.6, 9.9, 10.7, 11.4, 12.2, 13.0, 13.5, 14.0, 14.5, 15.1, 15.9, 16.4, 16.8, 17.7, 18.1, 19.1, 19.9, 20.6, 21.1, 21.7, 22.4, 23.1, 23.7, 24.6, and 25.2 degrees 2θ, plus or minus 0.10.

In one embodiment, the method is for analyzing a material for the presence or amount of Form 2 of the free base of Compound 1. In one embodiment, the characterization method is XRPD. In one embodiment, the characterization method is XRPD, and the signatory characteristic is XRPD peaks located at 1, 2, 3, 4, 5, 6, 7, 8, 9, 10, 11, 12, 13, 14, 15, or all of the following or approximately the following positions: 9.1, 10.9, 12.3, 15.0, 16.1, 16.8, 17.8, 18.1, 18.3, 19.3, 20.1, 20.5, 20.7, 20.8, 21.5, 21.9, 22.4, 22.7, 23.9, 24.9, 25.6, 26.2, 26.8, 27.2, and 27.5 degrees 2θ, plus or minus 0.10.

In one embodiment, the method is for analyzing a material for the presence or amount of Form 3 of the free base of Compound 1. In one embodiment, the characterization method is XRPD. In one embodiment, the characterization method is XRPD, and the signatory characteristic is XRPD peaks located at 1, 2, 3, 4, 5, 6, 7, 8, 9, 10, 11, 12, or all of the following or approximately the following positions: 4.9, 7.3, 10.6, 11.3, 12.0, 14.4, 14.9, 15.2, 16.9, 17.7, 20.0, 21.9, and 24.6 degrees 2θ, plus or minus 0.10.

In one embodiment, the method is for analyzing a material for the presence or amount of Form 4 of the free base of Compound 1. In one embodiment, the characterization method is XRPD. In one embodiment, the characterization method is XRPD, and the signatory characteristic is XRPD peaks located at 1, 2, 3, 4, 5, 6, 7, 8, 9, 10, 11, 12, 13, 14, 15, or all of the following or approximately the following positions: 5.0, 7.4, 10.7, 11.1, 11.5, 11.8, 13.0, 13.8, 14.5, 15.4, 16.4, 16.7, 17.5, 19.1, 20.0, 21.7, 22.2, 22.4, 23.2, and 23.9 degrees 2θ, plus or minus 0.10.

In one embodiment, the method is for analyzing a material for the presence or amount of Form 5 of the free base of Compound 1. In one embodiment, the characterization method is XRPD. In one embodiment, the characterization method is XRPD, and the signatory characteristic is XRPD peaks located at 1, 2, 3, 4, 5, 6, 7, 8, 9, 10, 11, 12, 13, 14, 15, or all of the following or approximately the following positions: 6.5, 9.0, 9.4, 10.0, 10.5, 10.7, 11.3, 11.7, 12.1, 12.9, 13.1, 14.0, 14.5, 15.5, 15.8, 16.0, 16.6, 17.3, 17.5, 17.7, 18.0, 18.5, 18.9, 19.1, and 19.4 degrees 2θ, plus or minus 0.10.

In one embodiment, the method is for analyzing a material for the presence or amount of Form 6 of the free base of Compound 1. In one embodiment, the characterization method is XRPD. In one embodiment, the characterization method is XRPD, and the signatory characteristic is XRPD peaks located at 1, 2, 3, 4, 5, 6, 7, 8, 9, 10, 11, 12, 13, 14, 15, or all of the following or approximately the following positions: 4.9, 7.2, 10.6, 11.1, 12.0, 12.2, 14.6, 15.3, 16.6, 17.3, 18.1, 18.7, 19.4, 20.2, 21.0, 21.2, 22.2, 23.4, and 23.9 degrees 2θ, plus or minus 0.10.

6. PHARMACEUTICAL COMPOSITIONS

In some embodiments, provided herein are pharmaceutical compositions comprising a compound provided herein, or an enantiomer, a mixture of enantiomers, or a mixture of two or more diastereomers thereof, or a pharmaceutically acceptable form thereof (e.g., pharmaceutically acceptable salts, hydrates, solvates, isomers, prodrugs, and isotopically labeled derivatives), and a pharmaceutically acceptable excipient, diluent, or carrier, including inert solid diluents and fillers, sterile aqueous solution and various organic solvents, permeation enhancers, solubilizers and adjuvants. In some embodiments, a pharmaceutical composition described herein includes a second active agent such as an additional therapeutic agent, (e.g., a chemotherapeutic agent).

6.1. Formulations

Pharmaceutical compositions can be specially formulated for administration in solid or liquid form, including those adapted for the following: oral administration, for example, drenches (aqueous or non-aqueous solutions or suspensions), tablets (e.g., those targeted for buccal, sublingual, and systemic absorption), capsules, boluses, powders, granules, pastes for application to the tongue, and intraduodenal routes; parenteral administration, including intravenous, intraarterial, subcutaneous, intramuscular, intravascular, intraperitoneal or infusion as, for example, a sterile solution or suspension, or sustained-release formulation; topical application, for example, as a cream, ointment, or a controlled-release patch or spray applied to the skin; intravaginally or intrarectally, for example, as a pessary, cream, stent or foam; sublingually; ocularly; pulmonarily; local delivery by catheter or stent; intrathecally, or nasally.

Examples of suitable aqueous and nonaqueous carriers which can be employed in pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents, dispersing agents, lubricants, and/or antioxidants. Prevention of the action of microorganisms upon the compounds described herein can be ensured by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

Methods of preparing these formulations or compositions include the step of bringing into association a compound described herein and/or the chemotherapeutic with the carrier and, optionally, one or more accessory ingredients. In general, the formulations are prepared by uniformly and intimately bringing into association a compound as provided herein with liquid carriers, or finely divided solid carriers, or both, and then, if necessary, shaping the product.

Preparations for such pharmaceutical compositions are well-known in the art. See, e.g., Anderson, Philip O.; Knoben, James E.; Troutman, William G, eds., *Handbook of Clinical Drug Data*, Tenth Edition, McGraw-Hill, 2002; Pratt and Taylor, eds., *Principles of Drug Action*, Third Edition, Churchill Livingston, New York, 1990; Katzung, ed., *Basic and Clinical Pharmacology*, Twelfth Edition, McGraw Hill, 2011; Goodman and Gilman, eds., *The Pharmacological Basis of Therapeutics*, Tenth Edition, McGraw Hill, 2001; *Remingtons Pharmaceutical Sciences*, 20th Ed., Lippincott Williams & Wilkins., 2000; Martindale, *The Extra Pharmacopoeia*, Thirty-Second Edition (The Pharmaceutical Press, London, 1999); all of which are incorporated by reference herein in their entirety. Except insofar as any conventional excipient medium is incompatible with the compounds provided herein, such as by producing any undesirable biological effect or otherwise interacting in a deleterious manner with any other component(s) of the pharmaceutically acceptable composition, the excipient's use is contemplated to be within the scope of this disclosure.

In some embodiments, the concentration of one or more of the compounds provided in the disclosed pharmaceutical compositions is equal to or less than about 100%, about 90%, about 80%, about 70%, about 60%, about 50%, about 40%, about 30%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about 0.0002%, or about 0.0001% w/w, w/v or v/v.

In some embodiments, the concentration of one or more of the compounds as provided herein is greater than about 90%, about 80%, about 70%, about 60%, about 50%, about 40%, about 30%, about 20%, about 19.75%, about 19.50%, about 19.25%, about 19%, about 18.75%, about 18.50%, about 18.25%, about 18%, about 17.75%, about 17.50%, about 17.25%, about 17%, about 16.75%, about 16.50%, about 16.25%, about 16%, about 15.75%, about 15.50%, about 15.25%, about 15%, about 14.75%, about 14.50%, about 14.25%, about 14%, about 13.75%, about 13.50%, about 13.25%, about 13%, about 12.75%, about 12.50%, about 12.25%, about 12%, about 11.75%, about 11.50%, about 11.25%, about 11%, about 10.75%, about 10.50%, about 10.25%, about 10%, about 9.75%, about 9.50%, about 9.25%, about 9%, about 8.75%, about 8.50%, about 8.25%, about 8%, about 7.75%, about 7.50%, about 7.25%, about 7%, about 6.75%, about 6.50%, about 6.25%, about 6%, about 5.75%, about 5.50%, about 5.25%, about 5%, about 4.75%, about 4.50%, about 4.25%, about 4%, about 3.75%, about 3.50%, about 3.25%, about 3%, about 2.75%, about 2.50%, about 2.25%, about 2%, about 1.75%, about 1.50%, about 1.25%, about 1%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about 0.0002%, or about 0.0001% w/w, w/v, or v/v.

In some embodiments, the concentration of one or more of the compounds as provided herein is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, or approximately 1% to approximately 10% w/w, w/v, or v/v.

In some embodiments, the concentration of one or more of the compounds as provided herein is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, or approximately 0.1% to approximately 0.9% w/w, w/v, or v/v.

In some embodiments, the amount of one or more of the compounds as provided herein is equal to or less than about 10 g, about 9.5 g, about 9.0 g, about 8.5 g, about 8.0 g, about 7.5 g, about 7.0 g, about 6.5 g, about 6.0 g, about 5.5 g, about 5.0 g, about 4.5 g, about 4.0 g, about 3.5 g, about 3.0 g, about 2.5 g, about 2.0 g, about 1.5 g, about 1.0 g, about 0.95 g, about 0.9 g, about 0.85 g, about 0.8 g, about 0.75 g, about 0.7 g, about 0.65 g, about 0.6 g, about 0.55 g, about 0.5 g, about 0.45 g, about 0.4 g, about 0.35 g, about 0.3 g, about 0.25 g, about 0.2 g, about 0.15 g, about 0.1 g, about 0.09 g, about 0.08 g, about 0.07 g, about 0.06 g, about 0.05 g, about 0.04 g, about 0.03 g, about 0.02 g, about 0.01 g, about 0.009 g, about 0.008 g, about 0.007 g, about 0.006 g, about 0.005 g, about 0.004 g, about 0.003 g, about 0.002 g, about 0.001 g, about 0.0009 g, about 0.0008 g, about 0.0007 g, about 0.0006 g, about 0.0005 g, about 0.0004 g, about 0.0003 g, about 0.0002 g, or about 0.0001 g.

In some embodiments, the amount of one or more of the compounds as provided herein is more than about 0.0001 g, about 0.0002 g, about 0.0003 g, about 0.0004 g, about 0.0005 g, about 0.0006 g, about 0.0007 g, about 0.0008 g, about 0.0009 g, about 0.001 g, about 0.0015 g, about 0.002 g, about 0.0025 g, about 0.003 g, about 0.0035 g, about 0.004 g, about 0.0045 g, about 0.005 g, about 0.0055 g, about 0.006 g, about 0.0065 g, about 0.007 g, about 0.0075 g, about 0.008 g, about 0.0085 g, about 0.009 g, about 0.0095 g, about 0.01 g, about 0.015 g, about 0.02 g, about 0.025 g, about 0.03 g, about 0.035 g, about 0.04 g, about 0.045 g, about 0.05 g, about 0.055 g, about 0.06 g, about 0.065 g, about 0.07 g, about 0.075 g, about 0.08 g, about 0.085 g, about 0.09 g, about 0.095 g, about 0.1 g, about 0.15 g, about 0.2 g, about 0.25 g, about 0.3 g, about 0.35 g, about 0.4 g, about 0.45 g, about 0.5 g, about 0.55 g, about 0.6 g, about 0.65 g, about 0.7 g, about 0.75 g, about 0.8 g, about 0.85 g, about 0.9 g, about 0.95 g, about 1 g, about 1.5 g, about 2 g, about 2.5 g, about 3 g, about 3.5 g, about 4 g, about 4.5 g, about 5 g, about 5.5 g, about 6 g, about 6.5 g, about 7 g, about 7.5 g, about 8 g, about 8.5 g, about 9 g, about 9.5 g, or about 10 g.

In some embodiments, the amount of one or more of the compounds as provided herein is in the range of about 0.0001 to about 10 g, about 0.0005 to about 9 g, about 0.001 to about 8 g, about 0.005 to about 7 g, about 0.01 to about 6 g, about 0.05 to about 5 g, about 0.1 to about 4 g, about 0.5 to about 4 g, or about 1 to about 3 g.

6.1.1. Formulations for Oral Administration

In some embodiments, provided herein are pharmaceutical compositions for oral administration containing a compound as provided herein, and a pharmaceutical excipient suitable for oral administration. In some embodiments, provided herein are pharmaceutical compositions for oral administration containing: (i) an effective amount of a disclosed compound; optionally (ii) an effective amount of one or more second agents; and (iii) one or more pharmaceutical excipients suitable for oral administration. In some embodiments, the pharmaceutical composition further contains: (iv) an effective amount of a third agent.

In some embodiments, the pharmaceutical composition can be a liquid pharmaceutical composition suitable for oral consumption. Pharmaceutical compositions suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more ingredients. In general, the pharmaceutical compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The present disclosure further encompasses anhydrous pharmaceutical compositions and dosage forms comprising an active ingredient, since water can facilitate the degradation of some compounds. For example, water can be added (e.g., about 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. For example, pharmaceutical compositions and dosage forms which contain lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous pharmaceutical compositions can be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the pharmaceutical compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. In some embodiments, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants can be used in the pharmaceutical compositions as provided herein to provide tablets that disintegrate when exposed to an aqueous environment. Too much of a disintegrant can produce tablets which can disintegrate in the bottle. Too little can be insufficient for disintegration to occur and can thus alter the rate and extent of release of the active ingredient(s) from the dosage form. Thus, a sufficient amount of disintegrant that is neither too little nor too much to detrimentally alter the release of the active ingredient(s) can be used to form the dosage forms of the compounds provided herein. The amount of disintegrant used can vary based upon the type of formulation and mode of administration, and can be readily discernible to those of ordinary skill in the art. About 0.5 to about 15 weight percent of disintegrant, or about 1 to about 5 weight percent of disintegrant, can be used in the pharmaceutical composition. Disintegrants that can be used to form pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein can be combined with various sweetening or flavoring agents, coloring matter or dyes and, for example, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms include, but are not limited to, hydrophilic surfactants, lipophilic surfactants, and mixtures thereof. That is, a mixture of hydrophilic surfactants can be employed, a mixture of lipophilic surfactants can be employed, or a mixture of at least one hydrophilic surfactant and at least one lipophilic surfactant can be employed.

A suitable hydrophilic surfactant can generally have an HLB value of at least about 10, while suitable lipophilic surfactants can generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants can be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants can be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants can include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of triglycerides, vegetable oils, and hydrogenated vegetable oils. The polyol can be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of glycerides, vegetable oils, hydrogenated vegetable oils, fatty acids and sterols; oil-soluble vitamins/vitamin derivatives; and mixtures thereof. Within this group, non-limiting examples of lipophilic surfactants include glycerol fatty acid esters, propylene glycol fatty acid esters, and mixtures thereof, or are hydrophobic transesterification products of a polyol with at least one member of vegetable oils, hydrogenated vegetable oils, and triglycerides.

In one embodiment, the pharmaceutical composition can include a solubilizer to ensure good solubilization and/or dissolution of a compound as provided herein and to minimize precipitation of the compound. This can be especially important for pharmaceutical compositions for non-oral use, e.g., pharmaceutical compositions for injection. A solubilizer can also be added to increase the solubility of the hydrophilic drug and/or other components, such as surfactants, or to maintain the pharmaceutical composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers can also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. In some embodiments, solubilizers include sorbitol, glycerol, triacetin, ethyl alcohol, PEG-400, glycofurol and propylene glycol.

The amount of solubilizer that can be included is not particularly limited. The amount of a given solubilizer can be limited to a bioacceptable amount, which can be readily determined by one of skill in the art. In some circumstances, it can be advantageous to include amounts of solubilizers far in excess of bioacceptable amounts, for example to maximize the concentration of the drug, with excess solubilizer removed prior to providing the pharmaceutical composition to a subject using conventional techniques, such as distillation or evaporation. Thus, if present, the solubilizer can be in a weight ratio of about 10%, 25%, 50%, 100%, or up to about 200% by weight, based on the combined weight of the drug, and other excipients. If desired, very small amounts of solubilizer can also be used, such as about 5%, 2%, 1% or even less. Typically, the solubilizer can be present in an amount of about 1% to about 100%, more typically about 5% to about 25% by weight.

The pharmaceutical composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, oils, odorants, opacifiers, suspending agents, binders, fillers, plasticizers, lubricants, and mixtures thereof.

Exemplary preservatives can include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils also include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

In addition, an acid or a base can be incorporated into the pharmaceutical composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl)-aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Examples can include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

6.1.2. Formulations for Parenteral Administration

In some embodiments, provided herein are pharmaceutical compositions for parenteral administration containing a compound as provided herein, and a pharmaceutical excipient suitable for parenteral administration. In some embodiments, provided herein are pharmaceutical compositions for parenteral administration containing: (i) an effective amount of a disclosed compound; optionally (ii) an effective amount of one or more second agents; and (iii) one or more pharmaceutical excipients suitable for parenteral administration. In some embodiments, the pharmaceutical composition further contains: (iv) an effective amount of a third agent.

The forms in which the disclosed pharmaceutical compositions can be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils can also be employed.

Aqueous solutions in saline are also conventionally used for injection. Ethanol, glycerol, propylene glycol, liquid polyethylene glycol, and the like (and suitable mixtures thereof), cyclodextrin derivatives, and vegetable oils can also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound as provided herein in the required amount in the appropriate solvent with various other ingredients as enumerated above, as appropriate, followed by filtered sterilization. Generally, dispersions are prepared by incorporating the various sterilized active ingredients into a sterile vehicle which contains the basic dispersion medium and the appropriate other ingredients from those enumerated above. In the case of sterile powders for the preparation of sterile injectable solutions, certain methods of preparation are vacuum-drying and freeze-drying techniques which yield a powder of the active ingredient plus any additional ingredient from a previously sterile-filtered solution thereof.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Injectable compositions can contain from about 0.1 to about 5% w/w of a compound as disclosed herein.

6.1.3. Formulations for Topical Administration

In some embodiments, provided herein are pharmaceutical compositions for topical (e.g., transdermal) administration containing a compound as provided herein, and a pharmaceutical excipient suitable for topical administration. In some embodiments, provided herein are pharmaceutical compositions for topical administration containing: (i) an effective amount of a disclosed compound; optionally (ii) an effective amount of one or more second agents; and (iii) one or more pharmaceutical excipients suitable for topical administration. In some embodiments, the pharmaceutical composition further contains: (iv) an effective amount of a third agent.

Pharmaceutical compositions provided herein can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation can provide more immediate exposure of the active ingredient to the chosen area.

The pharmaceutical compositions also can comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the disclosed methods employs transdermal delivery devices ("patches"). Such transdermal patches can be used to provide continuous or discontinuous infusion of a compound as provided herein in controlled amounts, either with or without another agent. The construction and use of transdermal patches for the delivery of pharmaceutical agents is well known in the art. See, e.g., U.S. Pat. Nos. 5,023,252, 4,992,445 and 5,001,139. Such patches can be constructed for continuous, pulsatile, or on demand delivery of pharmaceutical agents.

Suitable devices for use in delivering intradermal pharmaceutically acceptable compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Topically-administrable formulations can, for example, comprise from about 1% to about 10% (w/w) of a compound provided herein relative to the total weight of the formulation, although the concentration of the compound provided herein in the formulation can be as high as the solubility limit of the compound in the solvent. In some embodiments, topically-administrable formulations can, for example, comprise from about 1% to about 9% (w/w) of a compound provided herein, such as from about 1% to about 8% (w/w), further such as from about 1% to about 7% (w/w), further such as from about 1% to about 6% (w/w), further such as from about 1% to about 5% (w/w), further such as from about 1% to about 4% (w/w), further such as from about 1% to about 3% (w/w), and further such as from about 1% to about 2% (w/w) of a compound provided herein. Formulations for topical administration can further comprise one or more of the additional pharmaceutically acceptable excipients described herein.

6.1.4. Formulations for Inhalation Administration

In some embodiments, provided herein are pharmaceutical compositions for inhalation administration containing a compound as provided herein, and a pharmaceutical excipient suitable for topical administration. In some embodiments, provided herein are pharmaceutical compositions for inhalation administration containing: (i) an effective amount of a disclosed compound; optionally (ii) an effective amount of one or more second agents; and (iii) one or more pharmaceutical excipients suitable for inhalation administration. In some embodiments, the pharmaceutical composition further contains: (iv) an effective amount of a third agent.

Pharmaceutical compositions for inhalation or insufflation include solutions and suspensions in pharmaceutically acceptable, aqueous or organic solvents, or mixtures thereof, and powders. The liquid or solid pharmaceutical compositions can contain suitable pharmaceutically acceptable excipients as described herein. In some embodiments, the pharmaceutical compositions are administered by the oral or nasal respiratory route for local or systemic effect. Pharmaceutical compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder pharmaceutical compositions can be administered, e.g., orally or nasally, from devices that deliver the formulation in an appropriate manner.

6.1.5. Formulations for Ocular Administration

In some embodiments, the disclosure provides a pharmaceutical composition for treating ophthalmic disorders. The pharmaceutical composition can contain an effective amount of a compound as provided herein and a pharmaceutical excipient suitable for ocular administration. Pharmaceutical compositions suitable for ocular administration can be presented as discrete dosage forms, such as drops or sprays each containing a predetermined amount of an active ingredient a solution, or a suspension in an aqueous or non-aqueous liquid, an oil-in-water emulsion, or a water-in-oil liquid emulsion. Other administration forms include intraocular injection, intravitreal injection, topically, or through the use of a drug eluting device, microcapsule, implant, or microfluidic device. In some cases, the compounds as provided herein are administered with a carrier or excipient that increases the intraocular penetrance of the compound such as an oil and water emulsion with colloid particles having an oily core surrounded by an interfacial film. It is contemplated that all local routes to the eye can be used including topical, subconjunctival, periocular, retrobulbar, subtenon, intracameral, intravitreal, intraocular, subretinal, juxtascleral and suprachoroidal administration. Systemic or parenteral administration can be feasible including, but not limited to intravenous, subcutaneous, and oral delivery. An exemplary method of administration will be intravitreal or subtenon injection of solutions or suspensions, or intravitreal or subtenon placement of bioerodible or non-bioerodible devices, or by topical ocular administration of solutions or suspensions, or posterior juxtascleral administration of a gel or cream formulation.

Eye drops can be prepared by dissolving the active ingredient in a sterile aqueous solution such as physiological saline, buffering solution, etc., or by combining powder compositions to be dissolved before use. Other vehicles can be chosen, as is known in the art, including, but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. In some embodiments, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

In some cases, the colloid particles include at least one cationic agent and at least one non-ionic sufactant such as a poloxamer, tyloxapol, a polysorbate, a polyoxyethylene castor oil derivative, a sorbitan ester, or a polyoxyl stearate. In some cases, the cationic agent is an alkylamine, a tertiary alkyl amine, a quarternary ammonium compound, a cationic lipid, an amino alcohol, a biguanidine salt, a cationic compound or a mixture thereof. In some cases, the cationic agent is a biguanidine salt such as chlorhexidine, polyaminopropyl biguanidine, phenformin, alkylbiguanidine, or a mixture thereof. In some cases, the quaternary ammonium compound is a benzalkonium halide, lauralkonium halide, cetrimide, hexadecyltrimethylammonium halide, tetradecyltrimethylammonium halide, dodecyltrimethylammonium halide, cetrimonium halide, benzethonium halide, behenalkonium halide, cetalkonium halide, cetethyldimonium halide, cetylpyridinium halide, benzododecinium halide, chlorallyl methenamine halide, rnyristylalkonium halide, stearalkonium halide or a mixture of two or more thereof. In some cases, cationic agent is a benzalkonium chloride, lauralkonium chloride, benzododecinium bromide, benzethenium chloride, hexadecyltrimethylammonium bromide, tetradecyltrimethylammonium bromide, dodecyltrimethylammonium bromide or a mixture of two or more thereof. In some cases, the oil phase is mineral oil and light mineral oil, medium chain triglycerides (MCT), coconut oil; hydrogenated oils comprising hydrogenated cottonseed oil, hydrogenated palm oil, hydrogenate castor oil or hydrogenated soybean oil; polyoxyethylene hydrogenated castor oil derivatives comprising poluoxyl-40 hydrogenated castor oil, polyoxyl-60 hydrogenated castor oil or polyoxyl-100 hydrogenated castor oil.

6.1.6. Formulations for Controlled Release Administration

In some embodiments, provided herein are pharmaceutical compositions for controlled release administration containing a compound as provided herein, and a pharmaceutical excipient suitable for controlled release administration. In some embodiments, provided herein are pharmaceutical compositions for controlled release administration containing: (i) an effective amount of a disclosed compound; optionally (ii) an effective amount of one or more second agents; and (iii) one or more pharmaceutical excipients suitable for controlled release administration. In some embodiments, the pharmaceutical composition further contains: (iv) an effective amount of a third agent.

Active agents such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 each of which is incorporated herein by reference. Such dosage forms can be used to provide slow or controlled release of one or more active agents using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active agents provided herein. Thus, the pharmaceutical compositions provided encompass single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. In some embodiments, the use of a controlled release preparation in medical treatment is characterized by a minimum of drug substance being employed to cure or control the disease, disorder, or condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

In some embodiments, controlled release formulations are designed to initially release an amount of a compound as provided herein that promptly produces the desired therapeutic effect, and gradually and continually release other amounts of the compound to maintain this level of therapeutic or prophylactic effect over an extended period of time. In order to maintain this constant level of the compound in the body, the compound should be released from the dosage form at a rate that will replace the amount of drug being metabolized and excreted from the body. Controlled release of an active agent can be stimulated by various conditions including, but not limited to, pH, temperature, enzymes, water, or other physiological conditions or compounds.

In certain embodiments, the pharmaceutical composition can be administered using intravenous infusion, an implantable osmotic pump, a transdermal patch, liposomes, or other modes of administration. In one embodiment, a pump can be used (see, Sefton, *CRC Crit. Ref Biomed. Eng.* 14:201 (1987); Buchwald et al., *Surgery* 88:507 (1980); Saudek et al., *N. Engl. J. Med.* 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release*, 115-138 (vol. 2, 1984). Other controlled release systems are discussed in the review by Langer, *Science* 249:1527-1533 (1990). The one or more active agents can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The one or more active agents then diffuse through the outer polymeric membrane in a release rate controlling step. The percentage of active agent in such parenteral compositions is highly dependent on the specific nature thereof, as well as the needs of the subject.

6.2. Dosages

A compound described herein can be delivered in the form of pharmaceutically acceptable compositions which comprise a therapeutically effective amount of one or more compounds described herein and/or one or more additional therapeutic agents such as a chemotherapeutic, formulated together with one or more pharmaceutically acceptable excipients. In some instances, the compound described herein and the additional therapeutic agent are administered in separate pharmaceutical compositions and can (e.g., because of different physical and/or chemical characteristics) be administered by different routes (e.g., one therapeutic is administered orally, while the other is administered intravenously). In other instances, the compound described herein and the additional therapeutic agent can be administered separately, but via the same route (e.g., both orally or both intravenously). In still other instances, the compound described herein and the additional therapeutic agent can be administered in the same pharmaceutical composition.

The selected dosage level will depend upon a variety of factors including, for example, the activity of the particular compound employed, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

In general, a suitable daily dose of a compound described herein and/or a chemotherapeutic will be that amount of the compound which, in some embodiments, can be the lowest dose effective to produce a therapeutic effect. Such an effective dose will generally depend upon the factors described above. Generally, doses of the compounds described herein for a patient, when used for the indicated effects, will range from about 0.0001 mg to about 100 mg per day, or about 0.001 mg to about 100 mg per day, or about 0.01 mg to about 100 mg per day, or about 0.1 mg to about 100 mg per day, or about 0.0001 mg to about 500 mg per day, or about 0.001 mg to about 500 mg per day, or about 0.01 mg to 1000 mg, or about 0.01 mg to about 500 mg per day, or about 0.1 mg to about 500 mg per day, or about 1 mg to 50 mg per day, or about 5 mg to 40 mg. An exemplary dosage is about 10 to 30 mg per day. In some embodiments, for a 70 kg human, a suitable dose would be about 0.05 to about 7 g/day, such as about 0.05 to about 2.5 g/day. Actual dosage levels of the active ingredients in the pharmaceutical compositions described herein can be varied so as to obtain an amount of the active ingredient which is effective to achieve the desired therapeutic response for a particular patient, composition, and mode of administration, without being toxic to the patient. In some instances, dosage levels below the lower limit of the aforesaid range can be more than adequate, while in other cases still larger doses can be employed without causing any harmful side effect, e.g., by dividing such larger doses into several small doses for administration throughout the day.

In some embodiments, the compounds can be administered daily, every other day, three times a week, twice a week, weekly, or bi-weekly. The dosing schedule can include a "drug holiday," e.g., the drug can be administered for two weeks on, one week off, or three weeks on, one week off, or four weeks on, one week off, etc., or continuously, without a drug holiday. The compounds can be administered orally, intravenously, intraperitoneally, topically, transdermally, intramuscularly, subcutaneously, intranasally, sublingually, or by any other route.

In some embodiments, a compound as provided herein is administered in multiple doses. Dosing can be about once, twice, three times, four times, five times, six times, or more than six times per day. Dosing can be about once a month, about once every two weeks, about once a week, or about once every other day. In another embodiment, a compound as provided herein and another agent are administered together from about once per day to about 6 times per day. In another embodiment, the administration of a compound as provided herein and an agent continues for less than about 7 days. In yet another embodiment, the administration continues for more than about 6 days, about 10 days, about 14 days, about 28 days, about two months, about six months, or about one year. In some cases, continuous dosing is achieved and maintained as long as necessary.

Administration of the pharmaceutical compositions as provided herein can continue as long as necessary. In some embodiments, an agent as provided herein is administered for more than about 1, about 2, about 3, about 4, about 5, about 6, about 7, about 14, about 21, or about 28 days. In some embodiments, an agent as provided herein is administered for less than about 28, about 21, about 14, about 7, about 6, about 5, about 4, about 3, about 2, or about 1 day. In some embodiments, an agent as provided herein is administered for about 1, about 2, about 3, about 4, about 5, about 6, about 7, about 14, about 21, or about 28 days. In some embodiments, an agent as provided herein is administered chronically on an ongoing basis, e.g., for the treatment of chronic effects.

Since the compounds described herein can be administered in combination with other treatments (such as additional chemotherapeutics, radiation or surgery), the doses of each agent or therapy can be lower than the corresponding dose for single-agent therapy. The dose for single-agent therapy can range from, for example, about 0.0001 to about 200 mg, or about 0.001 to about 100 mg, or about 0.01 to about 100 mg, or about 0.1 to about 100 mg, or about 1 to about 50 mg per kilogram of body weight per day.

When a compound provided herein, is administered in a pharmaceutical composition that comprises one or more agents, and the agent has a shorter half-life than the compound provided herein unit dose forms of the agent and the compound provided herein can be adjusted accordingly.

6.3. Kits

In some embodiments, provided herein are kits. The kits can include a compound or pharmaceutical composition as described herein, in suitable packaging, and written material that can include instructions for use, discussion of clinical studies, listing of side effects, and the like. Such kits can also include information, such as scientific literature references, package insert materials, clinical trial results, and/or summaries of these and the like, which indicate or establish the activities and/or advantages of the pharmaceutical composition, and/or which describe dosing, administration, side effects, drug interactions, or other information useful to the health care provider. Such information can be based on the results of various studies, for example, studies using experimental animals involving in vivo models and studies based on human clinical trials.

In some embodiments, a memory aid is provided with the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . etc." Other variations of memory aids will be readily apparent. A "daily dose" can be a single tablet or capsule or several tablets or capsules to be taken on a given day.

The kit can further contain another agent. In some embodiments, the compound as provided herein and the agent are provided as separate pharmaceutical compositions in separate containers within the kit. In some embodiments, the compound as provided herein and the agent are provided as a single pharmaceutical composition within a container in the kit. Suitable packaging and additional articles for use (e.g., measuring cup for liquid preparations, foil wrapping to minimize exposure to air, and the like) are known in the art and can be included in the kit. In other embodiments, kits can further comprise devices that are used to administer the active agents. Examples of such devices include, but are not limited to, syringes, drip bags, patches, and inhalers. Kits described herein can be provided, marketed and/or promoted to health providers, including physicians, nurses, pharmacists, formulary officials, and the like. Kits can also, in some embodiments, be marketed directly to the consumer.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. The strength of the sheet is such that the tablets or capsules can be removed from the blister pack by manually applying pressure on the recesses whereby an opening is formed in the sheet at the place of the recess. The tablet or capsule can then be removed via said opening.

Kits can further comprise pharmaceutically acceptable vehicles that can be used to administer one or more active agents. For example, if an active agent is provided in a solid form that must be reconstituted for parenteral administration, the kit can comprise a sealed container of a suitable vehicle in which the active agent can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

The present disclosure further encompasses anhydrous pharmaceutical compositions and dosage forms comprising an active ingredient, since water can facilitate the degradation of some compounds. For example, water can be added (e.g., about 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. For example, pharmaceutical compositions and dosage forms which contain lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous pharmaceutical compositions can be packaged using materials known to prevent exposure to water such that they can be included in suitable formulary kits. Examples of suitable packaging include, but are not limited to, hermetically sealed foils, plastic or the like, unit dose containers, blister packs, and strip packs.

7. THERAPEUTIC METHODS

Phosphoinositide 3-kinases (PI3Ks) are members of a conserved family of lipid kinases that regulate numerous cell functions, including proliferation, differentiation, cell survival and metabolism. Several classes of PI3Ks exist in mammalian cells, including Class IA subgroup (e.g., PI3K-α, β, δ), which are generally activated by receptor tyrosine kinases (RTKs); Class IB (e.g., PI3K-γ), which is activated by G-protein coupled receptors (GPCRs), among others. PI3Ks exert their biological activities via a "PI3K-mediated signaling pathway" that includes several components that directly and/or indirectly transduce a signal triggered by a PI3K, including the generation of second messenger phophotidylinositol, 3,4,5-triphosphate (PIP3) at the plasma membrane, activation of heterotrimeric G protein signaling, and generation of further second messengers such as cAMP, DAG, and IP3, all of which leads to an extensive cascade of protein kinase activation (reviewed in Vanhaesebroeck, B. et al. (2001) *Annu Rev Biochem.* 70:535-602). For example, PI3K-δ is activated by cellular receptors through interaction between the PI3K regulatory subunit (p85) SH2 domains, or through direct interaction with RAS. PIP3 produced by PI3K activates effector pathways downstream through interaction with plextrin homology (PH) domain containing enzymes (e.g., PDK-1 and AKT [PKB]). (Fung-Leung W P. (2011) *Cell Signal.* 23(4):603-8). Unlike PI3K-δ, PI3K-γ is not associated with a regulatory subunit of the p85 family, but rather with a regulatory subunit in the p101 family. PI3K-γ is associated with GPCRs, and is responsible for the very rapid induction of PIP3. PI3K-γ can be also activated by RAS.

In some embodiments, provided herein are methods of modulating a PI3K kinase activity (e.g., selectively modulating) by contacting the kinase with an effective amount of a compound, or a pharmaceutically acceptable form (e.g., pharmaceutically acceptable salts, hydrates, solvates, isomers, prodrugs, and isotopically labeled derivatives) thereof, or pharmaceutical compositions as provided herein. Modulation can be inhibition (e.g., reduction) or activation (e.g., enhancement) of kinase activity. In some embodiments, provided herein are methods of inhibiting kinase activity by contacting the kinase with an effective amount of a compound as provided herein in solution. In some embodiments, provided herein are methods of inhibiting the kinase activity by contacting a cell, tissue, organ that express the kinase of interest with a compound provided herein. In some embodiments, provided herein are methods of inhibiting kinase activity in a subject by administering into the subject an effective amount of a compound as provided herein. In some embodiments, the kinase activity is inhibited (e.g., reduced) by more than about 25%, 30%, 40%, 50%, 60%, 70%, 80%, or 90% when contacted with a compound provided herein as compared to the kinase activity without such contact. In some embodiments, provided herein are methods of inhibiting PI3 kinase activity in a subject (including mammals such as humans) by contacting said subject with an amount of a compound as provided herein sufficient to inhibit or reduce the activity of the PI3 kinase in said subject.

In some embodiments, the kinase is a lipid kinase or a protein kinase. In some embodiments, the kinase is selected from a PI3 kinase including different isoforms such as PI3 kinase α, PI3 kinase β, PI3 kinase γ, PI3 kinase δ; DNA-PK; mTor; Abl, VEGFR, Ephrin receptor B4 (EphB4); TEK receptor tyrosine kinase (TIE2); FMS-related tyrosine kinase 3 (FLT-3); Platelet derived growth factor receptor (PDGFR); RET; ATM; ATR; hSmg-1; Hck; Src; Epidermal growth factor receptor (EGFR); KIT; Inulsin Receptor (IR); and IGFR.

As used herein, a "PI3K-mediated disorder" refers to a disease or condition involving aberrant PI3K-mediated signaling pathway. In one embodiment, provided herein is a method of treating a PI3K mediated disorder in a subject, the method comprising administering a therapeutically effective amount of a compound or a pharmaceutical composition as provided herein. In some embodiments, provided herein is a method of treating a PI3K-δ or PI3K-γ mediated disorder in a subject, the method comprising administering a therapeutically effective amount of a compound or a pharmaceutical composition as provided herein. In some embodiments, provided herein is a method for inhibiting at least one of PI3K-δ and PI3K-γ, the method comprising contacting a cell expressing PI3K in vitro or in vivo with an effective amount of the compound or composition provided herein. PI3Ks have been associated with a wide range of conditions, including immunity, cancer and thrombosis (reviewed in Vanhaesebroeck, B. et al. (2010) *Current Topics in Microbiology and Immunology*, DOI 10.1007/82_2010_65). For example, Class I PI3Ks, particularly PI3K-γ and PI3K-δ isoforms, are highly expressed in leukocytes and have been associated with adaptive and innate immunity; thus, these PI3Ks are believed to be important mediators in inflammatory disorders and hematologic malignancies (reviewed in Harris, S J et al. (2009) *Curr Opin Investig Drugs* 10(11): 1151-62); Rommel C. et al. (2007) *Nat Rev Immunol* 7(3): 191-201; Durand C A et al. (2009) *J Immunol*. 183(9):5673-84; Dil N, Marshall A J. (2009) *Mol. Immunol.* 46(10):1970-8; Al-Alwan M M et al. (2007) *J Immunol.* 178(4):2328-35; Zhang T T, et al. (2008) *J Allergy Clin Immunol.* 2008; 122(4):811-819.e2; Srinivasan L, et al. (2009) *Cell* 139(3): 573-86).

Numerous publications support roles of PI3K-δ, PI3K-γ, and PI3K-β in the differentiation, maintenance, and activation of immune and malignant cells, as described in more detail below.

The importance of PI3K-δ in the development and function of B-cells is supported from inhibitor studies and genetic models. PI3K-δ is an important mediator of B-cell receptor (BCR) signaling, and is upstream of AKT, calcium flux, PLCγ, MAP kinase, P70S6k, and FOXO3a activation. PI3K-δ is also important in IL4R, S1P, and CXCR5 signaling, and has been shown to modulate responses to toll-like receptors 4 and 9 Inhibitors of PI3K-δ have shown the importance of PI3K-δ in B-cell development (Marginal zone and B1 cells), B-cell activation, chemotaxis, migration and homing to lymphoid tissue, and in the control of immunoglobulin class switching leading to the production of IgE. Clayton E et al. (2002) *J Exp Med.* 196(6):753-63; Bilancio A, et al. (2006) *Blood* 107(2):642-50; Okkenhaug K. et al. (2002) *Science* 297(5583):1031-4; Al-Alwan M M et al. (2007) *J Immunol.* 178(4):2328-35; Zhang T T, et al. (2008) *J Allergy Clin Immunol.* 2008; 122(4):811-819.e2; Srinivasan L, et al. (2009) *Cell* 139(3):573-86)

In T-cells, PI3K-δ has been demonstrated to have a role in T-cell receptor and cytokine signaling, and is upstream of AKT, PLCγ, and GSK3b. In PI3K-δ deletion or kinase-dead knock-in mice, or in inhibitor studies, T-cell defects including proliferation, activation, and differentiation have been observed, leading to reduced T helper cell 2 (TH2) response, memory T-cell specific defects (DTH reduction), defects in antigen dependent cellular trafficking, and defects in chemotaxis/migration to chemokines (e.g., S1P, CCR7, CD62L). (Garçon F. et al. (2008) *Blood* 111(3):1464-71; Okkenhaug K et al. (2006). *J Immunol.* 177(8):5122-8; Soond D R, et al. (2010) *Blood* 115(11):2203-13; Reif K, (2004). *J. Immunol.* 2004; 173(4):2236-40; Ji H. et al. (2007) *Blood* 110(8): 2940-7; Webb L M, et al. (2005) *J Immunol.* 175(5):2783-7; Liu D, et al. (2010) *J Immunol.* 184(6):3098-105; Haylock- Jacobs S, et al. (2011) *J Autoimmun.* 2011; 36(3-4):278-87; Jarmin S J, et al. (2008) *J Clin Invest.* 118(3): 1154-64).

In neutrophils, PI3K-δ along with PI3K-γ, and PI3K-β, contribute to the responses to immune complexes, FCγRII signaling, including migration and neutrophil respiratory burst. Human neutrophils undergo rapid induction of PIP3 in response to formyl peptide receptor (FMLP) or complement component C5a (C5a) in a PI3K-γ dependent manner, followed by a longer PIP3 production period that is PI3K-δ dependent, and is essential for respiratory burst. The response to immune complexes is contributed by PI3K-δ, PI3K-γ, and PI3K-β, and is an important mediator of tissue damage in models of autoimmune disease (Randis T M et al. (2008)*Eur J. Immunol.* 38(5):1215-24; Pinho V, (2007) *J Immunol.* 179(11):7891-8; Sadhu C. et al. (2003) *J Immunol.* 170(5):2647-54; Condliffe A M et al. (2005) *Blood* 106(4): 1432-40). It has been reported that in certain autoimmune diseases, perfrential activation of PI3Kβ may be involved. (Kulkarni et al., *Immunology* (2011) 4(168) ra23: 1-11). It was also reported that PI3Kβ-deficient mice were highly protected in an FcγR-dependent model of autoantibody-induced skin blistering and partially protected in an FcγR-dependent model of inflammatory arthritis, whereas combined deficiency of PI3Kβ and PI3Kδ resulted in near complete protection in inflammatory arthritis. (Id.).

In macrophages collected from patients with chronic obstructive pulmonary disease (COPD), glucocorticoid responsiveness can be restored by treatment of the cells with inhibitors of PI3K-δ. Macrophages also rely on PI3K-δ and PI3K-γ for responses to immune complexes through the arthus reaction (FCgR and C5a signaling) (Randis T M, et al. (2008) *Eur J Immunol.* 38(5):1215-24; Marwick J A et al. (2009) *Am J Respir Crit. Care Med.* 179(7):542-8; Konrad S, et al. (2008) *J Biol. Chem.* 283(48):33296-303).

In mast cells, stem cell factor—(SCF) and IL3-dependent proliferation, differentiation and function are PI3K-δ dependent, as is chemotaxis. The allergen/IgE crosslinking of FCgR1 resulting in cytokine release and degranulation of the mast cells is severely inhibited by treatment with PI3K-δ inhibitors, suggesting a role for PI3K-δ in allergic disease (Ali K et al. (2004) *Nature* 431(7011):1007-11; Lee K S, et al. (2006) *FASEB J.* 20(3):455-65; Kim M S, et al. (2008) *Trends Immunol.* 29(10):493-501).

Natural killer (NK) cells are dependent on both PI3K-δ and PI3K-γ for efficient migration towards chemokines including CXCL10, CCL3, S1P and CXCL12, or in response to LPS in the peritoneum (Guo H, et al. (2008) *J Exp Med.* 205(10):2419-35; Tassi I, et al. (2007) *Immunity* 27(2):214-27; Saudemont A, (2009) *Proc Natl Acad Sci USA.* 106(14):5795-800; Kim N, et al. (2007) *Blood* 110(9): 3202-8).

The roles of PI3K-δ, PI3K-γ, and PI3K-β in the differentiation, maintenance, and activation of immune cells support a role for these enzymes in inflammatory disorders ranging from autoimmune diseases (e.g., rheumatoid arthritis, multiple sclerosis) to allergic inflammatory disorders, such as asthma, and inflammatory respiratory disease such as COPD. Extensive evidence is available in experimental animal models, or can be evaluated using art-recognized animal models. In an embodiment, described herein is a method of treating inflammatory disorders ranging from autoimmune diseases (e.g., rheumatoid arthritis, multiple sclerosis) to allergic inflammatory disorders, such as asthma and COPD using a compound described herein.

For example, inhibitors of PI3K-δ and/or -γ have been shown to have anti-inflammatory activity in several autoimmune animal models for rheumatoid arthritis (Williams, O. et al. (2010) *Chem Biol*, 17(2):123-34; WO 2009/088986; WO2009/088880; WO 2011/008302). PI3K-δ is expressed in the RA synovial tissue (especially in the synovial lining which contains fibroblast-like synoviocytes (FLS), and selective PI3K-δ inhibitors have been shown to be effective in inhibiting synoviocyte growth and survival (Bartok et al. (2010) *Arthritis Rheum* 62 Suppl 10:362). Several PI3K-δ and -γ inhibitors have been shown to ameliorate arthritic symptoms (e.g., swelling of joints, reduction of serum-induced collagen levels, reduction of joint pathology and/or inflammation), in art-recognized models for RA, such as collagen-induced arthritis and adjuvant induced arthritis (WO 2009/088986; WO2009/088880; WO 2011/008302).

The role of PI3K-δ has also been shown in models of T-cell dependent response, including the DTH model. In the murine experimental autoimmune encephalomyelitis (EAE) model of multiple sclerosis, the PI3K-γ/δ-double mutant mice are resistant. PI3K-δ inhibitors have also been shown to block EAE disease induction and development of TH-17 cells both in vitro and in vivo (Haylock-Jacobs, S. et al. (2011) *J. Autoimmunity* 36(3-4):278-87).

Systemic lupus erythematosus (SLE) is a complex disease that at different stages requires memory T-cells, B-cell polyclonal expansion and differentiation into plasma cells, and the innate immune response to endogenous damage associated molecular pattern molecules (DAMPS), and the inflammatory responses to immune complexes through the complement system as well as the $F_C$ receptors. The role of PI3K-δ and PI3K-γ together in these pathways and cell types suggest that blockade with an inhibitor would be effective in these diseases. A role for PI3K in lupus is also predicted by two genetic models of lupus. The deletion of phosphatase and tensin homolog (PTEN) leads to a lupus-like phenotype, as does a transgenic activation of Class 1A PI3Ks, which includes PI3K-δ. The deletion of PI3K-γ in the transgenically activated class 1A lupus model is protective, and treatment with a PI3K-γ selective inhibitor in the murine MLR/lpr model of lupus improves symptoms (Barber, D F et al. (2006) *J. Immunol.* 176(1): 589-93).

In allergic disease, PI3K-δ has been shown by genetic models and by inhibitor treatment to be essential for mast-cell activation in a passive cutaneous anaphalaxis assay (Ali K et al. (2008) *J Immunol.* 180(4):2538-44; Ali K, (2004) *Nature* 431(7011):1007-11). In a pulmonary measure of response to immune complexes (Arthus reaction) a PI3K-δ knockout is resistant, showing a defect in macrophage activation and C5a production. Knockout studies and studies with inhibitors for both PI3K-δ and PI3K-γ support a role for both of these enzymes in the ovalbumin induced allergic airway inflammation and hyper-responsiveness model (Lee K S et al. (2006) *FASEB J.* 20(3):455-65). Reductions of infiltration of eosinophils, neutrophils, and lymphocytes as well as TH2 cytokines (IL4, IL5, and IL13) were seen with both PI3K-δ specific and dual PI3K-δ and PI3K-γ inhibitors in the Ova induced asthma model (Lee K S et al. (2006) *J Allergy Clin Immunol* 118(2):403-9).

PI3K-δ and PI3K-γ inhibition can be used in treating COPD. In the smoked mouse model of COPD, the PI3K-δ knockout does not develop smoke induced glucocorticoid resistance, while wild-type and PI3K-γ knockout mice do. An inhaled formulation of dual PI3K-δ and PI3K-γ inhibitor blocked inflammation in a LPS or smoke COPD models as measured by neutrophilia and glucocorticoid resistance (Doukas J, et al. (2009) *J Pharmacol Exp Ther.* 328(3):758-65).

Class I PI3Ks, particularly PI3K-δ and PI3K-γ isoforms, are also associated with cancers (reviewed, e.g., in Vogt, P K et al. (2010) Curr Top Microbiol Immunol. 347:79-104; Fresno Vara, J A et al. (2004) *Cancer Treat Rev.* 30(2):193-204; Zhao, L and Vogt, P K. (2008) Oncogene 27(41):5486-96). Inhibitors of PI3K, e.g., PI3K-δ and/or -γ, have been shown to have anti-cancer activity (e.g., Courtney, K D et al. (2010) *J Clin Oncol.* 28(6):1075-1083); Markman, B et al. (2010) Ann Oncol. 21(4):683-91; Kong, D and Yamori, T (2009) Curr Med. Chem. 16(22):2839-54; Jimeno, A et al. (2009) J Clin Oncol. 27:156s (suppl; abstr 3542); Flinn, I W et al. (2009) *J Clin Oncol.* 27:156s (suppl; abstr 3543); Shapiro, G et al. (2009) J Clin Oncol. 27:146s (suppl; abstr 3500); Wagner, A J et al. (2009) *J Clin Oncol.* 27:146s (suppl; abstr 3501); Vogt, P K et al. (2006) Virology 344 (1):131-8; Ward, S et al. (2003) *Chem. Biol.* 10(3):207-13; WO 2011/041399; US 2010/0029693; US 2010/0305096; US 2010/0305084). In an embodiment, described herein is a method of treating cancer.

Types of cancer that can be treated with an inhibitor of PI3K (particularly, PI3K-δ and/or -γ) include, e.g., leukemia, chronic lymphocytic leukemia, acute myeloid leukemia, chronic myeloid leukemia (e.g., Salmena, L et al. (2008) *Cell* 133:403-414; Chapuis, N et al. (2010) *Clin Cancer Res.* 16(22):5424-35; Khwaja, A (2010) *Curr Top Microbiol Immunol.* 347:169-88); lymphoma, e.g., non-Hodgkin's lymphoma (e.g., Salmena, L et al. (2008) *Cell* 133:403-414); lung cancer, e.g., non-small cell lung cancer, small cell lung cancer (e.g., Herrera, V A et al. (2011) *Anticancer Res.* 31(3):849-54); melanoma (e.g., Haluska, F et al. (2007) *Semin Oncol.* 34(6):546-54); prostate cancer (e.g., Sarker, D et al. (2009) *Clin Cancer Res.* 15(15):4799-805); glioblastoma (e.g., Chen, J S et al. (2008) Mol Cancer Ther. 7:841-850); endometrial cancer (e.g., Bansal, N et al. (2009) Cancer Control. 16(1):8-13); pancreatic cancer (e.g., Furukawa, T (2008) *J Gastroenterol.* 43(12):905-11); renal cell carcinoma (e.g., Porta, C and Figlin, R A (2009) *J Urol.* 182(6):2569-77); colorectal cancer (e.g., Saif, M W and Chu, E (2010) *Cancer J.* 16(3):196-201); breast cancer (e.g., Torbett, N E et al. (2008) *Biochem J.* 415:97-100); thyroid cancer (e.g., Brzezianska, E and Pastuszak-Lewandoska, D (2011) *Front Biosci.* 16:422-39); and ovarian cancer (e.g., Mazzoletti, M and Broggini, M (2010) *Curr Med. Chem.* 17(36):4433-47).

Numerous publications support a role of PI3K-δ and PI3K-γ in treating hematological cancers. PI3K-δ and PI3K-γ are highly expressed in the heme compartment, and some solid tumors, including prostate, breast and glioblastomas (Chen J. S. et al. (2008) *Mol Cancer Ther.* 7(4):841-50; Ikeda H. et al. (2010) *Blood* 116(9):1460-8).

In hematological cancers including acute myeloid leukemia (AML), multiple myeloma (MM), and chronic lymphocytic leukemia (CLL), overexpression and constitutive activation of PI3K-δ supports the model that PI3K-δ inhibition would be therapeutic Billottet C, et al. (2006) *Oncogene* 25(50):6648-59; Billottet C, et al. (2009) *Cancer Res.* 69(3): 1027-36; Meadows, S A, 52$^{nd}$ Annual ASH Meeting and Exposition; 2010 Dec. 4-7; Orlando, Fla.; Ikeda H, et al. (2010) *Blood* 116(9):1460-8; Herman S E et al. (2010) *Blood* 116(12):2078-88; Herman S E et al. (2011). *Blood* 117(16): 4323-7. In an embodiment, described herein is a method of treating hematological cancers including, but not limited to acute myeloid leukemia (AML), multiple myeloma (MM), and chronic lymphocytic leukemia (CLL).

A PI3K-δ inhibitor (CAL-101) has been evaluated in a phase 1 trial in patients with haematological malignancies, and showed activity in CLL in patients with poor prognostic characteristics. In CLL, inhibition of PI3K-δ not only affects tumor cells directly, but it also affects the ability of the tumor cells to interact with their microenvironment. This microenvironment includes contact with and factors from stromal cells, T-cells, nurse like cells, as well as other tumor cells. CAL-101 suppresses the expression of stromal and T-cell derived factors including CCL3, CCL4, and CXCL13, as well as the CLL tumor cells' ability to respond to these factors. CAL-101 treatment in CLL patients induces rapid lymph node reduction and redistribution of lymphocytes into the circulation, and affects tonic survival signals through the BCR, leading to reduced cell viability, and an increase in apoptosis. Single agent CAL-101 treatment was also active in mantle cell lymphoma and refractory non Hodgkin's lymphoma (Furman, R R, et al. 52$^{nd}$ Annual ASH Meeting and Exposition; 2010 Dec. 4-7; Orlando, Fla.; Hoellenriegel, J, et al. 52$^{nd}$ Annual ASH Meeting and Exposition; 2010 Dec. 4-7; Orlando, Fla.; Webb, H K, et al. 52$^{nd}$ Annual ASH Meeting and Exposition; 2010 Dec. 4-7; Orlando, Fla.; Meadows, et al. 52$^{nd}$ Annual ASH Meeting and Exposition; 2010 Dec. 4-7; Orlando, Fla.; Kahl, B, et al. 52$^{nd}$ Annual ASH Meeting and Exposition; 2010 Dec. 4-7; Orlando, Fla.; Lannutti B J, et al. (2011) *Blood* 117(2):591-4).

PI3K-δ inhibitors have shown activity against PI3K-δ positive gliomas in vitro (Kashishian A, et al. Poster presented at: The American Association of Cancer Research 102$^{nd}$ Annual Meeting; 2011 Apr. 2-6; Orlando, Fla.). PI3K-δ is the PI3K isoform that is most commonly activated in tumors where the PTEN tumor suppressor is mutated (Ward S, et al. (2003) *Chem. Biol.* 10(3):207-13). In this subset of tumors, treatment with the PI3K-δ inhibitor either alone or in combination with a cytotoxic agent can be effective.

Another mechanism for PI3K-δ inhibitors to have an affect in solid tumors involves the tumor cells' interaction with their micro-environment. PI3K-δ, PI3K-γ, and PI3K-β are expressed in the immune cells that infiltrate tumors, including tumor infiltrating lymphocytes, macrophages, and neutrophils. PI3K-δ inhibitors can modify the function of these tumor-associated immune cells and how they respond to signals from the stroma, the tumor, and each other, and in this way affect tumor cells and metastasis (Hoellenriegel, J, et al. 52$^{nd}$ Annual ASH Meeting and Exposition; 2010 Dec. 4-7; Orlando, Fla.).

PI3K-δ is also expressed in endothelial cells. It has been shown that tumors in mice treated with PI3K-δ selective inhibitors are killed more readily by radiation therapy. In this same study, capillary network formation is impaired by the PI3K inhibitor, and it is postulated that this defect contributes to the greater killing with radiation. PI3K-δ inhibitors can affect the way in which tumors interact with their microenvironment, including stromal cells, immune cells, and endothelial cells and be therapeutic either on its own or in conjunction with another therapy (Meadows, S A, et al. Paper presented at: 52$^{nd}$ Annual ASH Meeting and Exposition; 2010 Dec. 4-7; Orlando, Fla.; Geng L, et al. (2004) *Cancer Res.* 64(14):4893-9).

In other embodiments, inhibition of PI3K (such as PI3K-δ and/or -γ) can be used to treat a neuropsychiatric disorder, e.g., an autoimmune brain disorder. Infectious and immune factors have been implicated in the pathogenesis of several neuropsychiatric disorders, including, but not limited to, Sydenham's chorea (SC) (Garvey, M. A. et al. (2005) *J. Child Neurol.* 20:424-429), Tourette's syndrome (TS), obsessive compulsive disorder (OCD) (Asbahr, F. R. et al. (1998) *Am. J. Psychiatry* 155:1122-1124), attention deficit/ hyperactivity disorder (AD/HD) (Hirschtritt, M. E. et al. (2008) *Child Neuropsychol.* 1:1-16; Peterson, B. S. et al. (2000) *Arch. Gen. Psychiatry* 57:364-372), anorexia nervosa (Sokol, M. S. (2000) *J. Child Adolesc. Psychopharmacol.* 10:133-145; Sokol, M. S. et al. (2002) *Am. J. Psychiatry* 159:1430-1432), depression (Leslie, D. L. et al. (2008) *J. Am. Acad. Child Adolesc. Psychiatry* 47:1166-1172), and autism spectrum disorders (ASD) (Hollander, E. et al. (1999) *Am. J. Psychiatry* 156:317-320; Margutti, P. et al. (2006) *Curr. Neurovasc. Res.* 3:149-157). A subset of childhood obsessive compulsive disorders and tic disorders has been grouped as Pediatric Autoimmune Neuropsychiatric Disorders Associated with Streptococci (PANDAS). PANDAS disorders provide an example of disorders where the onset and exacerbation of neuropsychiatric symptoms is preceded by a streptococcal infection (Kurlan, R., Kaplan, E. L. (2004) *Pediatrics* 113:883-886; Garvey, M. A. et al. (1998) *J. Clin. Neurol.* 13:413-423). Many of the PANDAS disorders share a common mechanism of action resulting from antibody responses against streptococcal associated epitopes, such as GlcNAc, which produces neurological effects (Kirvan. C. A. et al. (2006) *J. Neuroimmunol.* 179: 173-179). Autoantibodies recognizing central nervous system (CNS) epitopes are also found in sera of most PANDAS subjects (Yaddanapudi, K. et al. (2010) *Mol. Psychiatry.* 15:712-726). Thus, several neuropsychiatric disorders have been associated with immune and autoimmune components, making them suitable for therapies that include PI3K-δ and/or -γ inhibition.

In certain embodiments, a method of treating (e.g., reducing or ameliorating one or more symptoms of) a neuropsychiatric disorder, (e.g., an autoimmune brain disorder), using a PI3K-δ and/or -γ inhibitor is described, alone or in combination therapy. For example, one or more PI3K-δ and/or -γ inhibitors described herein can be used alone or in combination with any suitable therapeutic agent and/or modalities, e.g., dietary supplement, for treatment of neuropsychiatric disorders. Exemplary neuropsychiatric disorders that can be treated with the PI3K-δ and/or -γ inhibitors described herein include, but are not limited to, PANDAS disorders, Sydenham's chorea, Tourette's syndrome, obsessive compulsive disorder, attention deficit/hyperactivity disorder, anorexia nervosa, depression, and autism spectrum disorders. Pervasive Developmental Disorder (PDD) is an exemplary class of autism spectrum disorders that includes Autistic Disorder, Asperger's Disorder, Childhood Disintegrative Disorder (CDD), Rett's Disorder and PDD-Not Otherwise Specified (PDD-NOS) Animal models for evaluating the activity of the PI3K-δ and/or -γ inhibitor are known in the art. For example, a mouse model of PANDAS disorders is described in, e.g., Yaddanapudi, K. et al. (2010) supra; and Hoffman, K. I. et al. (2004) *J. Neurosci.* 24:1780-1791.

In some embodiments, provided herein are methods of using the compounds, or a pharmaceutically acceptable form (e.g., pharmaceutically acceptable salts, hydrates, solvates, isomers, prodrugs, and isotopically labeled derivatives) thereof, or pharmaceutical compositions as provided herein to treat disease conditions, including, but not limited to, diseases associated with malfunctioning of one or more types of PI3 kinase. A detailed description of conditions and disorders mediated by p110δ kinase activity is set forth in Sadu et al., WO 01/81346, which is incorporated herein by reference in its entirety for all purposes.

In some embodiments, the disclosure relates to a method of treating a hyperproliferative disorder in a subject that comprises administering to said subject a therapeutically effective amount of a compound, or a pharmaceutically acceptable form (e.g., pharmaceutically acceptable salts, hydrates, solvates, isomers, prodrugs, and isotopically labeled derivatives) thereof, or pharmaceutical compositions as provided herein. In some embodiments, said method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g., Lymphoma and Kaposi's Sarcoma) or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

Patients that can be treated with compounds, or a pharmaceutically acceptable form (e.g., pharmaceutically acceptable salts, hydrates, solvates, isomers, prodrugs, and isotopically labeled derivatives) thereof, or pharmaceutical compositions as provided herein, according to the methods as provided herein include, for example, but not limited to, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, NK cell leukemia (e.g., blastic plasmacytoid dendritic cell neoplasm), acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; lymphoma such as diffuse large B-cell lymphoma, B-cell immunoblastic lymphoma, NK cell lymphoma (e.g., blastic plasmacytoid dendritic cell neoplasm), and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma;

and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer.

In one embodiment, provided herein is a method of treating an inflammation disorder, including autoimmune diseases in a subject. The method comprises administering to said subject a therapeutically effective amount of a compound, or a pharmaceutically acceptable form (e.g., pharmaceutically acceptable salts, hydrates, solvates, isomers, prodrugs, and isotopically labeled derivatives) thereof, or pharmaceutical compositions as provided herein. Examples of autoimmune diseases includes but is not limited to acute disseminated encephalomyelitis (ADEM), Addison's disease, antiphospholipid antibody syndrome (APS), aplastic anemia, autoimmune hepatitis, autoimmune skin disease, coeliac disease, Crohn's disease, Diabetes mellitus (type 1), Goodpasture's syndrome, Graves' disease, Guillain-Barré syndrome (GBS), Hashimoto's disease, lupus erythematosus, multiple sclerosis, myasthenia gravis, opsoclonus myoclonus syndrome (OMS), optic neuritis, Ord's thyroiditis, oemphigus, polyarthritis, primary biliary cirrhosis, psoriasis, rheumatoid arthritis, Reiter's syndrome, Takayasu's arteritis, temporal arteritis (also known as "giant cell arteritis"), warm autoimmune hemolytic anemia, Wegener's granulomatosis, alopecia universalis (e.g., inflammatory alopecia), Chagas disease, chronic fatigue syndrome, dysautonomia, endometriosis, hidradenitis suppurativa, interstitial cystitis, neuromyotonia, sarcoidosis, scleroderma, ulcerative colitis, vitiligo, and vulvodynia. Other disorders include bone-resorption disorders and thrombosis.

Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammatory conditions include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gout flare, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, polymyalgia rheumatic, reperfusion injury, regional enteritis, rheumatic fever, systemic lupus erythematosus, scleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis. In certain embodiments, the inflammatory disorder is selected from arthritis (e.g., rheumatoid arthritis), inflammatory bowel disease, inflammatory bowel syndrome, asthma, psoriasis, endometriosis, interstitial cystitis and prostatistis. In certain embodiments, the inflammatory condition is an acute inflammatory condition (e.g., for example, inflammation resulting from infection). In certain embodiments, the inflammatory condition is a chronic inflammatory condition (e.g., conditions resulting from asthma, arthritis and inflammatory bowel disease). The compounds can also be useful in treating inflammation associated with trauma and non-inflammatory myalgia.

Immune disorders, such as auto-immune disorders, include, but are not limited to, arthritis (including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic, and juvenile arthritis), asthma, atherosclerosis, osteoporosis, bronchitis, tendonitis, bursitis, skin condition (e.g., psoriasis, eczema, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), relapsing polychondritis (e.g., atrophic polychondritis and systemic polychondromalacia), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)). In certain embodiments, a method of treating inflammatory or autoimmune diseases is provided comprising administering to a subject (e.g., a mammal) a therapeutically effective amount of a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, that selectively inhibit PI3K-δ and/or PI3K-γ as compared to all other type I PI3 kinases.

Such selective inhibition of PI3K-δ and/or PI3K-γ can be advantageous for treating any of the diseases or conditions described herein. For example, selective inhibition of PI3K-δ can inhibit inflammatory responses associated with inflammatory diseases, autoimmune disease, or diseases related to an undesirable immune response including, but not limited to asthma, emphysema, allergy, dermatitis, rheumatoid arthritis, psoriasis, lupus erythematosus, anaphylaxsis, or graft versus host disease. Selective inhibition of PI3K-δ can further provide for a reduction in the inflammatory or undesirable immune response without a concomittant reduction in the ability to reduce a bacterial, viral, and/or fungal infection. Selective inhibition of both PI3K-δ and PI3K-γ can be advantageous for inhibiting the inflammatory response in the subject to a greater degree than that would be provided for by inhibitors that selectively inhibit PI3K-δ or PI3K-γ alone. In one aspect, one or more of the subject methods are effective in reducing antigen specific antibody production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more. In another aspect, one or more of the subject methods are effective in reducing antigen specific IgG3 and/or IgGM production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more.

In one aspect, one of more of the subject methods are effective in ameliorating symptoms associated with rheumatoid arthritis including, but not limited to a reduction in the swelling of joints, a reduction in serum anti-collagen levels, and/or a reduction in joint pathology such as bone resorption, cartilage damage, pannus, and/or inflammation. In another aspect, the subject methods are effective in reducing ankle inflammation by at least about 2%, 5%, 10%, 15%, 20%, 25%, 30%, 50%, 60%, or about 75% to 90%. In another aspect, the subject methods are effective in reducing knee inflammation by at least about 2%, 5%, 10%, 15%, 20%, 25%, 30%, 50%, 60%, or about 75% to 90% or more. In still another aspect, the subject methods are effective in reducing serum anti-type II collagen levels by at least about 10%, 12%, 15%, 20%, 24%, 25%, 30%, 35%, 50%, 60%, 75%, 80%, 86%, 87%, or about 90% or more. In another aspect, the subject methods are effective in reducing ankle histopathology scores by about 5%, 10%, 15%, 20%, 25%, 30%, 40%, 50%, 60%, 75%, 80%, 90% or more. In still another aspect, the subject methods are effective in reducing knee histopathology scores by about 5%, 10%, 15%, 20%, 25%, 30%, 40%, 50%, 60%, 75%, 80%, 90% or more.

In some embodiments, provided herein are methods for treating disorders or conditions in which the δ isoform of PI3K is implicated to a greater extent than other PI3K isoforms such as PI3K-α and/or -β. Selective inhibition of PI3K-δ and/or PI3K-γ can provide advantages over using less selective compounds which inhibit PI3K-α and/or -β, such as an improved side effects profile or lessened reduction in the ability to reduce a bacterial, viral, and/or fungal infection.

In other embodiments, provided herein are methods of using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, to treat respiratory diseases including, but not limited to diseases affecting the lobes of lung, pleural cavity, bronchial tubes, trachea, upper respiratory tract, or the nerves and muscle for breathing. For example, methods are provided to treat obstructive pulmonary disease. Chronic obstructive pulmonary disease (COPD) is an umbrella term for a group of respiratory tract diseases that are characterized by airflow obstruction or limitation. Conditions included in this umbrella term include, but are not limited to: chronic bronchitis, emphysema, and bronchiectasis.

In another embodiment, the compounds, or a pharmaceutically acceptable form (e.g., pharmaceutically acceptable salts, hydrates, solvates, isomers, prodrugs, and isotopically labeled derivatives) thereof, or pharmaceutical compositions as provided herein are used for the treatment of asthma. Also, the compounds or pharmaceutical compositions described herein can be used for the treatment of endotoxemia and sepsis. In one embodiment, the compounds or pharmaceutical compositions described herein are used to for the treatment of rheumatoid arthritis (RA). In yet another embodiment, the compounds or pharmaceutical compositions described herein is used for the treatment of contact or atopic dermatitis. Contact dermatitis includes irritant dermatitis, phototoxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

In some embodiments, the disclosure provides a method of treating diseases related to vasculogenesis or angiogenesis in a subject that comprises administering to said subject a therapeutically effective amount of a compound, or a pharmaceutically acceptable form (e.g., pharmaceutically acceptable salts, hydrates, solvates, isomers, prodrugs, and isotopically labeled derivatives) thereof, or pharmaceutical compositions as provided herein. In some embodiments, said method is for treating a disease selected from tumor angiogenesis, chronic inflammatory disease such as rheumatoid arthritis and chronic inflammatory demyelinating polyneuropathy, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

In addition, the compounds described herein can be used for the treatment of arteriosclerosis, including atherosclerosis. Arteriosclerosis is a general term describing any hardening of medium or large arteries. Atherosclerosis is a hardening of an artery specifically due to an atheromatous plaque.

In some embodiments, provided herein is a method of treating a cardiovascular disease in a subject that comprises administering to said subject a therapeutically effective amount of a compound as provided herein, or a pharmaceutically acceptable form (e.g., pharmaceutically acceptable salts, hydrates, solvates, isomers, prodrugs, and isotopically labeled derivatives) thereof. Examples of cardiovascular conditions include, but are not limited to, atherosclerosis, restenosis, vascular occlusion and carotid obstructive disease.

In some embodiments, the disclosure relates to a method of treating diabetes in a subject that comprises administering to said subject a therapeutically effective amount of a compound as provided herein, or a pharmaceutically acceptable form (e.g., pharmaceutically acceptable salts, hydrates, solvates, isomers, prodrugs, and isotopically labeled derivatives) thereof, or pharmaceutical compositions as provided herein.

In addition, the compounds, or a pharmaceutically acceptable form (e.g., pharmaceutically acceptable salts, hydrates, solvates, isomers, prodrugs, and isotopically labeled derivatives) thereof, or pharmaceutical compositions as provided herein, can be used to treat acne. In certain embodiments, the inflammatory condition and/or immune disorder is a skin condition. In some embodiments, the skin condition is pruritus (itch), psoriasis, eczema, burns or dermatitis. In certain embodiments, the skin condition is psoriasis. In certain embodiments, the skin condition is pruritus.

In certain embodiments, the inflammatory disorder and/or the immune disorder is a gastrointestinal disorder. In some embodiments, the gastrointestinal disorder is selected from gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)). In certain embodiments, the gastrointestinal disorder is inflammatory bowel disease (IBD).

Further, the compounds, or a pharmaceutically acceptable form (e.g., pharmaceutically acceptable salts, hydrates, solvates, isomers, prodrugs, and isotopically labeled derivatives) thereof, or pharmaceutical compositions as provided herein, can be used for the treatment of glomerulonephritis. Glomerulonephritis is a primary or secondary autoimmune renal disease characterized by inflammation of the glomeruli. It can be asymptomatic, or present with hematuria and/or proteinuria. There are many recognized types, divided in acute, subacute or chronic glomerulonephritis. Causes are infectious (bacterial, viral or parasitic pathogens), autoimmune or paraneoplastic.

In some embodiments, provided herein are compounds, or a pharmaceutically acceptable form (e.g., pharmaceutically acceptable salts, hydrates, solvates, isomers, prodrugs, and isotopically labeled derivatives) thereof, or pharmaceutical compositions as provided herein, for the treatment of multiorgan failure. Also provided herein are compounds, or a pharmaceutically acceptable form (e.g., pharmaceutically acceptable salts, hydrates, solvates, isomers, prodrugs, and isotopically labeled derivatives) thereof, or pharmaceutical compositions as provided herein, for the treatment of liver diseases (including diabetes), gall bladder disease (including gallstones), pancreatitis or kidney disease (including proliferative glomerulonephritis and diabetes-induced renal disease) or pain in a subject.

In some embodiments, provided herein are compounds, or a pharmaceutically acceptable form (e.g., pharmaceutically acceptable salts, hydrates, solvates, isomers, prodrugs, and isotopically labeled derivatives) thereof, or pharmaceutical compositions as provided herein, for the prevention of blastocyte implantation in a subject.

In some embodiments, provided herein are compounds, or a pharmaceutically acceptable form (e.g., pharmaceutically acceptable salts, hydrates, solvates, isomers, prodrugs, and isotopically labeled derivatives) thereof, or pharmaceutical compositions as provided herein, for the treatment of disorders involving platelet aggregation or platelet adhesion, including, but not limited to Idiopathic thrombocytopenic purpura, Bernard-Soulier syndrome, Glanzmann's thrombasthenia, Scott's syndrome, von Willebrand disease, Hermansky-Pudlak Syndrome, and Gray platelet syndrome.

In some embodiments, compounds, or a pharmaceutically acceptable form (e.g., pharmaceutically acceptable salts, hydrates, solvates, isomers, prodrugs, and isotopically labeled derivatives) thereof, or pharmaceutical compositions as provided herein, are provided for treating a disease which is skeletal muscle atrophy, skeletal or muscle hypertrophy. In some embodiments, provided herein are compounds, or a pharmaceutically acceptable form (e.g., pharmaceutically acceptable salts, hydrates, solvates, isomers, prodrugs, and isotopically labeled derivatives) thereof, or pharmaceutical compositions as provided herein, for the treatment of disorders that include, but are not limited to, cancers as discussed herein, transplantation-related disorders (e.g., lowering rejection rates, graft-versus-host disease, etc.), muscular sclerosis (MS), allergic disorders (e.g., arthritis, allergic encephalomyelitis) and other immunosuppressive-related disorders, metabolic disorders (e.g., diabetes), reducing intimal thickening following vascular injury, and misfolded protein disorders (e.g., Alzheimer's Disease, Gaucher's Disease, Parkinson's Disease, Huntington's Disease, cystic fibrosis, macular degeneration, retinitis pigmentosa, and prion disorders) (as mTOR inhibition can alleviate the effects of misfolded protein aggregates). The disorders also include hamartoma syndromes, such as tuberous sclerosis and Cowden Disease (also termed Cowden syndrome and multiple hamartoma syndrome).

Additionally, the compounds, or a pharmaceutically acceptable form (e.g., pharmaceutically acceptable salts, hydrates, solvates, isomers, prodrugs, and isotopically labeled derivatives) thereof, or pharmaceutical compositions as provided herein, can be used for the treatment of bursitis, lupus, acute disseminated encephalomyelitis (ADEM), Addison's disease, antiphospholipid antibody syndrome (APS), amyloidosis (including systemic and localized amyloidosis; and primary and secondary amyloidosis), aplastic anemia, autoimmune hepatitis, coeliac disease, crohn's disease, diabetes mellitus (type 1), eosinophilic gastroenterides, goodpasture's syndrome, graves' disease, guillain-barré syndrome (GBS), hashimoto's disease, inflammatory bowel disease, lupus erythematosus (including cutaneous lupus erythematosus and systemic lupus erythematosus), myasthenia gravis, opsoclonus myoclonus syndrome (OMS), optic neuritis, ord's thyroiditis, ostheoarthritis, uveoretinitis, pemphigus, polyarthritis, primary biliary cirrhosis, reiter's syndrome, takayasu's arteritis, temporal arteritis, warm autoimmune hemolytic anemia, wegener's granulomatosis, alopecia universalis, chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis (e.g., ocular uveitis), vaginitis, vasculitis, or vulvitis.

In another aspect, provided herein are methods of disrupting the function of a leukocyte or disrupting a function of an osteoclast. The method includes contacting the leukocyte or the osteoclast with a function disrupting amount of a compound as provided herein.

In another aspect, methods are provided for treating ophthalmic disease by administering one or more of the subject compounds or pharmaceutical compositions to the eye of a subject.

In certain embodiments, provided herein are methods of treating, preventing and/or managing a disease or a disorder using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, wherein the disease or disorder is: Crohn's disease; cutaneous lupus; multiple sclerosis; rheumatoid arthritis; and systemic lupus erythematosus.

In other embodiments, provided herein are methods of treating, preventing and/or managing a disease or a disorder using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, wherein the disease or disorder is: ankylosing spondylitis; chronic obstructive pulmonary disease; myasthenia gravis; ocular uveitis, psoriasis; and psoriatic arthritis.

In other embodiments, provided herein are methods of treating, preventing and/or managing a disease or a disorder using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, wherein the disease or disorder is: adult-onset Still's disease; inflammatory alopecia; amyloidosis; antiphospholipid syndrome; autoimmune hepatitis; autoimmune skin disease, Behcet's disease; chronic inflammatory demyelinating polyneuropathy; eosinophilic gastroenteritis; inflammatory myopathies, pemphigus, polymyalgia rheumatica; relapsing polychondritis; Sjorgen's syndrome; temporal arthritis; ulcerative colitis; vasculis; vitiligo, and Wegner's granulomatosis.

In other embodiments, provided herein are methods of treating, preventing and/or managing a disease or a disorder using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, wherein the disease or disorder is: gout flare; sacoidosis; and systemic sclerosis.

In certain embodiments, provided herein are methods of treating, preventing and/or managing a disease or a disorder using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, wherein the disease or disorder is: asthma; arthritis (e.g., rheumatoid arthritis and psoriatic arthritis); psoriasis; scleroderma; myositis (e.g., dermatomyositis); lupus (e.g., cutaneous lupus erythematosus ("CLE") or systemic lupus erythematosus ("SLE")); or Sjogren's syndrome.

Efficacy of a compound provided herein in treating, preventing and/or managing the disease or disorder can be tested using various animal models known in the art. For example: efficacy in treating, preventing and/or managing asthma can be assessed using ova induced asthma model described, for example, in Lee et al. (2006) *J Allergy Clin Immunol* 118(2):403-9; efficacy in treating, preventing and/or managing arthritis (e.g., rheumatoid or psoriatic arthritis) can be assessed using autoimmune animal models described, for example, in Williams et al. (2010) *Chem Biol,* 17(2): 123-34, WO 2009/088986, WO2009/088880, and WO 2011/008302; efficacy in treating, preventing and/or managing psoriasis can be assessed using transgenic or knockout mouse model with targeted mutations in epidermis, vasculature or immune cells, mouse model resulting from spontaneous mutations, and immunodeficient mouse model with xenotransplantation of human skin or immune cells, all of which are described, for example, in Boehncke et al. (2007) *Clinics in Dermatology,* 25: 596-605; efficacy in treating, preventing and/or managing fibrosis or fibrotic condition can be assessed using the unilateral ureteral obstruction model of renal fibrosis (see Chevalier et al., *Kidney International* (2009) 75:1145-1152), the bleomycin induced model of pulmonary fibrosis (see Moore and Hogaboam, *Am. J. Physiol. Lung. Cell. Mol. Physiol.* (2008) 294:L152-L160), a variety of liver/biliary fibrosis models (see Chuang et al., *Clin Liver Dis* (2008) 12:333-347 and Omenetti, A. et al. (2007) *Laboratory Investigation* 87:499-514 (biliary duct-ligated model)), or a number of myelofibrosis mouse models (see Varicchio, L. et al. (2009) *Expert Rev. Hematol.* 2(3): 315-334); efficacy in treating, preventing and/or managing scleroderma can be assessed using mouse model induced by repeated local injections of bleomycin ("BLM") described, for example, in Yamamoto et al. (1999) *J Invest Dermatol* 112: 456-462; efficacy in treating, preventing and/or managing dermatomyositis can be assessed using myositis mouse model induced by immunization with rabbit myosin described, for example, in Phyanagi et al. (2009) *Arthritis & Rheumatism,* 60(10): 3118-3127; efficacy in treating, preventing and/or managing lupus (e.g., CLE or SLE) can be assessed using various animal models described, for example, in Ghoreishi et al. (2009) *Lupus,* 19: 1029-1035, Ohl et al. (2011) *Journal of Biomedicine and Biotechnology,* Article ID 432595 (14 pages), Xia et al. (2011) *Rheumatology,* 50:2187-2196, Pau et al. (2012) *PLoS ONE,* 7(5): e36761 (15 pages), Mustafa et al. (2011) *Toxicology,* 290: 156-168, Ichikawa et al. (2012) *Arthritis and Rheumatism,* 62(2): 493-503, Ouyang et al. (2012)*J Mol Med,* DOI 10.1007/s00109-012-0866-3 (10 pages), Rankin et al. (2012) *Journal of Immunology,* 188:1656-1667; and efficacy in treating, preventing and/or managing Sjögren's syndrome can be assessed using various mouse models described, for example, in Chiorini et al. (2009) *Journal of Autoimmunity,* 33: 190-196.

In one embodiment, provided herein is a method of treating, preventing and/or managing asthma. As used herein, "asthma" encompasses airway constriction regardless of the cause. Common triggers of asthma include, but are not limited to, exposure to an environmental stimulants (e.g., allergens), cold air, warm air, perfume, moist air, exercise or exertion, and emotional stress. Also provided herein is a method of treating, preventing and/or managing one or more symptoms associated with asthma. Examples of the symptoms include, but are not limited to, severe coughing, airway constriction and mucus production.

In one embodiment, provided herein is a method of treating, preventing and/or managing arthritis. As used herein, "arthritis" encompasses all types and manifestations of arthritis. Examples include, but are not limited to, crystalline arthritis, osteoarthritis, psoriatic arthritis, gouty arthritis, reactive arthritis, rheumatoid arthritis and Reiter's arthritis. In one embodiment, the disease or disorder is rheumatoid arthritis. In another embodiment, the disease or disorder is psoriatic arthritis. Also provided herein is a method of treating, preventing and/or managing one or more symptoms associated with arthritis. Examples of the symptoms include, but are not limited to, joint pain, which progresses into joint deformation, or damages in body organs such as in blood vessels, heart, lungs, skin, and muscles.

In one embodiment, provided herein is a method of treating, preventing and/or managing psoriasis. As used herein, "psoriasis" encompasses all types and manifestations of psoriasis. Examples include, but are not limited to, plaque psoriasis (e.g., chronic plaque psoriasis, moderate plaque psoriasis and severe plaque psoriasis), guttate psoriasis, inverse psoriasis, pustular psoriasis, pemphigus vulgaris, erythrodermic psoriasis, psoriasis associated with inflammatory bowel disease (IBD), and psoriasis associated with rheumatoid arthritis (RA). Also provided herein is a method of treating, preventing and/or managing one or more symptoms associated with psoriasis. Examples of the symptoms include, but are not limited to: red patches of skin covered with silvery scales; small scaling spots; dry, cracked skin that may bleed; itching; burning; soreness; thickened, pitted or ridged nails; and swollen and stiff joints.

In one embodiment, provided herein is a method of treating, preventing and/or managing fibrosis and fibrotic condition. As used herein, "fibrosis" or "fibrotic condition encompasses all types and manifestations of fibrosis or fibrotic condition. Examples include, but are not limited to, formation or deposition of tissue fibrosis; reducing the size, cellularity (e.g., fibroblast or immune cell numbers), composition; or cellular content, of a fibrotic lesion; reducing the collagen or hydroxyproline content, of a fibrotic lesion; reducing expression or activity of a fibrogenic protein; reducing fibrosis associated with an inflammatory response; decreasing weight loss associated with fibrosis; or increasing survival.

In certain embodiments, the fibrotic condition is primary fibrosis. In one embodiment, the fibrotic condition is idiopathic. In other embodiments, the fibrotic condition is associated with (e.g., is secondary to) a disease (e.g., an infectious disease, an inflammatory disease, an autoimmune disease, a malignant or cancerous disease, and/or a connective disease); a toxin; an insult (e.g., an environmental hazard (e.g., asbestos, coal dust, polycyclic aromatic hydrocarbons), cigarette smoking, a wound); a medical treatment (e.g., surgical incision, chemotherapy or radiation), or a combination thereof.

In some embodiments, the fibrotic condition is associated with an autoimmune disease selected from scleroderma or lupus, e.g., systemic lupus erythematosus. In some embodiments, the fibrotic condition is systemic. In some embodiments, the fibrotic condition is systemic sclerosis (e.g., limited systemic sclerosis, diffuse systemic sclerosis, or systemic sclerosis sine scleroderma), nephrogenic systemic fibrosis, cystic fibrosis, chronic graft vs. host disease, or atherosclerosis.

In certain embodiments, the fibrotic condition is a fibrotic condition of the lung, a fibrotic condition of the liver, a fibrotic condition of the heart or vasculature, a fibrotic condition of the kidney, a fibrotic condition of the skin, a fibrotic condition of the gastrointestinal tract, a fibrotic condition of the bone marrow or a hematopoietic tissue, a fibrotic condition of the nervous system, a fibrotic condition of the eye, or a combination thereof.

In other embodiment, the fibrotic condition affects a tissue chosen from one or more of muscle, tendon, cartilage, skin (e.g., skin epidermis or endodermis), cardiac tissue, vascular tissue (e.g., artery, vein), pancreatic tissue, lung tissue, liver tissue, kidney tissue, uterine tissue, ovarian tissue, neural tissue, testicular tissue, peritoneal tissue, colon, small intestine, biliary tract, gut, bone marrow, hematopoietic tissue, or eye (e.g., retinal) tissue.

In some embodiments, the fibrotic condition is a fibrotic condition of the eye. In some embodiments, the fibrotic condition is glaucoma, macular degeneration (e.g., age-related macular degeneration), macular edema (e.g., diabetic macular edema), retinopathy (e.g., diabetic retinopathy), or dry eye disease.

In certain embodiments, the fibrotic condition is a fibrotic condition of the lung. In certain embodiments, the fibrotic condition of the lung is chosen from one or more of: pulmonary fibrosis, idiopathic pulmonary fibrosis (IPF), usual interstitial pneumonitis (UIP), interstitial lung disease, cryptogenic fibrosing alveolitis (CFA), bronchiectasis, and scleroderma lung disease. In one embodiment, the fibrosis of the lung is secondary to a disease, a toxin, an insult, a medical treatment, or a combination thereof. For example, the fibrosis of the lung can be associated with (e.g., secondary to) one or more of: a disease process such as asbestosis and silicosis; an occupational hazard; an environmental pollutant; cigarette smoking; an autoimmune connective tissue disorders (e.g., rheumatoid arthritis, scleroderma and systemic lupus erythematosus (SLE)); a connective tissue disorder such as sarcoidosis; an infectious disease, e.g., infection, particularly chronic infection; a medical treatment, including but not limited to, radiation therapy, and drug therapy, e.g., chemotherapy (e.g., treatment with as bleomycin, methotrexate, amiodarone, busulfan, and/or nitrofurantoin). In one embodiment, the fibrotic condition of the lung treated with the methods of the invention is associated with (e.g., secondary to) a cancer treatment, e.g., treatment of a cancer (e.g., squamous cell carcinoma, testicular cancer, Hodgkin's disease with bleomycin). In one embodiment, the fibrotic condition of the lung is associated with an autoimmune connective tissue disorder (e.g., scleroderma or lupus, e.g., SLE).

In certain embodiments, the fibrotic condition is a fibrotic condition of the liver. In certain embodiments, the fibrotic condition of the liver is chosen from one or more of: fatty liver disease, steatosis (e.g., nonalcoholic steatohepatitis (NASH), cholestatic liver disease (e.g., primary biliary cirrhosis (PBC)), cirrhosis, alcohol induced liver fibrosis, biliary duct injury, biliary fibrosis, or cholangiopathies. In other embodiments, hepatic or liver fibrosis includes, but is not limited to, hepatic fibrosis associated with alcoholism, viral infection, e.g., hepatitis (e.g., hepatitis C, B or D), autoimmune hepatitis, non-alcoholic fatty liver disease (NA- FLD), progressive massive fibrosis, exposure to toxins or irritants (e.g., alcohol, pharmaceutical drugs and environmental toxins).

In certain embodiments, the fibrotic condition is a fibrotic condition of the heart. In certain embodiments, the fibrotic condition of the heart is myocardial fibrosis (e.g., myocardial fibrosis associated with radiation myocarditis, a surgical procedure complication (e.g., myocardial post-operative fibrosis), infectious diseases (e.g., Chagas disease, bacterial, trichinosis or fungal myocarditis)); granulomatous, metabolic storage disorders (e.g., cardiomyopathy, hemochromatosis); developmental disorders (e.g, endocardial fibroelastosis); arteriosclerotic, or exposure to toxins or irritants (e.g., drug induced cardiomyopathy, drug induced cardiotoxicity, alcoholic cardiomyopathy, cobalt poisoning or exposure). In certain embodiments, the myocardial fibrosis is associated with an inflammatory disorder of cardiac tissue (e.g., myocardial sarcoidosis). In some embodiments, the fibrotic condition is a fibrotic condition associated with a myocardial infarction. In some embodiments, the fibrotic condition is a fibrotic condition associated with congestive heart failure.

In certain embodiments, the fibrotic condition is a fibrotic condition of the kidney. In certain embodiments, the fibrotic condition of the kidney is chosen from one or more of: renal fibrosis (e.g., chronic kidney fibrosis), nephropathies associated with injury/fibrosis (e.g., chronic nephropathies associated with diabetes (e.g., diabetic nephropathy)), lupus, scleroderma of the kidney, glomerular nephritis, focal segmental glomerular sclerosis, IgA nephropathyrenal fibrosis associated with human chronic kidney disease (CKD), chronic progressive nephropathy (CPN), tubulointerstitial fibrosis, ureteral obstruction, chronic uremia, chronic interstitial nephritis, radiation nephropathy, glomerulosclerosis, progressive glomerulonephrosis (PGN), endothelial/thrombotic microangiopathy injury, HIV-associated nephropathy, or fibrosis associated with exposure to a toxin, an irritant, or a chemotherapeutic agent. In one embodiment, the fibrotic condition of the kidney is scleroderma of the kidney. In some embodiments, the fibrotic condition of the kidney is transplant nephropathy, diabetic nephropathy, lupus nephritis, or focal segmental glomerulosclerosis (FSGS).

In certain embodiments, the fibrotic condition is a fibrotic condition of the skin. In certain embodiments, the fibrotic condition of the skin is chosen from one or more of: skin fibrosis (e.g., hypertrophic scarring, keloid), scleroderma, nephrogenic systemic fibrosis (e.g., resulting after exposure to gadolinium (which is frequently used as a contrast substance for MRIs) in patients with severe kidney failure), and keloid.

In certain embodiments, the fibrotic condition is a fibrotic condition of the gastrointestinal tract. In certain embodiments, the fibrotic condition is chosen from one or more of: fibrosis associated with scleroderma; radiation induced gut fibrosis; fibrosis associated with a foregut inflammatory disorder such as Barrett's esophagus and chronic gastritis, and/or fibrosis associated with a hindgut inflammatory disorder, such as inflammatory bowel disease (IBD), ulcerative colitis and Crohn's disease. In some embodiments, the fibrotic condition of the gastrointestinal tract is fibrosis associated with scleroderma.

In certain embodiments, the fibrotic condition is a fibrotic condition of the bone marrow or a hematopoietic tissue. In certain embodiments, the fibrotic condition of the bone marrow is an intrinsic feature of a chronic myeloproliferative neoplasm of the bone marrow, such as primary myelofibrosis (also referred to herein as agnogenic myeloid metaplasia or chronic idiopathic myelofibrosis). In other embodiments, the bone marrow fibrosis is associated with (e.g., is secondary to) a malignant condition or a condition caused by a clonal proliferative disease. In other embodiments, the bone marrow fibrosis is associated with a hematologic disorder (e.g., a hematologic disorder chosen from one or more of: polycythemia vera, essential thrombocythemia, myelodysplasia, hairy cell leukemia, lymphoma (e.g., Hodgkin or non-Hodgkin lymphoma), multiple myeloma or chronic myelogeneous leukemia (CML)). In yet other embodiments, the bone marrow fibrosis is associated with (e.g., secondary to) a non-hematologic disorder (e.g., a non-hematologic disorder chosen from solid tumor metastasis to bone marrow, an autoimmune disorder (e.g., systemic lupus erythematosus, scleroderma, mixed connective tissue disorder, or polymyositis), an infection (e.g., tuberculosis), or secondary hyperparathyroidism associated with vitamin D deficiency. In some embodiments, the fibrotic condition is idiopathic or drug-induced myelofibrosis. In some embodiments, the fibrotic condition of the bone marrow or hematopoietic tissue is associated with systemic lupus erythematosus or scleroderma.

In one embodiment, provided herein is a method of treating, preventing and/or managing scleroderma. Scleroderma is a group of diseases that involve hardening and tightening of the skin and/or other connective tissues. Scleroderma may be localized (e.g., affecting only the skin) or systemic (e.g., affecting other systems such as, e.g., blood vessels and/or internal organs). Common symptoms of scleroderma include Raynaud's phenomenon, gastroesophageal reflux disease, and skin changes (e.g., swollen fingers and hands, or thickened patches of skin). In some embodiments, the scleroderma is localized, e.g., morphea or linear scleroderma. In some embodiments, the condition is a systemic sclerosis, e.g., limited systemic sclerosis, diffuse systemic sclerosis, or systemic sclerosis sine scleroderma.

Localized scleroderma (localized cutaneous fibrosis) includes morphea and linear scleroderma. Morphea is typically characterized by oval-shaped thickened patches of skin that are white in the middle, with a purple border. Linear scleroderma is more common in children. Symptoms of linear scleroderma may appear mostly on one side of the body. In linear scleroderma, bands or streaks of hardened skin may develop on one or both arms or legs or on the forehead. En coup de sabre (frontal linear scleroderma or morphea en coup de sabre) is a type of localized scleroderma typically characterized by linear lesions of the scalp or face.

Systemic scleroderma (systemic sclerosis) includes, e.g., limited systemic sclerosis (also known as limited cutaneous systemic sclerosis, or CREST syndrome), diffuse systemic sclerosis (also known as diffuse cutaneous systemic sclerosis), and systemic sclerosis sine scleroderma. CREST stands for the following complications that may accompany limited scleroderma: calcinosis (e.g., of the digits), Raynaud's phenomenon, esophageal dysfunction, sclerodactyl), and telangiectasias. Typically, limited scleroderma involves cutaneous manifestations that mainly affect the hands, arms, and face. Limited and diffuse subtypes are distinguished based on the extent of skin involvement, with sparing of the proximal limbs and trunk in limited disease. See, e.g., Denton, C. P. et al. (2006), *Nature Clinical Practice Rheumatology*, 2(3):134-143. The limited subtype also typically involves a long previous history of Raynaud's phenomenon, whereas in the diffuse subtype, onset of Raynaud's phenomenon can be simultaneous with other manifestations or might occur later. Both limited and diffuse subtypes may involve internal organs. Typical visceral manifestations of limited systemic sclerosis include isolated pulmonary hypertension, severe bowel involvement, and pulmonary fibrosis. Typical visceral manifestations of diffuse systemic sclerosis include renal crisis, lung fibrosis, and cardiac disease. Diffuse systemic sclerosis typically progresses rapidly and affects a large area of the skin and one or more internal organs (e.g., kidneys, esophagus, heart, or lungs). Systemic sclerosis sine scleroderma is a rare disorder in which patients develop vascular and fibrotic damage to internal organs in the absence of cutaneous sclerosis.

In one embodiment, provided herein is a method of treating, preventing and/or managing inflammatory myopathies. As used herein, "inflammatory myopathies" encompass all types and manifestations of inflammatory myopathies. Examples include, but are not limited to, muscle weakness (e.g., proximal muscle weakness), skin rash, fatigue after walking or standing, tripping or falling, dysphagia, dysphonia, difficulty breathing, muscle pain, tender muscles, weight loss, low-grade fever, inflamed lungs, light sensitivity, calcium deposits (calcinosis) under the skin or in the muscle, as well as biological concomitants of inflammatory myopathies as disclosed herein or as known in the art. Biological concomitants of inflammatory myopathies (e.g., dermatomyositis) include, e.g., altered (e.g., increased) levels of cytokines (e.g., Type I interferons (e.g., IFN-α and/or IFN-β), interleukins (e.g., IL-6, IL-10, IL-15, IL-17 and IL-18), and TNF-α), TGF-β, B-cell activating factor (BAFF), overexpression of IFN inducible genes (e.g., Type I IFN inducible genes). Other biological concomitants of inflammatory myopathies can include, e.g., an increased erythrocyte sedimentation rate (ESR) and/or elevated level of creatine kinase. Further biological concomitants of inflammatory myopathies can include autoantibodies, e.g., anti-synthetase autoantibodies (e.g., anti-Jo1 antibodies), anti-signal recognition particle antibodies (anti-SRP), anti-Mi-2 antibodies, anti-p155 antibodies, anti-PM/Sci antibodies, and anti-RNP antibodies.

The inflammatory myopathy can be an acute inflammatory myopathy or a chronic inflammatory myopathy. In some embodiments, the inflammatory myopathy is a chronic inflammatory myopathy (e.g., dermatomyositis, polymyositis, or inclusion body myositis). In some embodiments, the inflammatory myopathy is caused by an allergic reaction, another disease (e.g., cancer or a connective tissue disease), exposure to a toxic substance, a medicine, or an infectious agent (e.g., a virus). In some embodiments, the inflammatory myopathy is associated with lupus, rheumatoid arthritis, or systemic sclerosis. In some embodiments, the inflammatory myopathy is idiopathic. In some embodiments, the inflammatory myopathy is selected from polymyositis, dermatomyositis, inclusion body myositis, and immune-mediated necrotizing myopathy. In some embodiments, the inflammatory myopathy is dermatomyositis.

In another embodiment, provided herein is a method of treating, preventing and/or managing a skin condition (e.g., a dermatitis). In some embodiments, the methods provided herein can reduce symptoms associated with a skin condition (e.g., itchiness and/or inflammation). In some such embodiments, the compound provided herein is administered topically (e.g., as a topical cream, eyedrop, nose drop or nasal spray). In some such embodiments, the compound is a PI3K delta inhibitor (e.g., a PI3K inhibitor that demonstrates greater inhibition of PI3K delta than of other PI3K isoforms). In some embodiments, the PI3K delta inhibitor prevents mast cell degranulation.

As used herein, "skin condition" includes any inflammatory condition of the skin (e.g., eczema or dermatitis, e.g., contact dermatitis, atopic dermatitis, dermatitis herpetiformis, seborrheic dermatitis, nummular dermatitis, stasis dermatitis, perioral dermatitis), as well as accompanying symptoms (e.g., skin rash, itchiness (pruritus), swelling (edema), hay fever, anaphalaxis). Frequently, such skin conditions are caused by an allergen. As used herein, a "skin condition" also includes, e.g., skin rashes (e.g., allergic rashes, e.g., rashes resulting from exposure to allergens such as poison ivy, poison oak, or poison sumac, or rashes caused by other diseases or conditions), insect bites, minor burns, sunburn, minor cuts, and scrapes. In some embodiments, the symptom associated with inflammatory myopathy, or the skin condition or symptom associated with the skin condition, is a skin rash or itchiness (pruritus) caused by a skin rash.

The skin condition (e.g., the skin rash) may be spontaneous, or it may be induced, e.g., by exposure to an allergen (e.g., poison ivy, poison oak, or poison sumac), drugs, food, insect bite, inhalants, emotional stress, exposure to heat, exposure to cold, or exercise. In some embodiments, the skin condition is a skin rash (e.g., a pruritic rash, e.g., utricaria). In some embodiments, the skin condition is an insect bite. In some embodiments, the skin condition is associated with another disease (e.g., an inflammatory myopathy, e.g., dermatomyositis).

In some embodiments, the subject (e.g., the subject in need of treatment for an inflammatory myopathy and/or a skin condition) exhibits an elevated level or elevated activity of IFN-α, TNF-α, IL-6, IL-8, IL-1, or a combination thereof. In certain embodiments, the subject exhibits an elevated level of IFN-α. In some embodiments, treating (e.g., decreasing or inhibiting) the inflammatory myopathy, or the skin condition, comprises inhibiting (e.g., decreasing a level of, or decreasing a biological activity of) one or more of IFN-α, TNF-α, IL-6, IL-8, or IL-1 in the subject or in a sample derived from the subject. In some embodiments, the method decreases a level of IFN-α, TNF-α, IL-6, IL-8, or IL-1 in the subject or in a sample derived from the subject. In some embodiments, the method decreases a level of IFN-α in the subject or in a sample derived from the subject. In some embodiments, the level of IFN-α, TNF-α, IL-6, IL-8, or IL-1 is the level assessed in a sample of whole blood or PBMCs. In some embodiments, the level of IFN-α, TNF-α, IL-6, IL-8, or IL-1 is the level assessed in a sample obtained by a skin biopsy or a muscle biopsy. In some embodiments, the sample is obtained by a skin biopsy.

In one embodiment, provided herein is a method of treating, preventing and/or managing myositis. As used herein, "myositis" encompasses all types and manifestations of myositis. Examples include, but are not limited to, myositis ossificans, fibromyositis, idiopathic inflammatory myopathies, dermatomyositis, juvenile dermatomyositis, polymyositis, inclusion body myositis and pyomyositis. In one embodiment, the disease or disorder is dermatomyositis. Also provided herein is a method of treating, preventing and/or managing one or more symptoms associated with myositis. Examples of the symptoms include, but are not limited to: muscle weakness; trouble lifting arms; trouble swallowing or breathing; muscle pain; muscle tenderness; fatigue; fever; lung problems; gastrointestinal ulcers; intestinal perforations; calcinosis under the skin; soreness; arthritis; weight loss; and rashes.

In one embodiment, provided herein is a method of treating, preventing and/or managing lupus. As used herein, "lupus" refers to all types and manifestations of lupus. Examples include, but are not limited to, systemic lupus erythematosus; lupus nephritis; cutaneous manifestations (e.g., manifestations seen in cutaneous lupus erythematosus, e.g., a skin lesion or rash); CNS lupus; cardiovascular, pulmonary, hepatic, hematological, gastrointestinal and musculoskeletal manifestations; neonatal lupus erythematosus; childhood systemic lupus erythematosus; drug-induced lupus erythematosus; anti-phospholipid syndrome; and complement deficiency syndromes resulting in lupus manifestations. In one embodiment, the lupus is systemic lupus erythematosus (SLE), cutaneous lupus erythematosus (CLE), drug-induced lupus, or neonatal lupus. In another embodiment, the lupus is a CLE, e.g., acute cutaneous lupus erythematosus (ACLE), subacute cutaneous lupus erythematosus (SCLE), intermittent cutaneous lupus erythematosus (also known as lupus erythematosus tumidus (LET)), or chronic cutaneous lupus. In some embodiments, the intermittent CLE is chronic discloid lupus erythematosus (CDLE) or lupus erythematosus profundus (LEP) (also known as lupus erythematosus panniculitis). Types, symptoms, and pathogenesis of CLE are described, for example, in Wenzel et al. (2010), Lupus, 19, 1020-1028.

In one embodiment, provided herein is a method of treating, preventing and/or managing Sjögren's syndrome. As used herein, "Sjögren's syndrome" refers to all types and manifestations of Sjögren's syndrome. Examples include, but are not limited to, primary and secondary Sjögren's syndrome. Also provided herein is a method of treating, preventing and/or managing one or more symptoms associated with Sjögren's syndrome. Examples of the symptoms include, but are not limited to: dry eyes; dry mouth; joint pain; swelling; stiffness; swollen salivary glands; skin rashes; dry skin; vaginal dryness; persistent dry cough; and prolonged fatigue.

In some embodiments, a symptom associated with the disease or disorder provided herein is reduced by at least 10%, at least 20%, at least 30%, at least 40%, at least 50%, at least 60%, at least 70%, at least 80%, at least 90%, or at least 95% relative to a control level. The control level includes any appropriate control as known in the art. For example, the control level can be the pre-treatment level in the sample or subject treated, or it can be the level in a control population (e.g., the level in subjects who do not have the disease or disorder or the level in samples derived from subjects who do not have the disease or disorder). In some embodiments, the decrease is statistically significant, for example, as assessed using an appropriate parametric or non-parametric statistical comparison.

8. COMBINATION THERAPY

In some embodiments, the compound provided herein is administered in combination with one or more other therapies. In one embodiment, provided herein are methods for combination therapies in which an agent known to modulate other pathways, or other components of the same pathway, or even overlapping sets of target enzymes are used in combination with a compound provided herein, or a pharmaceutically acceptable form (e.g., pharmaceutically acceptable salts, hydrates, solvates, isomers, prodrugs, and isotopically labeled derivatives) thereof. In one aspect, such therapy includes, but is not limited to, the combination of the subject compound with chemotherapeutic agents, therapeutic antibodies, and/or radiation treatment, to provide a synergistic or additive therapeutic effect.

By "in combination with," it is not intended to imply that the other therapy and the PI3K modulator must be administered at the same time and/or formulated for delivery together, although these methods of delivery are within the scope of this disclosure. The compound provided herein can be administered concurrently with, prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before), or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after), one or more other therapies (e.g., one or more other additional agents). In general, each therapeutic agent will be administered at a dose and/or on a time schedule determined for that particular agent. The other therapeutic agent can be administered with the compound provided herein in a single composition or separately in a different composition. Triple therapy is also contemplated herein.

In general, it is expected that additional therapeutic agents employed in combination be utilized at levels that do not exceed the levels at which they are utilized individually. In some embodiments, the levels utilized in combination will be lower than those utilized individually.

In one aspect, a compound as provided herein, or a pharmaceutically acceptable form (e.g., pharmaceutically acceptable salts, hydrates, solvates, isomers, prodrugs, and isotopically labeled derivatives) thereof, orpharmaceutical compositions as provided herein, can present synergistic or additive efficacy when administered in combination with agents that inhibit IgE production or activity. Such combination can reduce the undesired effect of high level of IgE associated with the use of one or more PI3K-δ inhibitors, if such effect occurs. This can be particularly useful in treatment of autoimmune and inflammatory disorders (AIID) such as rheumatoid arthritis. Additionally, the administration of PI3K-δ or PI3K-δ/γ inhibitors as provided herein in combination with inhibitors of mTOR can also exhibit synergy through enhanced inhibition of the PI3K pathway.

In a separate but related aspect, provided herein is a combination treatment of a disease associated with PI3K-δ comprising administering to a PI3K-δ inhibitor and an agent that inhibits IgE production or activity. Other exemplary PI3K-δ inhibitors are applicable for this combination and they are described, e.g., U.S. Pat. No. 6,800,620. Such combination treatment is particularly useful for treating autoimmune and inflammatory diseases (AIID) including, but not limited to rheumatoid arthritis.

Agents that inhibit IgE production are known in the art and they include, but are not limited to, one or more of TEI-9874, 2-(4-(6-cyclohexyloxy-2-naphtyloxy)phenylacetamide)benzoic acid, rapamycin, rapamycin analogs (i.e., rapalogs), TORC1 inhibitors, TORC2 inhibitors, and any other compounds that inhibit mTORC1 and mTORC2. Agents that inhibit IgE activity include, for example, anti-IgE antibodies such as for example Omalizumab and TNX-901.

For treatment of autoimmune diseases, a compound as provided herein, or a pharmaceutically acceptable form (e.g., pharmaceutically acceptable salts, hydrates, solvates, isomers, prodrugs, and isotopically labeled derivatives) thereof, or pharmaceutical compositions as provided herein, can be used in combination with commonly prescribed drugs including, but not limited to Enbrel®, Remicade®, Humira®, Avonex®, and Rebif®. For treatment of respiratory diseases, the subject compounds or pharmaceutical compositions can be administered in combination with commonly prescribed drugs including, but not limited to Xolair®, Advair®, Singulair®, and Spiriva®.

The compounds as provided herein, or a pharmaceutically acceptable form (e.g., pharmaceutically acceptable salts, hydrates, solvates, isomers, prodrugs, and isotopically labeled derivatives) thereof, or pharmaceutical compositions as provided herein, can be formulated or administered in conjunction with other agents that act to relieve the symptoms of inflammatory conditions such as encephalomyelitis, asthma, and the other diseases described herein. These agents include non-steroidal anti-inflammatory drugs (NSAIDs), e.g., acetylsalicylic acid; ibuprofen; naproxen; indomethacin; nabumetone; tolmetin; etc. Corticosteroids are used to reduce inflammation and suppress activity of the immune system. An exemplary drug of this type is Prednisone. Chloroquine (Aralen) or hydroxychloroquine (Plaquenil) can also be used in some individuals with lupus. They can be prescribed for skin and joint symptoms of lupus. Azathioprine (Imuran) and cyclophosphamide (Cytoxan) suppress inflammation and tend to suppress the immune system. Other agents, e.g., methotrexate and cyclosporin are used to control the symptoms of lupus. Anticoagulants are employed to prevent blood from clotting rapidly. They range from aspirin at very low dose which prevents platelets from sticking, to heparin/coumadin. Other compounds used in the treatment of lupus include belimumab (Benlysta®).

In another aspect, provided herein is a pharmaceutical composition for inhibiting abnormal cell growth in a subject which comprises an amount of a compound as provided herein, or a pharmaceutically acceptable form (e.g., pharmaceutically acceptable salts, hydrates, solvates, isomers, prodrugs, and isotopically labeled derivatives) thereof, in combination with an amount of an anti-cancer agent (e.g., a chemotherapeutic agent). Many chemotherapeutics are presently known in the art and can be used in combination with the compounds as provided herein.

In some embodiments, the chemotherapeutic is selected from mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec® (Imatinib Mesylate), Velcade® (bortezomib), Casodex (bicalutamide), Iressa®, and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; BTK inhibitors such as ibrutinib (PCI-32765) and AVL-292; HDAC inhibitors such as vorinostat, romidepsin, panobinostat, valproic acid, belinostat, mocetinostat, abrexinostat, entinostat, SB939, resminostat, givinostat, CUDC-101, AR-42, CHR-2845, CHR-3996, 4SC-202, CG200745, ACY-1215 and kevetrin; JAK/STAT inhibitors such as lestaurtinib, tofacitinib, ruxolitinib, pacritinib, CYT387, baricitinib, fostamatinib, GLPG0636, TG101348, INCB16562 and AZD1480; nitrogen mustards such as bedamustine, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pralatrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™; razoxane; sizofiran; spirogermanium; tenuazonic acid; triaziquone; 2,2',2"-trichlorotriethyla-mine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL™, Bristol-Myers Squibb Oncology, Princeton, N.J.) and docetaxel (TAXOTERE™, Rhone-Poulenc Rorer, Antony, France) and ABRAXANE® (paclitaxel protein-bound particles); retinoic acid; esperamicins; capecitabine; and pharmaceutically acceptable forms (e.g., pharmaceutically acceptable salts, hydrates, solvates, isomers, prodrugs, and isotopically labeled derivatives) of any of the above. Also included as suitable chemotherapeutic cell conditioners are anti-hormonal agents that act to regulate or inhibit hormone action on tumors such as anti-estrogens including for example tamoxifen (Nolvadex™) raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Where desired, the compounds or pharmaceutical composition as provided herein can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, Crizotinib, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126, and Zosuquidar.

In some embodiments, the chemotherapeutic is selected from hedgehog inhibitors including, but not limited to IPI-926 (See U.S. Pat. No. 7,812,164). Other suitable hedgehog inhibitors include, for example, those described and provided in U.S. Pat. No. 7,230,004, U.S. Patent Application Publication No. 2008/0293754, U.S. Patent Application Publication No. 2008/0287420, and U.S. Patent Application Publication No. 2008/0293755, the entire disclosures of which are incorporated by reference herein. Examples of other suitable hedgehog inhibitors include those described in U.S. Patent Application Publication Nos. US 2002/0006931, US 2007/0021493 and US 2007/0060546, and International Application Publication Nos. WO 2001/19800, WO 2001/26644, WO 2001/27135, WO 2001/49279, WO 2001/74344, WO 2003/011219, WO 2003/088970, WO 2004/020599, WO 2005/013800, WO 2005/033288, WO 2005/032343, WO 2005/042700, WO 2006/028958, WO 2006/050351, WO 2006/078283, WO 2007/054623, WO 2007/059157, WO 2007/120827, WO 2007/131201, WO 2008/070357, WO 2008/110611, WO 2008/112913, and WO 2008/131354. Additional examples of hedgehog inhibitors include, but are not limited to, GDC-0449 (also known as RG3616 or vismodegib) described in, e.g., Von Hoff D. et al., *N. Engl. J. Med.* 2009; 361(12):1164-72; Robarge K. D. et al., *Bioorg Med Chem. Lett.* 2009; 19(19):5576-81; Yauch, R. L. et al. (2009) *Science* 326: 572-574; Sciencexpress: 1-3 (10.1126/science.1179386); Rudin, C. et al. (2009) *New England J of Medicine* 361-366 (10.1056/nejma0902903); BMS-833923 (also known as XL139) described in, e.g., in Siu L. et al., *J. Clin. Oncol.* 2010; 28:15s (suppl; abstr 2501); and National Institute of Health Clinical Trial Identifier No. NCT006701891; LDE-225 described, e.g., in Pan S. et al., *ACS Med. Chem. Lett.*, 2010; 1(3): 130-134; LEQ-506 described, e.g., in National Institute of Health Clinical Trial Identifier No. NCT01106508; PF-04449913 described, e.g., in National Institute of Health Clinical Trial Identifier No. NCT00953758; Hedgehog pathway antagonists provided in U.S. Patent Application Publication No. 2010/0286114; SMOi2-17 described, e.g., U.S. Patent Application Publication No. 2010/0093625; SANT-1 and SANT-2 described, e.g., in Rominger C. M. et al., *J. Pharmacol. Exp. Ther.* 2009; 329(3):995-1005; 1-piperazinyl-4-arylphthalazines or analogues thereof, described in Lucas B. S. et al., *Bioorg. Med. Chem. Lett.* 2010; 20(12):3618-22.

Other chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (Abraxane), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), Ca2+ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, caminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, caminomycin, aminopterin, and hexamethyl melamine.

Exemplary biotherapeutic agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. Herceptin (trastuzumab), T-DM1, AVASTIN (bevacizumab), ERBITUX (cetuximab), Vectibix (panitumumab), Rituxan (rituximab), Bexxar (tositumomab)).

In some embodiments, the chemotherapeutic is selected from HSP90 inhibitors. The HSP90 inhibitor can be a geldanamycin derivative, e.g., a benzoquinone or hygroquinone ansamycin HSP90 inhibitor (e.g., IPI-493 and/or IPI-504). Non-limiting examples of HSP90 inhibitors include IPI-493, IPI-504, 17-AAG (also known as tanespimycin or CNF-1010), BIIB-021 (CNF-2024), BIIB-028, AUY-922 (also known as VER-49009), SNX-5422, STA-9090, AT-13387, XL-888, MPC-3100, CU-0305, 17-DMAG, CNF-1010, Macbecin (e.g., Macbecin I, Macbecin II), CCT-018159, CCT-129397, PU-H71, or PF-04928473 (SNX-2112).

In some embodiments, the chemotherapeutic is selected from PI3K inhibitors (e.g., including those PI3K inhibitors provided herein and those PI3K inhibitors not provided herein). In some embodiment, the PI3K inhibitor is an inhibitor of delta and gamma isoforms of PI3K. In some embodiments, the PI3K inhibitor is an inhibitor of alpha isoforms of PI3K. In other embodiments, the PI3K inhibitor is an inhibitor of one or more alpha, beta, delta and gamma isoforms of PI3K. Exemplary PI3K inhibitors that can be used in combination are described in, e.g., WO 09/088,990, WO 09/088,086, WO 2011/008302, WO 2010/036380, WO 2010/006086, WO 09/114,870, WO 05/113556; US 2009/0312310, and US 2011/0046165. Additional PI3K inhibitors that can be used in combination with the pharmaceutical compositions, include but are not limited to, AMG-319, GSK 2126458, GDC-0980, GDC-0941, Sanofi XL147, XL499, XL756, XL147, PF-46915032, BKM 120, CAL-101 (GS-1101), CAL 263, SF1126, PX-886, and a dual PI3K inhibitor (e.g., Novartis BEZ235). In one embodiment, the PI3K inhibitor is an isoquinolinone.

In some embodiments, provided herein is a method for using the a compound as provided herein, or a pharmaceutically acceptable form (e.g., pharmaceutically acceptable salts, hydrates, solvates, isomers, prodrugs, and isotopically labeled derivatives) thereof, or pharmaceutical compositions as provided herein, in combination with radiation therapy in inhibiting abnormal cell growth or treating the hyperproliferative disorder in the subject. Techniques for administering radiation therapy are known in the art, and these techniques can be used in the combination therapy described herein. The administration of the compound as provided herein in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner as provided herein include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds as provided herein, or a pharmaceutically acceptable form (e.g., pharmaceutically acceptable salts, hydrates, solvates, isomers, prodrugs, and isotopically labeled derivatives) thereof, or pharmaceutical compositions as provided herein, can render abnormal cells more sensitive to treatment with radiation for purposes of killing and/or inhibiting the growth of such cells. Accordingly, provided herein is a method for sensitizing abnormal cells in a subject to treatment with radiation which comprises administering to the subject an amount of a compound as provided herein or pharmaceutically acceptable forms (e.g., pharmaceutically acceptable salts, hydrates, solvates, isomers, prodrugs, and isotopically labeled derivatives) thereof, which amount is effective is sensitizing abnormal cells to treatment with radiation. The amount of the compound used in this method can be determined according to the means for ascertaining effective amounts of such compounds described herein.

The compounds as provided herein, or a pharmaceutically acceptable form (e.g., pharmaceutically acceptable salts, hydrates, solvates, isomers, prodrugs, and isotopically labeled derivatives) thereof, or pharmaceutical compositions as provided herein, can be used in combination with an amount of one or more substances selected from anti-angiogenesis agents, signal transduction inhibitors, and anti-proliferative agents, glycolysis inhibitors, or autophagy inhibitors.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a compound as provided herein and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. In some embodiments, MMP-2 and MMP-9 inhibitors are those that have little or no activity inhibiting MMP-1. Other embodiments include those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some non-limiting examples of MMP inhibitors are AG-3340, RO 32-3555, and RS 13-0830.

Autophagy inhibitors include, but are not limited to, chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including, but not limited to ATG5 (which are implicated in autophagy), can also be used.

In some embodiments, provided herein is a method of and/or a pharmaceutical composition for treating a cardiovascular disease in a subject which comprises an amount of a compound as provided herein, or a pharmaceutically acceptable form (e.g., pharmaceutically acceptable salts, hydrates, solvates, isomers, prodrugs, and isotopically labeled derivatives) thereof, and an amount of one or more of therapeutic agents use for the treatment of cardiovascular diseases.

Exemplary agents for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetylsalicylic acid (ASA) and clopidrogel, vasodilating agents, e.g., nitrates, calcium channel blocking drugs, antiproliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings. Moreover, a coating can be used to effect therapeutic delivery focally within the vessel wall. By incorporation of the active agent in a swellable polymer, the active agent will be released upon swelling of the polymer.

The compounds as provided herein, or a pharmaceutically acceptable form (e.g., pharmaceutically acceptable salts, hydrates, solvates, isomers, prodrugs, and isotopically labeled derivatives) thereof, or pharmaceutical compositions as provided herein, can be formulated or administered in conjunction with liquid or solid tissue barriers also known as lubricants. Examples of tissue barriers include, but are not limited to, polysaccharides, polyglycans, seprafilm, interceed and hyaluronic acid.

Medicaments which can be administered in conjunction with the compounds as provided herein, or a pharmaceutically acceptable form (e.g., pharmaceutically acceptable salts, hydrates, solvates, isomers, prodrugs, and isotopically labeled derivatives) thereof, include any suitable drugs usefully delivered by inhalation for example, analgesics, e.g., codeine, dihydromorphine, ergotamine, fentanyl or morphine; anginal preparations, e.g., diltiazem; antiallergics, e.g. cromoglycate, ketotifen or nedocromil; anti-infectives, e.g., cephalosporins, penicillins, streptomycin, sulphonamides, tetracyclines or pentamidine; antihistamines, e.g., methapyrilene; anti-inflammatories, e.g., beclomethasone, flunisolide, budesonide, tipredane, triamcinolone acetonide or fluticasone; antitussives, e.g., noscapine; bronchodilators, e.g., ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (-)-4-amino-3,5-dichloro-α-[[[6-[2-(2-pyridinyl)ethoxy]hexyl]amino]methyl]benzenemethanol; diuretics, e.g., amiloride; anticholinergics e.g., ipratropium, atropine or oxitropium; hormones, e.g., cortisone, hydrocortisone or prednisolone; xanthines e.g., aminophylline, choline theophyllinate, lysine theophyllinate or theophylline; and therapeutic proteins and peptides, e.g., insulin or glucagon. It will be clear to a person skilled in the art that, where appropriate, the medicaments can be used in the form of salts (e.g., as alkali metal or amine salts or as acid addition salts) or as esters (e.g., lower alkyl esters) to optimize the activity and/or stability of the medicament.

Other exemplary therapeutic agents useful for a combination therapy include, but are not limited to, agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, α-adrenergic receptor antagonists, agents for the treatment of hypercholesterolemia, and agents for the treatment of dyslipidemia.

Other therapeutic agents contemplated herein include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents include, but are not limited to, those used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include, but are not limited to, antimicrobial agents, sulfonamides, trimethoprim-sulfamethoxazole quinolones, and agents for urinary tract infections, penicillins, cephalosporins, and other, β-Lactam antibiotics, an agent containing an aminoglycoside, protein synthesis inhibitors, drugs used in the chemotherapy of tuberculosis, *mycobacterium avium* complex disease, and leprosy, antifungal agents, antiviral agents including nonretroviral agents and antiretroviral agents.

Examples of therapeutic antibodies that can be combined with a subject compound include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

For treating renal carcinoma, one can combine a compound as provided herein, or a pharmaceutically acceptable form (e.g., pharmaceutically acceptable salts, hydrates, solvates, isomers, prodrugs, and isotopically labeled derivatives) thereof, or pharmaceutical compositions as provided herein, with sorafenib and/or avastin. For treating an endometrial disorder, one can combine a compound as provided herein with doxorubincin, taxotere (taxol), and/or cisplatin (carboplatin). For treating ovarian cancer, one can combine a compound as provided herein with cisplatin (carboplatin), taxotere, doxorubincin, topotecan, and/or tamoxifen. For treating breast cancer, one can combine a compound as provided herein with taxotere (taxol), gemcitabine (capecitabine), tamoxifen, letrozole, tarceva, lapatinib, PD0325901, avastin, herceptin, OSI-906, and/or OSI-930. For treating lung cancer, one can combine a compound as provided herein with taxotere (taxol), gemcitabine, cisplatin, pemetrexed, Tarceva, PD0325901, and/or avastin.

In some embodiments, the disorder to be treated, prevented and/or managed is hematological cancer, e.g., lymphoma (e.g., T-cell lymphoma; NHL), myeloma (e.g., multiple myeloma), and leukemia (e.g., CLL), and a compound provided herein is used in combination with: HDAC inhibitors such as vorinostat and romidepsin; mTOR inhibitors such as everolmus; anti-folates such as pralatrexate; nitrogen mustard such as bendamustine; gemcitabine, optionally in further combination with oxaliplatin; rituximab.cyclophosphamide combination; PI3K inhibitors such as GS-1101, XL 499, GDC-0941, and AMG-319; or BTK inhibitors such as ibrutinib and AVL-292.

In certain embodiments, wherein inflammation (e.g., arthritis, asthma) is treated, prevented and/or managed, a compound provided herein can be combined with, for example: PI3K inhibitors such as GS-1101, XL 499, GDC-0941, and AMG-319; BTK inhibitors such as ibrutinib and AVL-292; JAK inhibitors such as tofacitinib, fostamatinib, and GLPG0636.

In certain embodiments wherein asthma is treated, prevented and/or managed, a compound provided herein can be combined with, for example: beta 2-agonists such as, but not limited to, albuterol (Proventil®, or Ventolin®), salmeterol (Serevent®), formoterol (Foradil®), metaproterenol (Alupent®), pirbuterol (MaxAir®), and terbutaline sulfate; corticosteroids such as, but not limited to, budesonide (e.g., Pulmicort®), flunisolide (e.g., AeroBid Oral Aerosol Inhaler® or Nasalide Nasal Aerosol®), fluticasone (e.g., Flonase® or Flovent®) and triamcinolone (e.g., Azmacort®); mast cell stabilizers such as cromolyn sodium (e.g., Intal® or Nasalcrom®) and nedocromil (e.g., Tilade®); xanthine derivatives such as, but not limited to, theophylline (e.g., Aminophyllin®, Theo-24® or Theolair®); leukotriene receptor antagonists such as, but are not limited to, zafirlukast (Accolate®), montelukast (Singulair®), and zileuton (Zyflo®); and adrenergic agonists such as, but are not limited to, epinephrine (Adrenalin®, Bronitin®, EpiPen® or Primatene Mist®).

In certain embodiments wherein arthritis is treated, prevented and/or managed, a compound provided herein can be combined with, for example: TNF antagonist (e.g., a TNF antibody or fragment, a soluble TNF receptor or fragment, fusion proteins thereof, or a small molecule TNF antagonist); an antirheumatic (e.g., methotrexate, auranofin, aurothioglucose, azathioprine, etanercept, gold sodium thiomalate, hydroxychloroquine sulfate, leflunomide, sulfasalzine); a muscle relaxant; a narcotic; a non-steroid anti-inflammatory drug (NSAID); an analgesic; an anesthetic; a sedative; a local anesthetic; a neuromuscular blocker; an antimicrobial (e.g., an aminoglycoside, an antifungal, an antiparasitic, an antiviral, a carbapenem, cephalosporin, a fluoroquinolone, a macrolide, a penicillin, a sulfonamide, a tetracycline, another antimicrobial); an antipsoriatic; a corticosteroid; an anabolic steroid; a cytokine or a cytokine antagonist.

In certain embodiments wherein psoriasis is treated, prevented and/or managed, a compound provided herein can be combined with, for example: budesonide, epidermal growth factor, corticosteroids, cyclosporine, sulfasalazine, aminosalicylates, 6-mercaptopurine, azathioprine, metronidazole, lipoxygenase inhibitors, mesalamine, olsalazine, balsalazide, antioxidants, thromboxane inhibitors, IL-1 receptor antagonists, anti-IL-1β monoclonal antibodies, anti-IL-6 monoclonal antibodies, growth factors, elastase inhibitors, pyridinyl-imidazole compounds, antibodies or agonists of TNF, LT, IL-1, IL-2, IL-6, IL-7, IL-8, IL-15, IL-16, IL-18, EMAP-II, GM-CSF, FGF, and PDGF, antibodies of CD2, CD3, CD4, CD8, CD25, CD28, CD30, CD40, CD45, CD69, CD90 or their ligands, methotrexate, cyclosporine, FK506, rapamycin, mycophenolate mofetil, leflunomide, NSAIDs, ibuprofen, corticosteroids, prednisolone, phosphodiesterase inhibitors, adenosine agonists, antithrombotic agents, complement inhibitors, adrenergic agents, IRAK, NIK, IKK, p38, MAP kinase inhibitors, IL-1β converting enzyme inhibitors, TNFα converting enzyme inhibitors, T-cell signaling inhibitors, metalloproteinase inhibitors, sulfasalazine, azathioprine, 6-mercaptopurines, angiotensin converting enzyme inhibitors, soluble cytokine receptors, soluble p55 TNF receptor, soluble p75 TNF receptor, sIL-1RI, sIL-1RII, sIL-6R, anti-inflammatory cytokines, IL-4, IL-10, IL-11, IL-13 and TGFβ.

In certain embodiments wherein fibrosis or fibrotic condition of the bone marrow is treated, prevented and/or managed, a compound provided herein can be combined with, for example, a Jak2 inhibitor (including, but not limited to, INCB018424, XL019, TG101348, or TG101209), an immunomodulator, e.g., an IMID® (including, but not limited to thalidomide, lenalidomide, or panolinomide), hydroxyurea, an androgen, erythropoietic stimulating agents, prednisone, danazol, HDAC inhibitors, or other agents or therapeutic modalities (e.g., stem cell transplants, or radiation).

In certain embodiments wherein fibrosis or fibrotic condition of the heart is treated, prevented and/or managed, a compound provided herein can be combined with, for example, eplerenone, furosemide, pycnogenol, spironolactone, TcNC100692, torasemide (e.g., prolonged release form of torasemide), or combinations thereof.

In certain embodiments wherein fibrosis or fibrotic condition of the kidney is treated, prevented and/or managed, a compound provided herein can be combined with, for example, cyclosporine, cyclosporine A, daclizumab, everolimus, gadofoveset trisodium (ABLAVAR®), imatinib mesylate (GLEEVEC®), matinib mesylate, methotrexate, mycophenolate mofetil, prednisone, sirolimus, spironolactone, STX-100, tamoxifen, TheraCLEC™, or combinations thereof.

In certain embodiments wherein fibrosis or fibrotic condition of the skin is treated, prevented and/or managed, a compound provided herein can be combined with, for example, Bosentan (Tracleer), p144, pentoxifylline; pirfenidone; pravastatin, STI571, Vitamin E, or combinations thereof.

In certain embodiments wherein fibrosis or fibrotic condition of the gastrointestinal system is treated, prevented and/or managed, a compound provided herein can be combined with, for example, ALTU-135, bucelipase alfa (INN), DCI1020, EUR-1008 (ZENPEP™), ibuprofen, Lym-X-Sorb powder, pancrease MT, pancrelipase (e.g., pancrelipase delayed release), pentade canoic acid (PA), repaglinide, TheraCLECT™, triheptadecanoin (THA), ULTRASE MT20, ursodiol, or combinations thereof.

In certain embodiments wherein fibrosis or fibrotic condition of the lung is treated, prevented and/or managed, a compound provided herein can be combined with, for example, 18-FDG, AB0024, ACT-064992 (macitentan), aerosol interferon-gamma, aerosolized human plasma-derived alpha-1 antitrypsin, alpha1-proteinase inhibitor, ambrisentan, amikacin, amiloride, amitriptyline, antipseudomonas IgY gargle, ARIKACE™ AUREXIS® (tefibazumab), AZAPRED, azathioprine, azithromycin, azithromycin, AZLI, aztreonam lysine, BIBF1120, Bio-25 probiotic, bosentan, Bramitob®, calfactant aerosol, captopril, CC-930, ceftazidime, ceftazidime, cholecalciferol (Vitamin D3), ciprofloxacin (CIPRO®, BAYQ3939), CNTO 888, colistin CF, combined Plasma Exchange (PEX), rituximab, and corticosteroids, cyclophosphamide, dapsone, dasatinib, denufosol tetrasodium (INS37217), dornase alfa (PULMOZYME®), EPI-hNE4, erythromycin, etanercept, FG-3019, fluticasone, FTI, GC1008, GS-9411, hypertonic saline, ibuprofen, iloprost inhalation, imatinib mesylate (GLEEVEC®), inhaled sodium bicarbonate, inhaled sodium pyruvate, interferon gamma-1b, interferon-alpha lozenges, isotonic saline, IW001, KB001, losartan, lucinactant, mannitol, meropenem, meropenem infusion, miglustat, minocycline, Moli1901, MP-376 (levofloxacin solution for inhalation), mucoid exopolysaccharide P. aeruginosa immune globulin IV, mycophenolate mofetil, n-acetylcysteine, N-acetylcysteine (NAC), NaCl 6%, nitric oxide for inhalation, obramycin, octreotide, oligoG CF-5/20, Omalizumab, pioglitazone, piperacillin-tazobactam, pirfenidone, pomalidomide (CC-4047), prednisone, prevastatin, PRM-151, QAX576, rhDNAse, SB656933, SB-656933-AAA, sildenafil, tamoxifen, technetium [Tc-99 m]sulfur colloid and Indium [In-111] DTPA, tetrathiomolybdate, thalidomide, ticarcillin-clavulanate, tiotropium bromide, tiotropium RESPIMAT® inhaler, tobramycin (GERNEBCIN®), treprostinil, uridine, valganciclovir (VALCYTE®), vardenafil, vitamin D3, xylitol, zileuton, or combinations thereof.

In certain embodiments wherein fibrosis or fibrotic condition of the liver is treated, prevented and/or managed, a compound provided herein can be combined with, for example, adefovir dipivoxil, candesartan, colchicine, combined ATG, mycophenolate mofetil, and tacrolimus, combined cyclosporine microemulsion and tacrolimus, elastometry, everolimus, FG-3019, Fuzheng Huayu, GI262570, glycyrrhizin (monoammonium glycyrrhizinate, glycine, L-cysteine monohydrochloride), interferon gamma-1b, irbesartan, losartan, oltipraz, ORAL IMPACT®, peginterferon alfa-2a, combined peginterferon alfa-2a and ribavirin, peginterferon alfa-2b (SCH 54031), combined peginterferon alpha-2b and ribavirin, praziquantel, prazosin, raltegravir, ribavirin (REBETOL®, SCH 18908), ritonavir-boosted protease inhibitor, pentoxyphilline, tacrolimus, tauroursodeoxycholic acid, tocopherol, ursodiol, warfarin, or combinations thereof.

In certain embodiments wherein cystic fibrosis is treated, prevented and/or managed, a compound provided herein can be combined with, for example, 552-02, 5-methyltetrahydrofolate and vitamin B12, Ad5-CBCFTR, Adeno-associated virus-CFTR vector, albuterol, alendronate, alpha tocopherol plus ascorbic acid, amiloride HCl, aquADEK™, ataluren (PTC124), AZD1236, AZD9668, azithromycin, bevacizumab, biaxin (clarithromycin), BIIL 283 BS (amelubent), buprofen, calcium carbonate, ceftazidime, cholecalciferol, choline supplementation, CPX, cystic fibrosis transmembrane conductance regulator, DHA-rich supplement, digitoxin, cocosahexaenoic acid (DHA), doxycycline, ECGC, ecombinant human IGF-1, educed glutathione sodium salt, ergocalciferol (vitamin D2), fluorometholone, gadobutrol (GADOVIST®, BAY86-4875), gentamicin, ghrelin, glargine, glutamine, growth hormone, GS-9411, H5.001CBCFTR, human recombinant growth hormone, hydroxychloroquine, hyperbaric oxygen, hypertonic saline, IH636 grape seed proanthocyanidin extract, insulin, interferon gamma-1b, IoGen (molecular iodine), iosartan potassium, isotonic saline, itraconazole, IV gallium nitrate (GANITE®) infusion, ketorolac acetate, lansoprazole, L-arginine, linezolid, lubiprostone, meropenem, miglustat, MP-376 (levofloxacin solution for inhalation), normal saline IV, Nutropin AQ, omega-3 triglycerides, pGM169/GL67A, pGT-1 gene lipid complex, pioglitazone, PTC124, QAU145, salmeterol, SB656933, SB656933, simvastatin, sitagliptin, sodium 4-phenylbutyrate, standardized turmeric root extract, tgAAVCF, TNF blocker, TOBI, tobramycin, tocotrienol, unconjugated Isoflavones 100, vitamin: choline bitartrate (2-hydroxyethyl) trimethylammonium salt 1:1, VX-770, VX-809, Zinc acetate, or combinations thereof.

In some embodiments, a compound provided herein is administered in combination with an agent that inhibits IgE production or activity. In some embodiments, the PI3K inhibitor (e.g., PI3Kδ inhibitor) is administered in combination with an inhibitor of mTOR. Agents that inhibit IgE production are known in the art and they include but are not limited to one or more of TEI-9874, 2-(4-(6-cyclohexyloxy-2-naphtyloxy)phenylacetamide)benzoic acid, rapamycin, rapamycin analogs (i.e. rapalogs), TORC1 inhibitors, TORC2 inhibitors, and any other compounds that inhibit mTORC1 and mTORC2. Agents that inhibit IgE activity include, for example, anti-IgE antibodies such as for example Omalizumab and TNX-901.

In certain embodiments wherein scleroderma is treated, prevented and/or managed, a compound provided herein can be combined with, for example: an immunosuppressant (e.g., methotrexate, azathioprine (Imuran®), cyclosporine, mycophenolate mofetil (Cellcept®), and cyclophosphamide (Cytoxan®)); T-cell-directed therapy (e.g., halofuginone, basiliximab, alemtuzumab, abatacept, rapamycin); B-cell directed therapy (e.g., rituximab); autologous hematopoietic stem cell transplantation; a chemokine ligand receptor antagonist (e.g., an agent that targets the CXCL12/CSCR4 axis (e.g., AMD3100)); a DNA methylation inhibitor (e.g., 5-azacytidine); a histone dactylase inhibitor (e.g., trichostatin A); a statin (e.g., atorvastatin, simvastatin, pravastatin); an endothelin receptor antagonist (e.g., Bosentan®); a phosphodiesterase type V inhibitor (e.g., Sildenafil®); a prostacyclin analog (e.g., trepostinil); an inhibitor of cytokine synthesis and/or signaling (e.g., Imatinib mesylate, Rosiglitazone, rapamycin, antitransforming growth factor β1 (anti-TGFβ1) antibody, mycophenolate mofetil, an anti-IL-6 antibody (e.g., tocilizumab)); corticosteroids; nonsteroidal anti-inflammatory drugs; light therapy; and blood pressure medications (e.g., ACE inhibitors).

In certain embodiments wherein inflammatory myopathies are treated, prevented and/or managed, a compound provided herein can be combined with, for example: topical creams or ointments (e.g., topical corticosteroids, tacrolimus, pimecrolimus); cyclosporine (e.g., topical cyclosporine); an anti-interferon therapy, e.g., AGS-009, Rontalizumab (rhuMAb IFNalpha), Vitamin D3, Sifalimumab (MEDI-545), AMG 811, IFNα Kinoid, or CEP33457. In some embodiments, the other therapy is an IFN-α therapy, e.g., AGS-009, Rontalizumab, Vitamin D3, Sifalimumab (MEDI-545) or IFNα Kinoid; corticosteroids such as prednisone (e.g., oral prednisone); immunosuppressive therapies such as methotrexate (Trexall®, Methotrexate®, Rheumatrex®), azathioprine (Azasan®, Imuran®), intravenous immunoglobulin, tacrolimus (Prograf®), pimecrolimus, cyclophosphamide (Cytoxan®), and cyclosporine (Gengraf®, Neoral®, Sandimmune®); anti-malarial agents such as hydroxychloroquine (Plaquenil®) and chloroquine (Aralen®); total body irradiation; rituximab (Rituxan®); TNF inhibitors (e.g., etanercept (Enbrel®), infliximab (Remicade®)); AGS-009; Rontalizumab (rhuMAb IFNalpha); Vitamin D3; Sifalimumab (MEDI-545); AMG 811; IFNα Kinoid; CEP33457; agents that inhibit IgE production such as TEI-9874, 2-(4-(6-cyclohexyloxy-2-naphtyloxy)phenylacetamide)benzoic acid, rapamycin, rapamycin analogs (i.e. rapalogs), TORC1 inhibitors, TORC2 inhibitors, and any other compounds that inhibit mTORC1 and mTORC2; agents that inhibit IgE activity such as anti-IgE antibodies (e.g., Omalizumab and TNX-90); and additional therapies such as physical therapy, exercise, rest, speech therapy, sun avoidance, heat therapy, and surgery.

In certain embodiments wherein myositis (e.g., dermatomysitis) is treated, prevented and/or managed, a compound provided herein can be combined with, for example: corticosteroids; corticosteroid sparing agents such as, but not limited to, azathioprine and methotrexate; intravenous immunoglobulin; immunosuppressive agents such as, but not limited to, tacrolimus, cyclophosphamide and cyclosporine; rituximab; TNFα inhibitors such as, but not limited to, etanercept and infliximab; growth hormone; growth hormone secretagogues such as, but not limited to, MK-0677, L-162752, L-163022, NN703 ipamorelin, hexarelin, GPA-748 (KP102, GHRP-2), and LY444711 (Eli Lilly); other growth hormone release stimulators such as, but not limited to, Geref, GHRH (1-44), Somatorelin (GRF 1-44), ThGRF genotropin, L-DOPA, glucagon, and vasopressin; and insulin-like growth factor.

In certain embodiments wherein Sjögren's syndrome is treated, prevented and/or managed, a compound provided herein can be combined with, for example: pilocarpine; cevimeline; nonsteroidal anti-inflammatory drugs; arthritis medications; antifungal agents; cyclosporine; hydroxychloroquine; prednisone; azathioprine; and cyclophamide.

Further therapeutic agents that can be combined with a subject compound can be found in Goodman and Gilman's "*The Pharmacological Basis of Therapeutics*" Tenth Edition edited by Hardman, Limbird and Gilman or the Physician's Desk Reference, both of which are incorporated herein by reference in their entirety.

The compounds described herein can be used in combination with the agents provided herein or other suitable agents, depending on the condition being treated. Hence, in some embodiments, the compounds as provided herein will be co-administered with other agents as described above. When used in combination therapy, the compounds described herein can be administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound as provided herein and any of the agents described above can be simultaneously administered, wherein both the agents are present in separate formulations. In another alternative, a compound as provided herein can be administered just followed by and any of the agents described above, or vice versa. In the separate administration protocol, a compound as provided herein and any of the agents described above can be administered a few minutes apart, or a few hours apart, or a few days apart.

Administration of the compounds as provided herein can be effected by any method that enables delivery of the compounds to the site of action. An effective amount of a compound as provided herein can be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

When a compound as provided herein is administered in a pharmaceutical composition that comprises one or more agents, and the agent has a shorter half-life than the compound as provided herein, unit dose forms of the agent and the compound as provided herein can be adjusted accordingly.

The examples and preparations provided below further illustrate and exemplify the compounds as provided herein and methods of preparing such compounds. It is to be understood that the scope of the present disclosure is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers can be obtained by methods known to those skilled in the art.

| Abbreviations/Acronyms | Full Name/Description |
|---|---|
| ACN | acetonitrile |
| DCM | dichloromethane |
| DMF | dimethylformamide |
| EtOAc | ethyl acetate |
| IPA | Isopropyl alchol |
| IPAc | Isopropyl acetate |
| IPE | isopropyl ether |
| MEK | methyl ethyl ketone |
| 2-MeTHF | 2-methyltetrahydrofuran |
| MIBK | methyl iso-butyl ketone |
| MTBE or TBME | tert-butyl methyl ether |
| THF | tetrahydrofuran |
| TBME | Methyl tert-butyl ether |

9. EXAMPLES

Example 1

Free Base Soluability Assessment

Approximately 11 mg (0.022 mmol) portions of the free base Form 1 of Compound 1 (i.e., the compound of formula (I)) were weighed into 2 ml screw-topped HPLC vials. One of 15 solvents was added to each vial in a number of aliquots (up to 100 volumes), with shaking and if necessary with heating to 40° C., in an attempt to achieve dissolution.

It was observed that Compound 1 dissolved in MeOH (75 vol.), MIBK (40 vol.), chloroform (40 vol.), 2-MeTHF (50 vol.), THF (40 vol.), DMSO (5 vol.), and MeOH/anisole (50/50 v/v) (10 vol.); and that Compound 1 did not dissolve in EtOH, acetonitrile, EtOAC, acetone, TBME, anisole, $H_2O$, or EtOH/$H_2O$ in up to 100 vol.

Example 2

Salt Formation Assessment with the Hydrochloric Acid 25 ml of a 1M stock solution of HCl in THF (0.025 mmol-1.1 eq.) was added to each vial prepared for the solubility assessment (Example 1) at RT. All the samples were shaken at RT, then cooled to 5° C. (fridge) and left at this temperature for 24 hours. The suspensions were filtered and analyzed by XRPD; the clear solutions were evaporated at RT; and the gums were placed under maturation (RT/50° C. 4 hours cycle).

The results for the hydrochloride salts of Compound 1 are summarized in Table 1. The majority of the experiments resulted in gums or amorphous solids. Two different XRPD patterns (FIG. 21A and FIG. 21B) were identified: Hydrochloride pattern 1 from methanol, anisole and water. The $^1$H NMR analysis of the sample crystallized from methanol (data not shown) shows peak shifts compared to the Free Base Form 1 which is consistent with salt formation. Hydrochloride pattern 2 from 2-Methyl THF which contains 1.0 eq. of HCl as determined by IC (data not shown).

TABLE 1

Salt Formation Assessment with the Hydrochloride Salt Formation

| Solvent | Solvent vol. | Obs. after HCl addition | Obs. 5° C. | Further Exp. | Conclusion |
|---|---|---|---|---|---|
| MeOH | 75 vol. | Clear | Clear | Evaporation | HCl pattern 1 |
| EtOH | 100 vol. | Clear | Clear | Evaporation | Gum |
| acetonitrile | 100 vol. | Clear | Clear | Evaporation | Gum |
| EtOAC | 100 vol. | yellowish slurry | solid | N/A | Amorphous |
| Acetone | 100 vol. | Light slurry | Light slurry | N/A | Gum |
| MIBK | 40 vol. | slurry | Gum | Maturation | Gum |
| TBME | 100 vol. | slurry | solid | Filtration | Low cryst. |
| chloroform | 40 vol. | Light slurry | Gum | Maturation | Gum |
| anisole | 100 vol. | yellowish slurry | solid | N/A | Low cryst. HCl pattern 1 |
| 2-MeTHF | 50 vol. | slurry | solid | N/A | HCl pattern 2 |
| THF | 40 vol. | Light slurry | Gum | Maturation | Gum |
| $H_2O$ | 100 vol. | white slurry | solid | N/A | Low cryst. HCl pattern 1 |
| DMSO | 5 vol. | Clear | Clear | Evaporation | Gum |
| MeOH/Anisole (50/50 v/v) | 10 vol. | Clear | Clear | Evaporation | Gum |
| EtOH/$H_2O$ (50/50 v/v) | 100 vol. | Clear | Light slurry | Evaporation | Gum |

Key:
N/A = Not Applicable,
Low cryst. = Low crystallinity,
vol. = Volume,
Exp. = Experiment Methanol and 2-MeTHF were chosen as the solvents for further salt screening because it solubilized the free base and gave a crystalline salt with hydrochloric acid. MIBK was also chosen as solvent for the salt screening. TBME was identified as suitable anti-solvent.

Example 3

Salt Screening

Approximately 35 mg (0.07 mmol) of free base Form 1 of Compound 1 was weighed into 2 ml HPLC vial and dissolved in 43 vol. (1.50 ml) of MeOH, 25 vol. (0.87 ml) of 2-MeTHF, or suspended in 25 vol. (0.87 ml) of MIBK.

The solutions were heated to 50° C., and an appropriate volume of stock acid solution was added to each vial (2.2 eq. for targeted bis salts, 1.1 eq. for targeted mono salts, and 0.5 eq. for targeted hemi salts, 1M in THF except 1,2-ethane disulfonic acid, 2-hydroxyethanesulfonic acid, and L-aspartic acid) under magnetic stirring. The vials were then sealed and cooled to 5° C. within 8 hours to enhance the crystallization of the salts.

The clear solutions were cooled to −20° C. (freezer) and then evaporated at RT. The experiments which produced gums were fully evaporated. TBME/1-BuOH/Acetone were added respectively to the samples initially prepared in MeOH/MIBK/2-MeTHF. The samples were placed in maturation between RT/50° C. (4 hours at each temperature) for at least 24 hours, and then sonicated. The solids obtained during the sequence of manipulations were filtered and analyzed by XRPD.

The crystalline solids were filtered, dried at ambient conditions, and stored at 40° C./75% RH for 1 week and analyzed by $^1$H NMR/IC. The stable salts were further characterized by XRPD/TGA/DSC.

The results of the salt screen are summarized in Table 2. Several crystalline solids were isolated. The hydrochloride and the isethionate salts deliquesced after storage at 40° C./75% RH for up to 1 week. The salts stable on storage at 40° C./75% RH for at least 1 week include mono-1,2-ethanedisulfonic acid salt, mono-maleic acid salt, and bis-sulfuric acid salts. The bis-sulfuric acid salt was characterized by XRPD (FIG. 1A), TGA (FIG. 2A), and DSC (FIG. 3A). The mono-maleic acid salt was characterized by XRPD (FIG. 12A), TGA (FIG. 13A), and DSC (FIG. 14A). The mono-1,2-ethanedisulfonic acid salt was characterized by XRPD (FIG. 17A), TGA (FIG. 18A), and DSC (FIG. 19A). The isethionate salt was characterized by XRPD (FIG. 22).

TABLE 2

Results of the Salt Screen

| Counter-Ion | Target | Solvent | Method | XRPD | Storage 40° C./75% RH | $^1$H NMR | IC | Comment |
|---|---|---|---|---|---|---|---|---|
| Hydrobromic acid | Mono | MeOH | Ev./Maturation TBME/Sonication | Amorphous | N/A | N/A | N/A | No crystallization |
| | Mono | MIBK | Ev./Maturation 1-BuOH/Sonication | Amorphous | N/A | N/A | N/A | No crystallization |
| | Mono | 2-MeTHF | Ev./Maturation Acetone/Sonication | Amorphous | N/A | N/A | N/A | No crystallization |
| | Bis | MeOH | Ev./Maturation TBME/Sonication | Amorphous | N/A | N/A | N/A | No crystallization |
| | Bis | MIBK | Ev./Maturation 1-BuOH/Sonication | Amorphous | N/A | N/A | N/A | No crystallization |
| | Bis | 2-MeTHF | Ev./Maturation Acetone/Sonication | Amorphous | N/A | N/A | N/A | No crystallization |
| Hydrochloric acid | Mono | MeOH | Cooling at 5° C. | HCl Pattern 1 | Deliquesced | Salt formation | N/A | Deliquescent |
| | Mono | MIBK | Ev./Maturation 1-BuOH/Sonication | Amorphous | N/A | N/A | N/A | No crystallization |
| | Mono | 2-MeTHF | Ev./Maturation Acetone/Sonication | Low cryst. | N/A | N/A | N/A | Low cryst. |
| | Bis | MeOH | Ev./Maturation TBME/Sonication | Amorphous | N/A | N/A | N/A | No crystallization |
| | Bis | MIBK | Ev./Maturation 1-BuOH/Sonication | Amorphous | N/A | N/A | N/A | No crystallization |
| | Bis | 2-MeTHF | Ev./Maturation Acetone/Sonication | Low cryst. | N/A | N/A | N/A | Low cryst. |
| Sulfuric acid | Mono | MeOH | Ev./Maturation TBME/Sonication | Amorphous | N/A | N/A | N/A | No crystallization |
| | Mono | MIBK | Ev./Maturation 1-BuOH/Sonication | Amorphous | N/A | N/A | N/A | No crystallization |
| | Mono | 2-MeTHF | Ev./Maturation Acetone/Sonication | Low cryst. | N/A | N/A | N/A | Low cryst. |
| | Bis | MeOH | Ev./Maturation TBME/Sonication | N/A | N/A | N/A | N/A | Gum |
| | Bis | MIBK | Ev./Maturation 1-BuOH | Sulfuric acid salt Pattern 1 | N/A | N/A | N/A | Hit |
| | Bis | 2-MeTHF | Ev./Maturation Acetone | Sulfuric acid salt Pattern 1 | sulfuric acid salt Pattern 1 | Salt formation | 1.9 eq. Sulfuric acid | Hit |
| | Hemi | MeOH | Ev./Maturation TBME/Sonication | Amorphous | N/A | N/A | N/A | No crystallization |
| | Hemi | MIBK | Ev./Maturation 1-BuOH/Sonication | FB Pattern 6 | N/A | N/A | N/A | No crystallization |
| | Hemi | 2-MeTHF | Ev./Maturation Acetone/Sonication | N/A | N/A | N/A | N/A | Gum |
| 1-2-Ethane disulfonic acid | Mono | MeOH | Cooling at 5° C. | 1,2-ethanedisulfonic acid salt Pattern 1 | 1,2-ethanedisulfonic acid salt Pattern 1 | Salt formation 1.2 eq. of 1,2-ethanedisulfonic acid | N/A | Hit |

TABLE 2-continued

Results of the Salt Screen

| Counter-Ion | Target | Solvent | Method | XRPD | Storage 40° C./75% RH | $^1$H NMR | IC | Comment |
|---|---|---|---|---|---|---|---|---|
| | Mono | MIBK | Ev./Maturation 1-BuOH/Sonication | Low cryst. | N/A | N/A | N/A | Low cryst. |
| | Mono | 2-MeTHF | Ev./Maturation Acetone/Sonication | N/A | N/A | N/A | N/A | Gum |
| | Bis | MeOH | Cooling at 5° C. | 1,2-ethanedisulfonic acid salt Pattern 1 | N/A | N/A | N/A | Hit |
| | Bis | MIBK | Ev./Maturation 1-BuOH | 1,2-ethanedisulfonic acid salt Pattern 1 | N/A | N/A | N/A | Hit |
| | Bis | 2-MeTHF | Ev./Maturation Acetone/Sonication | N/A | N/A | N/A | N/A | Gum |
| 1-2-Ethane disulfonic acid | Hemi | MeOH | Ev./Maturation TBME/Sonication | Amorphous | N/A | N/A | N/A | No crystallization |
| | Hemi | MIBK | Ev./Maturation 1-BuOH | 1,2-ethanedisulfonic acid salt Pattern 1 | N/A | N/A | N/A | Hit |
| | Hemi | 2-MeTHF | Ev./Maturation Acetone/Sonication | N/A | N/A | N/A | N/A | Gum |
| p-Toluene sulfonic acid | Mono | MeOH | Ev./Maturation TBME/Sonication | Amorphous | N/A | N/A | N/A | No crystallization |
| | Mono | MIBK | Ev./Maturation 1-BuOH/Sonication | Amorphous | N/A | N/A | N/A | No crystallization |
| | Mono | 2-MeTHF | Ev./Maturation Acetone/Sonication | N/A | N/A | N/A | N/A | Gum |
| | Bis | MeOH | Ev./Maturation TBME/Sonication | N/A | N/A | N/A | N/A | Gum |
| | Bis | MIBK | Ev./Maturation 1-BuOH/Sonication | Amorphous | N/A | N/A | N/A | No crystallization |
| | Bis | 2-MeTHF | Ev./Maturation Acetone/Sonication | N/A | N/A | N/A | N/A | Gum |
| Methane sulfonic acid | Mono | MeOH | Ev./Maturation TBME/Sonication | Amorphous | N/A | N/A | N/A | No crystallization |
| | Mono | MIBK | Ev./Maturation 1-BuOH/Sonication | Amorphous | N/A | N/A | N/A | No crystallization |
| | Mono | 2-MeTHF | Ev./Maturation Acetone/Sonication | Amorphous | N/A | N/A | N/A | No crystallization |
| | Bis | MeOH | Ev./Maturation TBME/Sonication | N/A | N/A | N/A | N/A | Gum |
| | Bis | MIBK | Ev./Maturation 1-BuOH/Sonication | Amorphous | N/A | N/A | N/A | No crystallization |
| | Bis | 2-MeTHF | Ev./Maturation Acetone/Sonication | N/A | N/A | N/A | N/A | Gum |
| Oxalic acid | Mono | MeOH | Ev./Maturation TBME/Sonication | Low cryst. | N/A | N/A | N/A | N/A |
| | Mono | MIBK | Ev./Maturation 1-BuOH/Sonication | FB Pattern 5 | N/A | N/A | N/A | FB crystallization |
| | Mono | 2-MeTHF | Ev./Maturation Acetone/Sonication | N/A | N/A | N/A | N/A | Gum |
| | Bis | MeOH | Ev./Maturation TBME/Sonication | Amorphous | N/A | N/A | N/A | N/A |
| | Bis | MIBK | Ev./Maturation 1-BuOH/Sonication | FB Pattern 5 | N/A | N/A | N/A | FB crystallization |
| | Bis | 2-MeTHF | Ev./Maturation Acetone/Sonication | N/A | N/A | N/A | N/A | Gum |
| 2-Hydroxyethane sulfonic acid | Mono | MeOH | Ev. | Isethionate Pattern 1 | Deliquesced | N/A | N/A | Deliquescent |
| | Mono | MIBK | Ev./Maturation 1-BuOH/Sonication | FB P5 | N/A | N/A | N/A | FB crystallization |
| | Mono | 2-MeTHF | Ev./Maturation Acetone/Sonication | Low cryst. | N/A | N/A | N/A | Low cryst. |
| L-Aspartic acid | Mono | MeOH | Cooling at 5° C. | L-Aspartic acid | N/A | N/A | N/A | No salt formation |
| | Mono | MIBK | Ev./Maturation 1-BuOH/Sonication | FB Pattern 5 | N/A | N/A | N/A | FB crystallization |
| | Mono | 2-MeTHF | Ev./Maturation Acetone/Sonication | FB Pattern 5 | N/A | N/A | N/A | FB crystallization |
| | Bis | MeOH | Cooling at 5° C. | L-Aspartic acid | N/A | N/A | N/A | No salt formation |
| | Bis | MIBK | Ev./Maturation 1-BuOH/Sonication | FB Pattern 5 | N/A | N/A | N/A | FB crystallization |

TABLE 2-continued

Results of the Salt Screen

| Counter-Ion | Target | Solvent | Method | XRPD | Storage 40° C./75% RH | $^1$H NMR | IC | Comment |
|---|---|---|---|---|---|---|---|---|
| | Bis | 2-MeTHF | Ev./Maturation Acetone/Sonication | FB Pattern 5 | N/A | N/A | N/A | FB crystallization |
| Maleic acid | Mono | MeOH | Ev./Maturation TBME | Maleic acid salt Pattern 1 | Maleic acid salt Pattern 1 | Salt formation 1.1 eq. of Maleic acid | N/A | Hit |
| | Mono | MIBK | Cooling at 5° C. | Maleic acid salt Pattern 1 | N/A | N/A | N/A | Hit |
| | Mono | 2-MeTHF | Ev./Maturation Acetone/Sonication | N/A | N/A | N/A | N/A | Gum |
| Phosphoric acid | Mono | MeOH | Ev./Maturation TBME | Low cryst. | N/A | N/A | N/A | Low cryst. |
| | Mono | MIBK | Ev./Maturation 1-BuOH/Sonication | FB Pattern 5 | N/A | N/A | N/A | FB crystallization |
| | Mono | 2-MeTHF | Ev./Maturation Acetone/Sonication | FB Pattern 5 | N/A | N/A | N/A | FB crystallization |
| Ethane sulfonic acid | Mono | MeOH | Ev./Maturation TBME | Amorphous | N/A | N/A | N/A | No crystallization |
| | Mono | MIBK | Ev./Maturation 1-BuOH/Sonication | Amorphous | N/A | N/A | N/A | No crystallization |
| | Mono | 2-MeTHF | Ev./Maturation Acetone/Sonication | Amorphous | N/A | N/A | N/A | No crystallization |

Key:
Ev. = Evaporation,
FB = Free Base,
N/A = Not applicable

Example 4

Crystallization Tests

Prior to scale-up, crystallization tests were carried out to assess the propensity of the salts to crystallize directly from a solvent by addition of acid to a free base stock solution followed by cooling. Approximately 50 mg (0.102 mmol) of the free base Form 2 of Compound 1 was weighed into 2 ml screw-topped HPLC vial. An appropriate mass of acid was weighed into a separate 2 ml screw-topped HPLC vial, dissolved in the corresponding solvent and heated to 50° C. The acid solution was added to the free base under magnetic stirring. The vials were then sealed and cooled to 5° C. within 8 hours to enhance the crystallization of the salts. The solids were filtered and analysed by XRPD.

The results are summarized in Table 3. Based on the results, the most suitable methods for scale-up were: for mono-maleic acid salt Form 1, in MIBK with 1M THF acid stock solution; for bis-sulfuric acid Form 1, in Acetone/H$_2$O (90/10 v/v) with concentrated sulfuric acid diluted in water and seeding at 50° C.; and for mono-1,2-ethanedisulfonic acid salt pattern 1, in EtOH with 1M THF acid stock solution.

TABLE 3

Crystallisation Test Results

| Counter-Ion | Solvent | Vol. | Acid Stock Solution | Acid eq. | Method | XRPD |
|---|---|---|---|---|---|---|
| Maleic acid | MIBK | 50 | 1M THF | 1.1 | Cooling to 5° C. | Maleic acid salt Pattern 1 |
| | MIBK | 22 | 1M THF | 1.1 | Cooling to 5° C. | Maleic acid salt Pattern 1 |
| Sulfuric acid | 1-BuOH | 30 | 1M THF | 2.2 | Cooling to 5° C. | Gum |
| | Acetone | 17 | 1M THF | 2.2 | Cooling to 5° C. | Gum |
| | Acetone/H$_2$O (90/10 v/v) | 18 | Conc. in water | 2.2 | Seeded to 50° C. Cooling to 5° C. | Sulfuric acid salt Pattern 1 |
| 1-2-Ethane disulfonic acid | 1-BuOH | 50 | 1M THF | 1.1 | Cooling to 5° C. | Amorphous |
| | MeOH | 12 | 1M THF | 1.1 | Cooling to 5° C. | Gum |
| | EtOH | 34 | 1M THF | 1.1 | Cooling to 5° C. | 1,2-ethanedisulfonic acid salt Pattern 1 |

Key:
v/v = volume/volume,
vol. = volume,
eq. = equivalent

Example 5

0.5 g Scale-Up

Bis-Sulfuric Acid Salt:

Approximately 500 mg (1.02 mmol) of the free base Form 2 of Compound 1 was weighed into 30 ml reaction tube. The free base was suspended in 9 ml (18 vol.) of acetone. 2.2 eq.

of sulfuric acid (concentrated: 98%) was diluted in 1 ml of distilled water. The acid solution was added to the free base solution at 50° C. under magnetic stirring and the sample was seeded with bis-sulfuric acid salt Form 1. The experiment was kept at 50° C. for 10 minutes and then cooled to 5° C. (0.1° C./minute) to enhance the crystallization. The sample was filtered at RT and dried at RT for 20 minutes under reduced pressure, transferred to a vial and weighed. The sample was characterized by XRPD (FIG. 1B), TGA (FIG. 2B), DSC (FIG. 3B), GVS (FIG. 4), FT-IR (FIG. 5A and FIG. 5B), and VT-XRPD (FIG. 9).

free base was suspended in 20 mL (40 vol.) of ethanol. 1.1 eq. of 1,2-ethanedisulfonic acid was added to the free base suspension at 50° C. under magnetic stirring as 1M stock solution in THF. The experiment was kept at 50° C. for 10 minutes and then cooled to 5° C. (0.1° C./minute) to enhance the crystallization. The sample was filtered at RT and dried at RT for 20 minutes under reduced pressure, transferred to a vial and weighed. The sample was characterized by XRPD (FIG. 17B), TGA (FIG. 18B), DSC (FIG. 19B), and VT-XRPD (FIG. 20). The characterisation of the salts is summarised in Table 4.

TABLE 4

| Characterisation of the Salts Scaled-up at 0.5 gram | | | |
|---|---|---|---|
| Couter-Ion | Maleic acid | 1-2-Ethanedisulfonic acid | Sulfuric acid |
| Mass (mg) | 582.0 | 682.1 | 620.2 |
| Yield (%) | 94 | 99 | 88 |
| XRPD (D8) | Maleic acid salt Pattern 1 | 1,2-ethanedisulfonic acid salt Pattern 1 | Sulfuric acid salt Pattern 1 |
| $^1$H NMR | Salt Formation 1.1 eq. of Maleic acid | Salt Formation 1.0 eq. of 1,2-ethanedisulfonic acid 0.1 eq. of EtOH | Salt Formation |
| IC | N/A | N/A | 1.9 eq. of sulfuric acid |
| HPLC purity | 99.6% Peak Area | 99.4% Peak Area | 99.9% Peak Area |
| GVS Single cycle | Slightly hygroscopic | Moderately hygroscopic Loss of 4.0% w/w between 40% RH and 0% RH on desorption | Slightly hygroscopic |
| XRPD post GVS (C2) | Unchanged | Unchanged | Unchanged |
| TGA | Mass loss of 1.0% w/w between 40° C. and 170° C. | Mass loss of 3.6% w/w between 25° C. and 100° C. and of 3.0% w/w between 100° C. and 220° C. | Mass loss of 2.7% w/w between 40° C. and 180° C. |
| DSC | Endotherm at 191° C. | Broad endotherm 1 at 27° C. Broad endotherm 2 at 168° C. | Broad endotherm 1 at 127° C. Endotherm 2 at 219° C. |
| VT-XRPD (C2) | N/A | 1,2-ethanedisulfonic acid salt Pattern 1 at 25° C. 1,2-ethanedisulfonic acid salt Pattern 2 between 100° C. and 140° C. 1,2-ethanedisulfonic acid salt Pattern 3 at 220° C. Converts to 1,2-ethanedisulfonic acid salt Pattern 4 after cooling | Sulfuric acid salt Pattern 1 between 25° C. and 140° C. Sulfuric acid salt Pattern 2 above 180° C. Converts back to Sulfuric acid salt Pattern 1 after cooling |
| Storage 40° C./75% RH for 1 week | XRPD (D8): Unchanged HPLC Purity: 99.8% Peak Area | XRPD (D8): Unchanged HPLC Purity: Unchanged | XRPD (D8): Unchanged HPLC Purity: Unchanged |
| Storage 25° C./93% RH for 1 week | XRPD (D8): Unchanged HPLC Purity: 99.8% Peak Area | XRPD (D8): Unchanged HPLC Purity: Unchanged | XRPD (D8): Unchanged HPLC Purity: Unchanged |
| Thermodynamic Aqueous solubility | 1.9 mg/ml pH solution = 1.9 | 6.2 mg/ml pH solution = 1.7 | >51 mg/ml pH solution = 1.1 |
| XRPD (C2) post Aqueous solubility | FB pattern 2 | Low cryst. 1,2-ethanedisulfonic acid salt Pattern 1 | N/A |
| KF titration @ 150° C. | N/A | 7.2% w/w, 2.9 eq. of H$_2$O | 3.1% w/w, 1.2 eq. of H$_2$O |

Mono-Maleic Acid Salt:

Approximately 500 mg (1.02 mmol) of the free base Form 2 of Compound 1 was weighed into 30 ml reaction tube. The free base was suspended in 10 ml (20 vol.) of MIBK. 1.1 eq. of maleic acid was added to the free base suspension at 50° C. under magnetic stirring as 1M stock solution in THF. The sample was kept at 50° C. for 10 minutes and then cooled to 5° C. (0.1° C./minute) to enhance the crystallization. The sample was filtered at RT and dried at RT for 60 minutes under reduced pressure, transferred to a vial and weighed. The sample was characterized by XRPD (FIG. 12B), TGA (FIG. 13B), DSC (FIG. 14B), GVS (FIG. 15), and FT-IR (FIG. 16A and FIG. 16B).

Mono-1,2-Ethanedisulfonic Acid Salt:

Approximately 500 mg (1.02 mmol) of the free base Form 2 of Compound 1 was weighed into 30 ml reaction tube. The Example 6

1.5 g Scale-Up

Mono-Maleic Acid Salt:

Approximately 1.5 mg (3.06 mmol) of the free base Form 2 of Compound 1 was weighed into 100 ml reaction tube. The free base was suspended in 30 ml (20 vol.) of MIBK. 1.1 eq. of maleic acid was added to the free base suspension at 50° C. under magnetic stirring as 1M stock solution in THFThe experiment was kept at 50° C. for 10 minutes and then cooled to 5° C. (0.1° C./minute) to enhance the crystallisa.

tion. The sample was filtered at RT and dried at RT for 76 hours under reduced pressure, transferred to a vial and weighed. The sample was characterized by XRPD (FIG. 1C), TGA (FIG. 2C), and DSC (FIG. 3C).

Bis-Sulfuric Acid Salt:

Approximately 1.5 mg (3.06 mmol) of the free base Form 2 of Compound 1 was weighed into 100 ml reaction tube. The free base was suspended in 27 ml (18 vol.) of acetone. 2.2 eq. of sulfuric acid (concentrated: 98%) was diluted in 3 ml of distilled water. The acid solution was added to the free base solution at 50° C. under magnetic stirring and the sample was seeded with bis-sulfuric acid salt Form 1 (1% w/w, ~15 mg). The experiment was kept at 50° C. for 10 minutes and then cooled to 5° C. (0.1° C./minute) to enhance the crystallisation. The sample was filtered at RT and dried at RT for 76 hours under reduced pressure, transferred to a vial and weighed. The sample was characterized by XRPD (FIG. 12C), TGA (FIG. 13C), and DSC (FIG. 14C). The characterisation of the salts is summarised in Table 5.

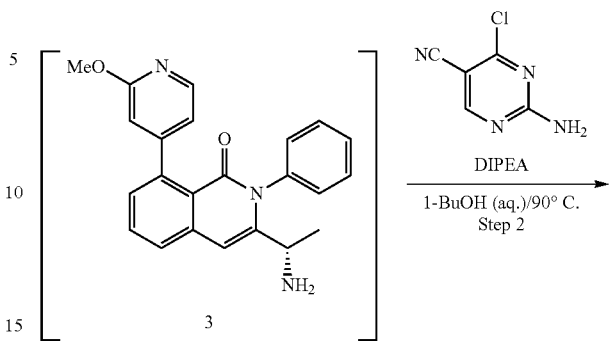

TABLE 5

Characterisation of the Salts Scaled-up at 1.5 gram

| Couter-Ion | Maleic acid | Sulfuric acid |
| --- | --- | --- |
| Mass (g) | 1.47 | 1.66 |
| Yield (%) | 81 | 79 |
| XRPD (D8) | Maleic acid salt Pattern 1 | Sulfuric acid salt Pattern 1 |
| $^1$H NMR | Salt Formation 1.1 eq. of Maleic acid | Salt Formation |
| IC | N/A | 1.9 eq. of sulfuric acid |
| HPLC purity | 99.7% Peak Area | 99.9% Peak Area |
| TGA | Mass loss of 0.6% w/w between 40° C. and 170° C. | Mass loss of 2.7% w/w between 40° C. and 180° C. corresponds to the loss of 1.0 eq. of $H_2O$ |
| DSC | Endotherm at 192° C. | Broad endotherm 1 at 132° C. Endotherm 2 at 219° C. |
| KF titration | N/A | @180° C.: 2.7% w/w corresponds to the loss of 1.0 eq. of $H_2O$ |

Key:
N/A = Not Applicable,
w/w = Weight/Weight,
eq. = Equivalent

Example 7

Synthesis of Bis-Sulfuric Acid Salt of Compound 1

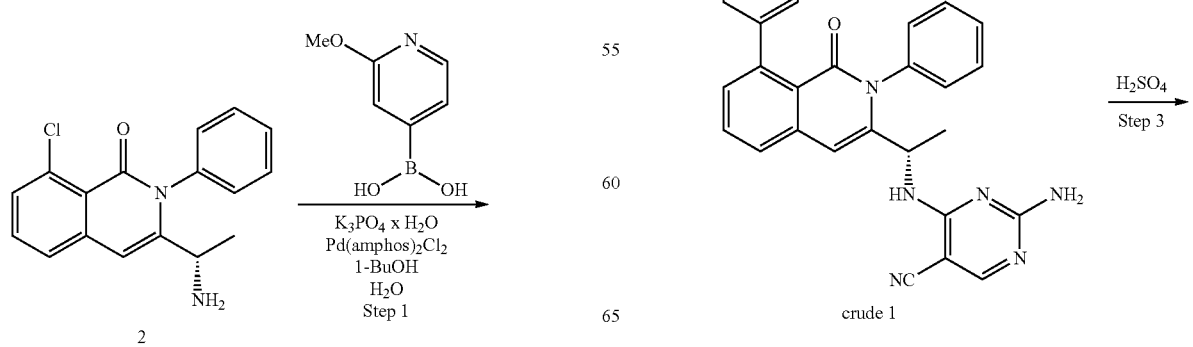

-continued

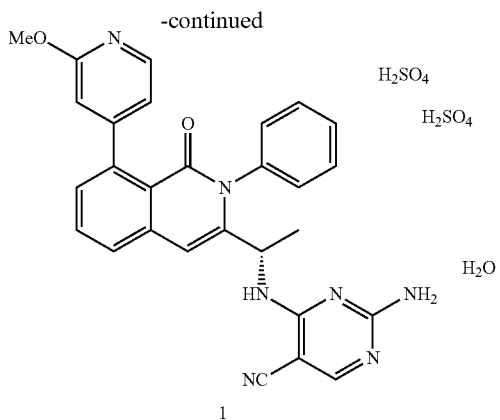

Step 1:

An appropriately sized reaction vessel was equipped with a mechanical stirrer, gas inlet/outlet, optical oxygen sensor (for headspace oxygen), reflux condenser and temperature probe. Compound 2 (1 kg, 1 wt., 1 equiv.), 2-methoxypyridine-4-boronic acid (1.1 equiv.) and potassium phosphate monohydrate (2 equiv.) were charged to the reaction vessel. 1-BuOH (8 vol) and water (4 vol) were charged to the reaction vessel. The mixture was stirred at 25±5° C. The content of the vessel was sparged with inert gas (nitrogen) for minimum of 30 min to remove dissolved oxygen. The palladium catalyst (0.01 equiv.) was charged via a solid charge port and the mixture was continuously sparged with inert gas for minimum of 10 min. The mixture was heated to 80±5° C. (target temperature 80-83° C.) under inert atmosphere, and stirred at this temperature under inert atmosphere for minimum of 4 hrs. After the reaction was found to be complete (≤1.0% Compound 2 relative to Compound 3 as determined by HPLC), the reaction mixture was cooled to 20±5° C. The two layers were split. The aqueous layer (bottom) was returned to the reactor and back extracted by stirring with 1-BuOH (2 vol.) for a minimum of 10 min. The two layers were split. The weight of the aqueous layer was determined and the aqueous layer was assayed by HPLC to estimate the yield loss of Compound 3. The organic layers were combined, and telescoped into the next step. Where the next step was not carried out on the same day, the solution was kept at 20±5° C. under inert head space.

Step 2:

An appropriately sized reaction vessel was equipped with mechanical stirrer, reflux condenser, temperature probe and inert gas inlet/outlet. The solution of Compound 3 (10 vol. based on Compound 2, 1 equiv.) from the previous step was charged to the vessel under an inert atmosphere. The funnel and port were rinsed with 1-butanol (0.5 volumes). The mixture was stirred at 20±5° C. 2-Amino-4-chloro-5-cyanopyrimidine (1.2 equiv.) was charged through a solid charge port under an inert atmosphere with stirring. N,N-Diisopropylethylamine (1.5 equiv.) was charged through the same charge port to the white suspension. The reaction mixture was heated to 90±5° C. (target temperature 89-91° C.) with stirring under argon. After the reaction was found to be complete (≤1.0% Compound 3 relative to Compound 1 as determined by HPLC), the reaction mixture was cooled down to 20±5° C. over approximately 2 hrs. The agitation was slowed down to minimize crystal attrition. Upon reaching 20±5° C., the suspension was aged for ≥6 hours. Where the product didn't nucleated upon reaching room temperature, the mixture was stirred at 20±5° C. until solid was observed then the batch was aged for a minimum of 6 hours. Potential hold point for up to 2 days at 20±5° C. The solid was filtered and the wet cake was washed with methyl tert-butyl ether (MTBE) (2×3 vol. with respect to the substrate). The solid was dried on the filter under vacuum for at least one hour, turned over regularly to help evenly dry the solid. The solid was transferred to a vacuum oven and dried at 40±5° C. under vacuum with nitrogen bleed until constant weight was achieved. Crude Compound 1 was collected as a pale yellow solid (1.48 kg, yield: ~90%).

Step 3.1 (Carbon Treatment):

A clean suitably sized vessel equipped with an overhead stirrer, reflux condenser, temperature probe, was assembled and flushed with nitrogen. Crude Compound 1 (20 g, 1 weight) was charged to the reaction vessel. Anisole (12 volumes) and methanol (8 volumes) were charged. Crude Compound 1 may not fully dissolve because it may contain some insoluble impurities. The reaction mixture was stirred and heated to 30±2° C. (target 30° C.), and was held for 15 minutes at 30±2° C. with stirring. 10 wt % of 3M activated carbon Type 5 (0.1 weight with respect to the charge weight of Compound 1 crude uncorrected for potency) was charged. The reaction mixture was stirred at 30±2° C. (target 30° C.) for a minimum of 4 hours. The black solid was filtered off (filter media Nylon 0.45 micron) under house vacuum. The cake was washed with a pre-mixed 40% methano/anisole solution (2×2 volumes), followed by methanol (2×4 volumes).

Step 3.2 (Distillation):

The filtrate was transferred to an appropriately sized jacketed reaction vessel equipped with a short path distillation head and overhead stirrer, and rinsed with methanol (minimum amount). The methanol was distilled off under reduced pressure (vacuum distillation) under 150 mmHg at 45° C. Compound 1 crashed out towards the end of the distillation. The heat was turned off, the vacuum was released, and the suspension was allowed to cool to 22±2° C. with stirring.

Step 3.3 (Salt Formation):

Ethanol (6 volumes) was charged to the slurry in the same jacketed reactor used to carry out the distillation. The mixture was heated to 50±5° C. (target 50° C.). A 4.5M solution of sulfuric acid was prepared by diluting concentrated sulfuric acid (18M) four folds. A 4.5M sulfuric acid aq. solution (1 volume, 2.2 equiv.) was charged dropwise at 50±5° C. over 5-20 minutes. The mixture was held at 50±5° C. for 1 hour, cooled to 5±5° C. (target 5° C.) over 2 hours, and held at 5±5° C. for 1 hour. The mixture was then heated to 50±5° C. over 1 hour, held at 50±5° C. for 1 hour, and cooled to 5±5° C. (target 5° C.) over 2 hours. Additional ethanol (3.4 volumes) was charged over 1 hour to increase the yield. The mixture was aged for a minimum of 6 hours at 5±5° C. with stirring. The solid was filtered off under house vacuum and washed with ethanol (3×4 volumes). The product was dried under house vacuum for a minimum of 2 hours, transferred to the vacuum oven, and dried at 40° C. under vacuum until constant weight was achieved. Compound 1 bis-sulfuric acid salt was collected as a white crystalline solid (yield: 90-95%).

Under additional exemplary studies, EtOH/water, instead of anisole/EtOH/water, was used as the solvent for Step 3. In one exemplary study, 0.75 g (yield: 54%) of bis-sulfuric acid salt monohydrate of Compound 1 was obtained from 1 g of crude Compound 1 using EtOH/water (21:1.5 v/v) as solvent and without the use of heating cycles in step 3.3. In another exemplary study, 3.8 g (yield: 54%) of bis-sulfuric acid salt monohydrate of Compound 1 was obtained from 5 g of crude Compound 1 using EtOH/water (30:1.5 v/v) as solvent and without the use of heating cycles in step 3.3. XRPD showed that the solid products prepared in these two studies (without use of the heating cycles) were Form 3 of the bis-sulfuric acid salt of Compound 1.

In another exemplary study, 1.1 g (yield: 78%) of bis-sulfuric acid salt monohydrate of Compound 1 was obtained from 1 g of crude Compound 1 using EtOH/water (12:1 v/v) as solvent, with the use of heating cycles in step 3.3, and without seeding. In another exemplary study, 1.1 g (yield: 78%) of bis-sulfuric acid salt monohydrate of Compound 1 was obtained from 1 g of crude Compound 1 using EtOH/water (12:1 v/v) as solvent, with the use of heating cycles in step 3.3, and with seeding. These studies showed that the use of heating cycles in step 3.3 can improve the yield of the product. XRPD showed that the solid products prepared in these two studies (with use of the heating cycles) were the more stable Form 1 of the bis-sulfuric acid salt of Compound 1.

In one exemplary study, to 1000 mg of crude Compound 1 hemi solvate (BuOH) was added 4 ml of EtOH and 800 ul of water. To the suspension was added 230 µL of sulfuric acid. The suspension was stirred at RT for 5 min. 100 mg of 3M activated Carbon Type 5 was added and the reaction mixture was stirred at RT for 50 min. to 1.0 hrs. The solid was filtered through a whatman filter unit, and the carbon cake was washed with 4 mL of EtOH containing 0.2 mL of water. The cake was then washed with 4 ml of EtOH. The pale yellow solution was stirred at RT for 20 min. The solution was seeded with Form 1 of the sulfuric acid salt of Compound 1 (20 mg). After over night at RT (15 hrs), the thick suspension was heated to 50° C. for 27 hrs, and then stirred at RT for 18 hrs. The solid was filtered, washed with 2 mL of EtOH, conditioned for 10 min, then dried in vacuum oven at 40° C. for 9 hrs till constant weight was achieved. XRPD showed that the solid was Form 1 of bis-sulfuric acid salt of Compound 1.

Example 8

Synthesis of Mono-Maleic Acid Salt of Compound 1

In one exemplary study, crude Compound 1 in anisole (from step 3.2 in Example 7, 2.043 mmol) was heated to 50° C. with stirring under air. 1.1 equiv. of maleic acid (0.261 g, 2.247 mmol) in THF (2.25 mL-1M solution) was added to the white suspension at 50° C. Solid dissolved to provide clear yellow solution. The reaction was held at 50° C. for 10 minutes. The heating was turned off and the reaction was allowed to cool to RT slowly. The reaction was cooled to 5° C. with an ice bath. After stirring for 4 days, a white solid crashed out of solution. The solid was filter off and washed with anisole (5 ml) and dried under vacuum, then placed in a vacuum oven at 40° C. overnight to afford mono-maleic acid salt (667 mg, 66.7% recovery) as a bright white solid. XRPD analysis of the solid showed it was Form 1 of mono-maleic acid salt of Compound 1.

The process was scaled up. To a four neck 250 ml round-bottom-flask was charged with 74.8 g of the anisole suspension containing crude Compound 1 (5.00 g, 10.21 mmol). The mixture was stirred under argon and heated to 50° C. Maleic acid (1M solution in THF, 11.24 ml, 11.24 mmol, 1.1 equiv.) was charged to the reaction. The reaction mixture was held at 50° C. for 60 minutes, and was cooled to 5° C. over 2 hours. The reaction mixture was held at 5° C. with stirring overnight. After stirring overnight the white suspension was filtered under vacuum, washed with MTBE (2×5 ml) and dried under vacuum for 1 hour before being transferred into the vacuum oven at 40° C. for 3 days to provide the mono-maleic acid salt of Compound 1 (5.7047 g, 9.42 mmol, 92% yield) as a white to off white solid. Purity (by HPLC and LCMS): 98.5%. $^1$H-NMR confirmed formation of the maleic acid salt. Palladium analysis (122 mg)=24.6 ppm. TGA showed 1.315% weight loss at 180° C. DSC showed a thermal event at 189.12° C. Water content by KF=0.07%.

Similar reactions were carried out using either EtOAc or IPA in place of THF as the solvent for maleic acid. These reactions provided solid products of maleic acid salt of Compound 1, which were determined to be Form 1 of mono-maleic acid salt of Compound 1.

In another exemplary study, similar reaction was carried out using 0.25M solution of maleic acid in ethyl acetate instead of 1M solution of maleic acid in THF. The process provided a solid maleic acid salt of Compound 1. Under the microscope the solid didn't blink when rotated through polarized light, indicating the solid was amorphous in nature.

Example 9

Synthesis of Hydrate of Free Base of Compound 1

An appropriate size reaction vessel was equipped with mechanical stirrer, reflux condenser, and temperature probe. Crude Compound 1 (from step 2 in Example 7) was charged to the reaction vessel. Acetic acid (4.5 vol.) was added. The internal temperature was adjusted to 25±5° C. (target temperature 23-26° C.) and the mixture was stirred for a minimum of 15 minutes. Water (4.5 vol.) was added. The temperature was increased to 32±5° C. (target temperature 29-33° C.) and the reaction mixture was stirred for a minimum of 15 minutes. Type 5 carbon (3M, 40 wt %) was charged and the mixture was stirred for a minimum of 30 minutes. The slurry was filtered on a 0.45 µm filter. The cake was washed with a 1:1 mixture of acetic acid/water (4.4 vol.).

28% NH$_4$OH (7.4-7.5 vol.) was charged to an appropriate size vessel equipped with mechanical stirrer, reflux condenser, and temperature probe. The acidic filtrate above was charged to the vessel with stirring at a rate to maintain the temperature ≤25° C. Water (4.5 vol.) was added (the pH should be neutral).

In one exemplary study, the suspension resulted from above was filtered and dried to provide a solid product of free base Compound 1. XRPD showed the solid product was Form 1 of the free base of Compound 1.

In another exemplary study, the suspension resulted from above was heated to 90±5° C. for 10-15 hrs, cooled to 20±5° C. over a minimum of 1 hr. The mixture was stirred at 20±5° C. for a minimum of 1 hr. The solid product was filtered, washed with water (2×4 vol.), and dried at 40° C. to constant weight to provide the hydrate of free base of Compound 1 as a white solid (yield: 75-90%). XRPD showed the solid product was the more stable Form 2 of the free base of Compound 1.

Example 10

Polymorphism Study: Maturation of Mono-Maleic Acid Salt Form 1

Approximately 35 mg (0.057 mmol) portions of mono-maleic acid salt Form 1 of Compound 1 were weighed into 2 ml screw-topped HPLC vials. One of 21 solvents was added to each vial in a number of aliquots (up to 30 volumes), with shaking. All the samples were then placed under maturation between RT to 50° C. (4 hours at each temperature) for 3 days. After maturation the samples were analysed by XRPD. Clear solutions were cooled to −20° C. (freezer). If no precipitation occurred samples were evaporated at RT.

The results are summarized in Table 6. Mono-maleic acid salt Form 1 was obtained from 8 out of 15 single-solvent systems and 2 out of 6 solvent mixtures. The samples didn't recrystallize in MEK, Acetone/Water (90/10 v/v), or methanol. The free base recrystallized in Ethanol, 2-Propanol, 1-Propanol, Acetone, THF, 2-Propanol/Water (90/10 v/v), EtOH/Water (90/10 v/v), Acetic acid/Water (25/75 v/v). The mono-maleic acid salt has a tendency to dissociate in these solvents.

TABLE 6

Polymorph Screen Results on Crystalline Mono-Maleic acid salt

| Solvent | Solvent vol. | Method | XRPD | $^1$H NMR | Comment |
|---|---|---|---|---|---|
| Ethanol | 30 vol. | Maturation | FB Pattern 5 | N/A | FB recrystallization |
| 2-Propanol | 30 vol. | Maturation | FB Pattern 5 | 0.4 eq. of maleic acid | FB recrystallization |
| 1-Propanol | 30 vol. | Maturation | FB Pattern 5 | N/A | FB recrystallization |
| 1-Butanol | 30 vol. | Maturation | Maleic acid salt Pattern 1 | 1.0 eq. of maleic acid | Stable salt |
| 2-Butanone | 30 vol. | Evaporation | Amorphous | 1.0 eq. of maleic acid | Amorphous |
| MIBK | 30 vol. | Maturation | Maleic acid salt Pattern 1 | N/A | Stable salt |
| Acetone | 30 vol. | Maturation | FB Pattern 5 | N/A | FB recrystallization |
| Ethyl acetate | 30 vol. | Maturation | Maleic acid salt Pattern 1 | N/A | Stable salt |
| Anisole | 30 vol. | Maturation | Maleic acid salt Pattern 1 | N/A | Stable salt |
| Anisole/Methanol (50/50 v/v) | 30 vol. | Evaporation | Maleic acid salt Pattern 1 | N/A | Stable salt |
| Toluene | 30 vol. | Maturation | Maleic acid salt Pattern 1 | N/A | Stable salt |
| Isopropylacetate | 30 vol. | Maturation | Maleic acid salt Pattern 1 | N/A | Stable salt |
| TBME | 30 vol. | Maturation | Maleic acid salt Pattern 1 | N/A | Stable salt |
| 2-Methyl-1-propanol | 30 vol. | Maturation | Maleic acid salt Pattern 1 | N/A | Stable salt |
| THF | 10 vol. | Maturation | FB Pattern 5 | No maleic acid detected | FB recrystallization |
| Acetone/Water (90/10 v/v) | 30 vol. | Evaporation | N/A | N/A | Gum |
| 2-Propanol/Water (90/10 v/v) | 30 vol. | Maturation | FB Pattern 2 | 0.2 eq. of maleic acid | FB recrystallization |
| EtOH/Water (90/10 v/v) | 30 vol. | Maturation | FB Pattern 5 | No maleic acid detected | FB recrystallization |
| Acetic acid/Water (25/75 v/v) | 5 vol. | Maturation | FB Pattern 2 | N/A | FB recrystallization |
| Anisole/TBME (50/50 v/v) | 30 vol. | Maturation | Maleic acid salt Pattern 1 | N/A | Stable salt |
| Methanol | 30 vol. | Evaporation | Amorphous | N/A | Amorphous |

Key:
FB = Free Base,
N/A = Not Applicable,
eq. = equivalent
Green = Stable salt

Example 11

Polymorphism Study: Maturation of Amorphous Mono-Maleic Acid Salt

The amorphous mono-maleic acid salt of Compound 1 was prepared by evaporation at RT of a methanolic solution saturated with mono-maleic acid salt Form 1. $^1$H-NMR data (not shown) demonstrated that the amorphous mono-maleic acid salt contains about 0.9 eq. of maleic acid salt and about 0.6 eq. of MeOH.

Aliquots of the selected solvents (10 vol.) were added to the amorphous mono-maleic acid salt in 2 ml HPLC vials at RT. Samples were placed under maturation between RT-50° C. (4 hours cycle) for 3 days. After maturation the samples were analyzed by XRPD. Clear solutions were then cooled to −20° C. (freezer). If no precipitation occurred, samples were evaporated at RT.

The results are summarized in Table 7. Mono-maleic acid salt Form 1 was obtained from 11 single-solvent systems. The samples didn't recrystallize in anisole/methanol (50/50 v/v), chloroform, 1-4-dioxane, or 1-1-1-trifluoroethanol.

TABLE 7

Polymorph Screen Results on Amorphous Mono-Maleic acid salt

| Solvent | Method | XRPD (C2) | Comment |
|---|---|---|---|
| 1-Butanol | Maturation | Maleic acid salt Pattern 1 | Stable salt |
| 2-Butanone | Maturation | Maleic acid salt Pattern 1 | Stable salt |
| MIBK | Maturation | Maleic acid salt Pattern 1 | Stable salt |
| Ethyl acetate | Maturation | Maleic acid salt Pattern 1 | Stable salt |
| Anisole | Maturation | Maleic acid salt Pattern 1 | Stable salt |
| Anisole/Methanol (50/50 v/v) | Evaporation | N/A | Gum |
| Toluene | Maturation | Maleic acid salt Pattern 1 | Stable salt |
| Isopropylacetate | Maturation | Maleic acid salt Pattern 1 | Stable salt |
| TBME | Maturation | Maleic acid salt Pattern 1 + 1 peak | Stable salt |
| 2-Methyl-1-propanol | Maturation | Maleic acid salt Pattern 1 | Stable salt |
| 2-MeTHF | Maturation | Maleic acid salt Pattern 1 | Stable salt |
| chloroform | Evaporation | N/A | Gum |
| acetonitrile | Maturation | Maleic acid salt Pattern 1 | Stable salt |

TABLE 7-continued

Polymorph Screen Results on Amorphous Mono-Maleic acid salt

| Solvent | Method | XRPD (C2) | Comment |
|---|---|---|---|
| 1-4-Dioxane | Evaporation | N/A | Gum |
| 1-1-1-Trifluoroethanol | Evaporation | N/A | Gum |

Key:
FB = Free Base,
N/A = Not Applicable,
eq. = equivalent,
Green = Stable salt Example 12

First Maleic Acid Salt Formation Experiments

Approximately 30 mg (0.06 mmol) of free base Form 1 of Compound 1 or free base Form 2 of Compound 1 was weighed separately into 2 ml HPLC vial and diluted in the selected solvents. The solutions were heated to 50° C. An appropriate volume of stock acid solution (prepared in water and prepared without water) was added to each vial under magnetic stirring. The vials were then sealed and cooled to 5° C. within 8 hours to enhance the crystallization of the salts. The clear solutions were cooled to −20° C. (freezer) and then evaporated at RT. Samples of the solids obtained during the sequence of manipulations were filtered and analysed by XRPD.

The results of the first salt formation series are summarized in Table 8. Free base of Compound 1 was crystallized in 13 out 20 experiments. Mono-maleic acid salt Form 1 was crystallized in 4 out of 20 experiments with 2-Butanone (MEK) or ethyl acetate as the solvent. The sample didn't recrystallize in 3 out of 20 experiments.

TABLE 8

Salt Formation Experiment Results

| Solvent | Solvent vol. | SM | Acid stock solution | XRPD | Comment |
|---|---|---|---|---|---|
| Ethanol | 30 | FB Form 1 | 1M in EtOH | FB Pattern 5 | FB crystallization |
| Ethanol | 30 | FB Form 1 | 1M in Water | FB Pattern 5 | FB crystallization |
| 1-Butanol | 30 | FB Form 1 | 1M in Water | FB Pattern 2 | FB crystallization |
| 2-Butanone | 10 | FB Form 1 | 1M in MEK | Maleic acid salt Pattern 1 | Stable salt |
| 2-Butanone | 10 | FB Form 1 | 1M in Water | FB Pattern 5 | FB crystallization |
| Ethyl acetate | 30 | FB Form 1 | 1M in EtOAc | Maleic acid salt Pattern 1 | Stable salt |
| Ethyl acetate | 30 | FB Form 1 | 1M in Water | FB Pattern 5 | FB crystallization |
| Anisole | 30 | FB Form 1 | 1M in Water | FB Pattern 5 | FB crystallization |
| Anisole/Methanol (50/50 v/v) | 10 | FB Form 1 | 1M in MeOH | N/A | Gum |
| Anisole/Methanol (50/50 v/v) | 10 | FB Form 1 | 1M in Water | Low cryst. FB Pattern 5 | FB crystallization |
| Ethanol | 30 | FB Form 2 | 1M in EtOH | Amorphous | No crystallization |
| Ethanol | 30 | FB Form 2 | 1M in Water | FB Pattern 5 | FB crystallization |
| 1-Butanol | 30 | FB Form 2 | 1M in Water | FB Pattern 2 | FB crystallization |
| 2-Butanone | 10 | FB Form 2 | 1M in MEK | Maleic acid salt Pattern 1 | Stable salt |
| 2-Butanone | 10 | FB Form 2 | 1M in Water | FB Pattern 2 | FB crystallization |
| Ethyl acetate | 30 | FB Form 2 | 1M in EtOAc | Maleic acid salt Pattern 1 | Stable salt |
| Ethyl acetate | 30 | FB Form 2 | 1M in Water | FB Pattern 2 | FB crystallization |
| Anisole | 30 | FB Form 2 | 1M in Water | FB Pattern 2 | FB crystallization |
| Anisole/Methanol (50/50 v/v)) | 10 | FB Form 2 | 1M in MeOH | N/A | Gum |
| Anisole/Methanol (50/50 v/v) | 10 | FB Form 2 | 1M in Water | Low cryst. FB Pattern 5 | FB crystallization |

Key:
vol. = volume,
v/v = volume/volume,
SM = Starting Material,
cryst. = crystallinity,
FB = Free Base,
N/A = Not Applicable.

Example 13

Second Maleic Acid Salt Formation Experiments

A second salt formation experiment series was made using various ratios of maleic acid stock solution to assess the process robustness. The results are summarised in Table 9. With 0.5 eq. of maleic acid, the free base crystallized; with 1.3 eq. and 1.5 eq. of maleic acid, maleic acid salt Form 1 was crystallized with an excess of maleic acid in the crystalline solid; and with 2.0 eq. of maleic acid, a low crystallinity maleic acid salt Form 1 was crystallized. In anisole with 1.0 eq. of maleic acid added as a 1M stock solution in THF, maleic acid salt Form 1 was crystallized.

TABLE 9

Salt Formation Experiment (2) Results

| Solvent | Solvent vol. | SM | acid stock solution | Acid eq. | XRPD | $^1$H NMR | Comment |
|---|---|---|---|---|---|---|---|
| MEK | 10 | FB Form 2 | 1M in MEK | 0.5 | FB Pattern 5 | N/A | FB crystallization |
| MEK | 10 | FB Form 2 | 1M in MEK | 1.3 | Maleic acid salt Pattern 1 | 1.2 eq. of maleic acid | Small excess of maleic acid |
| MEK | 10 | FB Form 2 | 1M in MEK | 1.5 | Maleic acid salt Pattern 1 | 1.4 eq. of maleic acid | Excess of maleic acid |
| MEK | 10 | FB Form 2 | 1M in MEK | 2.0 | Low cryst. Maleic acid salt Pattern 1 | N/A | Low cryst. Maleic acid salt Form 1 |
| Anisole | 30 | FB Form 2 | 1M in THF | 1.0 | Maleic acid salt Pattern 1 | N/A | Stable salt |
| Anisole | 10 | FB Form 2 | 1M in THF | 1.0 | Maleic acid salt Pattern 1 | N/A | Stable salt |

Key:
vol. = volume,
SM = Starting Material,
cryst. = crystallinity,
FB = Free Base,
N/A = Not Applicable,
eq. = equivalent Example 14

Polymorphism Study: Maturation of Bis-Sulfuric Acid Salt Form 1

Bis-Sulfuric acid salt Form 1 of Compound 1 (ca. 35 mg) was weighed into vials. The corresponding solvents and solvent mixtures were added in portions of (a total of) 5, 10, 20, and 30 volumes at 50° C., with shaking, aiming for clear solutions. After each addition, the vials were allowed to shake for 20 minutes, after which observations were made. Solutions were allowed to evaporate, whereas slurries were set for 8 hour temperature cycling maturation, between RT and 50° C., for 5 days.

The results are summarized in Table 10. The material showed clear solutions in 5 volumes of acetic acid/water 1:3 and methanol at 50° C. Slow evaporation of these solutions yielded oils, which were subjected to maturation, producing the bis-sulfuric acid salt Form 1 in the case of the methanol experiment. The experiment in ethanol/water (90/10 v/v) initially showed a slurry in 30 volumes but a clear solution was observed after maturation for three days. Evaporation produced an oil, which crystallized to the bis-sulfuric acid salt Form 1 after maturation. All other experiments showed slurries in 30 volumes of solvent, and maturation for five days did not show any changes.

TABLE 10

Polymorph Screen with the Crystalline Bis-Sulfuric acid salt

| Solvent | solvent vol. | Procedure | XRPD |
|---|---|---|---|
| Ethanol | 30 vol. | Maturation | Sulfuric acid salt Pattern 1 |
| 2-Propanol | 30 vol. | Maturation | Sulfuric acid salt Pattern 1 |
| 1-Propanol | 30 vol. | Maturation | Sulfuric acid salt Pattern 1 |
| 1-Butanol | 30 vol. | Maturation | Sulfuric acid salt Pattern 1 |
| 2-Butanone | 30 vol. | Maturation | Sulfuric acid salt Pattern 1 |
| MIBK | 30 vol. | Maturation | Sulfuric acid salt Pattern 1 |
| Acetone | 30 vol. | Maturation | Sulfuric acid salt Pattern 1 |
| Ethyl acetate | 30 vol. | Maturation | Sulfuric acid salt Pattern 1 |
| Anisole | 30 vol. | Maturation | Sulfuric acid salt Pattern 1 |
| Anisole/Methanol (50/50 v/v) | 30 vol. | Maturation | Sulfuric acid salt Pattern 1 |
| Toluene | 30 vol. | Maturation | Sulfuric acid salt Pattern 1 |
| IPAc | 30 vol. | Maturation | Sulfuric acid salt Pattern 1 |
| TBME | 30 vol. | Maturation | Sulfuric acid salt Pattern 1 |
| 2-Methyl-1-propanol | 30 vol. | Maturation | Sulfuric acid salt Pattern 1 |
| THF | 30 vol. | Maturation | Sulfuric acid salt Pattern 1 |
| Acetone/Water (90/10 v/v) | 30 vol. | Maturation - filtrate formed gum on standing | n/a |
| 2-Propanol/Water (90/10 v/v) | 30 vol. | Maturation | Sulfuric acid salt Pattern 1 |
| EtOH/Water (90/10 v/v) | 30 vol. | Evaporation | Sulfuric acid salt Pattern 1 |
| Acetic acid/Water (25/75 v/v) | 5 vol. | Evaporation/Maturation | n/a Oil |
| Anisole/TBME (50/50 v/v) | 30 vol. | Maturation | Sulfuric acid salt Pattern 1 |
| Methanol | 5 vol. | Evaporation/Maturation | Maturation of oil Sulfuric acid salt Pattern 1 |

Example 15

Polymorphism Study: Maturation of Amorphous Bis-Sulfuric Acid Salt

Bis-sulfuric acid salt Form 1 (ca. 100 mg) was weighed in a round bottom flask and dissolved in methanol (2.5 mL). Rotary evaporation was carried out at 45 mbar, in a 50° C. water bath. After 20 minutes, an oil was observed on the flask walls, which became a solid after scratching with a spatula. The amorphous character was confirmed by XRPD and $^1$H-NMR confirmed the structure, as well as the presence of residual methanol (0.3 equivalents).

Further amorphous material was prepared in vials, to be used as input material for a maturation screen. Bis-Sulfuric acid salt Form 1 (ca. 250 mg) was dissolved in 1.25 mL methanol, and pipetted into HPLC vials. The temperature was set at 80° C. to aid solvent evaporation, which yielded oils after 20 minutes. The oils were placed in a vacuum oven at 40° C. in order to remove residual solvent.

Basic characterisation of these oils highlighted that the oils were wet (broad water peak by NMR and weight loss of 7% below 100° C.). The DSC was typical of an amorphous material, and no crystallization was observed below degradation.

The oils obtained by solvent evaporation were used for the maturation screen. Anhydrous solvents (5 volumes; 100 μL) were used in order to minimise the amount of water present. Any solutions were allowed to slowly evaporate, whereas slurries were set for 8 hour temperature cycling maturation, between RT and 50° C. After 24 hours, most oils had not mixed with the solvents, and these were scratched with a spatula, producing slurries. These were matured for a further 24 hours before performing XRPD analysis.

The results are summarized in Table 11. The bis-sulfuric acid salt is difficult to crystallise in an anhydrous environment. The experiment in methanol produced a clear solution, which then became an oil after solvent evaporation. The experiment in acetonitrile produced a slurry, for which maturation yielded a poorly crystalline solid, with an XRPD pattern slightly different to the bis-sulfuric acid salt Form 1 (FIG. 6). The remaining experiments had to be mixed manually with a spatula, and maturation of the slurries for 24 hours did not induce crystallisation. Basic characterisation of the slurry in acetonitrile experiment showed a poorly crystalline solid, whose crystallinity decreased on standing at room conditions for 24 hours. $^1$H-NMR showed residual solvent (0.3 equivalents of methanol and 0.2 equivalents of acetonitrile). The DSC trace showed an irregular baseline with a small endothermic event at 191° C.

TABLE 11

Maturation of Amorphous Oils in Anhydrous Solvents

| Anhydrous Solvent | Amount (μL) | Maturation 24 h | Maturation 48 h | XRPD |
| --- | --- | --- | --- | --- |
| Methanol | 100 | Solution - set for evaporation | n/a | Oil |
| Acetonitrile | 100 | White Slurry | White Slurry | Poorly crystalline solid, slightly different |
| Toluene | 100 | Oil did not mix with solvent - scratching produces slurry | Yellow slurry | Amorphous |
| DCM | 100 | | Yellow slurry | Amorphous |
| THF | 100 | | Yellow slurry | Amorphous |
| EtOAc | 100 | | Yellow slurry | Amorphous |
| BuOAc | 100 | | Yellow slurry | Amorphous |
| TBME | 100 | | Yellow slurry | Amorphous |
| Dioxane | 100 | | Yellow slurry | Amorphous glass |
| IPA | 100 | | Yellow slurry | Amorphous glass |
| DIPE | 100 | | Yellow slurry | Amorphous |

Example 16

Bis-Sulfuric Acid Salt Formation Experiments

Free Base Form 1 and Form 2 of Compound 1 (~25 mg) was weighed into vials and dissolved or suspended in the selected solvents (20 volumes, 500 μL) at 50° C. Sulfuric acid (2.2 equivalents, 112 μL solution in THF, 50 μL solution in water, or 50 μL solution in ethanol) was added at 50° C. A cooling ramp to 20° C. was set up at 0.1° C./minute. All solids observed were isolated and analysed by XRPD. Solutions were set for slow evaporation.

The results are summarized in Table 12. Experiments in anisole/methanol and MEK started as solutions of the free base at 50° C., whereas experiments in ethanol and ethyl acetate started as slurries. After the addition of the acid, most experiments remained unchanged, although some solutions showed immediate precipitation. Most isolated solids were amorphous by XRPD. A low crystalline solid was crystallised from the system anisole/methanol/THF, showing an XRPD pattern slightly different to that of the bis-sulfuric acid salt Form 1 (FIG. 7). Basic characterisation suggested that this material could be an unstable solvate (FIG. 8A and FIG. 8B). Three experiments yielded the bis-sulfuric acid salt Form 1 (ethanol/THF, from evaporation; and MEK/THF, from maturation of gums).

TABLE 12

Results from salt formation experiments

| Input | Solvent | Appearance 50° C. | Acid solution | Appearance on addition | After cooling ramp | XRPD |
| --- | --- | --- | --- | --- | --- | --- |
| Form 1 | anisole/methanol | Solution | THF | Yellow solution | Yellow solution | Oil |
| Form 2 | anisole/methanol | Solution | THF | Yellow solution | Yellow solution | Evaporation yielded crystals Slightly different to Pattern 1 |
| Form 1 | | Solution | water | Yellow solution | Yellow solution | Oil |
| Form 2 | | Solution | water | Yellow solution | Yellow solution | Oil |
| Form 1 | | Solution | Ethanol | Yellow solution | Yellow solution | Oil |
| Form 2 | | Solution | Ethanol | Yellow solution | Yellow solution | Oil |

TABLE 12-continued

Results from salt formation experiments

| Input | Solvent | Appearance 50° C. | Acid solution | Appearance on addition | After cooling ramp | XRPD |
|---|---|---|---|---|---|---|
| Form 1 | ethanol | Slurry | THF | Yellow solution | Yellow solution | Low crystalline solid obtained Sulfuric acid salt Pattern 1 |
| Form 2 | | Slurry | THF | Yellow solution | Yellow solution | Evaporation yielded amorphous particles |
| Form 1 | | Slurry | water | Yellow solution | Yellow solution | Oil |
| Form 2 | | Slurry | water | Yellow solution | Yellow solution | Oil |
| Form 1 | | Slurry | Ethanol | Cloudy yellow solution | Yellow slurry | Filtrate turns to gum on standing, scratching yields solid = Amorphous |
| Form 2 | | Slurry | Ethanol | Cloudy yellow Solution | Yellow slurry | Filtrate turns to gum on standing, scratching yields solid = Amorphous |
| Form 1 | MEK | Solution | THF | Yellow solution | Gum on walls | White solid after maturation = Sulfuric acid salt Pattern 1 |
| Form 2 | | Solution | THF | Yellow solution | Gum on walls | White solid after maturation = Sulfuric acid salt Pattern 1 |
| Form 1 | | Solution | water | Two phases | Two phases | n/a |
| Form 2 | | Solution | water | Two phases | Two phases | n/a |
| Form 1 | | Solution | Ethanol | Precipitation | Yellow slurry | Amorphous |
| Form 2 | | Solution | Ethanol | Precipitation | Yellow slurry | Amorphous |
| Form 1 | EtOAc | Slurry | THF | Yellow slurry | Yellow slurry | Amorphous |
| Form 2 | | Slurry | THF | Yellow slurry | Yellow slurry | Gum |
| Form 1 | | Slurry | water | Two phases | Two phases | n/a |
| Form 2 | | Slurry | water | Two phases | Two phases | n/a |
| Form 1 | | Slurry | Ethanol | Yellow slurry | Yellow slurry | Amorphous |
| Form 2 | | Slurry | Ethanol | Yellow slurry | Yellow slurry | Amorphous |

Example 17

Characterization of the Free Base Form 1

The results of the characterization of Form 1 of the free base of Compound 1 are summarized in Table 13. Free base Form 1 was analysed to be a hydrate (~0.6 equivalents water by KF). Thermal analysis showed dehydration to Form 4 (anhydrous) from around 75° C., followed by a melt (onset at 161° C.). GVS suggested that Form 1 material hydrates to a higher hydrate above 80% RH, but this re-converts to Form 1 on desorption. One week storage at 25° C./93% RH showed conversion to Form 3, whereas storage at 40° C./75% RH over the same period of time did not show any changes.

TABLE 13

Characterization data for Compound 1 Free Base Form 1

| | |
|---|---|
| XRPD (FIG. 23) | Crystalline Free Base Form 1 |
| $^1$H-NMR | Consistent with structure. No residual solvent observed. |
| Purity by HPLC | 99.3 area % Sum of total impurities greater than 0.1 area % = 0.48 area % |
| TGA(FIG. 24) and DSC (FIG. 25) | TGA shows a weight loss of 1.9% (0.53 eqs. Water) corresponding to a very broad endotherm by DSC. Melting endotherm with onset at 161° C. followed by decomposition from 340° C. |
| VT-XRPD | Conversion to a anhydrous form, Form 4, between 40-75° C. Melt at 183° C. |
| GVS (FIG. 26) | 0.7% w/w moisture on loading. 4.0% w/w uptake between 80-90% RH, with hysteresis on desorption. Between 0-10% RH, the sample starts losing more water but the mass does not reach equilibrium. No changes by XRPD after the experiment. |
| Stability at 40° C./75% RH | No changes in form after 1 week |
| Stability at 25° C./93% RH | Conversion to Form 3 (FIG. 31) |
| KF | 2.15% w/w water (0.60 eqs. Water) |
| Thermodynamic aqueous solubility | 0.004 mg/mL, at pH 6.85 |

Example 18

Characterization of the Free Base Form 2

The results of the characterization of Form 2 of the free base of Compound 1 are summarized in Table 14. Free base Form 2 was analysed to be a highly crystalline hydrate (~0.8 equivalents water by KF). Thermal analysis showed a very slight change in the XRPD pattern on heating above 75° C., followed by a melt (onset at 172° C.). GVS showed slight moisture uptake on loading (1% w/w) between 40-50% RH, remaining stable with 5.7% w/w moisture content between 90-10% on desorption. Slight evidence of hysteresis (re-uptake is slower between 0-10% RH) and very slight changes in the XRPD after the experiment. One week storage at 25° C./93% RH and 40° C./75% RH also showed mainly the same pattern with a few differences. The fact that the XRPD patterns hardly change with moisture content varying between 0 and 6% w/w water (0 to 2 equivalents) suggests that this material is a channel hydrate where water can easily move in and out of the crystal lattice.

TABLE 14

Characterisation data for Compound 1 Free Base Form 2

| | |
|---|---|
| XRPD (FIG. 27) | Crystalline Free Base Form 2 |
| $^1$H-NMR | Consistent with structure. No residual solvent observed. |

TABLE 14-continued

Characterisation data for Compound 1 Free Base Form 2

| | |
|---|---|
| Purity by HPLC | 99.6 area % Sum of total impurities greater than 0.1 area % = 0.30 area % |
| TGA (FIG. 28) and DSC (FIG. 29) | TGA shows a weight loss of 3.0% (0.53 eqs. water) corresponding to a very broad endotherm by DSC. Melting endotherm with onset at 172° C. followed by decomposition from 340° C. |
| VT-XRPD | Slight changes in pattern from 75% RH. No further changes up to a melt at around 190° C. |
| Drying experiments | Heating in an oven at 125° C. for two hours showed very slight changes by XRPD |
| GVS (FIG. 30) | 4.7% w/w moisture on loading. Immediate moisture uptake (40-50% RH up to 5.7% w/w) which remains stable on sorption up to 90% RH, and on desorption down to 10% RH. Between 0-10% RH, the sample starts losing more water but the mass does not reach equilibrium. Re-sorption up to 5.7% w/w on unloading at 40% RH. Slight changes by XRPD after the experiment. |
| Stability at 40° C./75% RH | Very slight changes after 1 week |
| Stability at 25° C./93% RH | Very slight changes after 1 week |
| KF | 2.80% w/w water (0.8 eqs. Water) |
| Thermodynamic aqueous solubility | 0.005 mg/mL, at pH 6.47 |

Example 19

Characterization of the Amorphous Free Base

In one exemplary study, to 5 g of crude Compound 1 (from step 2 in Example 7) was added 400 mL of t-BuOH: water (95:5). The mixture was heated up with heat gun until a solution was obtained, then 100 mL of water was added. After 30 min at RT the solution was still homogeneous and brownish. The solution was freeze dried (lyophilization) for 9 days to provide 4.7 g of Compound 1 as a solid material. Picture under microscope of the solid material showed that it was amorphous. NMR showed that the material contained about ⅓ molar of t-BuOH. The solid material was put into vacuum over at 40° C. for 4 days, and NMR showed that it contained about 20% molar ratio of t-BuOH.

The results of the characterization of the amorphous free base of Compound 1 are summarized in Table 15. The amorphous free base of Compound 1 was analysed to be amorphous, with high chemical purity and some residual tert-butanol content. Thermal analysis showed some solvent loss but no evidence of crystallisation before decomposition. No crystallisation after storage at elevated humidity.

TABLE 15

Characterization data for amorphous free base Compound 1

| | |
|---|---|
| XRPD | Amorphous |
| $^1$H-NMR | Consistent with structure. ~0.3 equivalents residual tert-butanol |
| Purity by HPLC | 99.0 area % Sum of total impurities greater than 0.1 area % = 0.83 area % |
| TGA and DSC | Weight loss in two steps, of 1.0% (below 100° C., with a broad endotherm by DSC) and 3.1% below 180° C. Small evidence of an endotherm by DSC at around 170° C., similar to melting temperature of hydrates, could be evidence of some crystalline content. |
| Stability at 40° C./75% RH | No changes after 1 week |
| Stability at 25° C./93% RH | No changes after 1 week |

Example 20

Polymorphism Study: Screening Using Amorphous Free Base Compound 1

Amorphous free base Compound 1 (ca. 25 mg) was weighed into vials. The selected solvents and solvent mixtures (5 to 20 volumes) were added with stirring. Any solutions were allowed to slowly evaporate, whereas slurries were set for 8 hour temperature cycling maturation, between RT and 50° C., for 2 days.

The results are summarized in Table 16. Most vials showed an off-white solid in a brown solution after solvent addition. These suspensions were set for temperature cycling, and most of them converted to thick slurries after 24 hours. These were allowed to cycle for a further 24 hours prior to analysis. Most of these solids showed a very similar XRPD pattern, and were denoted as Form 5 (FIG. 36). Slight differences were observed, suggesting that these are isostructural solvates, where differences in the solvent result in slight differences by XRPD. The only experiment that gave a different XRPD was the experiment in water, which showed Form 4. Finally, maturation in isopropyl acetate resulted in material with similar XRPD to Form 5.

TABLE 16

Polymorph screen using amorphous material

| Solvent | Solvent amount (µL) | Observations on solvent addition | After 24 hours cycling | XRPD |
|---|---|---|---|---|
| MeOH | 250 | White solid in brown solution | Off-white slurry | Crystalline Form 5 |
| EtOH | 250 | White solid in brown solution | Off-white slurry | Crystalline Form 5 |
| Acetonitrile | 200 | White solid in brown solution | Off-white slurry | Crystalline Form 5 |
| EtOAc | 100 | White solid in brown solution | Off-white slurry | Crystalline Form 5 |
| Acetone | 100 | White solid in brown solution | Off-white slurry | Crystalline Form 5 |
| MIBK | 100 | White solid in brown solution | Off-white slurry | Crystalline Form 5 |
| TBME | 300 | White solid in brown solution | Off-white slurry | Crystalline Form 5 |
| 2-MeTHF | 200 | White solid in brown solution | Off-white slurry | Crystalline Form 5 |
| THF | 150 | White solid in brown solution | Off-white slurry | Crystalline Form 5 |
| DCM | 150 | White solid in brown solution | Off-white slurry | Crystalline Form 5 |
| IPA | 150 | White solid in brown solution | Off-white slurry | Crystalline Form 5 |

TABLE 16-continued

Polymorph screen using amorphous material

| Solvent | Solvent amount (μL) | Observations on solvent addition | After 24 hours cycling | XRPD |
|---|---|---|---|---|
| DME | 150 | White solid in brown solution | Off-white slurry | Crystalline Form 5 |
| DCM:MeOH 1:1 | 150 | White solid in brown solution | Off-white slurry | Crystalline Form 5 |
| H2O | 450 | White solid in brown solution | Off-white slurry | Partially crystalline = matches FB Pattern 4 |
| EtOH/5% water | 150 | White solid in brown solution | Off-white slurry | Crystalline Form 5 |
| THF/5% water | 150 | White solid in brown solution | Off-white slurry | Crystalline Form 5 |
| MeCN/5% water | 150 | White solid in brown solution | Off-white slurry | Crystalline Form 5 |
| IPAc | 300 (16 hours maturation) | White solid in brown solution | Off-white slurry | Crystalline Form 5 |

Example 21

Polymorphism Study: Screening Using Form 2 of Free Base Compound 1

Crystalline Hydrate Form 2 of Compound 1 showed changes in solubility in the whole range of solvent systems investigated. The best solvent systems (clear solutions) were methanol:anisole 1:1 and DMSO (10 volumes, at RT), dioxane (10 volumes, 50° C.), chloroform (20 volumes, RT).

Experiments in 2-methyltetrahydrofuran, THF:5% water and ethanol:anisole showed clear solutions using 50 volumes, and methanol, DCM, THF, DME, DCM:methanol 1:1 and acetonitrile/5% water using 100 volumes.

The results are summarized in Table 17. Solutions were placed at 4° C., where eight experiments showed crystallisation. Crystals were ground in order to analyse them by XRPD. Suspensions were set for temperature cycling for a total of five days after which time XRPD analysis was carried out. Most solids obtained from both procedures showed Form 5. Similar to the screen in Example 20, these XRPD patterns show slight differences (FIG. 37). However, solids from both screens obtained from the same solvent show a matching XRPD pattern, also supporting that this is a series of isostructural solvates.

The solid obtained from ethanol:water 1:1 showed the unchanged Form 2. Solutions from 2-methyltetrahydrofuran and dioxane yielded oils, which crystallised (to Form 5 or a mixture of Forms 5 and 3 respectively) after temperature cycling for two days (same program).

TABLE 17

Solubility assessment and polymorph screen using FB Hydrate Form 2

| | Solubility at 50° C. | | | | | |
|---|---|---|---|---|---|---|
| Solvent | 10 vols | 20 vols | 50 vols | 75 vols | Comments | XRPD |
| EtOH | x | x | x | x | Maturation | Crystalline Form 5 |
| acetonitrile | x | x | x | x | Maturation | Crystalline Form 5 |
| EtOAc | x | x | x | x | Maturation | Crystalline Form 5 |
| Acetone | x | x | x | x | Maturation | Crystalline Form 5 |
| MIBK | x | x | x | x | Maturation | Crystalline Form 5 |
| chloroform | x | ✓ (RT) | n/a | n/a | Cooling in fridge yielded oil | Maturation of oil produced Crystalline Form 5 |
| 2-MeTHF | x | x | ✓ | n/a | Evaporation yielded oil | Maturation of oil produced Crystalline Form 5 |
| THF | x | x | Almost | ✓ | Crystallization in fridge | Crystalline Form 5 |
| Dioxane | ✓ | n/a | n/a | n/a | Evaporation yielded oil | Maturation of oil produced Crystalline Form 5 + Form 3 |
| DCM | x | x | x | ✓ | Crystallization in fridge | Crystalline Form 5 |
| IPA | x | x | x | x | Maturation | Crystalline Form 5 |
| DCM:MeOH 1:1 | x | x | x | ✓ | Crystallization in fridge | Crystalline Form 5 + Form 1 |
| EtOH/5% water | x | x | x | x | Maturation | Crystalline Form 5 |
| MeCN/5% water | x | x | x | ✓ | Crystallization in fridge | Crystalline Form 5 |
| IPAc | x | x | x | x | Maturation | Crystalline Form 5 |
| 1-butanol | x | x | x | x | Maturation | Crystalline Form 5 |
| MeOH/anisole | ✓ (RT) | n/a | n/a | n/a | Crystallization in fridge | Crystalline Form 5 |
| EtOH/water 1:1 | x | x | x | x | Maturation | Crystalline Form 2 |
| DMSO | ✓ (RT) | n/a | n/a | n/a | No crystallization in fridge; set for evaporation | Amorphous |

Example 22

Polymorphism Study: Maturation in Acetic Acid:Water

Maturation of the hydrate Form 1 of free base Compound 1 and the amorphous material in acetic acid:water 1:1 for three days yielded an XRPD pattern denoted as Form 6. However, maturation of the hydrate Form 2 of free base Compound 1 did not show any changes in form. The results are summarized in Table 18.

TABLE 18

Maturation experiments in acetic acid:water 1:1

| Input material | Scale/ Solvent amount | Observations on solvent addition | After 72 hours cycling | XRPD |
|---|---|---|---|---|
| Amorphous | 10 mg/100 µL | White solid in brown solution | White solid in brown solution | Crystalline Form 6 |
| Form 1 | 25 mg/100 µL | White slurry | White slurry | Crystalline Form 6 |
| Form 2 | 25 mg/100 µL | White slurry | White slurry | Crystalline Form 2 |

Example 23

Characterization of Screening Samples

Samples from the screen using amorphous free base Compound 1 were analysed by $^1$H-NMR and DSC, and re-analysis by XRPD was also carried out after drying at 50° C./vacuum and storage at 40° C./75% RH (the same sample was dried and stored at elevated humidity).

The results are summarized in Table 19. $^1$H-NMR revealed different amounts of residual organic solvent in most solids, with the exception of that from methanol. DSC analysis varied significantly between different solids. Generally, a melting endotherm was observed (onsets between 159 and 178° C.) and some traces show solvent loss broad endotherms. VT-XRPD on selected samples did not show any form changes below the melt. TGA on selected samples showed a weight loss on the melt area, which suggests that these solvates only release the solvents on melting, which is consistent with the lack of form change by XRPD. Drying at 50° C. under vacuum did not show any changes by XRPD, and neither did storage at 40° C./75% RH, suggesting that water could have replaced the organic solvent. $^1$H-NMR of selected samples after storage showed that these had lost their organic solvent to some extent.

TABLE 19

Characterization of screening samples (Form 5/Form 4)

| Solvent | Residual solvent by $^1$H-NMR | DSC (and TGA if applicable) | VT-XRPD | XRPD after drying at 50° C./vacuum | XRPD after Storage at 40° C./75% RH |
|---|---|---|---|---|---|
| MeOH | 0.04 eqs | Broad endotherm low T Melt at 176° C. | No changes below melt | No changes | No changes |
| EtOH | 0.6 eqs | Broad endotherm low T Melt at 173° C. | n/a | No changes | No changes |
| Acetonitrile | 0.5 eqs | Melt at 177° C.; TGA: Weight loss at low T and during melt | n/a | No changes | No changes; NMR showed no MeCN |
| EtOAc | 0.6 eqs | Double endotherm (onset 172° C.) | n/a | No changes | No changes |
| Acetone | 1 eq | Melt at 177° C. | n/a | No changes | No changes |
| MIBK | Very wet; >12 eqs. | Poor baseline, unable to integrate | n/a | No changes | No changes |
| TBME | 0.5 eqs | Poor baseline; Small endotherm at 159° C. | n/a | No changes | No changes |
| 2-MeTHF | 0.75 eqs | Melt at 72° C. | No changes below melt | No changes | No changes |
| THF | 0.95 eqs | DSC: Double endotherm (onset 172° C.) TGA: Weight loss at low T and during melt | n/a | No changes | No changes; NMR showed lower THF (0.75 eqs) |
| DCM | 0.67 eqs | Melt at 78° C. | No changes below melt | No changes | No changes |
| IPA | 0.85 eqs | Melt at 170° C. | n/a | No changes | No changes |
| DME | 0.45 eqs | Melt at 175° C. | n/a | No changes | No changes |
| DCM:MeOH 1:1 | 0.1 eqs MeOH; 0.5 eqs DCM | Melt at 178° C. | No changes below melt | No changes | No changes |
| H$_2$O | No organic solvent | Poor baseline, unable to integrate | n/a | No changes | No changes |
| EtOH/5% water | Very wet; >12 eqs ethanol | Poor baseline, unable to integrate | n/a | No changes | No changes |
| THF/5% water | Very wet; >8 eqs THF | Double endotherm (onset 174° C.) | n/a | No changes | No changes |
| MeCN/5% water | Very wet; >30 eqs MeCN | Melt at 173° C.; TGA: Weight loss at low T and during melt | n/a | No changes | No changes |

Example 24

Characterization of Form 4 of Free Base of Compound 1

Hydrate Form 1 of free base Compound 1 (~90 mg) was heated in an oven to 125° C. for two hours. The resulting solid was analysed to be the anhydrous Form 4, consistent with the dehydration of Form 1 by VT-XRPD. Basic characterisation was carried out and it is summarized in Table 20. Form 4 was analysed to be anhydrous, and resulted from dehydration of the Hydrate Form 1. This material adsorbs some moisture, as shown in thermal analysis and KF. GVS suggests this material hydrates above 80% RH, but reversibly dehydrates back at 40% RH.

TABLE 20

Characterization of the anhydrous Form 4

| Technique | Form 4 of Free Base Compound 1 |
|---|---|
| XRPD (FIG. 32) | Form 4 |
| $^1$H-NMR | Consistent with structure. No residual solvent. |
| TGA (FIG. 33) and DSC (FIG. 34) | TGA shows a weight loss of 1.5 (0.25 eqs. water) corresponding to a very broad endotherm by DSC. Melting endotherm with onset at 161° C. followed by decomposition from 340° C. |
| GVS (FIG. 35) | 0.3% w/w moisture on loading. 4.8% w/w uptaken between 70-90% RH, with hysteresis on desorption. No changes by XRPD after the experiment. |
| KF | 2.04% w/w water |

Example 25

Characterization of Form 6 of Free Base of Compound 1

Batch 1 of Form 6 of free base of Compound 1 was obtained from maturation of Form 1 of free base of Compound 1 in acetic acid:water as described in Example 22. Batch 2 of Form 6 was obtained in a similar manner. Form 1 (~22 mg) of free base of Compound 1 was suspended in acetic acid:water 1:1 (100 µL; 5 volumes) and set for temperature cycling maturation (between room temperature and 50° C., 4 hours at each temperature) for a total of 16 hours. Very small amount of solid was present so the liquors were evaporated.

Basic characterisation was carried out and it is summarised in Table 21. Form 6 was analysed to be an acetic acid solvate containing 0.5 equivalents of acetic acid. Desolvation to the anhydrous Form 4 occurred at around 100° C. by VT-XRPD and at 0% RH on the GVS. TGA and DSC showed complex thermal behaviour above those temperatures. Storage at elevated humidity conditions showed conversion to Hydrate Form 3. The fact that both Solvate Form 6 and Hydrate Form 3 show very similar diffractograms suggests that they could be another set of isostructural solvates/hydrates.

TABLE 21

Characterization of Form 6

| Technique | Batch 1 of Form 6 | Batch 2 of Form 6 |
|---|---|---|
| XRPD (FIG. 38) | Acetic acid solvate Form 6 | Acetic acid solvate Form 6 |
| $^1$H-NMR | Consistent with structure. 0.5 eqs. Acetic acid | Consistent with structure. 0.5 eqs. Acetic acid |
| TGA (FIG. 39) and DSC (FIG. 40) | n/a | TGA shows two weight losses of 3.0% and 3.6% (combined equivalent to 0.5 eqs. Acetic acid) corresponding to two broad endotherms by DSC. Double endotherm with onsets at 165 and 175° C. followed by decomposition from 340° C. |
| VT-XRPD | Conversion to Form 4 from 100° C. Slight change at 185° C., closely followed by melt. | n/a |
| GVS (FIG. 41) | 6.3% w/w moisture on loading. (0.5 eqs. Acetic acid), which is released on desorption. Second cycle shows 4.9% reversible moisture uptake between 0-90% RH. Re-analysis by XRPD showed the anhydrous Form 4 | n/a |
| Stability at 40° C./75% RH | n/a | Very slight changes after 1 week |
| Stability at 25° C./93% RH | n/a | Very slight changes after 1 week |

Example 26

Stability of Hydrate Form 2 of Free Base of Compound 1

Hydrate Form 2 of free base of Compound 1 (~50 mg) was suspended in pure water or a mixture acetic acid:water 1:3 (10 volumes) and set to mature at constant temperature (25° C. or 90° C.) for a total of 40 hours. Aliquots of the suspensions were filtered and analysed by XRPD, and the results are summarized in Table 22. Both solids obtained from maturation at 25° C. (from water and the aqueous acetic acid mixture) showed the unchanged Form 2. At 90° C., the solid from pure water also showed Form 2, but the solid from acetic acid:water showed some evidence of the acetic acid solvate Form 6 mixed with a majority of Form 2. Thermal analysis of Form 2 shows dehydration above 80° C., and the presence of acetic acid could favour the solvate when the water content is not too high.

TABLE 22

Stability experiments on Form 2 of free base of Compound 1

| Solvent | Temperature | XRPD |
|---|---|---|
| Water | 25° C. | Hydrate Form 2 |
| Water | 90° C. | Hydrate Form 2 |
| Acetic acid:water 1:3 | 25° C. | Hydrate Form 2 |
| Acetic acid:water 1:3 | 90° C. | Hydrate Form 2 + Solvate Form 6 |

Example 27

Single Crystal Experiments

A sample of Form 5 of free base of Compound 1 (acetonitrile solvate) was submitted for single crystal X-ray diffraction studies. The results are shown in Table 23. The structure solution was obtained by direct methods, full-matrix least-squares refinement on $F^2$ with weighting $w^{-1}=\sigma^2(F_o^2)+(0.0453P)^2+(0.0000P)$, where $P=(F_o^2+2F_c^2)/3$, anisotropic displacement parameters, empirical absorption correction using spherical harmonics, implemented in SCALE3 ABSPACK scaling algorithm. Final $wR^2=\{\Sigma[w(F_o^2-F_c^2)^2)]/\Sigma[w(F_o^2)^2]^{1/2}\}=0.1088$ for all data, conventional $R_1=0.0454$ on F values of 9209 reflections with $F_o>4\sigma(F_o)$, S=1.036 for all data and 762 parameters. Final $\Delta/\sigma(max)$ 0.001, $\Delta/\sigma$ (mean), 0.000. Final difference map between +0.410 and -0.350 e Å$^{-3}$.

FIG. 42 shows a view of a molecule of the acetonitrile solvate (Form 5) from the crystal structure showing the numbering scheme employed. Anisotropic atomic displacement ellipsoids for the non-hydrogen atoms are shown at the 50% probability level. Hydrogen atoms are displayed with an arbitrarily small radius. FIG. 43 shows a view of part of the crystal packing of the acetonitrile solvate (Form 5) in the unit cell looking approximately down the [0,1,1] direction of the unit cell. For clarity all hydrogen atoms other than the O—H and N—H are removed. FIG. 44 shows the experimental and calculated XRPD patterns of the acetonitrile solvate (Form 5).

TABLE 23

Single Crystal Structure of the acetonitrile solvate

| | | | | | |
|---|---|---|---|---|---|
| Molecular formula | $C_{30}H_{26}N_8O_2$ | | | | |
| Molecular weight | 530.59 | | | | |
| Crystal system | Orthorhombic | | | | |
| Space group | P2(1)2(1)2(1) | a | 14.4157(3) Å | α | 90° |
| | | b | 18.7487(4) Å | β | 90° |
| | | c | 20.0103(5) Å | γ | 90° |
| V | 5408.3(2) Å$^3$ | | | | |
| Z | 8 | | | | |
| $D_c$ | 1.303 g·cm$^{-3}$ | | | | |
| μ | 0.696 mm$^{-1}$ | | | | |
| Source, λ | Cu—K(alpha), 1.54178 Å | | | | |
| F(000) | 2224 | | | | |
| T | 100(1) K | | | | |
| Crystal | Colourless columnar, 0.18 × 0.05 × 0.02 mm | | | | |
| Data truncated to | 0.80 Å | | | | |
| $\theta_{max}$ | 74.48° | | | | |
| Completeness | 99.9% | | | | |
| Reflections | 29981 | | | | |
| Unique reflections | 11007 | | | | |
| $R_{int}$ | 0.0597 | | | | |

Example 28

Solid Form Characterization

X-Ray Powder Diffraction (XRPD)

Bruker AXS C2 GADDS:

X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Gael multilayer mirror coupled with a pinhole collimator of 0.3 mm. The beam divergence, i.e., the effective size of the X-ray beam on the sample, was approximately 4 mm. A θ-θ continuous scan mode was employed with a sample—detector distance of 20 cm which gives an effective 2θ range of 3.2°-29.7°. Typically the sample would be exposed to the X-ray beam for 120 seconds. The software used for data collection was GADDS for XP/2000 4.1.43 and the data were analyzed and presented using Diffrac Plus EVA v13.0.0.2 or v15.0.0.0. Samples run under ambient conditions were prepared as flat plate specimens using powder as received without grinding. Approximately 1-2 mg of the sample was lightly pressed on a glass slide to obtain a flat surface. Samples run under non-ambient conditions were mounted on a silicon wafer with heat-conducting compound. The sample was then heated to the appropriate temperature at 10° C./min and subsequently held isothermally for 1 minute before data collection was initiated.

Bruker AXS D8 Advance:

X-Ray Powder Diffraction patterns were collected on a Bruker D8 diffractometer using Cu Kα radiation (40 kV, 40 mA), θ-2θ goniometer, and divergence of V4 and receiving slits, a Ge monochromator and a Lynxeye detector. The software used for data collection was Diffrac Plus XRD Commander v2.6.1 and the data were analysed and presented using Diffrac Plus EVA v13.0.0.2 or v15.0.0.0. Samples were run under ambient conditions as flat plate specimens. The sample was gently packed into a cavity cut into polished, zero-background (510) silicon wafer. The sample was rotated in its own plane during analysis. The details of the data collection are: Angular range: 2 to 42°2θ, Step size: 0.05°2θ, and Collection time: 0.5 s/step.

$^1$H NMR

NMR spectra were collected on a Bruker 400 MHz instrument equipped with an auto-sampler and controlled by a DRX400 console. Automated experiments were acquired using ICON-NMR v4.0.7 running with Topspin v1.3 using the standard Bruker loaded experiments. For non-routine spectroscopy, data were acquired through the use of Topspin alone. Samples were prepared in DMSO-d$_6$, unless otherwise stated. Off-line analysis was carried out using Topspin v1.3 or ACD SpecManager v12.5.

Differential Scanning Calorimetry (DSC)

DSC data were collected on a Mettler DSC 823E equipped with a 34 position auto-sampler. The instrument was calibrated for energy and temperature using certified indium. Typically 0.5-1.5 mg of each sample, in a pin-holed aluminium pan, was heated at 10° C./min from 25° C. to 300° C. A nitrogen purge at 50 ml/min was maintained over the sample. The instrument control and data analysis software was STARe v9.20.

Thermo-Gravimetric Analysis (TGA)

TGA data were collected on a Mettler TGA/SDTA 851e equipped with a 34 position auto-sampler. The instrument was temperature calibrated using certified indium. Typically 5-10 mg of each sample was loaded onto a pre-weighed aluminium crucible and was heated at 10° C./min from ambient temperature to 350° C. A nitrogen purge at 50 ml/min was maintained over the sample. The instrument control and data analysis software was STARe v9.20.

Polarised Light Microscopy (PLM)

Samples were studied on a Leica LM/DM polarised light microscope with a digital video camera for image capture. A small amount of each sample was placed on a glass slide, mounted in immersion oil and covered with a glass slip, the individual particles being separated as well as possible. The sample was viewed with appropriate magnification and partially polarised light, coupled to a λ false-colour filter.

Water Determination by Karl Fischer Titration (KF)

The water content of each sample was measured on a Metrohm 874 Oven Sample Processor at 150° C. or 180° C. with 851 Titrano Coulometer using Hydranal Coulomat AG oven reagent and nitrogen purge. Weighed solid samples were introduced into a sealed sample vial. Approx 10 mg of sample was used per titration and duplicate determinations were made.

Gravimetric Vapour Sorption (GVS)

Sorption isotherms were obtained using a Hiden IGASorp moisture sorption analyser, controlled by CFRSorp software. The sample temperature was maintained at 25° C. by a Huber re-circulating water bath. The humidity was controlled by mixing streams of dry and wet nitrogen, with a total flow rate of 250 ml/min. The relative humidity (RH) was measured by a calibrated Vaisala RH probe (dynamic range of 0-95% RH), located near the sample. The weight change, (mass relaxation) of the sample as a function of % RH was constantly monitored by the microbalance (accuracy ±0.001 mg). Typically 10-20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0-90% RH range.

| Parameters | Values |
| --- | --- |
| Adsorption - Scan 1 | 40-90 |
| Desorption/Adsorption - Scan 2 | 85 - Dry, Dry - 40 |
| Intervals (% RH) | 10 |
| Number of Scans | 2 |
| Flow rate (ml/min) | 250 |
| Temperature (° C.) | 25 |
| Stability (° C./min) | 0.05 |
| Minimum Sorption Time (hours) | 1 |
| Maximum Sorption Time (hours) | 4 |
| Mode | AF2 |
| Accuracy (%) | 98 |

The software uses a least squares minimisation procedure together with a model of the mass relaxation, to predict an asymptotic value. The measured mass relaxation value must be within 5% of that predicted by the software, before the next % RH value is selected. The minimum equilibration time was set to 1 hour and the maximum to 4 hours. The sample was recovered after completion of the isotherm and re-analysed by XRPD.

Ion Chromatography (IC)

Data were collected on a Metrohm 861 Advanced Compact IC (for anions) using IC Net software v2.3. Accurately weighed samples were prepared as stock solutions in an appropriate dissolving solution and diluted appropriately prior to testing. Quantification was achieved by comparison with standard solutions of known concentration of the ion being analysed.

| Type of method | Anion exchange |
| --- | --- |
| Column | Metrosep A Supp 5 - 250 (4.0 × 250 mm) |
| Column Temperature (° C.) | Ambient |
| Injection (μl) | 10 |
| Detection | Conductivity detector |
| Flow Rate (ml/min) | 0.7 |
| Eluent | 3.2 mM sodium carbonate, 1.0 mM sodium hydrogen carbonate in 5% aqueous acetone. |

Fourier Transform-Infra-Red (FTIR)

Data were collected on a Perkin-Elmer Spectrum One fitted with a universal Attenuated Total Reflectance (ATR) sampling accessory. The data were collected and analysed using Spectrum v10.0.1 software.

Example 29

Comparative Studies for Free Base Hydrate, Bis-Sulfuric Acid Salt, and Mono-Maleic Acid Salt of Compound 1

Stability:

2-Week comparative stability studies were conducted for Form 2 of free base hydrate, Form 1 of bis-sulfuric acid salt monohydrate, and Form 1 of mono-maleic acid salt of Compound 1 in the following conditions: (i) 5° C. (closed); (ii) ambient (closed); (iii) ambient (closed-exposed to light); (iv) ambient (open); (v) 60° C. (closed); (vi) RT/75% RH (open); and (vii) 40° C./75% RH (open). No change in appearance was observed for any form across all conditions tested. No significant change of water content was observed, as determined by KF (data not shown), for any form across all conditions tested.

Solubility:

The solubility date for free base hydrate, Form 1 of bis-sulfuric acid salt monohydrate, and Form 1 of mono-maleic acid salt of Compound 1 are summarized in Table 24. When compared to the hydrate, both salts, particularly the bis-sulfuric acid salt, showed significantly higher solubility up to pH 3.

TABLE 24

Solubility of free base hydrate, bis-sulfuric acid salt, and mono-maleic acid salt

| Solubility | Hydrate | Bis-sulfuric acid salt | | | Maleic acid salt | | |
| --- | --- | --- | --- | --- | --- | --- | --- |
| Water | 0 | >60 mg/mL (pH 1.16) | | | ~0.2 mg/mL (pH 4.43) | | |
| | | pH | RT | 37° C. | pH | RT | 37° C. |
| Other pH's | ~0 | 1.65 | >12 | >12 | 1.6 | >4 | >4 |
| | | 1.9 | >12 | >12 | 2.5 | 3.57 | 3.07 |
| | | 2.5 | >12 | >12 | 2.9 | 1.39 | 1.62 |
| | | 3.0 | 1.58 | 3.45 | 3.8 | 0.24 | 0.31 |
| | | 3.8 | 0.29 | 0.28 | | | |

TABLE 24-continued

Solubility of free base hydrate, bis-sulfuric acid salt, and mono-maleic acid salt

| Solubility | Hydrate | Bis-sulfuric acid salt | Maleic acid salt |
|---|---|---|---|
| citrate buffer, pH 2.5 | 0.2-0.3 mg/mL | >12 mg/mL at RT and 37° C. | 1.8 mg/mL at RT; 3.13 mg/mL at 37° C. |
| 0.1N HCl, 37° C., at saturation | 16 mg/mL | >90 mg/mL | 34 mg/mL |
| Simulated Gastric Fluid | 8.13 mg/mL | >17 mg/mL | >19 mg/mL |
| Simulated Intestinal Fluid | 0.002 mg/mL | 0.04 mg/mL | 0.01 mg/mL |

Dissolution:

The dissolution date for Form 2 of free base hydrate, Form 1 of bis-sulfuric acid salt monohydrate, and Form 1 of mono-maleic acid salt of Compound 1 are shown in FIG. 45A and FIG. 45B. The dissolution rate for the hydrate was about 80% in 15 min at pH 1.2 and about 20% in 60 min at pH 2.5. The dissolution rate of the bis-sulfuric acid salt was 100% in 15 min at both pH 1.2 and pH 2.5. The dissolution rate of the mono-maleic acid salt was 100% in 15 min at pH 1.2 and about 20% in 60 min at pH 2.5.

Particle Size and Flowability:

The density and flowability date for Form 2 of free base hydrate, Form 1 of bis-sulfuric acid salt monohydrate, and Form 1 of mono-maleic acid salt of Compound 1 are summarized in Table 25. The Hausner ratio and the Carr index are correlated to the flowability of a powder or granular material. The data showed that both the bis-sulfuric acid salt and the mono-maleic acid salts have improved flowability than the hydrate has. The flowability of both salts are acceptable for manufacturing.

The particle size distribution of the bis-sulfuric acid salt and the mono-maleic acid salts are shown in FIG. 46.

Dog PK Study:

Dog PK studies were conducted with four formulations (Form 2 of free base hydrate in capsule; Form 2 of free base hydrate in solution; Form 1 of maleic acid salt in capsule; and Form 1 of bis-sulfuric acid salt in capsule) of Compound 1. The study group consisted with 3 male dogs (10 kg each). There was a 72-hour wash-out period between each dose. Blood samples were drawn at T=0, 0.25, 0.5, 1, 2, 4, 8, 12, and 24 h. The results were summarized in Table 25. The bis-sulfuric acid salt capsule (50 mg) formulation achieved a dose-normalized $AUC_{0-24}$ that was comparable to that of the hydrate solution (4.5 mg/kg) formulation, about 30% higher than the maleic acid salt capsule (50 mg) formulation, and about 120% higher than the hydrate capsule (50 mg) formulation. The dog PK data for IPAc solvate (Form 5 of free base) of Compound 1 and Form 2 of free base hydrate suspension from similar studies are also listed in Table 25.

TABLE 25

Dog PK data of various Compound 1 formulations in Male Dogs

| Formulation | $C_{max}$ (ng/mL) | $T_{max}$ (h) | $AUC_{0-24}$ (ng*h/mL) | $AUC_{0-24}/$ Dose (ng*h/mL) | $t_{1/2}$ (h) |
|---|---|---|---|---|---|
| Form 2 of Free Base Hydrate Capsule (50 mg) | 935 | 1.5 | 6494 | 1185 | 6.1 |
| Form 2 of Free Base Hydrate Solution (4.5 mg/kg) | 1677 | 0.8 | 12766 | 2837 | 7.7 |
| Form 1 of Maleic acid salt Capsule (50 mg) | 1093 | 1.7 | 10842 | 2005 | 7.5 |
| Form 1 of Bis Sulfuric acid salt Capsule (50 mg) | 1893 | 1.0 | 14480 | 2650 | 7.8 |
| IPAc Solvate (Form 5 of Free base) Suspension (5 mg/kg) | 1012 | 1.0 | 12047 | 2409 | 14.7 |
| Form 2 of Free Base Hydrate Suspension (5 mg/kg) | 723 | 1.5 | 4130 | 825 | 4.2 |

While exemplary embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments described herein can be employed in practicing the subject matter of the disclosure. It is intended that the following claims define the scope of the invention and that methods and structures within the scope of these claims and their equivalents be covered thereby.

What is claimed is:

1. A solid form of a compound of formula (I):

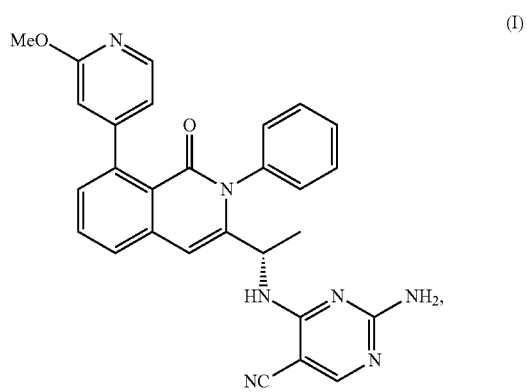 [SMILES: COc1cc(-c2cccc3cc([C@H](C)Nc4nc(N)ncc4C#N)n(-c4ccccc4)c(=O)c23)ccn1]

or a salt, solvate, or solvate of a salt of the compound, wherein the solid form is Form 1 of a sulfuric acid salt of the compound of formula (I), having an X-ray powder diffraction pattern comprising peaks at approximately 10.7, 12.4, and 23.6 degrees 2θ;

Form 3 of a sulfuric acid salt of the compound of formula (I), having an X-ray powder diffraction pattern comprising peaks at approximately 13.7, 15.5, and 20.9 degrees 2θ;

Form 1 of a maleic acid salt of the compound of formula (I), having an X-ray powder diffraction pattern comprising peaks at approximately 9.0, 16.0, and 22.6 degrees 2θ;

Form 1 of a 1,2-ethanedisulfonic acid salt of the compound of formula (I), having an X-ray powder diffraction pattern comprising peaks at approximately 10.3, 12.7, and 23.3 degrees 2θ;

Form 1 of a free base of the compound of formula (I), having an X-ray powder diffraction pattern comprising peaks at approximately 11.4, 16.8, and 19.9 degrees 2θ;

Form 2 of a free base of the compound of formula (I), having an X-ray powder diffraction pattern comprising peaks at approximately 9.1, 10.9, and 16.8 degrees 2θ;

Form 3 of a free base of the compound of formula (I), having an X-ray powder diffraction pattern comprising peaks at approximately 7.3, 10.6, and 11.3 degrees 2θ;

Form 4 of a free base of the compound of formula (I), having an X-ray powder diffraction pattern comprising peaks at approximately 11.1, 11.5, and 20.0 degrees 2θ;

Form 5 of a free base of the compound of formula (I), having an X-ray powder diffraction pattern comprising peaks at approximately 9.0, 10.5, and 18.9 degrees 2θ; or Form 6 of a free base of the compound of formula (I), having an X-ray powder diffraction pattern comprising peaks at approximately 7.2, 10.6, and 11.1 degrees 2θ.

2. The solid form of claim 1, which is Form 1 of a sulfuric acid salt of the compound of formula (I), having an X-ray powder diffraction pattern comprising peaks at approximately 10.7, 12.4, and 23.6 degrees 2θ.

3. The solid form of claim 2, having an X-ray powder diffraction pattern further comprising peaks at approximately 19.2 and 20.4 degrees 2θ.

4. The solid form of claim 3, having an X-ray powder diffraction pattern further comprising peaks at approximately 17.7 and 22.2 degrees 2θ.

5. The solid form of claim 2, which exhibits a weight loss of about 2.70% of the total sample weight upon heating from about 30 to about 220° C.

6. The solid form of claim 2, which exhibits a thermal event, as characterized by DSC, with a peak temperature of about 151° C. and an onset temperature of about 133° C.

7. The solid form of claim 2, which is a bis-sulfuric acid monohydrate salt of the compound of formula (I).

8. The solid form of claim 1, which is Form 3 of a sulfuric acid salt of the compound of formula (I), having an X-ray powder diffraction pattern comprising peaks at approximately 13.7, 15.5, and 20.9 degrees 2θ.

9. The solid form of claim 8, having an X-ray powder diffraction pattern further comprising peaks at approximately 24.6 and 24.9 degrees 2θ.

10. The solid form of claim 9, having an X-ray powder diffraction pattern further comprising peaks at approximately 11.8 and 18.3 degrees 2θ.

11. The solid form of claim 1, which is Form 1 of a maleic acid salt of the compound of formula (I), having an X-ray powder diffraction pattern comprising peaks at approximately 9.0, 16.0, and 22.6 degrees 2θ.

12. The solid form of claim 11, having an X-ray powder diffraction pattern further comprising peaks at approximately 18.6 and 24.4 degrees 2θ.

13. The solid form of claim 12, having an X-ray powder diffraction pattern further comprising peaks at approximately 12.9 and 13.0 degrees 2θ.

14. The solid form of claim 1, which is Form 1 of a 1,2-ethanedisulfonic acid salt of the compound of formula (I), having an X-ray powder diffraction pattern comprising peaks at approximately 10.3, 12.7, and 23.3 degrees 2θ.

15. The solid form of claim 14, having an X-ray powder diffraction pattern further comprising peaks at approximately 14.3 and 18.1 degrees 2θ.

16. The solid form of claim 15, having an X-ray powder diffraction pattern further comprising peaks at approximately 17.2 and 21.9 degrees 2θ.

17. The solid form of claim 1, which is Form 1 of a free base of the compound of formula (I), having an X-ray powder diffraction pattern comprising peaks at approximately 11.4, 16.8, and 19.9 degrees 2θ.

18. The solid form of claim 17, having an X-ray powder diffraction pattern further comprising peaks at approximately 5.0 and 7.6 degrees 2θ.

19. The solid form of claim 18, having an X-ray powder diffraction pattern further comprising peaks at approximately 22.4 and 23.7 degrees 2θ.

20. The solid form of claim 1, which is Form 2 of a free base of the compound of formula (I), having an X-ray powder diffraction pattern comprising peaks at approximately 9.1, 10.9, and 16.8 degrees 2θ.

21. The solid form of claim 20, having an X-ray powder diffraction pattern further comprising peaks at approximately 17.8 and 24.9 degrees 2θ.

22. The solid form of claim 21, having an X-ray powder diffraction pattern further comprising peaks at approximately 19.3 and 26.8 degrees 2θ.

23. The solid form of claim 1, which is Form 3 of a free base of the compound of formula (I), having an X-ray powder diffraction pattern comprising peaks at approximately 7.3, 10.6, and 11.3 degrees 2θ.

24. The solid form of claim 23, having an X-ray powder diffraction pattern further comprising peaks at approximately 4.9 and 20.0 degrees 2θ.

25. The solid form of claim 24, having an X-ray powder diffraction pattern further comprising peaks at approximately 21.9 and 24.6 degrees 2θ.

26. The solid form of claim 1, which is Form 4 of a free base of the compound of formula (I), having an X-ray powder diffraction pattern comprising peaks at approximately 11.1, 11.5, and 20.0 degrees 2θ.

27. The solid form of claim 26, having an X-ray powder diffraction pattern further comprising peaks at approximately 7.4 and 21.7 degrees 2θ.

28. The solid form of claim 27, having an X-ray powder diffraction pattern further comprising peaks at approximately 5.0 and 11.8 degrees 2θ.

29. The solid form of claim 1, which is Form 5 of a free base of the compound of formula (I), having an X-ray powder diffraction pattern comprising peaks at approximately 9.0, 10.5, and 18.9 degrees 2θ.

30. The solid form of claim 29, having an X-ray powder diffraction pattern further comprising peaks at approximately 9.4 and 15.5 degrees 2θ.

31. The solid form of claim 30, having an X-ray powder diffraction pattern further comprising peaks at approximately 10.0 and 16.0 degrees 2θ.

32. The solid form of claim 1, which is Form 6 of a free base of the compound of formula (I), having an X-ray powder diffraction pattern comprising peaks at approximately 7.2, 10.6, and 11.1 degrees 2θ.

33. The solid form of claim 32, having an X-ray powder diffraction pattern further comprising peaks at approximately 14.6 and 18.1 degrees 2θ.

34. The solid form of claim 33, having an X-ray powder diffraction pattern further comprising peaks at approximately 4.9 and 22.2 degrees 2θ.

35. A pharmaceutical composition comprising a solid form of claim 1, and one or more pharmaceutically acceptable excipients.

\* \* \* \* \*